US011207511B2

(12) United States Patent
Barman et al.

(10) Patent No.: US 11,207,511 B2
(45) Date of Patent: Dec. 28, 2021

(54) METHODS FOR TREATING BALDNESS AND PROMOTING HAIR GROWTH

(71) Applicant: FOLLICA, INC., Boston, MA (US)

(72) Inventors: Shikha P. Barman, Bedford, MA (US); William D. Ju, Mendham, NJ (US); Scott C. Kellogg, Mattapoisett, MA (US); Stephen M. Prouty, Doylestown, PA (US); Eric Schweiger, New York, NY (US); Seth Lederman, New York, NY (US); Mary Osbakken, Philadelphia, PA (US); Alan D. Schinazi, Providence, PR (US)

(73) Assignee: Follica, Inc., Boston, MA (US)

( * ) Notice: Subject to any disclaimer, the term of this patent is extended or adjusted under 35 U.S.C. 154(b) by 0 days.

(21) Appl. No.: 16/164,344

(22) Filed: Oct. 18, 2018

(65) Prior Publication Data

US 2019/0381296 A1 Dec. 19, 2019

Related U.S. Application Data

(63) Continuation of application No. 13/991,874, filed as application No. PCT/US2011/063557 on Dec. 6, 2011, now abandoned.

(60) Provisional application No. 61/513,906, filed on Aug. 1, 2011, provisional application No. 61/478,689, filed on Apr. 25, 2011, provisional application No. 61/453,919, filed on Mar. 17, 2011, provisional application No. 61/453,902, filed on Mar. 17, 2011, provisional application No. 61/420,282, filed on Dec. 6, 2010.

(51) Int. Cl.
| | |
|---|---|
| *A61M 37/00* | (2006.01) |
| *A61K 8/63* | (2006.01) |
| *A61K 8/69* | (2006.01) |
| *A61Q 7/00* | (2006.01) |
| *A61K 8/49* | (2006.01) |
| *A61B 17/54* | (2006.01) |
| *A61B 17/00* | (2006.01) |
| *A61H 7/00* | (2006.01) |
| *A61N 5/06* | (2006.01) |
| *A61B 18/20* | (2006.01) |
| *A61K 38/48* | (2006.01) |
| *A61B 18/00* | (2006.01) |
| *A61B 17/32* | (2006.01) |
| *A61H 23/02* | (2006.01) |
| *A61N 5/067* | (2006.01) |

(52) U.S. Cl.
CPC ....... *A61M 37/00* (2013.01); *A61B 17/00491* (2013.01); *A61B 17/54* (2013.01); *A61B 18/203* (2013.01); *A61H 7/005* (2013.01); *A61K 8/4953* (2013.01); *A61K 8/63* (2013.01); *A61K 8/69* (2013.01); *A61K 38/4893* (2013.01); *A61N 5/0617* (2013.01); *A61Q 7/00* (2013.01); *A45D 2200/1054* (2013.01); *A61B 2017/00398* (2013.01); *A61B 2017/00495* (2013.01); *A61B 2017/00734* (2013.01); *A61B 2017/00747* (2013.01); *A61B 2017/00761* (2013.01); *A61B 2017/320004* (2013.01); *A61B 2018/00476* (2013.01); *A61B 2018/00577* (2013.01); *A61H 23/0245* (2013.01); *A61H 2201/10* (2013.01); *A61H 2201/105* (2013.01); *A61H 2201/1215* (2013.01); *A61H 2201/1604* (2013.01); *A61H 2201/1671* (2013.01); *A61H 2205/021* (2013.01); *A61K 2800/884* (2013.01); *A61N 5/067* (2021.08); *A61N 2005/0644* (2013.01)

(58) Field of Classification Search
None
See application file for complete search history.

(56) References Cited

U.S. PATENT DOCUMENTS

| | | |
|---|---|---|
| 4,139,619 A | 2/1979 | Chidsey, III |
| 4,490,365 A | 10/1984 | Panaretto et al. |
| 4,919,664 A | 4/1990 | Oliver et al. |
| 5,183,817 A | 2/1993 | Bazzano |
| 5,223,271 A | 6/1993 | Horrobin |
| 5,424,298 A | 6/1995 | Takasugi et al. |
| 5,466,695 A | 11/1995 | Poulos et al. |
| 5,514,672 A | 5/1996 | Bazzano |
| 5,861,432 A | 1/1999 | Sklar |
| 6,075,005 A | 6/2000 | Raziel |
| 6,159,950 A | 12/2000 | Crystal et al. |
| 6,187,796 B1 | 2/2001 | Steiner et al. |
| 6,262,105 B1 | 7/2001 | Johnstone |
| 6,409,736 B1 | 6/2002 | Bemabei et al. |
| 6,416,769 B1 | 7/2002 | Vromen |
| 6,458,387 B1 | 10/2002 | Scott et al. |

(Continued)

FOREIGN PATENT DOCUMENTS

| | | |
|---|---|---|
| JP | 63-045212 A | 2/1988 |
| JP | 04/290813 A | 10/1992 |

(Continued)

OTHER PUBLICATIONS

U.S. Appl. No. 14/946,512, Cotsarelis et al.

(Continued)

*Primary Examiner* — Blaine Lankford
(74) *Attorney, Agent, or Firm* — Jones Day

(57) ABSTRACT

The invention relates to methods of treating baldness, treating alopecia, promoting hair growth, and/or promoting hair follicle development and/or activation or stimulation on an area of the skin of a subject (for example, a human) by subjecting said area of the skin to integumental perturbation. Integumental perturbation can be used in combination with other treatments for promoting hair growth. The invention provides devices for integumental perturbation for promoting hair growth, and provides pharmaceutical compositions for use in combination with integumental perturbation for promoting hair growth.

19 Claims, 34 Drawing Sheets

(56) References Cited

U.S. PATENT DOCUMENTS

| | | |
|---|---|---|
| 6,527,716 B1 | 3/2003 | Eppstein |
| 6,720,427 B2 | 4/2004 | Sanner et al. |
| 6,831,186 B2 | 12/2004 | Bauman et al. |
| 6,848,451 B2 | 2/2005 | Postal et al. |
| 6,926,681 B1 | 8/2005 | Ramey et al. |
| 6,936,044 B2 | 8/2005 | McDeniel |
| 8,252,749 B2 | 8/2012 | Steinberg et al. |
| 8,431,400 B2 | 4/2013 | Hoffmann et al. |
| 8,871,711 B2 | 10/2014 | Cotsarelis et al. |
| 9,220,926 B2 | 12/2015 | Cotsarelis et al. |
| 9,254,293 B2 | 2/2016 | Cotsarelis et al. |
| 2002/0013298 A1 | 1/2002 | Hunter et al. |
| 2002/0065314 A1 | 5/2002 | Nielsen et al. |
| 2002/0114772 A1 | 8/2002 | Morgan et al. |
| 2002/0132792 A1 | 9/2002 | Prien et al. |
| 2002/0172672 A1 | 11/2002 | Seiberg et al. |
| 2003/0007941 A1 | 1/2003 | Cornelius |
| 2003/0083381 A1 | 5/2003 | Kumagai et al. |
| 2003/0134424 A1 | 7/2003 | Canham et al. |
| 2004/0153131 A1 | 8/2004 | Yorke et al. |
| 2004/0236269 A1 | 11/2004 | Marchitto et al. |
| 2005/0037038 A1 | 2/2005 | Gupta |
| 2005/0049625 A1 | 3/2005 | Shaya et al. |
| 2005/0154333 A1 | 7/2005 | Mulholland et al. |
| 2005/0222220 A1 | 10/2005 | Padilla et al. |
| 2006/0008505 A1 | 1/2006 | Brandon et al. |
| 2006/0018966 A1 | 1/2006 | Lin et al. |
| 2006/0058238 A1 | 3/2006 | Laurent-Applegate et al. |
| 2006/0063736 A1 | 3/2006 | Bertozzi et al. |
| 2006/0073117 A1 | 4/2006 | Li |
| 2006/0088505 A1 | 4/2006 | Hoffmann et al. |
| 2006/0129209 A1 | 6/2006 | McDaniel et al. |
| 2006/0135583 A1 | 6/2006 | Tachibana et al. |
| 2006/0165617 A1 | 7/2006 | Lemer et al. |
| 2006/0241696 A1 | 10/2006 | Krco |
| 2006/0269494 A1 | 11/2006 | Gupta |
| 2006/0286063 A1 | 12/2006 | Shebuski et al. |
| 2006/0287385 A1 | 12/2006 | Baxter et al. |
| 2007/0020213 A1 | 1/2007 | Tamarkin et al. |
| 2007/0077201 A1 | 4/2007 | Reading et al. |
| 2007/0078290 A1 | 4/2007 | Esenaliev |
| 2007/0092496 A1 | 4/2007 | Zheng et al. |
| 2007/0129353 A1 | 6/2007 | Kahn |
| 2007/0190075 A1 | 8/2007 | Suzuki et al. |
| 2007/0243132 A1 | 10/2007 | Russell-Jones et al. |
| 2007/0249714 A1 | 10/2007 | Hattendorf et al. |
| 2008/0182859 A1 | 7/2008 | Brunton et al. |
| 2008/0193423 A1 | 8/2008 | Brunton et al. |
| 2008/0269732 A1 | 10/2008 | Pyun |
| 2009/0004122 A1 | 1/2009 | Modak et al. |
| 2009/0074886 A1 | 3/2009 | Bennett et al. |
| 2009/0196945 A1 | 8/2009 | Walsh et al. |
| 2009/0214628 A1 | 8/2009 | De Rijk |
| 2009/0269418 A1 | 10/2009 | Albeck et al. |
| 2009/0304635 A1 | 12/2009 | Cotsarelis et al. |
| 2010/0120768 A1 | 5/2010 | Steinberg et al. |
| 2010/0278784 A1 | 11/2010 | Pojasek et al. |
| 2010/0298760 A1 | 11/2010 | Olle et al. |
| 2011/0021599 A1 | 1/2011 | Cotsarelis et al. |
| 2011/0086007 A1 | 4/2011 | Kemp et al. |
| 2011/0092421 A1 | 4/2011 | Cotsarelis et al. |
| 2011/0130706 A1 | 6/2011 | Kellogg et al. |
| 2011/0130711 A1 | 6/2011 | Lederman et al. |
| 2011/0130748 A1 | 6/2011 | Kellogg et al. |
| 2011/0152746 A1 | 6/2011 | Cotsarelis et al. |
| 2011/0282267 A1 | 11/2011 | Cotsarelis et al. |
| 2012/0121693 A1 | 5/2012 | Cotsarelis et al. |
| 2012/0156228 A1 | 6/2012 | Steinberg et al. |
| 2013/0204238 A1 | 8/2013 | Lederman et al. |
| 2015/0072963 A1 | 3/2015 | Cotsarelis et al. |
| 2015/0216934 A1 | 8/2015 | Cotsarelis et al. |

FOREIGN PATENT DOCUMENTS

| | | |
|---|---|---|
| JP | 07-048230 A | 2/1995 |
| JP | 2003 081866 | 3/2003 |
| JP | 2003 192541 | 7/2003 |
| WO | WO 1999/01034 | 1/1999 |
| WO | WO 2000/31134 | 6/2000 |
| WO | WO 2000/045736 | 8/2000 |
| WO | WO 2001/32840 | 5/2001 |
| WO | WO 2001/58413 | 8/2001 |
| WO | WO 2001/074164 | 10/2001 |
| WO | WO 2002/060396 | 8/2002 |
| WO | WO 2002/092771 | 11/2002 |
| WO | WO 2003/039478 | 5/2003 |
| WO | WO 2003/061362 | 7/2003 |
| WO | WO 2003/068248 | 8/2003 |
| WO | WO 2004/043415 | 5/2004 |
| WO | WO 2004/060488 | 7/2004 |
| WO | WO 2004/111012 | 12/2004 |
| WO | WO 2005/017107 | 2/2005 |
| WO | WO 2006/050368 | 5/2006 |
| WO | WO 2006/105109 | 10/2006 |
| WO | WO 2007/149312 | 12/2007 |
| WO | WO 2008/042216 | 4/2008 |
| WO | WO 2008/143928 | 11/2008 |
| WO | WO 2009/061349 | 5/2009 |
| WO | WO 2010/056759 | 5/2010 |
| WO | WO 2011/031977 | 3/2011 |
| WO | WO 2011/031990 | 3/2011 |
| WO | WO 2011/123218 | 6/2011 |
| WO | WO 2012/065065 | 5/2012 |
| WO | WO 2012/067630 | 5/2012 |
| WO | WO 2012/067631 | 5/2012 |
| WO | WO 2012/067632 | 5/2012 |
| WO | WO 2012/125941 | 9/2012 |
| WO | WO 2013/142295 | 9/2013 |
| WO | WO 2003/104443 | 12/2013 |

OTHER PUBLICATIONS

Anonymous: "Operation and maintenance instruction manual AEU-12C Torque Plus+ Electric Dental Motor System". Nov. 2, 2012 pp. 1-8. Retrieved from the Internet on Apr. 13, 2016: URL: http://www.aseptico.com/wp-content/uploads/AEU-12C_420292_SnglePg_Rev-D.pdf.

Argyris et al., 1962, "Factors affecting the stimulation of hair growth during wound healing." Anat Rec. 142(2):139-45.

Argyris et al., 1964, "On the mechanism of hair growth stimulation in wound healing." Dev Biol. 9:230-54.

Argyris, T., 1976, "Kinetics of epidermal production during epidermal regeneration following abrasion in mice." Am J Pathol. 83(2):329-40.

Argyris, TS., 1962, "The growth-promoting effects of wounds on hair follicles already stimulated by plucking." Anat Rec. 143:183-8.

Beiley, B.J. et al., "193 Dermabrasion" in *Atlas of Head & Neck Surgery-Otolaryngology*, Jan. 1, 2002, Lippincott Williams & Wilkins, p. FP1-3, 526, 527.

Bennett et al., 2003, "Introduction to cosmetic dermatology." Current Problems in Dermatology, Mosby, 15(2)43-48.

Bernstein EF., 2002, "Chemical peels." Semin Cutan Med Surg. 21(1):27-45.

Bharti et al., "Demabrastion," eMedicine, Jan. 5, 2015.

Botchkarev et al., 1999, "Noggin is a mesenchymally derived stimulator of hair-follicle induction." Nat Cell Biol. 1(3):158-64.

Botchkarev et al., 2001, "Noggin is required for induction of the hair follicle growth phase in postnatal skin." FASEB J. 15(12):2205-14.

Botchkarev et al., 2005, "Edar signaling in the control of hair follicle development." J Investig Dermatol Symp Proc. 10(3):247-51.

Breedis et al., 1954, "Regeneration of hair follicles and sebaceous glands from the epithelium of scars in the rabbit." Cancer Research 14(8): 575-579.

Brown et al., 1998, "Acne vulgaris." Lancet. 351(9119):1871-6.

Buckland et al., 1986, "Effect of scalp burns on common male pattern baldness." Br Med J (Clin Res Ed). 293(6562):1645.

(56) References Cited

OTHER PUBLICATIONS

Danilenko et al., 1995, "Keratinocyte growth factor is an important endogenous mediator of hair follicle growth, development, and differentiation. Normalization of the nu/nu follicular differentiation defect and amelioration of chemotherapy-induced alopecia." Am J Pathol. 147(1):145-54.
Dreno B. 2004, "Acne: physical treatment." Clin Dermatol. 22(5):429-33.
Du Cros DL., 1993, "Fibroblast growth factor and epidermal growth factor in hair development." J Invest Dermatol. 101(1 Suppl):106S-113S.
Fuchs et al., 2000, "Stem cells: a new lease on life." Cell. 100(1):143-55.
Hallmans et al., 1974, "Regeneration of hair follicles from experimental wounds on the rabbit ear." Scand J Plast Reconstr Surg. 8(3):207-10.
Han et al., 2004, "Effect of minoxidil on proliferation and apoptosis in dermal papilla cells of human hair follicle." J. Dermatol Sci. 34(2):91-8.
Huelsken et al., 2001, "beta-Catenin controls hair follicle morphogenesis and stem cell differentiation in the skin." Cell. 105(4):533-45.
Ito et al., 2004, "Hair follicle stem cells in the lower bulge form the secondary germ, a biochemically distinct but functionally equivalent progenitor cell population, at the termination of catagen." Differentiation 72(9-10):548-57.
Jahoda et al., 1992, "Cellular and extracellular involvement in the regeneration of the rat lower vibrissa follicle." Development 114(4):887-97.
Johnson et al., 1964, "The effect of plucking hairs during different phases of the follicular cycle." J Embryol Exp Morphol. 12:465-74.
Kashiwagi et al., 1997, "Specific inhibition of hair follicle formation by epidermal growth factor in an organ culture of developing mouse skin." Dev. Biol. 189(1):22-32.
Katsuyuki, 1994, "Effects of epidermal growth factor and transforming growth factor on cultured hair follicle cells from human scalp." Skin 36(2):125-33 (English Abstract).
Kawano et al., 2005, "Comprehensive analysis of FGF and FGFR expression in skin: FGF18 is highly expressed in hair follicles and capable of inducing anagen from telogen stage hair follicles." J Invest Dermatol. 124(5):877-85.
Kligman Am., 1959, "Neogenesis of human hair follicles." Ann N Y Acad Sci. 83:507-11.
Kligman et al., 1956, "The formation of vellus hair follicles from human adult epidermis." J Invest Dermatol. 27(1):19-23.
Komi-Kuramochi et al., 2005, "Expression of fibroblast growth factors and their receptors during full-thickness skin wound healing in young and aged mice." J Endocrinol. 186(2):273-89.
Kwon, O. et al., 2009, "Fibroblast growth factor 9 from dentritic epidermal T cells promotes hari follicle neogenesis after wounding in adult skin", J. of Investigative Dermatology 129(S1): S104, & 69 Annual Meeting of the Society-of-Investigative-Dermatology; Montreal, Canada; May 6-9, 2009 (abstract).
Ley et al., 1987, "Hair growth induction by ultraviolet radiation in the marsupial Monodelphis domestica." Arch Dermatol. 123(8):1032-5.
Li et al., 2005, "Early epidermal destruction with subsequent epidermal hyperplasia is a unique feature of the papilloma-independent squamous cell carcinoma phenotype in PKCepsilon overexpressing transgenic mice." Toxicol Pathol. 33(6):684-94.
Lo Celso et al., 2004, "Transient activation of beta-catenin signaling in adult mouse epidermis is sufficient to induce new hair follicles but continuous activation is required to maintain hair follicle tumours." Development, 131: 1787-1799.
Lübbe and Harms, 1998, "Therapy of acne vulgaris". Ther Umsch. 55(8):478-83 (English Abstract).
Mahé et al., 1996, "Pro-inflammatory cytokine cascade in human plucked hair." Skin Pharmacol. 9(6):366-75.
Mak et al., 2003, "Epidermal growth factor as a biologic switch in hair growth cycle." J Biol Chem. 278(28):26120-6.

Mattar et al., 1993, "Inhibition of the epidermal growth factor receptor tyrosine kinase activity by leflunomide." FEBS Lett. 334(2):161-4.
McElwee et al., 2003, "Cultured peribulbar dermal sheath cells can induce hair follicle development and contribute to the dermal sheath and dermal papilla." J Invest Dermatol. 121(6):1267-75.
Messenger AG, 2004, "Minoxidil: mechanisms of action on hair growth." Br J Dermatol. 150(2):186-94.
Millar SE., 2002, "Molecular mechanisms regulating hair follicle development." J Invest. Dermatol. 118(2):216-25.
Moore et al., 1985, "Epidermal hyperplasia and wool follicle regression in sheep infused with epidermal growth factor." J Invest Dermatol. 84(3):172-5.
Muller SA., 1971, "Hair neogenesis." J Invest Dermatol. 56(1):1-9.
Ota et al., 2002, "Fibroblast growth factor 5 inhibits hair growth by blocking dermal papilla cell activation." Biochem Biophys Res Commun. 290(1):169-76.
Pestana et al., 1987, "Effect of ultraviolet light on topical minoxidil-induced hair growth in advanced male pattern baldness." J Am. Acad Dermatol. 16(5 Pt 1):971-6.
Reynolds et al., 1991, "Inductive properties of hair follicle cells." Ann N Y Acad Sci. :226-41; discussion 241-2.
Rubenstein et al., 1986, "Atypical keloids after dermabrasion of patients taking isotretinoin." J Am Acad Dermatol. 15(2Pt 1):280-5.
Srivastava et al., 2001, "Ectodysplasin-A1 is sufficient to rescue both hair growth and sweat glands in Tabby mice." Hum Mol Genet. 10(26):2973-81.
Suzuki et al., 2000, "Dual-mode regulation of hair growth cycle by two Fgf-5 gene products." J Invest Dermatol. 114(3):456-63.
Van Mater et al., 2003, "Transient activation of beta -catenin signaling in cutaneous keratinocytes is sufficient to trigger the active growth phase of the hair cycle in mice." Genes Dev. 17(10):1219-24.
International Search Report for PCT Application No. PCT/US06/11319, dated: May 28, 2008.
International Search Report for PCT Application No. PCT/US2010/048439, dated: Oct. 28, 2010.
Written Opinion for PCT Application No. PCT/US2010/048439, dated Oct. 28, 2010.
International Search Report for PCT Application No. PCT/US2010/048457, date of completion Oct. 22, 2010.
Written Opinion for PCT Application No. PCT/US2010/048457, date of completion Oct. 22, 2010.
International Search Report for PCT Application No. PCT/US2011/063557, dated Apr. 25, 2012.
Written Opinion for PCT Application No. PCT/US2011/063557, dated Apr. 25, 2012.
International Search Report for PCT Application No. PCT/US2007/020842, dated Aug. 8, 2008.
Written Opinion for PCT Application No. PCT/US2007/020842, dated Aug. 8, 2008.
International Search Report for PCT Application No. PCT/US2009/064049, dated Feb. 3, 2010.
Written Opinion for PCT Application No. PCT/US2009/064049, dated Feb. 3, 2010.
International Search Report for PCT Application No. PCT/US2008/006224, dated Oct. 9, 2008.
Written Opinion for PCT Application No. PCT/US2008/006224, dated Oct. 9, 2008.
International Search Report for PCT Application No. PCT/US2008/011979, dated Feb. 24, 2009.
Written Opinion for PCT Application No. PCT/US2008/011979, dated Feb. 24, 2009.
International Search Report for PCT Application No. PCT/US2011/060375, dated Mar. 23, 2012.
Written Opinion for PCT Application No. PCT/US2011/060375, dated Mar. 23, 2012.
International Search Report for PCT Application No. PCT/US2012/029475, dated Jun. 25, 2012.
Written Opinion for PCT Application No. PCT/US2012/029475, dated Jun. 25, 2012.

(56) References Cited

OTHER PUBLICATIONS

Blanpain et al., 2004, Self-renewal, multipotency, and the existence of two cell populations within an epithelial stem cell niche. 118(5): 635-648.

Dhurat et al., 2013, "A Randomized Evaluator Blinded Study of Effect of Microneedling in Androgenetic Alopecia: A Pilot Study." Int. J. Trichology, 5(1):6-11.

Kimura-Ueki et al., 2012, "Hair cycle resting phase is regulated by cyclic epithelial FGF18 signaling" J. Invest. Dermatol., 132(5): 1338-1345.

Mimura et al., Functional Cosmetics II, 1996, Chapter 9, Mechanism of hair loss and application of hair growing agent, pp. 124-130.

Vandervoort and Ludwig, 2008, "Microneedles for transdermal drug delivery: a minireview." Frontiers in Bioscience 13:1711-1715.

Verbaan et al., 2007, "Assembled microneedle arrays enhance the transport of compounds varying over a large range of molecular weight across human dermatomed skin." Journal of Controlled Release, 117:238-245.

Ledger, "Hair Brained," PENNMedicine, Dec. 1, 2008, p. FP1-2, 1-42; http://plannedgiving.med.upenn.edu/newsletters/PENNMedicine_2009_01_winter.pdf.

Hopkin, 2007, "Skin's own cells could beat baldness: Nature News"., http://www.nature.com/news/2007/070516/full/news070514-12.htm.

Ito et al., 2007, "Wnt-dependent de novo hair follicle regeneration in adult mouse skin after wounding", Nature, 447(7142):316-321.

Sung-Kyun et al., 2010, "Effect of applying modes of the polymer microneedle-roller on the permeation of L-ascorbic acid in rats", Journal of Drug Targeting, 18(1):15-20.

'Mesotherapy—Hair Loss & Hair Regrowth', Mesotherapy Worldwide [retrieved from internet on May 22, 2017] <URL: https://web.archive.org/web/20071025052754/http://www.mesotherapyworldwide.com/Hair_Loss.htm.> published on Oct. 25, 2007 as per Wayback Macine.

'MTS-Roller™- Clinical Use' [retrieved from internet on May 22, 2017] <URL:https://web.archive.org/web/20090328023028/http://www.clinicalresolution.com/main/mtsclinical.html> published on Mar. 28, 2009 as per Wayback Machine.

'Follica Announces Positive Topline Data from Clinical Study in Male Androgenetic Alopecia', Business Wire, [retrieved from internet on Mar. 22, 2020] <URL:https://www.businesswire.com/news/home/20191218005795/en/Follica-Announces-Positive-Topline-Data-Clinical-Study> published on Dec. 19, 2019.

Ro et al., "Therapeutic Effects of Growth Factor Cocktail Treatment in Patients with Androgenetic Alopecia According to the Depth of Microneedle," Korean Journal of Dermatology (2016) 54(3):184-189.

PELA = pre-existing-like, attached
PEL = pre-existing-like
NL = neogenic-like
DP = dermal papilla
Red = marker is negative
Green = marker is positive
Gray = marker is inconclusive

METHODS FOR TREATING BALDNESS AND PROMOTING HAIR GROWTH

This application is a continuation of U.S. patent application Ser. No. 13/991,874, which is a national stage entry of International patent application No. PCT/US2011/063557, filed Dec. 6, 2011, which claims priority to U.S. provisional application No. 61/420,282, filed Dec. 6, 2010, U.S. provisional application No. 61/453,919, filed Mar. 17, 2011, U.S. provisional application No. 61/453,902, filed Mar. 17, 2011, U.S. provisional application No. 61/478,689, filed Apr. 25, 2011, and U.S. provisional application No. 61/513,906, filed Aug. 1, 2011, the entire contents of each of which is incorporated herein by reference in its entirety.

1. INTRODUCTION

The invention relates to methods of treating baldness, treating alopecia, promoting hair growth, and/or promoting hair follicle development and/or activation on an area of the skin of a subject (for example, a human) by subjecting said area of the skin to integumental perturbation. Integumental perturbation can be used in combination with other treatments for promoting hair growth. The invention provides devices for integumental perturbation for promoting hair growth, and provides pharmaceutical compositions for use in combination with integumental perturbation for promoting hair growth.

2. BACKGROUND

The skin of an adult human is essentially covered with hair follicles and contains approximately five million hair follicles, with approximately 100,000-150,000 covering the scalp. The portions of human skin that lack visible hair contain, for the most part, hair follicles that produce "vellus hair" while certain other hair follicles may contain or produce no hair (see FIG. 1). Essentially, only the glaborous skin on palmar and plantar aspects of hands and feet, respectively, and the lips and labia lack hair follicles. Only a minority of human hair follicles produce a hair fiber that can be readily appreciated visibly (a "terminal hair") and these specialized follicles are localized on specific regions of skin; on the normal scalp, terminal hair follicles typically outnumber vellus hair follicles by 7:1. Accordingly, both the presence and absence of visible hair on human non-glaborous skin is mediated by regulation of activity of specialized follicles.

Hair follicles, and particularly human hair follicles, are crypt structures comprised of distinct components, each comprised of several different specialized cells (see FIGS. 2 and 3). In addition to the cells and structures associated with making and anchoring the hair shaft, the vast majority of hair follicles contain units called sebaceous glands (which produce sebum). Some hair follicles have apocrine glands attached to them, and are located in the axilla and other specific areas of the body.

In addition to the hair shaft, the structures of the hair follicle include the follicular papilla (FP) and the germinative epithelium (GE) (together, the bulb). The FP is comprised of mesenchymal cells (and connective tissue). The other cells of the follicle are epithelial and include at least 8 cellular lineages including the outer root sheath (ORS), the companion layer (CL), the internal root sheath Henle's layer (He), internal root sheath Huxley's layer (Hu), the cuticle of the internal root sheath (Csth), the cuticle of the hair shaft (Csft), the cortex of the hair shaft, and the medulla of the shaft (Med). (Stenn & Paus, 2001, Physiol. Revs. 81: 449-494.) (See also FIGS. 2-4.)

Scalp and certain other hair in humans tend to grow in follicular units. A follicular unit of scalp hair is typically composed of two to four terminal hair follicles; one, rarely two vellus hair follicles; their associated sebaceous glands, neurovascular plexus, an erector pilorum muscle and a circumferential band of adventitial collagen, termed the "perifolliculum" (Headington J T, 1984, Arch. Dermatol. 120:449-456; Bernstein R M, 2005, "Follicular Unit Hair Transplantation," Ch. 34 in *Surgery of the Skin*, Robinson et al., eds., St. Louis: Mosby, pp. 549-574).

Hair follicles are believed to produce approximately 20 individual hair shafts over the life of the follicle as the follicle progresses through cycles of hair production, shedding (ejection), involution and new growth. The regulation of hair growth and follicle regeneration have been investigated in murine systems. However, the biology of hair follicles in the mouse is different from those of the human in several important aspects. In the mouse, a thick fur coating is essential to healthy life (because hair plays roles in thermoregulation and other functions.) Mouse skin is covered with hair follicles that produce terminal hair (fur), whereas significant regions of human skin are covered with hair follicles that produce vellus hair, which is much less visible or even invisible. Mouse and other non-primate mammals have synchronous Follicle Cycles in early life, although the hair follicle cycles become less synchronous with age. Human follicles progress through the Follicle Cycle in an asynchronous fashion. On an adult human scalp, at any particular time approximately 80-90% are in anagen; 10-20% in telogen and 1-2% in catagen. While the mouse has certain specialized follicles (e.g., whiskers, guard, awl, auchene, and zigzag hair), mouse follicles are generally not subject to developmental and gender-specific hair patterning. In contrast, a significant number of human follicles are individual participants in choreographed hair patterning that affects the type, length and color of shaft produced at different times in development and aging and in a gender specific manner.

2.1 Hair Follicle Morphogenesis and Regeneration

It is believed that follicle formation occurs but once in a lifetime (in utero), so that a mammal, and particularly a human, is born with a fixed number of follicles, which does not normally increase thereafter. Despite suggestions of the regenerative capacity of the adult mammalian skin to recreate the embryonic follicle, until recently, follicle neogenesis was not proven because of the lack of tools needed to demonstrate the occurrence or hair follicle neogenesis (see, Argyris et al., 1959, Dev. Biol. 1: 269-80; Miller, 1973, J. Invest. Dermatol. 58:1-9; and Kligman, 1959, Ann NY Acad Sci 83: 507-511).

It has been proposed, however, that hair follicle neogenesis can be associated with wound healing in animals (e.g., rabbits, mice). See, Stenn & Paus, 2001, Physiol. Revs. 81:449-494. More recently, a series of murine experiments definitively showed that hair follicle-derived epithelial stem cell progenitors migrate out of the follicle and contribute to the re-epithelialization of injured skin (see, Morris et al., 2004, Nature Biotechnology 22:411-417; Ito et al., 2004, Differentiation 72:548-57; and Ito et al., 2005, Nature Medicine 11:1351-1354). In animal studies designed to explore the role of Wnt in hair follicle development, Fathke showed that prolonged activation of Wnt signaling during wound healing in mice resulted in generation of rudiments of hair follicles but did not result in the formation of hair follicles or growth of more hair (Fathke et al., 2006, BMC Cell Biol. 7:4).

As noted by Fathke, cutaneous repair in adult mammals following full thickness wounding is understood to result in scar tissue and the loss of the regenerative capability of the hair follicle. Severe wounds and burns are usually associated with a form of cutaneous repair that results in scar tissue and no hair follicles (see, Fathke et al., 2006, BMC Cell Biol. 7:4). However, in a mouse study, Cotsarelis showed that physically disrupting the skin and existing follicles, in a defined fashion, can lead to follicle neogenesis (Ito et al., 2007, Nature 447:316-321). Cotsarelis showed that following closure of large healed wounds created by full thickness excision (FTE) (1 cm$^2$ square wounds) in mice, new hairs are formed at the center of the wound (Ito et al., 2007, Nature 447:316-321). (Argyris, 1976, *Amer J Pathol* 83:329-338). In humans, dermabrasion was performed by planing to an approximate depth of 2 mm about halfway through the dermis of the facial skin and the formation of vellus hair follicles was observed (Kligman, 1956, J Invest Dermatol 27: 19-23). These findings have not been translated to clinical regimens for treatment of hair loss.

Other preclinical studies have identified a therapeutic window after epithelial disruption where the skin reverts to an embryonic state, allowing manipulation of skin and follicle phenotype by addition of compounds. For example, because new hair patterns after wounding are not predetermined, the regulatory pathways relevant to follicle formation (e.g. Wnt, EGFR) can be influenced dramatically, e.g., to increase the number and size of follicles. See, Ito et al. Nature. 2007; 447(7142):316-320; Fathke et al. BMC Cell Biol. 2006; 7:4; Snippert et al. Science. 2010; 327(5971): 1385-1389.

Motorized devices for performing dermabrasion for skin resurfacing and scar restoration have been around for decades. Over these years, the traditional embodiment of a motorized rotating grinding wheel hasn't changed much. Essentially, when power is applied to an abrasive wheel it grinds off stratum corneum and epidermis and sometimes part of the dermis, until the desired clinical effect is achieved. See, Argyris T S, Am J Pathol. 1977; 88(3):575-582. Conventional dermabrasion units have significant drawbacks, however. For example, the rotating wheel presents significant challenges when used in areas of thinning hair as part of a follicular growth treatment. Specifically, as can be seen in FIGS. 5A and 5B, because the traditional dermabrasion wheel 202 rotates through 360 degrees, the rotating wheel 202 tends to wind up and pull out existing hair 204. Also, the rotational inertia of a rotating wheel becomes transferred to blood and debris thereby causing the blood and debris created by the dermabrasion process to splatter, raising safety concerns and visual unpleasantness. Further, as can be seen in FIG. 6, a rotating wheel 202 tends to track and move or "walk" in the direction of rotation, resulting in poor overall control by the technician. Additionally, the axial orientation of conventional dermabraders provides for poor ergonomics. As can be seen in FIG. 7, with conventional dermabrasion hand pieces 210, the clinician's hand continually interferes with the patient and standard human factors engineering teaches that this is a poor way to hold a finesse instrument.

2.2 Human Hair Patterning is Mediated by Distinct Hair Follicle Types with Specific Features At a microscopic level, human skin is essentially covered with hair follicles. The portions of human skin where hair is not readily visible contain, for the most part, hair follicles that produce "vellus hair" which is thin and short (i.e., less than 2 mm in length and/or less than 30 microns in diameter), and can have a fine or "fuzzy" appearance, and is often colorless. Certain other hair follicles may contain or produce no hair. Only a minority of human hair follicles produce a hair fiber that can be readily appreciated visibly (a "terminal hair") and these specialized follicles are localized on specific regions of skin. Another follicle type is the "sebaceous" follicle, which is, from its inception, a hair follicle with a very small hair shaft, a very large sebaceous gland, and a large canal and pore.

Accordingly, both the presence and absence of noticeable hair on human skin is mediated by regulation of the activity of specialized hair follicles.

The spatial and temporal aspects of human hair patterning are believed to depend on the localization of specialized hair follicles with unique features during embryogenesis. It is further believed that this complement of hair follicles is maintained throughout life without renewal or replacement. Human fetus follicles may produce lanugo hair during gestation, which is intermediate fine, short, and poorly pigmented and is typically shed by the time of normal birth. By the time of birth, distinct specialized follicle types are positioned in specific areas of the skin where they will each play a programmed role in hair patterning over the life of the human individual, producing various hair types (lanugo, vellus or terminal hair) either constitutively or depending on certain signals, such as sex hormones or other factors (e.g., lanugo hair can reappear in starvation or in eating disorders such as anorexia nervosa and bulimia and also postnatally in congenital hypertrichosis lanuginosa, and acquired hypertrichosis lanuginosa, in the latter case associated with cancer).

Gender is associated with specific patterning of human hair. The growth and loss of visible hair in specific areas of the skin, in stereotypical gender dimorphic patterns, are regarded as "Secondary Sexual Characteristics." This terminology relates "secondary" features such as hair patterning to the genitals and reproductive organs, which are termed "Primary Sexual Characteristics." The distinctive genitals and reproductive organs of males and females acquired during embryonic development undergo further changes in puberty and menopause/andropause. In addition to hair growth and loss, breasts in females are also considered Secondary Sexual Characteristics.

Certain human hair follicles are targeted to specific skin areas and develop specialized characteristics during embryogenesis under the influence of sex hormones such as testosterone and dihydrotestosterone ("androgens") and/or estrogens. Further, certain human hair follicles are driven to change activity by sex hormones during puberty and in menopause/andropause.

The appearance and intensity of secondary sex characteristics can be described as being regulated by ratios of androgens and estrogens, since to a certain extent either of these groups of hormones (androgens and estrogens) can act to induce certain activities or to inhibit the effect of the other group (i.e., androgens inhibit estrogen effects and estrogens inhibit androgen effects). For example, androgens induce male characteristics and suppress female characteristics while estrogens induce female characteristics and suppress male characteristics. Male and female, as used herein, refer to the extremes of genetic gender dimorphism and include by reference the various conditions and states that represent a spectrum of male and female features (such as XO syndromes or conditions that result from exogenous sex steroid administration).

Specialized human hair follicles have quantitative variation in activity as well as qualitative variation. For example, sex steroids have qualitative effects on hair patterning either in embryogenesis or in adult life or both (e.g., males have beard hair follicles that produce terminal hair after puberty whereas females do not). Males and females also vary in the amount of gender-specific hair patterning (e.g., a higher density of leg hair follicles produce terminal hair on male rather than female legs). Also, individuals of the same gender exhibit quantitative variation. For example, male chest and back hair presents in different individuals as a spectrum from almost hairless to dense hair and from small regions of follicles producing terminal hair to large regions.

Gender specific human hair patterning highlights the distinct biological programming of specific hair follicles. Distinct hair follicles in relative proximity on the male scalp and face respond to high androgen/estrogen ratios in diametrically opposite ways: high androgen/estrogen ratios induce vellus to terminal hair transformation in male moustache/beard skin (particularly during puberty), but induce terminal to vellus follicle transformation change in male frontal/temporal scalp (progressively post puberty) in male pattern hair loss.

The effects of androgen/estrogen levels on other regions evidences further variations in the biological programming of specific hair follicles. Hair follicles on the occipital scalp are relatively insensitive to high androgen/estrogen ratios (but later, after more prolonged androgen exposure, undergo age-related thinning). Hair follicles in the axillary and pubic regions (anogenital region) appear to be more sensitive to androgen than moustache/beard follicles; since terminal hair in axillae/pubis grows: (a) in females with relatively low levels of androgen; (b) early in male puberty before beard/moustache; and (c) in patients with genetic 5-alpha-Reductase Type II deficiency.

2.2.1 Male Pattern Hair Loss

Male pattern hair loss (MPHL) is a type of "androgenetic alopecia." Androgenetic alopecia is a genetically-mediated disorder that occurs in approximately 50% of men by the age of 50 years (see review, Stough et al, 2005). In women, the histological features of the condition are the same as in men, but susceptibility, age at onset, rate of progression and pattern of hair loss differ between genders (Dinh and Sinclair, 2007).

After puberty, males begin to lose the scalp hair over the vertex, crown and frontal/parietal areas in a relatively characteristic pattern that is a continuum (described by, e.g., the Hamilton Norwood scale; see FIG. 8). The process of hair loss occurs at the level of the hair follicles by "miniaturization" through which the hair follicle becomes progressively smaller both in depth and circumference, and the hair shaft produced becomes shorter and thinner. The ratio of terminal-to-vellus-like hairs may be reduced from approximately 7:1 to less than 2:1. Miniaturization results in increased proportions of club hair shafts or vellus hair shafts. The loss of scalp hair in men is known to be a process driven by the androgen dihydrotestosterone (DHT), which can be inhibited and to some extent reversed by finasteride, which inhibits 5-alpha-reductase II (which converts testosterone to DHT). In advanced stages of MPHL, the affected hair follicles on the bald vertex or temples are considered to be atrophied, or perhaps involuted irreparably ("senescent"). The process by which this occurs is not completely understood. One theory holds that androgens change the length of anagen and telogen phases, so that a normal ratio of anagen to telogen ratio of approximately 9:1 can become approximately 2:1 or less in MPHL. Telogen hairs are more loosely anchored and prone to shedding or being pulled out (for example, by combing or brushing hair). At the end of telogen, a club hair is produced that is a fully keratinized hair. The hair follicles on MPHL affected areas also undergo follicular miniaturization in which a growing proportion of terminal follicles become vellus follicles. Additionally, androgenetic alopecia is thought to involve the progressive conversion of hair follicle units with 3 or more terminal hairs to follicular units having fewer terminal hairs (e.g., units with 2 terminal hairs progress to units with 1 terminal hair). Thinning of the hair, especially on the top of head, in addition to affecting younger individuals, can also occur in older individuals when amounts of testosterone and DHT in the body are decreasing. This can either be an extension of MPHL from the earlier years or even start in the latter decades of life (i.e. age-related hair thinning).

MPHL is associated with specific polymorphisms of the androgen receptor, the EDA2R gene. Men who are genetically deficient in Type II 5-alpha-reductase do not experience MPHL (see Jenkins et al., 1992, J Clin Invest 89:293-300).

Several lines of investigation have elucidated mechanistic aspects of the sensitivity to androgen of male frontal parietal and coronal hair follicles. Androgen activity may be mediated by a co-factor to the androgen receptor Hic-5/ARA55 (Inui, 2007, J Invest Dermatol 127:2302-2306). Hic-5/ARA55 mRNA expression was high in dermal papilla cells from the beard and bald frontal scalp but low in cells from the occipital scalp. Another androgen receptor coactivator ARA70/ELE1 had decreased expression of a splice variant form (ARA70beta/ELElbeta) in the dermal papilla of balding recipient areas than non-balding areas (Lee et al., 2005, J Cutan Pathol 32:567-571). There is evidence that there is increased methylation of the Hic-5/ARA55 gene in occipital hair follicles which may "protect" these hair follicles from androgen mediated hair loss. See Cobb et al. Br J Dermatol. 2011; 165(1):210-213.

2.2.2 Female Pattern Hair Loss

In addition to the progression of MPHL, both males and females develop diffuse hair loss in the frontal/parietal scalp called "thinning," which begins between 12 and 40 years of age. Collectively, MPHL and diffuse thinning in males and females is termed "androgenetic alopecia." Perhaps more than males, females notice (and complain of) diffuse hair thinning progressively in middle age more than males, perhaps because diffuse alopecia is more noticeable and problematic for females because they do not suffer from MPHL and retain the frontal hairline. In females, thinning is known as "Female Pattern Hair Loss (FPHL)" and may be caused or exacerbated by androgens (Price, 2003, J. Investig. Dermatol. Symp. Proc. 8:24-27).

Mechanistically, FPHL is thought to share some features with MPHL in terms of progressive reduction in the duration of anagen and progressive follicular miniaturization, although recent studies have found a prolongation of kenogen. As with MPHL, thinning of the hair, especially on the top of head, in addition to affecting younger individuals, can also occur in older individuals when amounts of testosterone and DHT in the body are decreasing. This can either be an extension of FPHL from the earlier years or even start in the latter decades of life (i.e. age-related hair thinning).

2.2.3 Cicatricial Alopecia

Scarring alopecia, also known as cicatricial alopecia, includes primary cicatricial alopecia (PCA) and secondary cicatricial alopecia. Primary cicatricial alopecia describes a rare group of diverse hair disorders that cause permanent destruction and scarring of the hair follicle in otherwise healthy men and women of all ages (http://www.carfintl.org/faq.html; Price V H, 2006, "The medical treatment of cicatricial alopecia," Semin Cutan Med Surg 25:56-9). In PCA, the hair follicle is the primary target of a folliculocentric inflammatory attack that results in destruction and replacement of the sebaceous gland and follicular stem cells with fibrous (scar) tissue. Secondary cicatricial alopecia describes an incidental destruction of the follicular unit following severe infections, tumors, burns, or radiation.

Primary cicatricial alopecia represents at least eight rare diseases that cause permanent hair loss. The clinical course of these diseases is highly variable and unpredictable. Hair loss may slowly progress over many years, or may occur rapidly within months. Itching, pain and burning are often severe and incapacitating. Primary cicatricial alopecia is currently classified by the histopathological analysis of scalp biopsies, which stratifies those with a predominantly lymphocytic inflammation from those with a predominantly neutrophilic inflammation, and from those with a mixed infiltrate. Lymphocyte-mediated PCA includes lichen planopilaris (LPP), frontal fibrosing alopecia (FFA), central centrifugal cicatricial alopecia (CCCA), and pseudopelade (Brocq). Neutrophil-mediated PCA includes folliculitis decalvans and tufted folliculitis. A mixed inflammatory infiltrate occurs in dissecting cellulitis and folliculitis keloidalis, both of which are secondary to follicular rupture.

The etiology and pathogenesis of these inflammatory disorders are poorly understood (see, Mirmirani et al., 2005, "Primary cicatricial alopecia: histopathologic findings do not distinguish clinical variants," J Am Acad Dermatol 52:637-43). They are not contagious and, unlike alopecia areata and androgenetic alopecia, are not inherited. Clinical hallmarks of PCA include the loss of follicular orifices over the affected scalp and the presence of loosely anchored anagen hair in a "pull test," a clinical marker of activity. Similar features are described in spontaneous mutant strains of mice, namely Asebia (Josefowicz & Hardy, 1978, "The expression of the gene asebia in the laboratory mouse. I. Epidermis and dermis," Genet Res 31:53-65) and defolliculated (Porter et al., 2002, "Defolliculated (Dfl): a dominant mouse mutation leading to poor sebaceous gland differentiation and total elimination of pelage follicles," J Invest Dermatol 119:32-37), with their hypoplastic sebaceous glands, destruction of hair follicles, progressive hair loss, and permanent replacement of follicles with fibrous tissue. Recently, an accumulation of evidence including microarray data and immunohistochemical analyses of patients' scalp biopsies, other in vitro studies, and transgenic studies in mouse models of scarring alopecia have led to speculation that decreased expression or loss of function of a specific transcription factor, peroxisome proliferator-activated receptor gamma (PPAR-γ) triggers the progressive loss of peroxisomes, proinflammatory lipid accumulation, and infiltration of inflammatory cells which ultimately destroys the pilosebaceous unit in LPP patients (Karnik et al., 2009, "Hair follicle stem cell-specific PPAR-gamma deletion causes scarring alopecia," J Invest Dermatol 129(5):1243-1257).

2.2.4 Donor Dominance

The unique features of specialized human hair follicles continue to show the characteristics of the donor site when skin, hair follicles, or hair follicle units are transplanted, which has been referred to as "donor dominance" (Orentreich N, 1959, Ann NY Acad Sci. 83:463-479). This principle is evidenced by the results of the commonly performed procedure of transplanting scalp hair (skin, follicles or follicle units) in males from areas that are not subject to androgen-triggered, MPHL (e.g. occipital scalp) to areas in which specialized follicles have begun producing vellus hair or have stopped producing hair under the influence of androgens (e.g. frontal/temporal; crown or vertex scalp. The transplanted follicles retain the programmed terminal hair producing features from their original location. However, more recent studies suggest that the recipient site may affect some characteristics of transplanted hairs. See Hwang et al., 2002, Dermatol. Surg. 28:795-799.

2.3 Current Treatments for Hair Loss in Human Subjects

Human hair loss can be categorized as (1) gender specific hair patterning, (2) pathological hair loss, or (3) hair loss after wounding, all which can be associated with effects on self-esteem and self-image, and many individuals explore whether their hair loss process can be treated. Current treatments offered involve a limited selection of agents and regimens, such as chemical and surgical approaches that either stimulate or transplant pre-existing hair.

Chemical treatments involve the use of drugs for the treatment of certain MPHL. These include, for example, minoxidil (trade name Rogaine™), which is an antihypertensive drug that opens K+ channels; and antiandrogens such as finasteride (trade names Propecia™, Proscar™), dutasteride or ketoconazole. Minoxidil and antiandrogens are reasonably effective in stimulating the growth of vellus and miniaturized hair in certain MPHL conditions. While these types of treatments are reasonably effective in delaying MPHL, they are less effective in both preventing MPHL and stimulating the growth of significant terminal hair in scalp of MPHL after baldness has advanced, consistent with some kind of terminal senescence or involution of the follicle. Even when effective, these drugs do no create hair follicles of the kind that were there before balding, and the resultant hair follicles are smaller and the scalp has less density of terminal hairs.

Importantly, both minoxidil and finasteride are effective only for as long as it is taken; the hair gained or maintained is lost within 6-12 months of ceasing therapy. See, e.g., Rossi, ed., 2004, Australian Medicines Handbook. Adelaide: Australian Medicines Handbook. Thus, minoxidil and finasteride require continuous treatment for lasting effects. In addition, patients with advanced MPHL may express dissatisfaction with even statistically significant, but cosmetically insignificant increase in hair counts and such frustration may contribute to poor compliance and further unsatisfactory outcomes. Recently, bimatoprost (a prostaglandin analog used to control the progression of glaucoma in the management of ocular hypertension) has been FDA approved to lengthen eyelashes and is marketed under the name Latisse®, with the claim of growing eyelashes, making them longer, thicker and darker.

Finasteride is not approved for females, while minoxidil is FDA approved for both males and females. Kopexil (e.g., Keranique™), is a modified form of minoxidil that has been proposed to have fewer side effects, and therefore has been proposed for treatment of hair loss in females. However, patient dissatisfaction with statistically significant, but cosmetically insignificant increase in hair counts contribute to poor compliance and unsatisfactory outcomes. minoxidil use is further complicated by the fact that it is messy and can leave a residue. In addition, many patients are dissatisfied with the side effects from persistent finasteride or minoxidil treatment, such as sexual dysfunction in the case of the 5-alpha-reductase inhibitors.

A device that uses low level light energy directly on the scalp (the HairMax Lasercomb) has received FDA clearance as a 510K device. Although the device is advertised as a "Laser," it operates by applying low level monochromatic light energy directly to the scalp, which is thought to stimulate hair growth through "photo-biostimulation" of hair follicles. Various types of devices operating on similar principles were referenced as the predicate for HairMax (see, Lolis et al., 2006, J. Cosmetic Dermatol. 5:274-276).

Finally, more drastic measures for treating hair loss involve hair transplantation—in which scalp strips, hair follicles or follicular units from the occipital scalp (which are resistant to the effects of androgens in inducing AGA-type alopecia) are excised and transplanted to a person's balding or thinning areas. Another surgical method that has been used is scalp reduction; in this procedure, the skin in the balding area of the scalp is surgically excised and the surrounding skin (with hair) is pulled together and sutured. Surgical methods are best for focal hair loss, and are less effective for diffuse hair loss, are less effective for women, and younger patients are not ideal candidates because the pattern and extent of future hair loss is variable. For all patients, hair transplantation can be inconvenient because of the invasive nature of the surgery, recovery time, duration of time to show a cosmetic effect (around 6-12 months), creation of scarring, and expense. Despite surgical advances in hair transplantation, cosmetic coverage is constrained by the area of and the number of hairs in a patient's donor sites.

Primary cicatricial alopecia (PCA) disorders are currently treated as inflammatory disorders. Patients with lymphocytic PCA are typically prescribed oral, topical or intralesional injections of anti-inflammatory drugs. Oral drugs include hydroxychloroquine, doxycycline, mycophenolate mofetil, cyclosporine, or corticosteroids; topical drugs include corticosteroids, topical tacrolimus, or topical pimecrolimus; and triamcinolone acetonide is used as an injected drug. Antimicrobial drugs are prescribed for neutrophilic (neutrophil-mediated) PCA after culture and sensitivities direct the appropriate selection. Dissecting cellulitis, with its mixed infiltrate, responds to isotretinoin treatment. None of these treatments is curative and, at best, the symptoms are arrested and clinical signs resolve. Hair loss often continues slowly and insidiously. In contrast to alopecia areata, a rapid diagnosis and treatment may reduce the permanent hair loss and scarring which contributes to its considerable morbidity. Hair transplantation for some is also considered a clinical option.

Because of limited effective treatment options, there is substantial interest among individuals for novel, safe and effective treatments for hair loss, including those that lead to hair follicle neogenesis, resulting in visible hair.

3. SUMMARY OF THE INVENTION

Integumental perturbation is used to promote the growth of hair in a subject, in particular, a human subject. Provided herein are devices and methods for using integumental perturbation to promote the growth of hair. In certain aspects, a method provided herein for using integumental perturbation to promote the growth of hair results in an increase in the amount or thickness of hair on an area of skin of a subject. In certain aspects, a method provided herein for using integumental perturbation to promote the growth of hair results in an increase of vellus hair on an area of skin of a subject. In certain aspects, the methods of integumental perturbation provided herein are accompanied by administration of a non-occlusive, topical pharmaceutical composition. In certain aspects, the methods of integumental perturbation are accompanied by administration of a pharmaceutical composition comprising a hair growth-promoting agent. In particular aspects, the methods of integumental perturbation are accompanied by administration of a pharmaceutical composition comprising an agent that promotes the transition of vellus hair to terminal hair. Thus, in one aspect of the invention, provided herein are methods for promoting the growth of terminal hair in a subject, comprising integumental perturbation accompanied by (i.e., before, during, and/or after) administration of one or more hair growth-promoting agents, which may be, in a particular aspect, an agent that promotes the transition of vellus hair to terminal hair or the transition of resting or telogen hair follicles into growing or anagen hair follicles. In certain aspects, a method provided herein for using integumental perturbation in combination with one or more hair growth-promoting agents to promote the growth of hair results in an increase in terminal hair on an area of skin of a subject. In certain aspects, a method is provided herein comprising using integumental perturbation to promote the transition of the number of vellus hairs to terminal hairs followed by administration of one or more hair growth-promoting agents to sustain and/or further increase the size of these new terminal hairs from the perturbation, which otherwise would revert back to vellus-sized hairs. In certain aspects, a method is provided herein comprising using integumental perturbation to increase the number of new terminal hairs followed by administration of one or more hair growth-promoting agents to sustain and/or further increase the size of these new terminal hairs from the perturbation, which otherwise decrease in size and become vellus-sized hairs. In certain aspects, a method is provided herein for using integumental perturbation in combination with one or more hair growth-promoting agents to promote the growth of hair results in an increase in the amount or thickness of hair on an area of skin of a subject.

As used herein, integumental perturbation refers to any treatment of the skin and/or other tissues of the integumentary system that results in debriding, peeling, or wounding, or other perturbation of the skin. The procedure can be controlled to limit perturbation to part or all of the epidermis, to part or all of the stratum corneum, or deeper into the papillary dermis, reticular dermis, and/or hypodermis. In one aspect, the epidermis is removed and, e.g., the papillary dermis is disrupted. In one aspect, the occurrence of pinpoint bleeding would indicate removal of the stratum corneum, epidermis (or part thereof) and portions of the upper layer of the dermis, such as the superficial papillary dermis. The occurrence of increased bleeding would indicate deeper penetration (and thus perturbation) into the deeper papillary dermis and reticular dermis layer. Thus, in certain aspects, the integumental perturbation method causes only superficial wounding to the area of skin on which hair growth is desired. In certain aspects, the extent of wounding is minimized by controlling the depth of perturbation. In certain aspects, the extent of wounding is minimized by controlling the size of the perturbed area of skin; for example, by making a series of small wounds to effect wounding of a large area rather than a single large wound. In these aspects, removal of the epidermis can be detected by the appearance of a shiny, whitish, and smooth layer of skin. The disruption of the superficial papillary dermis can be detected, e.g., by the appearance of small pinpoints of blood over a shiny, whitish, smooth surface in the treated area. Perturbing to the deeper papillary dermis results in more bleeding and the treated surface appears rougher. After entering the reticular dermis, bleeding becomes confluent and brisk, the surface appearance is rougher than the deep papillary dermis, representing exposed dermal collagen.

In certain embodiments, integumental perturbation results in partial removal of the epithelium. In other embodiments, integumental perturbation results in complete removal of the epithelium but does not go deeper into the dermis.

In one aspect, a method of integumental perturbation described herein disrupts skin to a depth of between 30 μm to 200 μm (e.g., to a maximum depth of 30, 40, 50, 60, 70, 80, 85, 90, 95, 100, 105, 110, 120, 130, 140, 150, 160, 170, 180, 190 or 200 μm), and preferably to approximately 100-150 μm. In one aspect, a method of integumental perturbation described herein disrupts skin to a depth of 100 μm. In one aspect, a method of integumental perturbation described herein disrupts skin to a depth of 150 μm.

In certain aspects, integumental perturbation is accomplished using chemical treatments (e.g., an inflammatory agent, caustic agent, etc.), or mechanical or electromagnetic or physical treatments including but not limited to dermabrasion (DA), particle-mediated dermabrasion (PMDA), microdermabrasion, microneedles, laser (e.g., a laser that delivers ablative, non-ablative, fractional, non-fractional, superficial, or deep treatment, and/or that is $CO_2$-based, or erbium-YAG-based, erbium-glass based (e.g. Sciton Laser), neodymium:yttrium aluminum garnet (Nd:YAG) laser, etc.), a low-level (low-intensity) laser therapy treatment (e.g., Hair-Max Laser comb), laser abrasion, irradiation, radio frequency (RF) ablation, dermatome planing (e.g. dermaplaing), a coring needle, a puncture device, a punch tool or other surgical tool, suction tool or instrument, electrology, electromagnetic disruption, electroporation, sonoporation, low voltage electric current, intense pulsed light, or surgical treatments (e.g., skin graft, hair transplantation, strip harvesting, scalp reduction, hair transplant, follicular unit extraction (FUE), robotic FUE, etc.), or supersonically accelerated saline (jetpeel; Golan et al., Ann Plast Surg. 2005; 54(4):369-374.) that promote the growth of hair. Methods and devices for integumental perturbation in accordance with this aspect are described in Section 5.1 infra.

In certain aspects, the invention excludes freezing or chemically treating the area of skin to be integumentally perturbed. In certain aspects, integumental perturbation is performed using a diamond fraize. In certain aspects, integumental perturbation is performed at a depth that results in the histological presence of the PEL and PELA structures. In certain aspects, integumental perturbation is performed on a transitional area of the scalp in subjects with AGA-type alopecia. In certain aspects, integumental perturbation is performed on subjects with Fitzpatric skin types 1-4.

Provided herein is an improved dermabrasion tip for use on a dermabrasion hand piece that addresses the above-discussed drawbacks with conventional dermabrasion devices. In certain embodiments, a dermabrasion tip for use on a dermabrasion hand piece comprises:
(a) a housing having a first opening substantially aligned with a longitudinal axis of the housing and a second opening disposed at an angle to the longitudinal axis;
(b) a transmission unit disposed in the housing, the transmission unit comprising:
  (i) a first set of gears;
  (ii) a linkage assembly adjacent to the first set of gears; and
  (iii) a second set of gears adjacent to the linkage assembly; and
(c) a platform to receive an abrasive disk,
(d) wherein the transmission unit converts a rotational motion of the dermabrasion hand piece to a reciprocating motion causing the platform to reciprocate.

In another embodiment, a dermabrasion tip for use on a dermabrasion hand piece comprises:
(a) a housing having a first opening substantially aligned with a longitudinal axis of the housing and a second opening disposed at an angle to the longitudinal axis;
(b) a transmission unit disposed in the housing, the transmission unit comprising:
  (i) a first set of gears;
  (ii) a second set of gears; and
  (iii) a linkage assembly disposed between the first set of gears and the second set of gears; and
(c) an abrasive disk,
(d) wherein the transmission unit converts a rotational motion of the dermabrasion hand piece to a reciprocating motion causing the abrasive disk to reciprocate, and
(e) wherein the abrasive disk is disposed at an angle with the longitudinal axis of the housing.

In yet another embodiment, a dermabrasion tip for use on a dermabrasion hand piece comprises:
(a) a housing having a first opening substantially aligned with a longitudinal axis of the housing and a second opening disposed at an angle to the longitudinal axis;
(b) a transmission unit disposed in the housing, the transmission unit comprising:
  (i) a first set of bevel gears;
  (ii) a linkage assembly adjacent to the first set of gears, the linkage assembly including an input drive wheel, an output drive wheel and at least one coupling rod; and
  (iii) a second set of bevel gears adjacent to the linkage assembly; and
(c) an abrasive disk,
(d) wherein the transmission unit converts a rotational motion of the dermabrasion hand piece to a reciprocating motion causing the abrasive disk to reciprocate, and
(e) wherein the abrasive disk is disposed at an angle with the longitudinal axis of the housing.

In a further embodiment, a dermabrasion tip for use on a dermabrasion hand piece comprises:
(a) a housing having a first opening substantially aligned with a longitudinal axis of the housing and a second opening disposed at an angle to the longitudinal axis;
(b) a means for converting a rotational motion of the dermabrasion hand piece to a reciprocating motion; and
(c) an abrasive disk,
(d) wherein the abrasive disk is disposed at an angle with the longitudinal axis of the housing.

In another embodiment, a dermabrader comprises:
(A) a control unit;
(B) a hand piece having a longitudinal axis and comprising:
  (i) a housing;
  (ii) a transmission unit disposed in the housing, the transmission unit comprising:
    (a) a first set of gears;
    (b) a linkage assembly adjacent to the first set of gears; and
    (c) a second set of gears adjacent to the linkage assembly; and (iii) an abrasive disk, and
(C) a cord that connects the hand piece to the control unit;
(D) wherein the transmission unit converts a rotational motion of the dermabrasion hand piece to a reciprocating motion causing the abrasive disk to reciprocate, and
(E) wherein the abrasive disk is disposed at an angle with the longitudinal axis of the hand piece.

In a still further embodiment, a kit for dermabrasion comprises:
(A) a pharmaceutical composition described in Sections 5.2, 5.3, and/or 5.4 infra;
(B) a disposable dermabrasion tip comprising:
  (i) a housing having a first opening substantially aligned with a longitudinal axis of the housing and a second opening disposed at an angle to the longitudinal axis;
  (ii) a transmission unit disposed in the housing, the transmission unit comprising:
    (a) a first set of gears;
    (b) a second set of gears; and
    (c) a linkage assembly disposed between the first set of gears and the second set of gears; and
  (iii) an abrasive disk,
(C) wherein the transmission unit converts a rotational motion of the dermabrasion hand piece to a reciprocating motion causing the abrasive disk to reciprocate, and
(D) wherein the abrasive disk is disposed at an angle with the longitudinal axis of the housing.

In another embodiment, a kit for dermabrasion comprises:
(A) a pharmaceutical composition described in Sections 5.2, 5.3, and/or 5.4 infra;
(B) a disposable dermabrasion tip comprising:
  (i) a housing having a first opening substantially aligned with a longitudinal axis of the housing and a second opening disposed at an angle to the longitudinal axis;
  (ii) a means for converting a rotational motion of a dermabrasion hand piece to a reciprocating motion; and
  (iii) a platform to receive an abrasive disk,
(C) wherein the transmission unit converts a rotational motion of the dermabrasion hand piece to a reciprocating motion causing the platform to reciprocate, and
(D) wherein the platform is disposed at an angle with the longitudinal axis of the housing.

Also provided herein are methods for using integumental perturbation for promoting hair growth on an area of skin of a subject, wherein the integumental perturbation comprises dermabrasion. In particular embodiments, dermabrasion is accomplished using the dermabrasion tip, dermabrader, and/or kit for dermabrasion described in Section 5.1 infra. In one embodiment, dermabrasion is performed using a diamond fraize.

Objects of the invention are to promote generation of new hair follicles ("follicle neogenesis"); to promote formation of neogenic-like (NL) follicular structures; to promote activation (possibly by reorganization) of existing hair follicles; to promote formation of pre-existing-like (PEL) or pre-existing-like, attached (PELA) follicular structures; to promote development of hair follicles, for example, to promote the growth of terminal hair (in preference to vellus hair); to promote the branching of pre-existing hair follicles (seen as an increased number of hair shafts per pore); to increase the width of hair follicles (thereby promoting growth of an increased shaft width); and/or to delay or prevent follicle senescence. Further objects of the invention are to promote the growth of hair; to promote growth of vellus hair; to promote the transition of vellus hair to terminal hair; to increase the amount of hair follicles in anagen, to prolong anagen, to shorten telogen, to promote growth of terminal hair; to increase the amount of hair; to increase the thickness of hair; and/or to reduce or prevent hair loss.

Additional objects of the invention are to promote activation, reorganization, or regeneration of hair follicle units or generation of new hair follicle units; to promote development of hair units, for example, to promote the growth of terminal hair (in preference to vellus hair) for or in follicular units; to promote the branching of pre-existing hair follicle units (seen as an increased number of hair shafts per pore); to increase the width of hair in hair follicle units (thereby promoting growth of increased shaft widths); and/or to delay or prevent follicle unit senescence. Further objects of the invention are to promote the growth of hair in follicular units; to promote growth of vellus hair in follicular units, to promote the transition of vellus hair in follicular units to terminal hair in follicular units; to promote growth of terminal hair in follicular units; to increase the amount of hair in follicular units; to increase the thickness of hair in follicular units; and/or to reduce or prevent hair loss or hair miniaturization in follicular units.

Without being bound by any theory, the treatments described herein may achieve these results by increasing the capacity of the skin to generate new hair follicles and/or new follicle units; increasing the capacity of the skin to reprogram hair follicle and/or hair follicle unit development; increasing the capacity of the skin to reorganize and activate existing hair follicles and follicular structures; regulating the unique human processes that regulate visible hair growth; regulating the activity of specialized human hair follicles and/or hair follicle units; regulating specific activities of specialized human hair follicles and/or hair follicle units; regulating gender-specific specialized human hair follicles and/or hair follicle units, including those under the influence of sex-steroid regulation; altering the activity of specialized human hair follicles and/or hair follicle units, sometimes in conjunction with transplantation; regulating the differentiation of stem cells into gender-specific specialized human hair follicles and/or hair follicle units, that may result in follicles having features that are different from natural follicles in the target location of skin (e.g., normal sized follicles with terminal hair where previously miniaturized follicles with vellus hair were present); regulating or altering age-related changes in human hair follicles and/or hair follicle units and hair, including those under the influence of sex-steroid regulation; or altering, delaying or preventing programmed senescence of hair follicles and/or hair follicle units.

The invention is based, in part, on the principle that human skin is replenished by stem cells, such as bone-marrow derived and tissue-derived stem cells, throughout life. Follicle Stem Cells can be derived from (1) other Follicle Stem Cells, (2) from other tissue stem cells, termed "pre-Follicle Stem Cells" (from the interfollicular skin), (3) from bone marrow-derived stem cells ("BMST"), and/or (4) from mesenchymal stem cells such as adipocyte stem cells. In the case of bone marrow derived stem cells (BMST), their differentiation into Follicle Stem Cells requires intact follicles, whose cells can play the role of "nurse cells" and provide appropriate signals to guide the differentiation of bone marrow derived stem cells into Follicle Stem Cells. Integumental perturbation (1) provides signals for Follicle Stem Cells to divide symmetrically to begin the process of forming new follicles; (2) mobilizes tissue stem cells ("pre-Follicle Stem Cells") from interfollicular skin to differentiate into stem cells, (3) increases the trafficking of bone marrow derived stem cells to affected areas of skin and promotes their differentiation into Follicle Stem Cells by nurse cells in existing follicles, and (4) encourages the "mixing" of hair follicles, hair follicle precursor cells, and other types of inductive cells, which may enable signals from precursor cells to induce hair follicle activation and development. In one aspect, a method described herein comprises contacting a precursor cell with an inductive cell.

Accordingly, and without being bound by theory, the invention is based in part on the discovery that, while hair growth can be promoted by true hair follicle neogenesis, other follicular structures that need not arise from de novo formation of neofollicles can be stimulated, activated and reorganized in order to promote hair growth. Many conventional pharmacologic treatments for hair growth promotion encourage the switch from vellus to terminal hair. The integumental perturbation methods described herein promote the formation of stimulated, activated and reorganized hair follicle structures which correlate with increased vellus hair, if not terminal hair. By increasing the number of stimulated and activated hair follicles, and vellus hair or terminal hair, the methods of the invention may provide additional substrates for the action of these pharmacologic treatments. Thus, in certain aspects, a combination of integumental perturbation and one or more pharmacologic treatments, which may be administered in combination or sequentially or cyclically, results in increased hair, increased hair thickness, and/or longer lasting hair. In certain aspects, such a combination treatment results in a 1.25-fold, 1.5-fold, 2-fold, 2.5-fold, 3-fold, 3.5-fold, or 4-fold or more increase in the amount of hair compared to treatment with a pharmacologic treatment alone.

In certain aspects, the present invention can exclude the administration of other therapeutic agents, for example, hair growth-promoting agents. In certain aspects, the present invention comprises serial perturbations in the same treated area, either with or without pharmaceutical agents, to produce an additive hair growth effect. In certain aspects, the present invention comprises one or more perturbations in the same treated area, either with or without one or more pharmaceutical agents, to produce a synergistic effect, i.e., to grow more hair than would be expected of the additive effect of either of the treatments alone. In certain aspects, the present invention comprises integumental perturbation in combination with one or more additional therapeutic agents. In certain aspects, the present invention comprises integumental perturbation in combination with an additional treatment, wherein the additional treatment may or may not include an active pharmaceutical ingredient (see, e.g., Section 5.2 infra). In some aspects, only anesthetic or pain relieving compounds (e.g., lidocaine) are administered in the additional treatment. In certain aspects, the additional treatment comprises an active pharmaceutical ingredient or active pharmaceutical ingredients for promoting the growth of hair, including vellus hair or terminal hair, preventing infection, and/or promoting healing of perturbed skin. Methods and pharmaceutical compositions for use in accordance with this aspect are described in Sections 5.2, 5.3, and 5.4 infra.

In one aspect, an integumental perturbation method of the invention is used in combination with other agents or treatments that stimulate hair growth. For example, an integumental perturbation method of the invention can be administered before, concurrently, after, or alternating with one or more hair growth-promoting agents. Hair growth-promoting agents for use, alone or in combination, in accordance with this aspect include but are not limited to: agents affecting prostaglandins, such as Prostaglandin F2α analogs, e.g. latanoprost (trade name Xalatan™), travoprost (trade name Travatan™), tafluprost, unoprostone, dinoprost (trade name Prostin F2 Alpha™), AS604872, BOL303259X, PF3187207, carboprost (trade name Hemabate™); Prostamides, e.g., bimatoprost (trade names Latisse™, Lumigan™); Prostanoid receptor agonists, e.g. fluprostenol; Prostaglandin D2 receptor antagonists, e.g. laropiprant, AM211; Prostglandin E2 analogs, e.g. sulprostone; and EP 2 receptor agonists, e.g. butaprost; 5α-reductase inhibitors, such as, e.g., finasteride, dutasteride, turosteride, bexlosteride, izonsteride, epristeride, epigallocatechin, Fluridil (Sovak et al, $Dermatol\ Surg.$ 2002; 28(8):678-685), RU 58841 (Pan et al. Endocrine. 1998; 9(1):39-43), N,N-diethyl-4-methyl-3-oxo-4-aza-5 alpha-androstane-17 beta-carboxamide (Rittmaster et al., J Clin Endocrinol Metab. 1987; 65(1):188-193), MK-386, azelaic acid, FCE 28260, SKF 105,111; minoxidil; ATP-sensitive potassium channel openers, e.g. diazoxide; and the hair growth-promoting agents described herein or otherwise known in the art, such as, e.g., kopexil (for example, the product Keranique™), $CaCl_2$, botilinum toxin A, adenosine, ketoconazole, DoxoRx, docetaxel, FK506, GP11046, GP11511, LGD 1331, ICX-TRC, MTS-01, NEOSH101, HYG-102440, HYG-410, HYG-420, HYG-430, HYG-440, spironolactone, CB-03-01, RK-023, abatacept, Viviscal®, MorrF, ASC-J9, NP-619, AS101, Metron-F-1, PSK 3841, Targretin™ (bexrotene, e.g., 1% gel), MedinGel, PF3187207, BOL303259X, AS604872, THG11331, PF-277343, PF-3004459, Raptiva™ (efalizumab), caffeine, and coffee. Other hair-growth promoting agents include arginine, isoleucine, leucine, lysine, methionine, phenylalanine, threonine, tryptophan, valine, gamma linoleic acid and polyphenol catechins, copper peptides. Other hair-growth promoting agents that can be formulated as a hair wash tonic could include but are not limited to, jojoba oil, extract of apple, saw palmetto, emu oil, beta carotene and green tea. In one aspect, an integumental perturbation method of the invention is used in combination with drugs for alopecia being developed by SWITCH Biotech LLC.

In accordance with this aspect, one or more of the foregoing may be used in its commercially available form. In other aspects, the dosage of one or more of the foregoing is adjusted to optimize a combination treatment (e.g., integumental perturbation or treatment with another active ingredient or active ingredients) described herein. In other aspects, the formulation of one or more of the foregoing is adjusted to optimize a combination treatment (e.g., integumental perturbation or treatment with another active ingredient or active ingredients) described herein. In a particular aspect, one or more of the foregoing is formulated for topical administration, e.g., by incorporation into a pharmaceutical composition for post-perturbation treatment described in Section 5.2 infra.

In particular aspects, the hair growth-promoting agent used in accordance with this aspect enhances conversion of vellus hair to nonvellus hair. In one such aspect, the hair growth-promoting agent enhances conversion of vellus hair to terminal hair. Exemplary hair growth-promoting agents that promote conversion of vellus to nonvellus or terminal hair that may be used in accordance with this aspect are prostaglandin F2α analogs (in one aspect, latanoprost), prostamides (in one aspect, e.g., bimatoprost), minoxidil, etc. In one embodiment, minoxidil is administered in combination with a prostaglandin F2α analog. In one embodiment, minoxidil is administered in combination with a prostamide. In one embodiment, minoxidil is administered in combination with a 5α-reductase inhibitor. In one such embodiment, minoxidil is administered in combination with finasteride. Methods and pharmaceutical compositions comprising "hair growth-promoting agents" for use in accordance with this aspect are described in Section 5.3 infra.

In certain aspects, a method is provided herein comprising using integumental perturbation to promote the transition of the number of vellus hairs to terminal hairs followed by administration of a hair growth-promoting agent to sustain and/or further increase the size of these new terminal hairs from the perturbation, which otherwise would revert back to vellus-sized hairs. In certain aspects, a method is provided herein comprising using integumental perturbation to increase the number of new terminal hairs followed by administration of a hair growth-promoting agent to sustain and/or further increase the size of these new terminal hairs from the perturbation, which otherwise decrease in size and become vellus-sized hairs. In certain aspects, a method provided herein for using integumental perturbation in combination with a hair growth-promoting agent to promote the growth of hair results in an increase in the amount or thickness of hair on an area of skin of a subject.

In certain aspects, the invention provides a method for promoting hair growth on the scalp of a male or a female subject with androgenetic alopecia wherein the method comprises in the following order: (i) applying integumental perturbation; (ii) optionally applying a non-occlusive wound dressing to the integumentally perturbed skin area; and (iii) administering minoxidil topically. In more specific embodiments, integumental perturbation is performed using dermabrasion with an estimated depth of 100-150 microns, a hydrogel is administered to the skin, and minoxidil is administered in the form of 5% minoxidil foam. Minoxidil can be administered as a liquid, gel, and/or foam at a concentration of 2-5% minoxidil. In specific embodiments, the hydrogel is administered topically immediately following dermabrasion twice daily for about 1 week, followed by a 3 week period without treatment, which in turn is followed by a period of at least 5 months of minoxidil treatment. In specific embodiments, the hydrogel is administered topically immediately following dermabrasion twice daily for 12 days, which in turn is followed by a period of 6 months of minoxidil treatment. In an embodiment, the treatment regimen is repeated multiple times to build up hair density over time.

In certain aspects, the invention provides a method for inducing hair growth on the scalp of a male or female subject with androgenetic alopecia, wherein the method comprises:
(i) Dermabrasion (estimated depth 100-150 microns) at Day 0;
(ii) Commencing at Day 0, topical administration of hydrogel for about 11 days;
(iii) Immediately following step (ii), topical administration of minoxidil 2-5% solution and/or minoxidil 2-5% gel and/or minoxidil 2-5% foam for at least 3 months, or in another embodiment, at least 6 months.
(iv) In certain specific embodiments, the dermabrasion tip described in Section 5.1 infra is used in step (i)
(v) In certain specific embodiments, the subject receives an additional treatment with topically administered 0.005% or 0.01% or 0.1% latanoprost.
(vi) In certain specific embodiments, the subject receives an additional treatment with topically administered 0.01% or 0.03% bimatoprost.
(vii) In certain specific embodiments, the subject receives a treatment with topically administered 0.005% or 0.01% or 0.1% latanoprost after step(ii) instead of minoxidil.
(vi) In certain specific embodiments, the subject receives a treatment with topically administered 0.01% or 0.03% bimatoprost after step(ii) instead of minoxidil.

In certain aspects, the invention provides a treatment regimen that starts minoxidil as soon as re-epithelialization is complete. In one embodiment, re-epithelialization is complete between 11 days and 14 days after post integumental perturbation.

Provided herein are devices that can be used to deliver a therapeutic compound, such as a hair growth-promoting agent, to the treated skin, including drug spraying devices. In certain aspects, a drug spraying device disclosed herein comprises a drug cartridge having two separate chambers that keep drug components isolated until the therapeutic compound is to be dispensed. In certain aspects, a drug spraying device disclosed herein enables the sustained release of a hair growth-promoting agent, without the use of highly hydrophobic, occlusive matrices. In certain aspects, a drug spraying device disclosed herein enables the sustained release of a hair growth-promoting agent and uptake by the skin through a scab. In certain aspects, a drug spraying device disclosed herein enables the concurrent delivery of two or more drugs. In one aspect, a drug spraying device disclosed herein enables the cleansing of the integumentally perturbed skin and administration of one or more drugs with one single device. Exemplary devices and their use with exemplary pharmaceutical compositions for the practice of this aspect of the invention are described in Section 5.5.2.1 infra.

In certain aspects the methods described herein are used to replenish hair in scalp that was used or could be used as a donor site for hair transplant surgery.

Success of a method of the invention can be measured by, for example:
improved overall cosmetic outcome (e.g., using the Visual Analogue Scale (VAS))
patient assessment of his/her hair growth (e.g., based on questionnaire)
investigator assessment of hair growth in a patient (e.g., based on a rating scale)
patient assessment of his/her hair growth in photographs
investigator assessments of hair growth in patient photographs
increased hair count (e.g., by measuring new hair growth as an increased number of fibers in an affected area of the skin)
increased hair density
increased thickness of hair or hair shaft (e.g., based on diameter)
increased hair weight
hair cuttings
longer hair
increase in the amount of terminal hair (by, e.g., measuring new hair growth as an increased number of fibers in an affected area of the skin, or increased thickness (e.g., diameter) or length of hair fibers)
increase in the amount of vellus hair (by, e.g., measuring new hair growth as an increased number of fibers in an affected area of the skin) (e.g., as measured photographically)
increase in the amount of nonvellus hair, e.g., intermediate or terminal hair
an increase in the ratio of terminal-to-vellus hair increased number of hair germs
increased number of hair follicles (e.g., as evaluated by a skin biopsy)
increased number of hair follicles at a more mature stage of development
increased numbers of follicular units with 3 or more hair follicles
increased hair follicle branching
formation of new hair follicles ("hair follicle neogenesis")
formation of new hair follicles with vellus-sized hair shafts (i.e., hair shafts with diameters less than 30 microns in diameter)
formation of new hair follicles with nonvellus-sized hair shafts (i.e., hair shafts with diameters 30 microns or greater in diameter)
hair follicle regeneration
increased activation of existing hair follicles
increased number of hair follicles
increased number of activated hair follicles
increased number of activated pre-existing hair follicles
presence or increased numbers of neogenic-like (NL) hair follicles (based on, e.g., examination of a biopsy or by confocal microscope, by assessing number of hair follicles, and/or by assessing morphology of hair follicles compared to baseline or a negative control)
presence or increased numbers of pre-existing hair follicles (based on, e.g., examination of a biopsy or by confocal microscope, by assessing number of hair follicles, and/or by assessing morphology of hair follicles compared to baseline or a negative control)
presence or increased numbers of primitive structures of interest (SOIs), such as neogenic-like (NL), pre-existing-like (PEL), and/or pre-existing-like, attached (PELA) follicular structures (based on, e.g., examination of a biopsy or by confocal microscope, by assessing number of hair follicles, and/or by assessing morphology of hair follicles compared to baseline or a negative control, as described for example in Section 5.8.4 infra)
increased number of pre-existing hair follicles with vellus-sized hair shafts in a treated area of skin of a subject
increased number of neogenic-like hair follicles with vellus-sized hair shafts in a treated area of skin of a subject
increase in the amount of anagen hair
increase in the amount of telogen hair
increased proportion of hair follicles in anagen or decreased proportion of hair follicles in telogen (i.e., an increase in the ratio of anagen-to-telogen hair) (based on, e.g., examination of a biopsy or phototrichogram)
increased proliferation of dermal papilla (based on, e.g., examination of a biopsy)
increased recruitment or proliferation of stem cells to the follicle (based on, e.g., examination of a biopsy).

Human subjects who are candidates for the treatments disclosed herein include any subject for whom increased hair growth is desired including, but not limited to, subjects with nonscarring (noncicatricial) alopecia, such as androgenetic alopecia (AGA), including male pattern hair loss (MPHL) or female pattern hair loss (FPHL), age-related hair loss (senescence), or any other form of hair loss caused by androgens, toxic alopecia, alopecia areata (including alopecia universalis), scarring (cicatricial) alopecia, pathologic alopecia (caused by, e.g., medication, chemotherapy, trauma, wounds, burns, stress, autoimmune diseases), trichotillomania, malnutrition, or endocrine dysfunction), or hypotrichosis, or any other disease, disorder, or form of hair loss as discussed infra and/or known in the art.

In a particular aspect, a human subject who is a candidate for such treatments is a human subject with scarring (cicatricial) alopecia. Forms of cicatricial alopecia that may be treated in accordance with the methods described herein include primary cicatricial alopecia (PCA) and secondary cicatricial alopecia. Primary cicatricial alopecias that may be treated in accordance with the methods described herein include lymphocyte-mediated PCAs, such as lichen planopilaris (LPP), frontal fibrosing alopecia (FFA), central centrifugal cicatricial alopecia (CCCA), and pseudopelade (Brocq); neutrophil-mediated PCAs, such as folliculitis decalvans and tufted folliculitis; and PCAs involving a mixed inflammatory infiltrate, such as occurs in dissecting cellulitis and folliculitis keloidalis.

In a particular aspect, provided herein is a method for enhancing hair growth in a patient with scarring alopecia comprising controlled integumental perturbation using dermabrasion, followed by twice daily topical administration of a hydrogel for 7-14 days, preferably 12 days, followed by administration of one or more hair growth promoting agents. In certain embodiments, the hydrogel treatment is begun on the same day as the laser treatment. In one embodiment, the patient has primary scarring alopecia. In one embodiment, the patient has lichen planopilaris. In another embodiment, the patient has frontal fibrosing alopecia.

Success of a treatment for scarring alopecia may be measured using the methods described above. In some embodiments, successful treatment is determined as an increase in the number of visually or photographically detected hairs. In other embodiments, successful treatment is evaluated by a skin biopsy for hair follicle structures and scar attributes. Success may also be measured as a reduction or elimination of itching, burning, pain, and tenderness associated with the condition, or a reduction of scalp redness, scaling, and/or pustules. Success may also be measured as a reduction or elimination of inflammation of the scalp.

3.1 Glossary of Terms for Hair and Disorders of Hair Growth

The following terms are used herein consistently with their art-accepted meanings summarized below.

Alopecia: Abnormal hair loss:

Alopecia areata: Hair loss in patches, thought to be caused by an autoimmune response to hair follicles in the anagen stage; extensive forms of the disorder are called alopecia areata totalis (hair loss over the entire scalp) and alopecia areata universalis (hair loss over the entire body).

Anagen: Growth stage of the hair-Follicle Cycle.

Anagen effluvium: Abrupt shedding of hair caused by interruption of active hair-follicle growth (e.g., in patients undergoing chemotherapy).

Androgenetic alopecia (AGA): Baldness caused by miniaturization of genetically predisposed follicles in the MPHL pattern (frontal recession and thinning at the vertex) or the FPHL pattern (loss of hair primarily over the crown, with sparing of frontal hair).

Bulb: Lowermost portion of the hair follicle, including the dermal papilla (also known as the follicular papilla), containing rapidly proliferating matrix cells that produce the hair.

Bulge: Portion of the outer-root sheath of the hair follicle, located at the region of the insertion of the arrector pili muscle; thought to contain epithelial stem cells responsible for regenerating follicles in the anagen stage.

Catagen: Stage of the hair cycle characterized by regression and involution of the follicle.

Club hair: Fully keratinized, dead hair—the final product of a follicle in the telogen stage; 50 to 150 club hairs are shed daily from a normal scalp.

Female Pattern Hair Loss (FPHL): form of gender specific hair patterning in females (also sometimes referred to as female pattern alopecia).

Follicle cycle: Hair growth in each follicle occurs in a cycle that includes the following phases: anagen (growth phase), catagen (involuting/regressing stage), telogen (the quiescent phase), exogen (shedding phase), kenogen, and re-entry into anagen.

Kenogen: Latent phase of hair cycle after hair shaft has been shed and growth is suspended in follicle.

Hirsutism: Excessive hair growth in androgen-dependent areas in women.

Hypertrichosis: Excessive hair growth (usually diffuse) beyond that considered normal according to age, race, sex, and skin region.

Integumental: Pertaining to the integumentary system, which comprises the skin (epidermis, dermis, hypodermis (or subcutanea)) and all cells contained therein regardless of origin, and its appendages (including, e.g., hair and nails).

Intermediate hair: A subset of "Terminal hair". Hair shaft diameters typically 30 μm or greater, but less than 60 μm.

Lanugo hair: Fine hair on the body of the fetus, usually shed in utero or within weeks after birth.

Male Pattern Hair Loss (MPHL): form of gender specific hair patterning in men (also sometimes referred to as male pattern alopecia).

Miniaturization: Primary pathological process in androgenetic alopecia, resulting in conversion of large (terminal) hairs into small (vellus) hairs.

NL (Neogenic-Like) follicular structure: In certain embodiments, an unattached primitive follicular structure, with only one of the following "small" traits: shaft, sebaceous gland, or pore. Dermal channel is absent or inconclusive. Further subcategories of NL include: NL with DP (dermal papilla)/active, NL with DP/inactive, NL without DP/active, and NL without DP/inactive.

Nonvellus hair: Same as "Terminal hair."

PEL (Pre-Existing-Like) follicular structure: In certain embodiments, an unattached primitive follicular structure, with one or more of the following "large" traits or two or more of the following "small" traits: shaft, sebaceous gland, or pore. Dermal channel is present. Further subcategories of PEL include: PEL with DP (dermal papilla)/active, PEL with DP/inactive, PEL without DP/active, and PEL without DP/inactive.

PELA (Pre-Existing-Like, Attached) follicular structure: In certain embodiments, a primitive follicular structure that is attached to larger, mature, pilosebaceous unit that extends to the epidermis.

Permanent alopecia: Caused by destruction of hair follicles as a result of inflammation, trauma, fibrosis, or unknown causes; examples include lichen planopilaris and discoid lupus erythematosus. Includes diseases referred to as scarring alopecia.

Telogen: Resting stage of the hair cycle; club hair is the final product and is eventually shed.

Telogen effluvium: Excessive shedding of hair caused by an increased proportion of follicles entering the telogen stage; common causes include drugs and fever.

Terminal hair: Large, usually pigmented hairs on scalp and body. Hair shaft diameters typically 30 μm or greater.

Vellus hair: Very short, often nonpigmented hairs (e.g., those found diffusely over nonbeard area of face and bald scalp as a result of miniaturization of terminal hairs). In certain embodiments, as used herein, a "vellus" hair is a hair that is less than 2 mm in length and less than 30 μm in diameter. In certain embodiments, as used herein, a "vellus" hair is a hair that is determined histologically as having a hair shaft diameter of less than 30 μm and not exceeding the thickness of its surrounding internal root sheath.

4. DESCRIPTION OF THE FIGURES

FIGS. 1A, 1B, 1C, 1D, 1E, 1F, 1G, 1H, and 1I. Types of human hair follicles.

FIG. 2. Architecture of the skin.

FIG. 3. Diagram of human hair follicle histology.

FIG. 4. Cellular structure of the human hair bulb.

FIGS. 5A and 5B. FIG. 5A depicts a prior art dermabrasion rotating wheel;

FIG. 5B depicts a prior art dermabrasion rotating wheel in use.

FIG. 6. Depicts a prior art dermabrasion rotating wheel in use.

FIG. 7. Depicts a prior art dermabrasion hand piece in use.

FIGS. 8A, 8B, 8C, 8D, 8E, 8F, 8G, 8H, 8I, 8J, 8K, and 8L. Hamilton-Norwood classification of male pattern hair loss (MPHL).

FIGS. 9A and 9B. Depict different views of an inventive dermabrasion tip attached to a conventional dermabrasion hand piece, according to an embodiment of the present invention.

FIG. 10. Depicts a conventional dermabrader.

FIG. 11. Is a schematic drawing of a dermabrasion tip, according to an embodiment of the present invention.

FIG. 12. Is a schematic drawing of a linkage assembly, according to an embodiment of the present invention.

FIG. 13. Depicts a dermabrasion tip, according to an embodiment of the present invention.

FIG. 14. Depicts a dermabrasion tip, according to an embodiment of the present invention.

FIG. 15. Depicts an inventive dermabrasion tip in use, according to an embodiment of the present invention.

FIG. 16. Depicts a portion of the transmission assembly, according to an embodiment of the present invention.

FIGS. 17A and 17B. FIG. 17A is a front perspective view of a spraying device, according to an embodiment of the present invention; FIG. 17B is a rear perspective view of a spraying device, according to an embodiment of the present invention.

FIG. 18. A front perspective view of a spraying device, according to an embodiment of the present invention.

FIGS. 19A and 19B. FIG. 19A is a plan view of showing the components of a hand piece depicted in FIGS. 17A and 17B. FIG. 19B is a rear perspective view of a hand piece, according to an embodiment of the present invention.

FIGS. 20A, 20B, 20C, and 20D. FIG. 20A is a plan view of a drug cartridge, according to an embodiment of the present invention. FIG. 20B is a plan view of a drug cartridge and the front end of a hand piece, according to an embodiment of the present invention. FIG. 20C is a plan view of a drug cartridge and the front end of a hand piece, according to an embodiment of the present invention. FIG. 20D is a plan view of a drug cartridge and the front end of a hand piece, according to an embodiment of the present invention.

FIGS. 21A, 21B, 21C, 21D, and 21E. FIG. 21A shows plan view of a drug cartridge and the front end of a hand piece, according to an embodiment of the present invention; FIG. 21B is a plan view of a drug cartridge and the front end of a hand piece, according to an embodiment of the present invention; FIG. 21C is a plan view of a drug cartridge and the front end of a hand piece, according to an embodiment of the present invention; FIG. 21D is a plan view of a drug cartridge and the front end of a hand piece, according to an embodiment of the present invention; and FIG. 21E is a plan view of a drug cartridge and the front end of a hand piece, according to an embodiment of the present invention.

FIGS. 22A and 22B. Criteria for categorizing follicular structures of interest.

FIGS. 23A, 23B, 23C, 23D, 23E, and 23F. Photographs of skin of a subject treated with integumental perturbation by dermabrasion ("DA") (FIG. 23A) before DA; (FIG. 23B) after DA; (FIG. 23C) day 14 post-DA (before biopsy); (FIG. 23D) day 28 post-DA, after suture removal; and (FIG. 23E) another image taken after DA, enlarged to show the appearance of pinpoint bleeding. FIG. 23F provides an illustration of the skin's epidermal ridges which enclose the vascularized dermal papillae. Epidermal rete pegs, capillary loops within the dermal papillae, and dermal papillae are indicated. Disruption to the depth marked by the uppermost dotted line may be expected to produce pinpoint bleeding. Disruption to the depth marked by the lowermost dotted line may be expected to produce pinpoint bleeding as well as more homogenous bleeding as the skin depth transitions from the dermal papillae to the superficial vascular plexus.

FIG. 24 is a graph depicting the gel time as a function of pH for PEG-NHS/PEG-AM hydrogels.

FIGS. 25A and 25B. FIGS. 25A and 25B are graphs depicting the gel time as a function of PEG concentration for PEG-NHS/PEG-AM hydrogels.

5. DESCRIPTION OF THE INVENTION

Figure 1A:
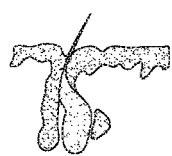
Figure 1B:
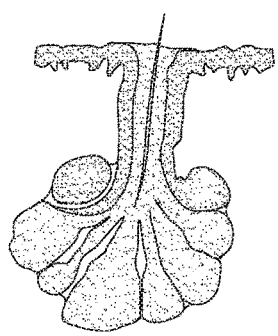
Figure 1C:
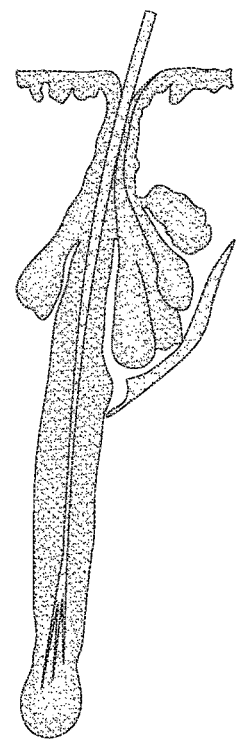
Figure 1D:
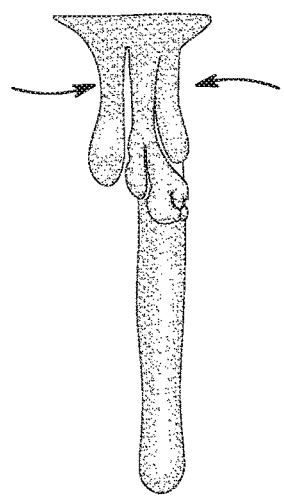
Figure 1E:
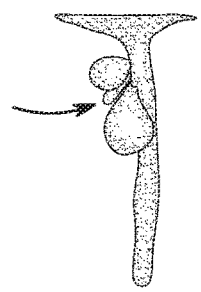
Figure 1F:
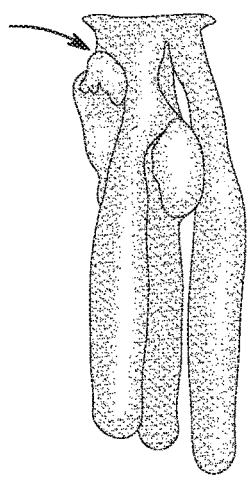
Figure 1G:
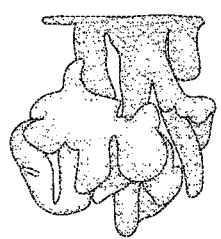
Figure 1H:
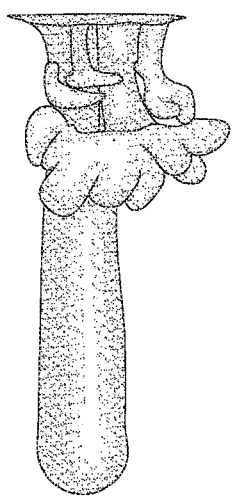
Figure 1I:
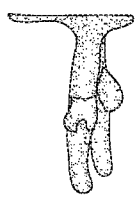
Figure 2:
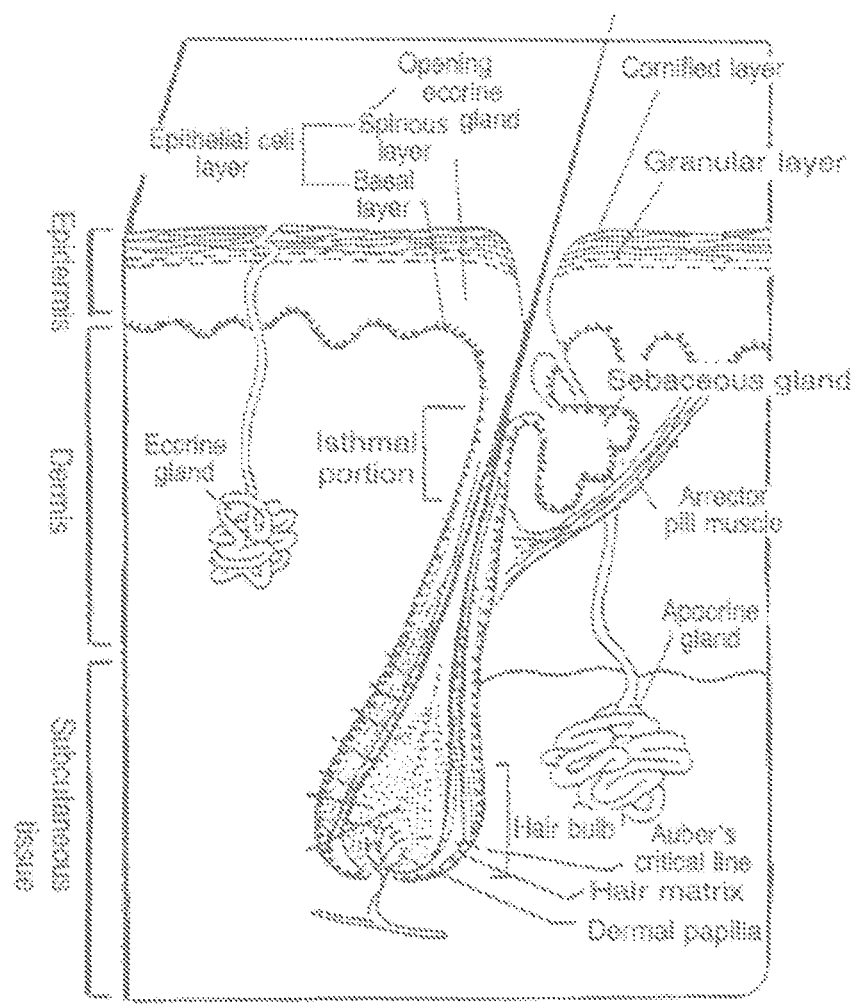
Figure 3:
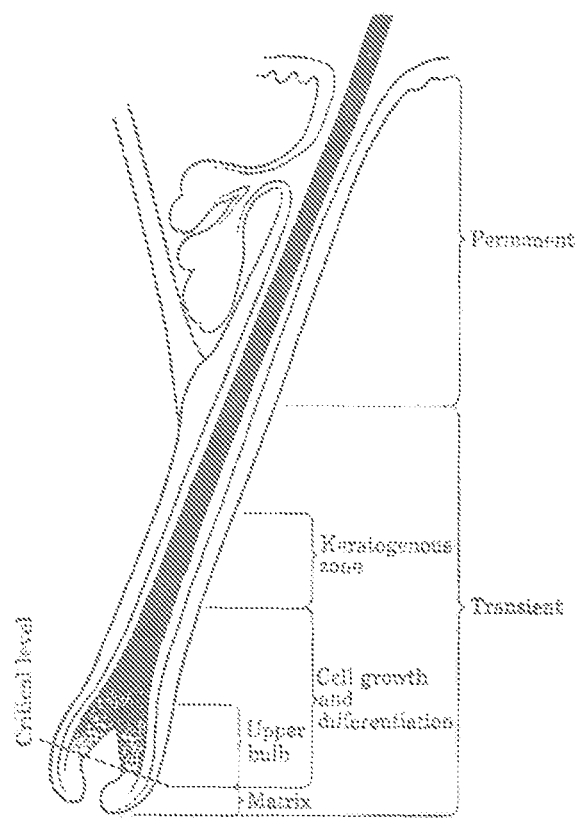
Figure 4:
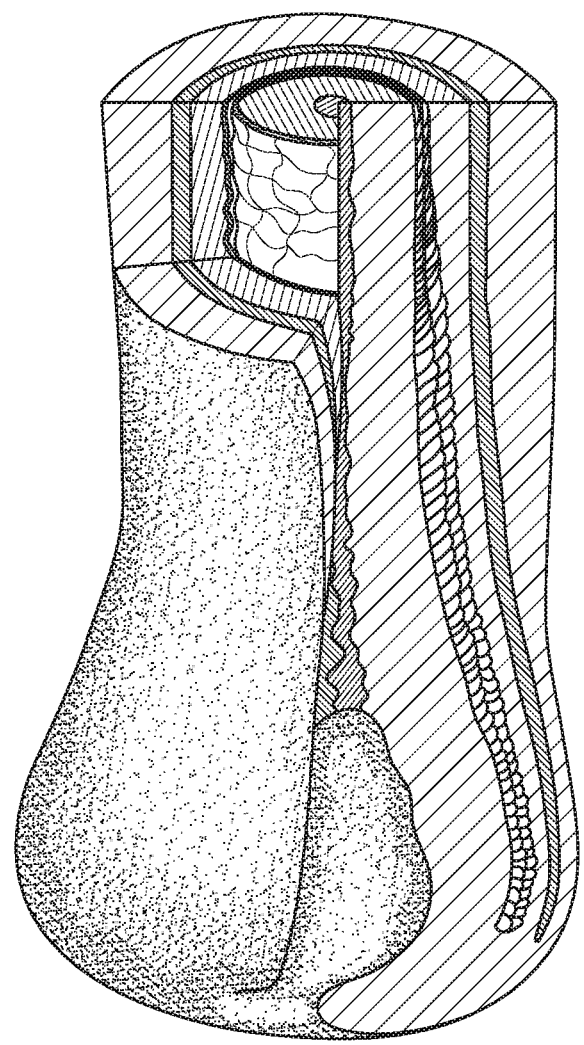
Figure 5A:
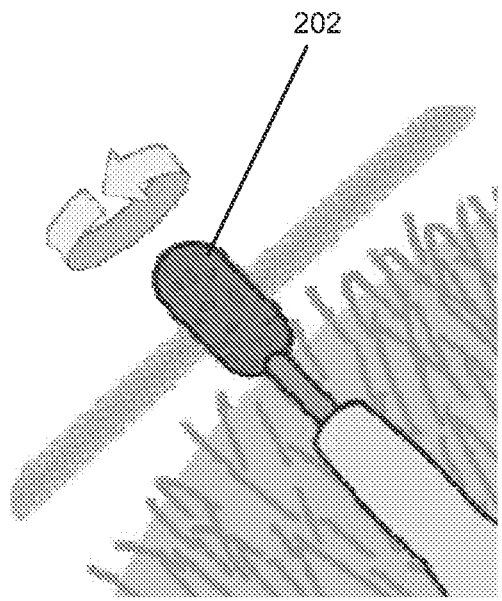
Figure 5B:
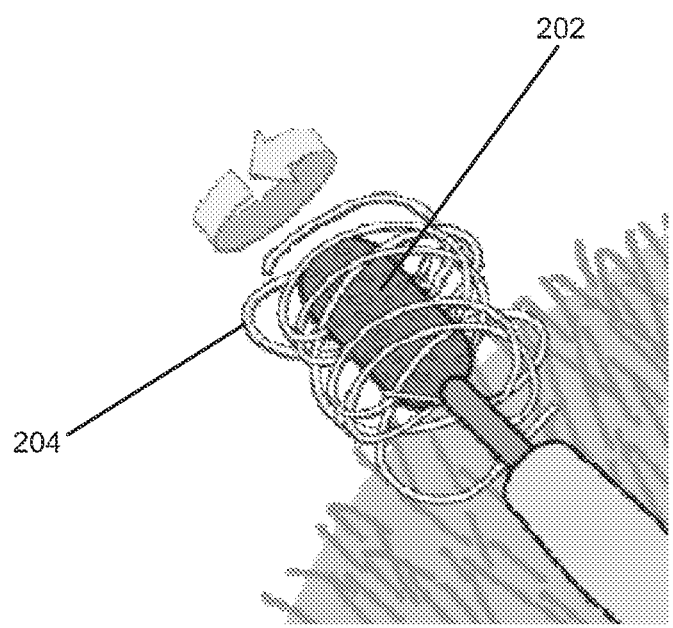
Figure 6:
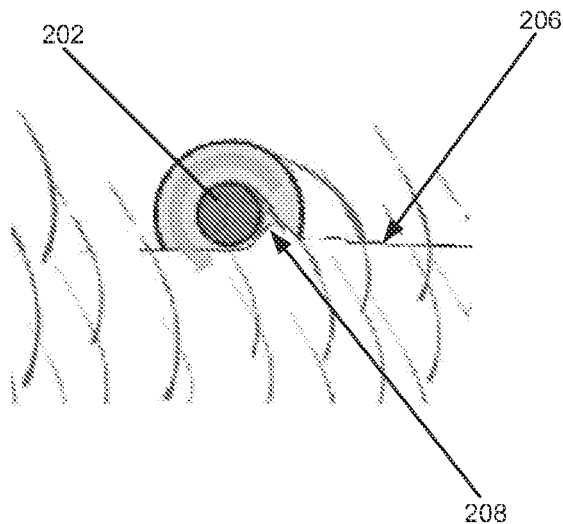
Figure 7:
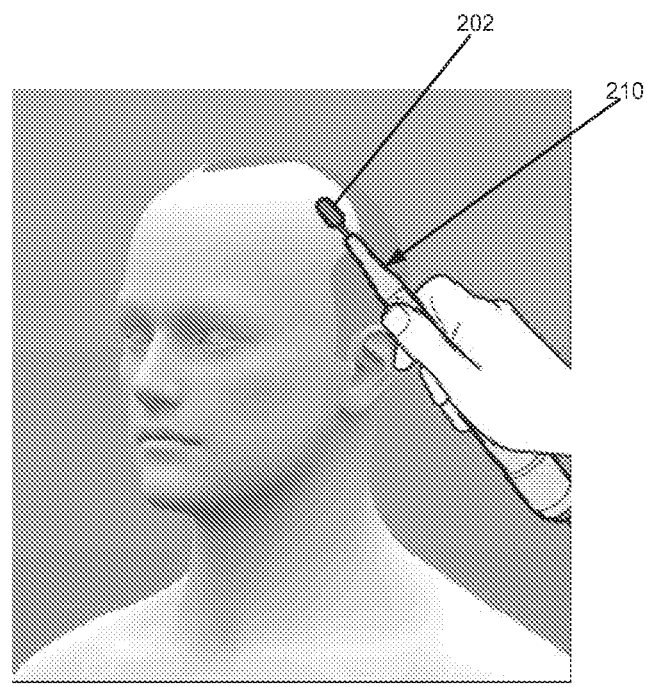
Figure 8A:
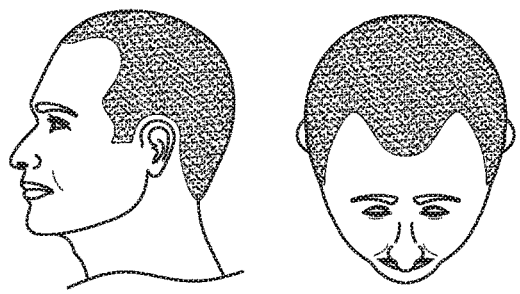
Figure 8B:
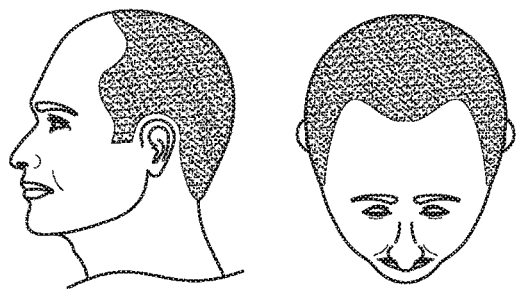
Figure 8C:
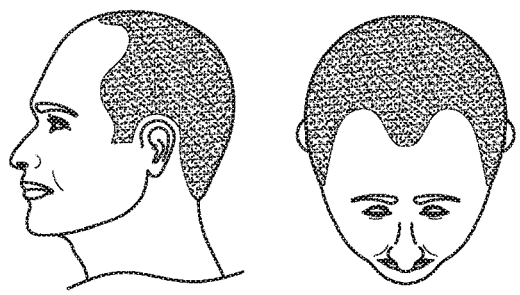
Figure 8D:
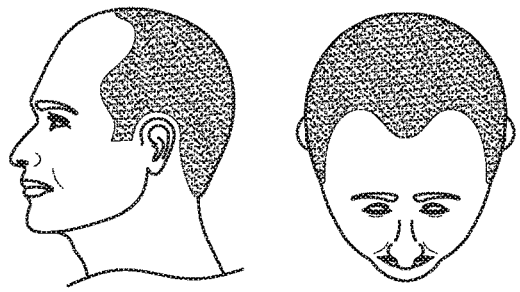
Figure 8E:
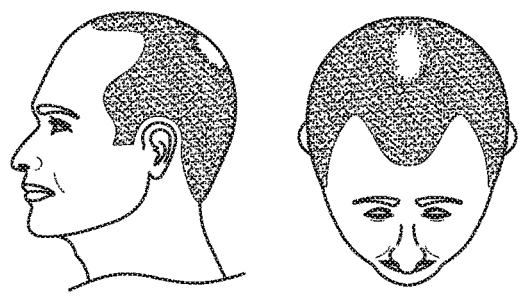
Figure 8F:
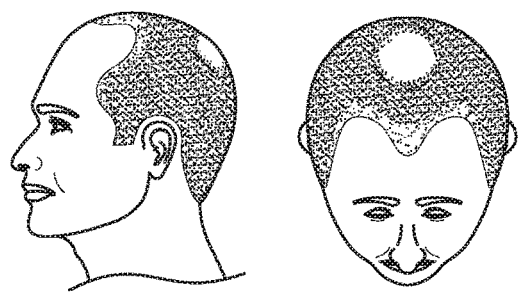
Figure 8G:
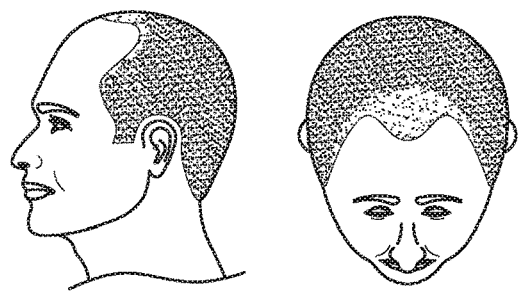
Figure 8H:
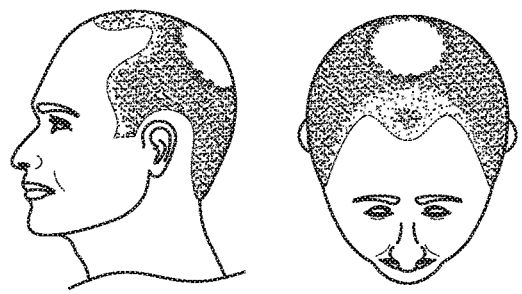
Figure 8I:
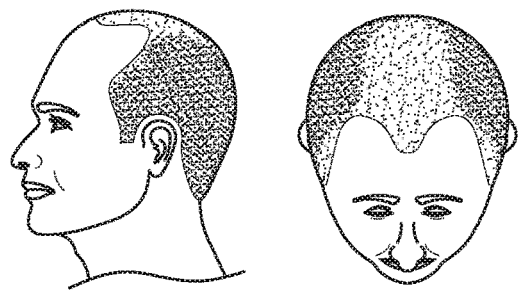
Figure 8J:
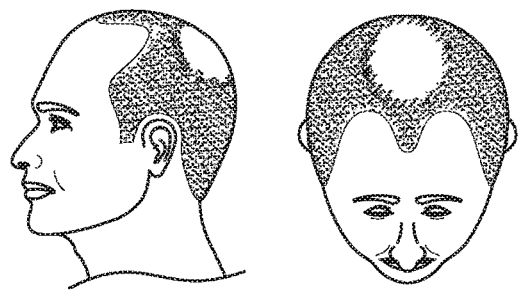
Figure 8K:
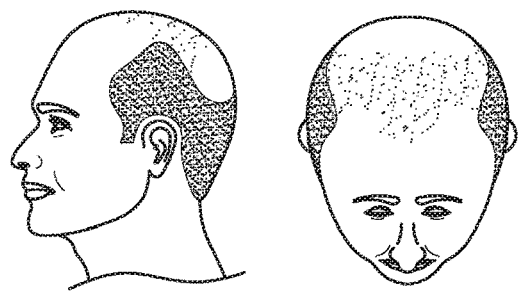
Figure 8L:
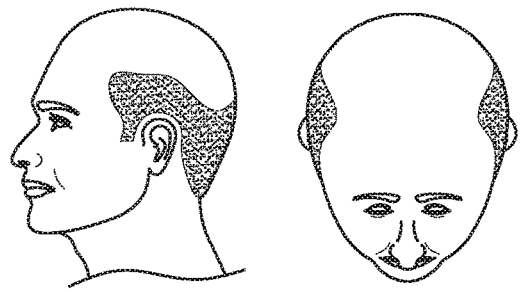

Provided herein are methods of treating baldness or alopecia in a subject (e.g., a human subject), the methods comprising subjecting an affected area of the skin to integumental perturbation. Also provided herein are methods of enhancing, stimulating, or increasing hair growth or enhancing or increasing the thickness of hair (in some embodiments collectively referred to herein as "promoting" hair growth or hair thickness) on an area of skin of a subject (e.g., a human), the methods comprising subjecting an affected area of the skin to integumental perturbation. In certain embodiments, the method of treating baldness or alopecia or promoting hair growth or thickness of hair results in formation of new hair follicles ("hair follicle neogenesis"), the formation of neogenic-like hair follicles, activation of existing hair follicles, reorganization of existing hair follicles, an increase in the numbers of vellus hairs, an increase in the numbers of nonvellus hairs (e.g., intermediate or terminal), and/or an increase in the numbers of terminal hairs in the treated area. In some embodiments, the integumental perturbation step is carried out in combination with a second treatment step, the second treatment step referred to herein as a "post-perturbation treatment." In some embodiments, the integumental perturbation step, alone or in combination with a post-perturbation treatment step, is carried out in combination with a step comprising treatment with one or more hair growth-promoting agents. Also provided herein are methods and devices for integumental perturbation, which may be used, inter alia, to promote the growth of hair. Also provided herein are pharmaceutical compositions for use in the post-perturbation step, and pharmaceutical compositions for use in the hair growth-promoting agent treatment step.

In one embodiment, a method of integumental perturbation provided herein promotes growth of hair on an area of skin of a subject. In some embodiments, a method of integumental perturbation provided herein increases the amount or thickness of hair on a treated area of skin of a subject. In some embodiments, a method of integumental perturbation provided herein results in an increase in the amount of vellus hair on a treated area of skin of a subject. In some embodiments, a method of integumental perturbation provided herein results in an increase in the amount of terminal hair on a treated area of skin of a subject. In some embodiments, a method of integumental perturbation provided herein results in formation of new hair follicles ("hair follicle neogenesis") in a treated area of skin of a subject. In certain embodiments, a method of integumental perturbation provided herein results in an increased number of hair follicles in a treated area of skin of a subject. In particular embodiments, the method of integumental perturbation results in formation of new hair follicles with vellus-sized hair shafts (i.e., hair shafts with diameters less than 30 microns in diameter) in a treated area of skin of a subject. In some embodiments, a method of integumental perturbation results in an increased number of stimulated and activated hair follicles, such as pre-existing hair follicles, in a treated area of skin of a subject. In particular embodiments, the method of integumental perturbation results in an increased number of pre-existing hair follicles with vellus-sized hair shafts in a treated area of skin of a subject. In particular embodiments, the method of integumental perturbation results in the presence and/or increased numbers of NL, PEL, and PELA follicular structures.

In particular embodiments, a method of integumental perturbation described herein comprises dermabrasion, using, e.g., a device described herein. In other embodiments, a method of integumental perturbation comprises treatment with laser. Various methods of integumental perturbation are described in Section 5.1 infra, however, the invention is not to be so limited, and any method of integumental perturbation may be used in accordance with the methods described herein.

Also provided herein are "post-perturbation" treatments. Provided herein are methods for treating an integumentally perturbed area of the skin with a post-perturbation treatment for promoting the growth of hair, including vellus hair or terminal hair, preventing infection and/or promoting healing of perturbed skin. In some embodiments, the post-perturbation treatment promotes healing with no or reduced scarring. In certain embodiments, the post-perturbation treatment is a topical treatment. Pharmaceutical compositions for use in post-perturbation treatment methods are also provided herein.

In some embodiments, the post-perturbation treatment step comprises topical administration of a pharmaceutical composition that is intended to promote the growth of hair, including vellus hair, terminal hair, increase hair thickness, prevent infection and/or promote healing, e.g., scarless healing, of the perturbed skin. In some embodiments, a pharmaceutical composition for use in the post-perturbation treatment step is formulated for topical administration. In particular embodiments, the pharmaceutical composition formulated for topical administration is non-occlusive. In some embodiments, the non-occlusive pharmaceutical composition formulated for topical administration is an aqueous formulation (e.g., hydrogel), a non-aqueous formulation, an ointment, a suspension, or a cream (e.g., emulsion). In certain embodiments, the pharmaceutical composition formulated for post-perturbation topical administration does not contain an active pharmaceutical ingredient (API). In certain embodiments, a post-perturbation topical treatment comprises a wound healing gel that does not contain an API. In certain embodiments the wound healing gel is applied immediately after integumental perturbation and every day for about a week. In certain other embodiments, the pharmaceutical composition formulated for post-perturbation topical administration contains an active pharmaceutical ingredient or pharmaceutical ingredients, which can be any agent described herein (e.g., in Section 5.3 or 5.4) or otherwise known in the art.

In some embodiments, a post-perturbation treatment is administered immediately after integumental perturbation. In some embodiments, a post-perturbation treatment is administered a certain period of time after integumental perturbation. Although referred to herein as "post-perturbation" treatments, the post-perturbation treatment methods described herein are not by definition limited to treatment steps after integumental perturbation. In some embodiments, a post-perturbation treatment is administered before or during integumental perturbation. In particular embodiments, a post-perturbation treatment is present at more than one time period before, during, and/or after integumental perturbation.

In one embodiment, a method of integumental perturbation in combination with a post-perturbation treatment provided herein promotes growth of hair on an area of skin of a subject. In some embodiments, a method of integumental perturbation in combination with a post-perturbation treatment provided herein increases the amount or thickness of hair on a treated area of skin of a subject. In some embodiments, a method of integumental perturbation in combination with a post-perturbation treatment provided herein results in an increase in the amount of vellus hair on a treated area of skin of a subject. In some embodiments, a method of integumental perturbation in combination with a post-perturbation treatment provided herein results in an increase in the amount of terminal hair on a treated area of skin of a subject. In some embodiments, a method of integumental perturbation in combination with a post-perturbation treatment provided herein results in hair follicle neogenesis in a treated area of skin of a subject. In certain embodiments, a method of integumental perturbation in combination with a post-perturbation treatment provided herein results in an increased number of hair follicles in a treated area of skin of a subject. In particular embodiments, the method of integumental perturbation in combination with post-perturbation treatment results in formation of new hair follicles with vellus-sized hair shafts (i.e., hair shafts with diameters less than 30 microns in diameter) in a treated area of skin of a subject. In some embodiments, a method of integumental perturbation in combination with a post-perturbation treatment provided herein results in an increased number of stimulated or activated hair follicles, such as pre-existing hair follicles, in a treated area of skin of a subject. In particular embodiments, the method of integumental perturbation in combination with post-perturbation treatment results in an increased number of pre-existing hair follicles with vellus-sized hair shafts in a treated area of skin of a subject. In particular embodiments, the method of integumental perturbation in combination with post-perturbation treatment results in the presence and/or increased numbers of NL, PEL, and PELA follicular structures.

In some embodiments, a method of integumental perturbation in combination with a post-perturbation treatment provided herein prevents infection of a treated area of skin. In some embodiments, a method of integumental perturbation in combination with a post-perturbation treatment provided herein promotes healing of perturbed skin. In some embodiments, a method of integumental perturbation in combination with a post-perturbation treatment provided herein promotes healing of perturbed skin with no or reduced scarring.

Various post-perturbation pharmaceutical compositions and treatment methods are described in Section 5.2 infra, however, the invention is not to be so limited, and any topical pharmaceutical composition may be used in accordance with the post-perturbation treatment steps described herein.

Also provided herein are methods of treating baldness or alopecia in a subject (e.g., a human subject), the methods comprising (i) subjecting an affected area of the skin to integumental perturbation, optionally carried out in combination with a post-perturbation treatment step, (ii) in combination with a step comprising treatment with one or more hair growth-promoting agents. Also provided herein are methods of promoting hair growth or hair thickness on an area of skin of a subject (e.g., a human), the methods comprising (i) subjecting an affected area of the skin to integumental perturbation, optionally carried out in combination with a post-perturbation treatment step, (ii) in combination with a step comprising treatment with one or more hair growth-promoting agents. In certain embodiments, the method of treating baldness or alopecia or promoting hair growth or thickness of hair comprising integumental perturbation (optionally in combination with a post-perturbation treatment step) in combination with a step comprising treatment with one or more hair growth-promoting agents results in hair follicle neogenesis, stimulation, activation or reorganization of existing hair follicles, the formation or an increase in NL, PEL, or PELA follicular structures, an increase in the numbers of vellus hairs, an increase in the numbers of terminal hairs, and/or an increase in the numbers of terminal hairs in the treated area. Also provided herein are pharmaceutical compositions for use in the hair growth-promoting agent treatment step.

As used herein, the term "hair growth-promoting agent" refers to any agent that promotes hair growth or hair thickness, or is intended for such purpose, and/or treats a disease or condition associated with hair loss, or is intended for such purpose. In some embodiments, the hair growth-promoting agent is an agent that promotes, or is intended to promote, the transition of vellus hair to terminal hair. In some embodiments, the hair growth-promoting agent increases vellus hair growth. In some embodiments, the hair growth-promoting agent increases terminal hair growth. In some embodiments, the hair growth-promoting agent increases the ratio of terminal-to-vellus hair on an area of skin of a subject. In some embodiments, the hair growth-promoting agent maintains terminal hair growth, i.e. helps prevent miniaturization of terminal hairs. In some embodiments, the hair growth-promoting agent increases the number of anagen hairs or increases anagen hair growth. In some embodiments, the hair growth-promoting agent increases the ratio of anagen-to-teleogen hair on an area of skin of a subject.

In one embodiment, a method of integumental perturbation (optionally in combination with a post-perturbation treatment step) in combination with a step comprising treatment with one or more hair growth-promoting agents provided herein promotes growth of hair on an area of skin of a subject. In some embodiments, a method of integumental perturbation (optionally in combination with a post-perturbation treatment step) in combination with a step comprising treatment with one or more hair growth-promoting agents provided herein increases the amount or thickness of hair on a treated area of skin of a subject. In some embodiments, a method of integumental perturbation (optionally in combination with a post-perturbation treatment step) in combination with a step comprising treatment with one or more hair growth-promoting agents provided herein results in an increase in the amount of vellus hair on a treated area of skin of a subject. In some embodiments, a method of integumental perturbation (optionally in combination with a post-perturbation treatment step) in combination with a step comprising treatment with one or more hair growth-promoting agents provided herein results in an increase in the amount of terminal hair on a treated area of skin of a subject. In some embodiments, a method of integumental perturbation (optionally in combination with a post-perturbation treatment step) in combination with a step comprising treatment with one or more hair growth-promoting agents provided herein results in the maintenance of terminal hair growth, i.e. helps prevent miniaturization of terminal hairs. In some embodiments, a method of integumental perturbation (optionally in combination with a post-perturbation treatment step) in combination with a step comprising treatment with one or more hair growth-promoting agents provided herein results in an increase in the ratio of terminal-to-vellus hair on a treated area of skin of a subject. In some embodiments, a method of integumental perturbation (optionally in combination with a post-perturbation treatment step) in combination with a step comprising treatment with one or more hair growth-promoting agents provided herein results in an increase in the amount of anagen hair or increases anagen growth on a treated area of skin of a subject. In some embodiments, a method of integumental perturbation (optionally in combination with a post-perturbation treatment step) in combination with a step comprising treatment with one or more hair growth-promoting agents provided herein results in an increase in the ratio of anagen-to-telogen hair on a treated area of skin of a subject. In some embodiments, a method of integumental perturbation (optionally in combination with a post-perturbation treatment step) in combination with a step comprising treatment with one or more hair growth-promoting agents provided herein results in hair follicle neogenesis in a treated area of skin of a subject. In certain embodiments, a method of integumental perturbation (optionally in combination with a post-perturbation treatment step) in combination with a step comprising treatment with one or more hair growth-promoting agents provided herein results in an increased number of hair follicles in a treated area of skin of a subject. In particular embodiments, the method of integumental perturbation (optionally in combination with a post-perturbation treatment step) in combination with a step comprising treatment with one or more hair growth-promoting agents results in formation of new hair follicles with nonvellus-sized hair shafts (i.e., hair shafts with diameters equal to or greater than 30 microns in diameter) in a treated area of skin of a subject. In some embodiments, a method of integumental perturbation (optionally in combination with a post-perturbation treatment step) in combination with a step comprising treatment with one or more hair growth-promoting agents provided herein results in an increased number of stimulated and activated hair follicles, such as pre-existing hair follicles, in a treated area of skin of a subject. In particular embodiments, the method of integumental perturbation (optionally in combination with a post-perturbation treatment step) in combination with a step comprising treatment with one or more hair growth-promoting agents results in an increased number of pre-existing hair follicles with nonvellus-sized hair shafts in a treated area of skin of a subject. In particular embodiments, the method of integumental perturbation (optionally in combination with a post-perturbation treatment step) in combination with a step comprising treatment with one or more hair growth-promoting agents results in the presence and/or increased numbers of NL, PEL, and PELA follicular structures.

Various pharmaceutical compositions and treatment methods comprising hair growth-promoting agents are described in Section 5.3 infra, however, the invention is not to be so limited, and any pharmaceutical composition may be used in accordance with the hair growth-promoting treatment steps described herein.

5.1 Integumental Perturbation

As used herein, integumental perturbation refers to any treatment of the skin and/or other tissues of the integumentary system that results in debriding, peeling, or wounding, or other perturbation of the skin. In certain embodiments, a treatment with integumental perturbation refers to any treatment that results in an increase in the number of neogenic-like (NL) hair follicles, stimulated or activated or reorganized follicles, such as pre-existing-like (PEL) or pre-existing-like, attached (PELA) follicular structures (as these terms are described herein; see e.g., Section 5.8.4 infra). In certain embodiments, a treatment with integumental perturbation refers to any treatment that results in an increase in the number of vellus hairs or terminal hairs or anagen hairs. Integumental perturbation can be achieved by any means known in the art or described herein or that may become available in the future, such as, for example, using chemical, mechanical, physical, or electromagnetic means. In one embodiment, the integumental perturbation treatment increases the number of NL, PEL, or PELA follicular structures in an area of skin adjacent to the integumentally perturbed skin site. In another embodiment, the integumental perturbation treatment increases the number of NL, PEL, or PELA follicular structures in the integumentally perturbed skin site, for example, beneath the site of integumental perturbation. In another embodiment, the integumental perturbation treatment increases the number of NL, PEL, or PELA follicular structures in the integumentally perturbed skin site and in an area of skin adjacent to the integumentally perturbed skin site. In one embodiment, integumental perturbation comprises disrupting the skin of the subject (for example, resulting in the induction of re-epithelialization of the skin of the subject). In some embodiments, a certain area of the epithelium is partially or wholly disrupted. In some embodiments, a certain area of both the epithelium and stratum corneum are partially or wholly disrupted. For a discussion of skin disruption and re-epithelialization, including methods for disrupting skin and inducing and detecting re-epithelialization, see PCT Publication Nos. WO 2008/042216 and WO 2006/105109, each of which is incorporated herein by reference. Integumental perturbation can be used to induce, for example, a burn, excision, dermabrasion, full-thickness excision, blister, or other form of abrasion or wound.

Chemical means of integumental perturbation can be achieved, for example, using phenol, trichloroacetic acid, ascorbic acid, an enzyme that cleaves the basement membrane (Fein et al., Dermatol Surg. 2005; 31(2):139-47); discussion 147-8, or an inflammatory agent. In one embodiment, a chemical means of integumental perturbation is by inducing inflammation, which can be accomplished by, e.g., application of an adjuvant. In one embodiment, the adjuvant is one or more of sodium dodecyl sulfate, aluminum salts, monophosphoryl lipid A, or cetyl triammonium bromide (CTAB). In one embodiment, inflammation is induced by application of a cytokine (e.g., IL-1beta). In one embodiment, inflammation is induced by application of an antigen (e.g. tetanus toxoid).

Physical and mechanical means of integumental perturbation include, for example, dermabrasion (DA), particle-mediated dermabrasion (PMDA), microdermabrasion, microneedles, microneedle rollers, dermatome planning (e.g., dermaplaining), a coring needle, a puncture device, a punch tool or other surgical tool, suction tool or instrument, use of sandpaper, a felt wheel, ultrasound, sonoporation, supersonically accelerated mixture of saline and oxygen, tape-stripping, spiky patch, or peels, or surgical treatments (e.g., biopsy, skin graft, hair transplant, cosmetic surgery, strip harvesting, scalp reduction, hair transplant, follicular unit extraction (FUE), robotic FUE, etc.).

Electromagnetic means of integumental perturbation include, for example, use of heat or thermal injury. In some embodiments, electromagnetic means of integumental perturbation is by laser (e.g., using lasers, such as those that deliver ablative, non-ablative, fractional, non-fractional, superficial or deep treatment, and/or are $CO_2$-based, or erbium-YAG-based, erbium-glass, neodymium:yttrium aluminum garnet (Nd:YAG) laser, etc.), a low-level laser therapy treatment (e.g., HairMax), or laser abrasion. In some embodiments, the integumental perturbation is carried by "photo-biostimulation" of the hair follicles. For example, the Hairmax Lasercomb or the Leimo laser are non-limiting examples of devices that can be used to stimulate growth of hair, and can be used alone, in combination with another form of integumental perturbation described herein, or in combination with a treatment described in Section 5.2-5.4 or elsewhere herein or known in the art.

Integumental perturbation can also be achieved through, for example, the use of irradiation, such as, e.g., visible, infrared, ultraviolet, radio, or X-ray irradiation. In one embodiment, integumental perturbation is by light energy, such as described in Leavitt et al., 2009, Clin. Drug. Invest. 29:283-292, or intense pulsed light. Electrical or magnetic means of disruption of the epidermis can be achieved, for example, through the application of an electrical current, through electroporation, radio frequency (RF) ablation, electrology, low voltage electric current, iontophoresis, electrophoresis, or any other form of electromagnetic disruption. Electric or magnetic means can also include the induction of an electric or a magnetic field, or an electromagnetic field. For example, an electrical current can be induced in the skin by application of an alternating magnetic field. A radiofrequency power source can be coupled to a conducting element, and the currents that are induced will heat the skin, resulting in an alteration or disruption of the skin.

In some embodiments, a fractional like hole pattern (similar to that achieved with a fractional laser or full thickness excision) is achieved with using an array of punch biopsy needles. For example, 1-mm punch biopsies can be arranged with 1-mm hole spacing. When inserted into the scalp or other area of skin to be treated, the cored skin samples can be removed and, thus, an effect approximating the full thickness excision model is invoked within each hole. Similarly, and for smaller holes, microneedles (e.g., 19 or 21 gauge needles) and/or micro-coring needles could be used.

In one embodiment, integumental perturbation is accomplished using a microneedle array. In one such embodiment, the microneedle array is in the form of a roller or flat plate. In one embodiment, the microneedle array can disrupt a skin area of 1.5 cm×1.5 cm to 15 cm×15 cm. In one embodiment, the microneedle array can disrupt skin at a depth of 100 microns to 4000 microns. In some embodiments, the microneedle array has hollow needles. In some embodiments, the microneedle array top has a luer-lock fitting that can accommodate a syringe to deliver drug. In a certain embodiment, the volume of the syringe is 1 ml to 3 ml.

In specific embodiments, a device or method of integumental perturbation described in US Patent Application Publication Nos. US 2011-0130711, US 2011-0130748, or US 2011-0130706, each published Jun. 2, 2011, or International Patent Application Publication No. WO 11/123218, published Jun. 10, 2011, each of which is incorporated by reference herein in its entirety, may be used in accordance with the invention.

In some embodiments, a technique of integumental perturbation for use in the invention excludes freezing of the skin. In some embodiments, a technique of integumental perturbation for use in the invention includes freezing of the skin.

In one embodiment, a method of treatment—either the integumental perturbation step, and/or post-perturbation treatment(s) step, and/or hair growth-promoting agent(s) treatment step—is carried out over a small area of skin, e.g., 1×1 cm, or 1.5×1.5 cm, or 2×2 cm, or 2.5×2.5 cm, or 3×3 cm or more). In some embodiments, the method of treatment is carried out over a larger area of skin, such as, e.g, an entire balding area of scalp. In some embodiments, treatment of a small area of skin is followed by treatment of a larger area of skin. In some embodiments, a step or steps of the treatment is carried out over alternating areas of skin, by applying, for example, a mesh or grid-like covering to the area to be treated so that areas contacted with the treatment alternate with areas that are not contacted with the treatment.

5.1.1 Dermabrasion

In particular embodiments, integumental perturbation is by dermabrasion (also referred to herein as "DA"), a well-established dermatological procedure that has been used for decades as a skin resurfacing technique (Grimes, 2005, Microdermabrasion. Dermatol Surg 31:1351-1354). While the popularity of mechanical dermabrasion has decreased in recent years with the advent of laser-based procedures, dermabrasion is still used for removing facial scars resulting from acne and other trauma. Small, portable mechanical dermabrasion equipment uses interchangeable diamond fraises operated at different rotation speeds to remove the epidermis and dermis to differing skin depth levels. Adult human skin treated with dermabrasion completely re-epithelializes in 5-7 days with minor redness lasting up to a few weeks. Dermabrasion may be carried out using any technique known in the art, described elsewhere herein (e.g., as described in the examples), or that becomes available in the future. For example, dermabrasion may be carried out using standard DA with aluminum oxide crystals using the Aseptico Econo-Dermabrader, Advance Microderm DX system, or M2-T system; standard DA with Bell Hand Engine with diamond fraise; wire brush; etc. In a specific embodiment, dermabrasion can be carried out using a hand-held dermabrader with a standard grit diamond fraise to achieve pinpoint capillary bleeding (estimated depth 100-150 microns, not anticipated to cause scarring). In some embodiments, the method of dermabrasion is alumina-, silica- or ice-based dermabrasion (as described by, e.g., Weber, U.S. Pat. Nos. 6,764,493; 6,726,693; and 6,306,119).

In some embodiments, DA is carried out using an abrasive wheel. In some embodiments, DA with an abrasive wheel is used in order to achieve pinpoint bleeding. In other embodiments, dermabrasion may be carried out using an abrasive wheel to achieve larger globules of bleeding and frayed collagen. Non-powered devices such as abrasive cloths can also be used to achieve the dermabrasion, with the optional achievement of the same endpoint.

In some embodiments, DA is accomplished using a device typically used for microdermabrasion (also referred to herein as "MDA"). For example, in such DA protocols, a microdermabrasion device is used to remove a greater depth and/or area of skin than is typical for microdermabrasion. In some embodiments, the microdermabrasion device is used under sterile conditions. In some embodiments, dermabrasion is achieved by using a device for microdermabrasion to the point where treatment is stopped upon the observation of pinpoint bleeding, which signals the removal of the stratum corneum and epidermis into the papillary dermis. In other embodiments, dermabrasion is achieved by using a device for microdermabrasion to the point where treatment is stopped upon the observation of larger globules of bleeding and frayed collagen, which signals the removal of the stratum corneum and epidermis into the deeper papillary and reticular dermis. In some embodiments, this extended use is reduced by using a microdermabrasion device with increased output pressure and increased abrasion particle size, which may accelerate the skin removal process.

In some embodiments, DA is accomplished by removal of surface skin by particle bombardment (also referred to herein as "particle mediated dermabrasion" ("PMDA")), for example, with alumina-, ice- or silica-based particles. In some such embodiments, micron-sized particles are propelled toward the surface of the skin via short strokes of a handpiece, such as a particle gun, as known in the art. The velocity of particles is controlled through positive or negative pressure. The depth of skin removed by particle bombardment DA (e.g., PMDA) is a function of the volume of particles impacting the skin, the suction or positive pressure, the speed of movement of the handpiece, and the number of passes per area of the skin.

In some embodiments, a technique of dermabrasion for use in the invention excludes freezing of the skin. In some embodiments, a technique of dermabrasion for use in the invention includes freezing of the skin. Freezing is done with wheel dermabraders to make the skin more firm for a more controlled and consistent dermabrarding.

In order to address the above-discussed drawbacks of conventional hand held dermabrasion devices, described herein is a dermabrasion tip that converts the rotational output of conventional dermabraders to a reciprocating motion. Additionally, the present dermabrasion tip uses an angle offset in order to improve ergonomics for the user. Embodiments of the present invention have several advantages over conventional dermabrasion tips including improved ergonomics, less blood and splatter, better clinician control, better suitability for use in areas of thinning hair, being hair-sparing, and use as a single use disposable unit.

Figure 9:
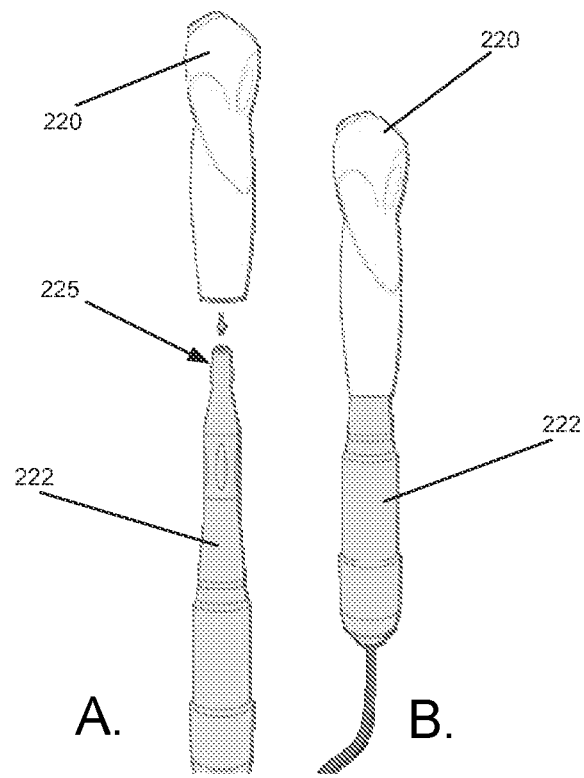
Figure 10:
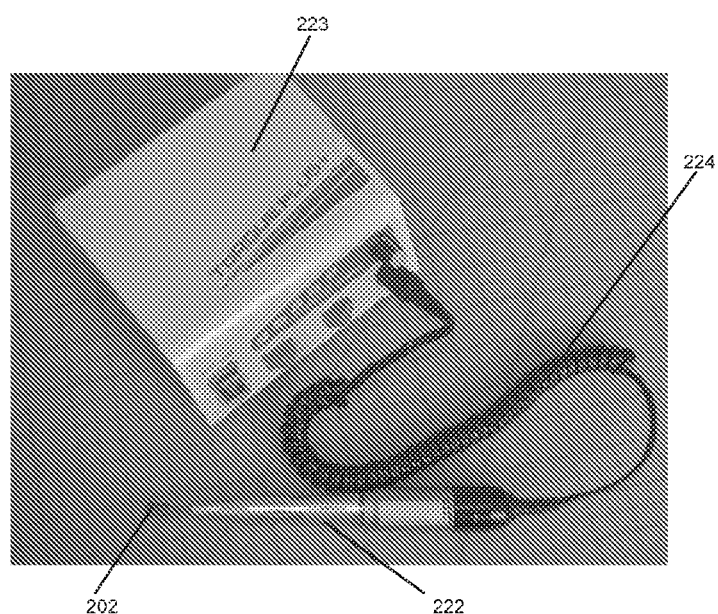

Depicted in FIG. 9 is an embodiment of a dermabrasion tip 220 that can be used with conventional dermabraders and which converts the rotational motion of a standard dermabrader to a reciprocating motion. As depicted, this embodiment is designed to be compatible as a direct replacement for a standard dermabrasion tip and thus, can be used with a standard dermabrasion hand piece 222. An example of a standard dermabrader with which the present dermabrasion tip can be used is depicted in FIG. 10, which is a Torque Plus+ dermabrader, Model AEU-12C, manufactured by Aseptico, Inc. in Woodinville, Wash. Typically, the dermabrader includes a control unit 223, a dermabrasion hand piece 222, and a cord 224 that connects the hand piece 222 to the control unit 223. As depicted in FIG. 9, the present dermabrasion tip 220 simply fits over the front end 225 of a conventional dermabrasion hand piece 222 thereby converting the hand piece's rotational motion to a reciprocating motion.

Conversion of the rotational motion of a conventional dermabrasion tip to the reciprocating motion in the present dermabrasion tip is achieved by way of a transmission. Although there are many ways to construct a means that that converts rotational motion to reciprocating motion, such as gear based transmission, transmissions that use flexible linkages, or a combination of both gears and flexible linkages, one embodiment of a transmission will be described with reference to FIG. 11.

Figure 11:
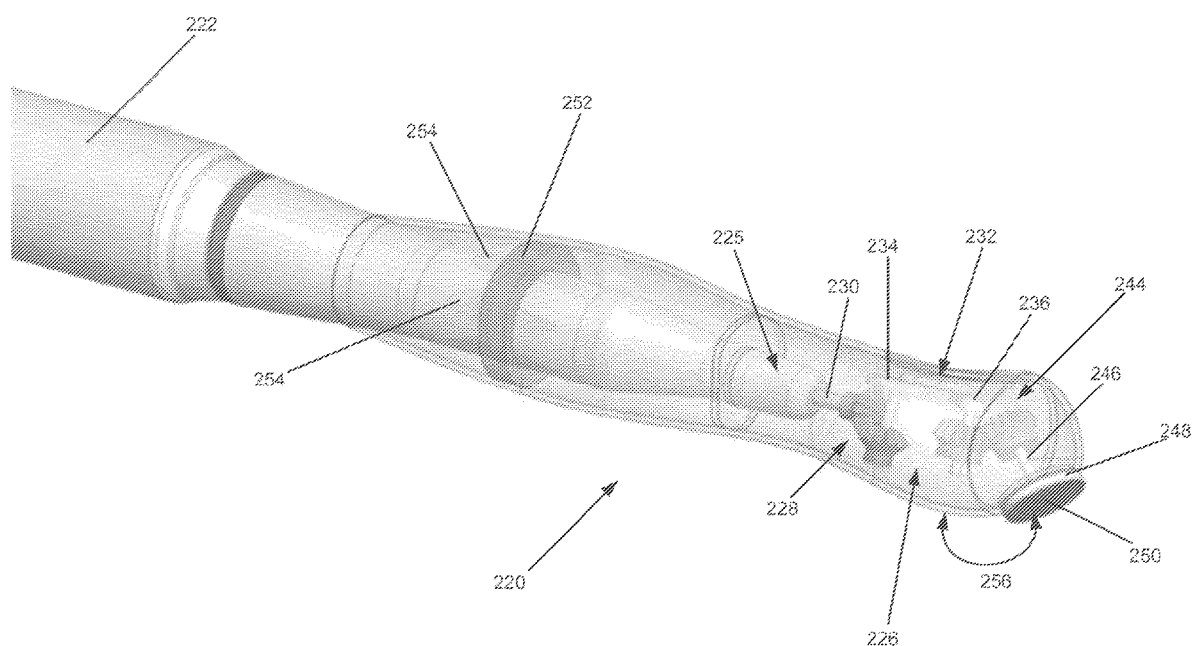
Figure 12:
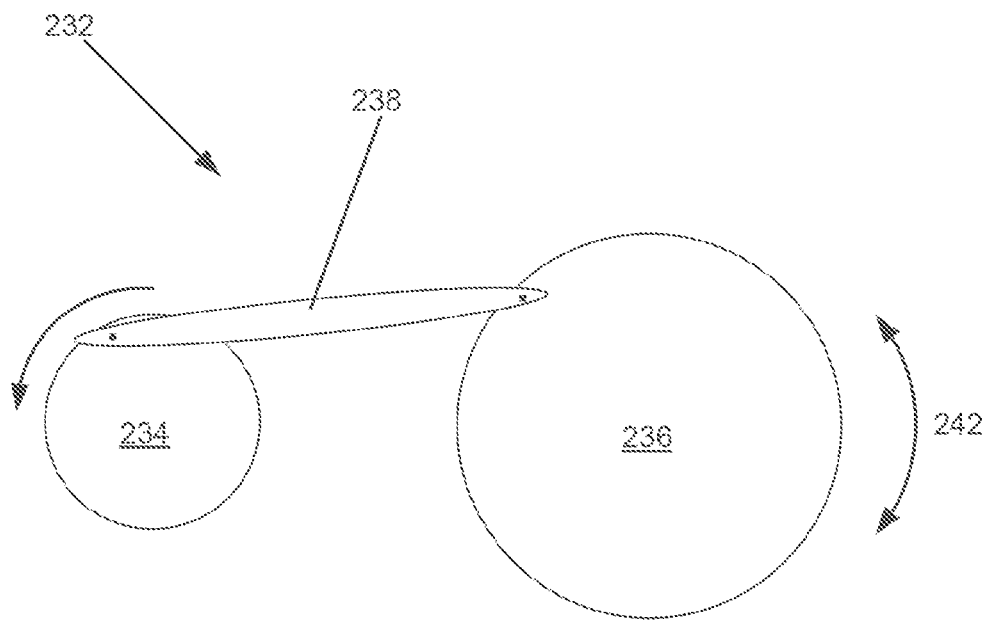

As depicted in FIG. 11, in the present embodiment, the dermabrasion tip 220 houses a gear/linkage converting transmission 226. In this embodiment, a first pair of bevel miter gears 228 converts the rotational output of the hand piece 222 to rotational output that is essentially orthogonal to the direction of rotation of the drive unit of the hand piece 222. The gears 228 can be constructed of Nylon, Acetal, or other suitable durable low-friction plastic, can be approximately 6.35 mm in diameter, and will typically have approximately 1.9 teeth/mm. The first set of bevel gears 228 is driven by a drive shaft 230 that can be made, for example, from stainless steel and is approximately 2.36 mm in diameter. Such a drive shaft 230 is suitable for insertion into the front end 225 of the hand piece 222 for connection to the hand piece's drive unit. The first set of bevel gears 228 connect to a linkage assembly 232 that is similar to a locomotive linkage. The linkage assembly 232 converts the orthogonal rotational motion of the conventional hand piece 222 to orthogonal reciprocating motion. As can be seen in FIG. 12, the linkage assembly 232 includes an input drive wheel 234, an output drive wheel 236, and at least one coupling rod 238. As can also be seen in FIG. 12, a first end of the coupling rod 238 attaches to an edge portion of the input drive wheel 234 and the second end of the coupling rod 238 attaches to an edge portion of the output drive wheel 236.

As depicted in FIG. 12, in the linkage assembly 232, the input drive wheel 234 rotates through a radius that is smaller than the diameter of the output drive wheel 236. Therefore, as the input drive wheel 234 completes 360 degrees of rotation, the output drive wheel 236 reciprocates through a motion of less than +/−180 degrees. That is, the output drive wheel 234 never completes a complete 360 degree rotation and instead reciprocates back in forth as indicated by arrow 242. By changing the diameters of the input drive wheel 234 and output drive wheel 236 of the linkage assembly 32, one can adjust the reciprocating swing downward from +/−180 degrees. In the present embodiment, the input drive wheel 234 is approximately 6.35 mm inches in diameter and the output drive wheel 236 is approximately 9.53 mm in diameter and the coupling rod 238 is approximately 12.7 mm in length. Preferably, this provides for approximately +/−45 degrees of reciprocating output. However, as will be readily apparent to those skilled in the art, the diameters of the input and output drive wheels, 234, 236, and/or the length of the coupling rod 238, can be changed in order to change the degree of reciprocating motion, which can range anywhere from 1 degree to 179 degrees. The linkage assembly 232 can be constructed, for example, of Nylon, Acetal, or other suitable durable low-friction plastics.

Figure 13:
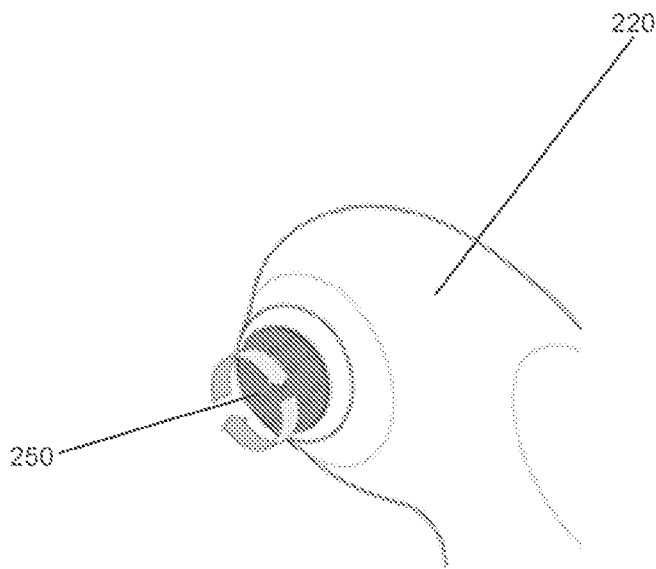
Figure 14:
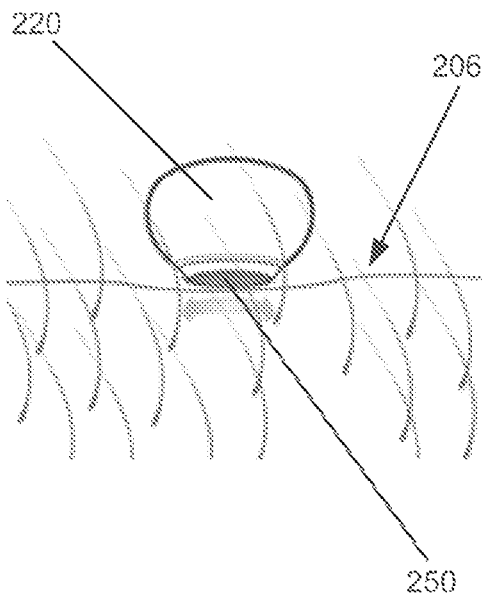

Referring again to FIG. 11, the reciprocating output drive wheel 236 of the linkage assembly 232 connects to a second pair of similar (size, material, pitch, etc.) bevel miter gears 244 that convert the reciprocating output of the linkage assembly 232 to a reciprocating output that is, in the present embodiment, at an angle of approximately 45 degrees to the elongated axis of the hand piece 222. The 45 degree reciprocating output connects to a second drive shaft 246, which, for example, can be made of stainless steel. This second drive shaft 246 is connected to a circular pad 248, which can be made, for example, of polypropylene, and which can have a diameter of approximately 12.7 mm. Supported by pad 248 is an abrasive disk 250, which may be composed of bonded aluminum oxide particles with a course CAMI grit of 24, 30, or 36. In addition, Johnson Abrasives, Jaffery N.H. Wet-Kut water proof abrasive backed clothed may be adequately secured to the support pad with very-high-bond tape such as 3M-4952. Thus, as can be seen in FIGS. 13 and 14, the reciprocating motion of the second drive shaft 246 is transferred to the abrasive disk 250. In all of the gearing described herein, the diameters can be varied to achieve the desired transmission speed and torque conversions.

All of the transmission components described above may be housed in, for example, a polypropylene housing or a housing made of other suitable materials. The housing can be approximately 63.5 mm in length with an external surface contoured to achieve maximum ergonomics. The inside proximal diameter is designed to be approximately 15 mm, which allows the housing and hence, the entire dermabrasion tip 220 to be inserted onto the front end portion 225 of a conventional dermabrasion hand piece 222 as depicted in FIG. 9. In order to provide securement to the hand piece 222, a co-molded low durometer thermoplastic rubber (TPR) or thermoplastic elastomer (TPE) insert 252 having an inside diameter of approximately 14.4 mm, is included on the inside of the dermabrasion tip 220. As can be seen in FIG. 11, the insert 252 is designed to engage the distal flats 254 of a conventional dermabrasion hand piece 222, thereby forming a friction fit between the dermabrasion tip 220 and the hand piece 222.

Figure 15:
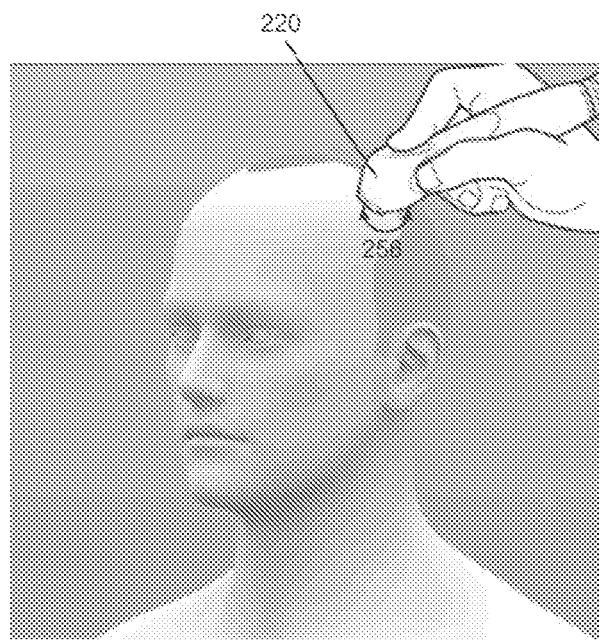

Furthermore, as can be seen in FIGS. 11 and 15, the present dermabrasion tip 220 includes an angle 256 of approximately 45 degrees between the longitudinal axis of the hand piece and the end effector. As previously discussed, such an angle improves ergonomics and allows the hand piece to be held more like a pen or artist paint brush. The added angle also improves clinician comfort and overall control. As will be readily apparent to those skilled in the art, different angles may be used to change the ergonomics of the dermabrasion tip. Furthermore, in another embodiment, the dermabrasion tip 220 can include an adjustable end effector such that the angle between the longitudinal axis of the hand piece 222 and the end effector can be adjusted by the clinician in order to better adapt the dermabrasion tip 220 to the clinician and/or patient and/or procedure being performed.

Figure 16:
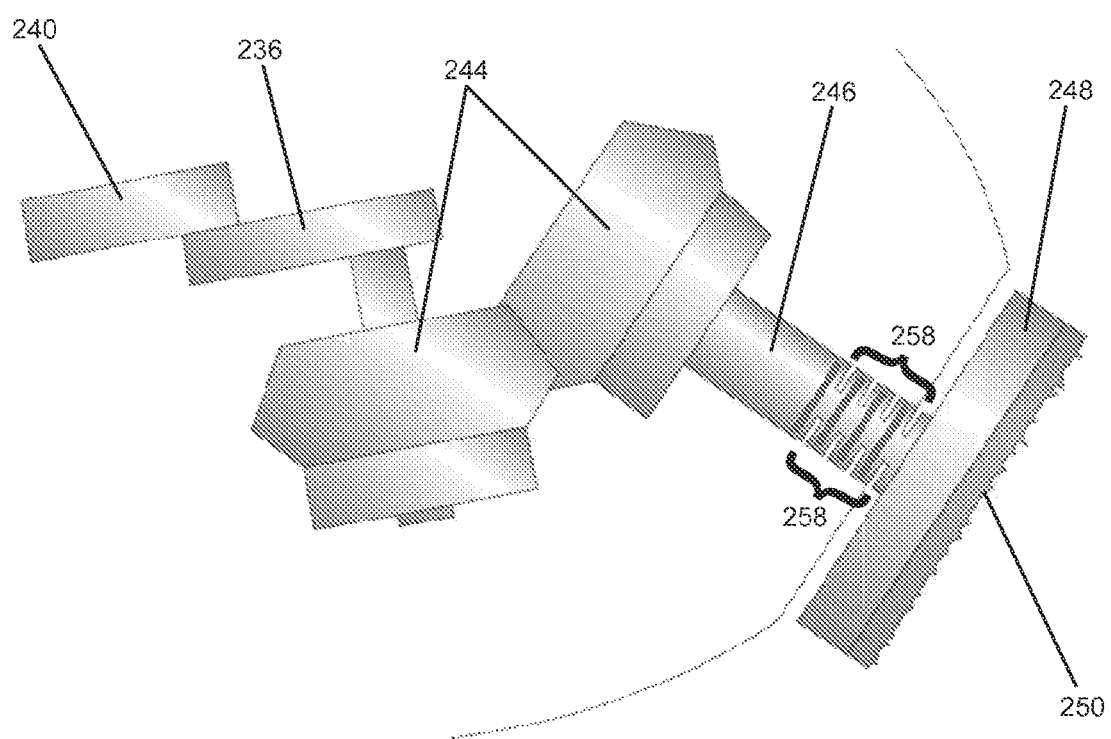
Figure 17A:
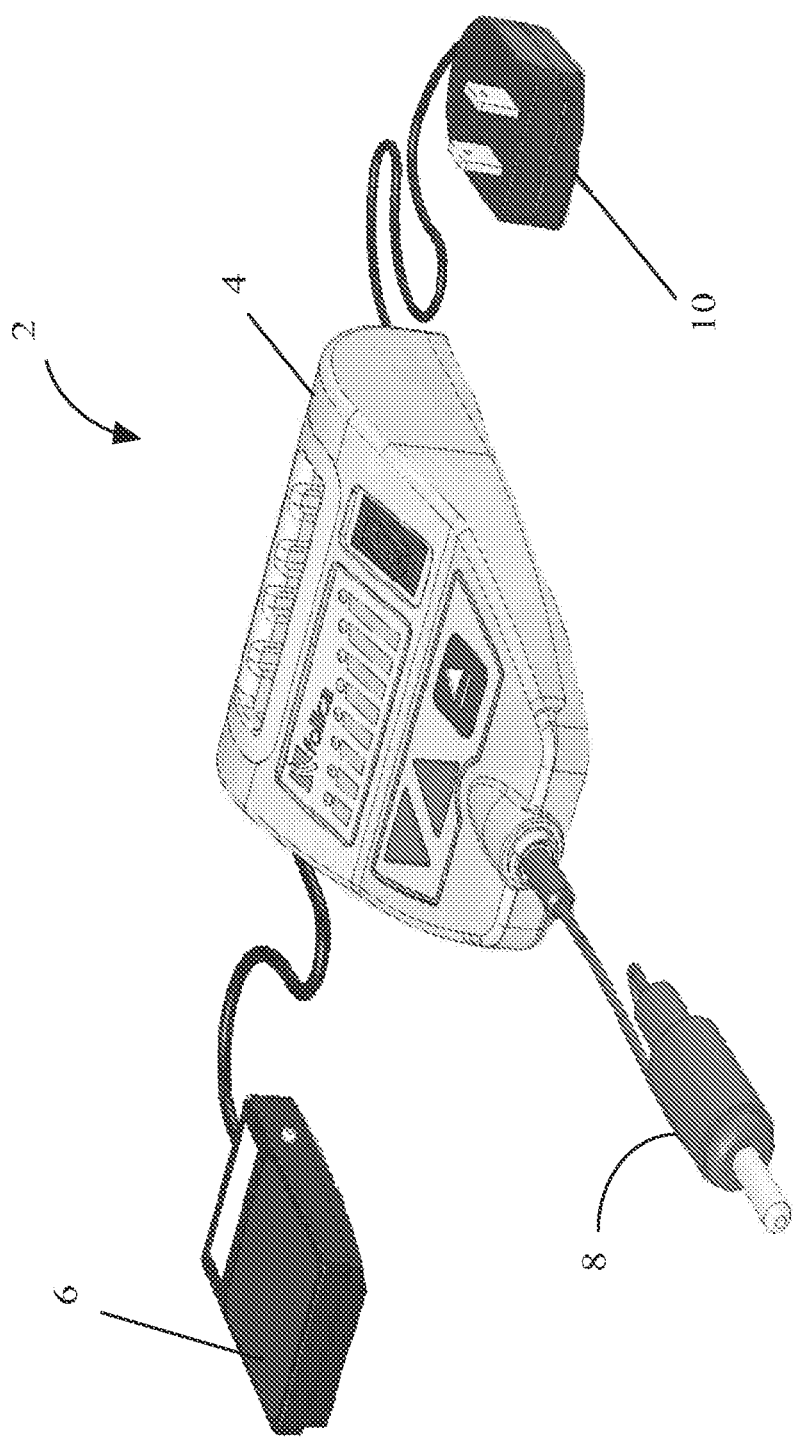
Figure 17B:
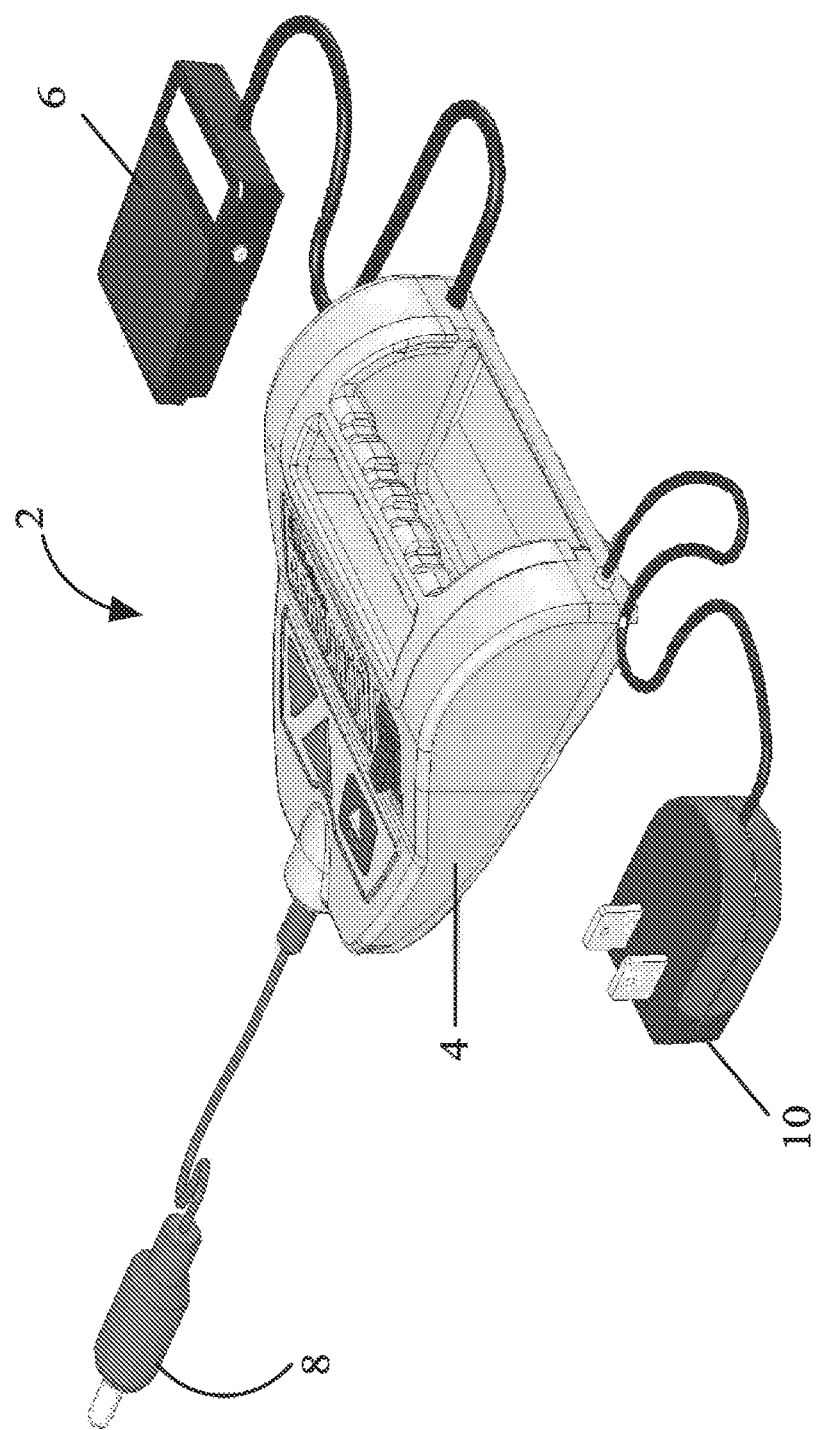

Moreover, in order to allow the end effector, which includes the abrasive disk 250, to better conform to the skin surface, as depicted in FIG. 16, the second drive shaft 246 can include a plurality of notches 258. These notches 258 permit the second drive shaft 244 to flex, thereby allowing the abrasive disk 250 to conform to the skin surface. Other ways to achieve conformability of the abrasive pad 250 to the skin surface include, but are not limited to, use of a ball and socket joint or a universal joint.

In another embodiment of the dermabrasion tip, all the inexpensive plastic transmission parts previously described for use in a single use disposable dermabrasion tip can be made from stainless steel and incorporated into the body of a dermabrasion tip that can be reusable. Essentially, all the parts of the reciprocating dermabrasion tip would then be reusable with the exception of the abrasive disk, which could be peeled off after use and discarded. Thus, after the reusable dermabrasion tip is cleaned, a new abrasive disk could be attached prior to use.

As an added convenience to the clinician, the above-described dermabrasion tip can be packaged in a kit with a tube (or other similar container) containing a pharmaceutical composition for use in conjunction with the procedure, examples of which include the post-perturbation treatments described in Section 5.2, hair growth-promoting agents described in Section 5.3, other drugs described in Section 5.4, or described elsewhere herein or otherwise known in the art. Thus, the kit would include all the necessary consumables to perform the follicular procedure in the clinic.

In another embodiment, the present invention is directed to a method of inducing hair growth that comprises disrupting a skin surface with a dermabrasion tip disclosed herein and then applying one or more post-perturbation treatment described in Section 5.2, one or more hair growth-promoting agents described in Section 5.3, other drugs described in Section 5.4, or described elsewhere herein or otherwise known in the art.

5.1.2 Laser

In other particular embodiments, integumental perturbation is by laser treatment. Exemplary laser treatments for integumental perturbation include or fractional laser (e.g., Fraxel), laser abrasion, erbium-YAG laser, erbium-glass laser, Ultrapulse $CO_2$ fractional laser, Ultrapulse $CO_2$ ablative laser, Smooth Peel Full-ablation Erbium laser (Candela), or neodymium:yttrium aluminum garnet (Nd:YAG) laser. Any other laser treatment described herein, known in the art, or described in the future may also be used in the methods described herein. In one embodiment, a laser treatment is chosen in which the integumental perturbation achieved most resembles that achieved by dermabrasion (for example, a dermabrasion method described herein). In one embodiment, integumental perturbation by laser treatment is by a fractional laser. See, e.g., the laser treatments described in U.S. Provisional Application Nos. 61/262,820, 61/262,840, 61/262,831, each of which is incorporated herein by reference in its entirety. One example of a fractional laser treatment is treatment with an erbium-YAG laser at around 1540 nm or around 1550 nm (for example, using a Fraxel® laser (Solta Medical)). Treatment with an erbium-YAG laser at 1540 or 1550 nm is typically non-ablative, and pinpoint bleeding typical of laser treatment is not observed since the stratum corneum is left intact. The column of dead (epidermal and/or dermal) cells in the path of the laser treatment is termed a "coagulum." In another embodiment, integumental perturbation by laser treatment is by a fractional laser, using, e.g., a $CO_2$ laser at 10,600 nm. Treatment with a $CO_2$ laser at 10,600 nm is typically ablative, and typically leads to the appearance of pinpoint bleeding. In another embodiment, the laser is a fractional erbium-glass laser, used at, e.g., 1550 nm. In a particular embodiment, a subject receives one or more (2-10 or more) treatments with a 1550 nm fraction Er:Glass Laser at 2-week intervals using a 5-10 mm tip, 6 mJ pulse energy, 800 spot/$cm^2$ density, and static mode, as described in Lee et al., 2011, *Journal of the European Academy of Dermatology and Venereology* 25:1450-1454, which is incorporated by reference herein in its entirety. See also Kim et al., 2011, *Dermatol Surg* 37:41-51, also incorporated by reference herein in its entirety.

A standard $CO_2$ or erbium-YAG or erbium-glass laser can be used to create superficial and, optionally, broad based, integumental perturbation similar to dermabrasion (discussed below). Although the pinpoint bleeding clinical endpoint may not be achieved due to the coagulation properties of (particularly non-ablative) lasers, use of a laser has an advantage making it possible to select the specific depth of skin disruption to effectively remove the stratum corneum and epidermis, or portions thereof.

In one embodiment, the laser treatment is ablative. For example, full ablation of tissue is generated by the targeting of tissue water at wavelengths of 10,600 nm by a $CO_2$ laser or 2940 nm by an erbium-YAG laser. In this mode of laser treatment, the epidermis is removed entirely and the dermis receives thermal tissue damage. The depth of tissue ablation may be a full ablation of the epidermis, or a partial ablation of the epidermis, with both modes causing adequate wounding to the skin to induce the inflammatory cascade requisite for regeneration. In another variation, the depth of ablation may extend partially into the dermis, to generate a deep wound. The denuded skin surface is then treated with one or more hair growth-promoting agents; alternatively, the one or more hair growth-promoting agents can be delivered into the skin after the initial re-epithelialization has occurred already, to prevent clearance and extrusion of the hair growth-promoting agent-containing depots from the tissue site by the biological debris-clearance process. In one embodiment, one or more hair growth-promoting agents is delivered by a sustained release depot that is comprised of biocompatible, bioabsorbable polymers that are compatible to tissue.

The standard full thickness excision model is created using scissors or with a scalpel in animal models (see, also, the examples of Sections 28-30 and 32 in International Patent Application Publication No. WO 2011/031990, which is incorporated by reference herein in its entirety). Full thickness excision, while contemplated for use herein, carries with it the risk of scarring. However, various fractional laser modalities could be used to achieve a similarly deep disruption on a grid pattern. A fractional laser can be use to "drill," for example, 1-mm diameter holes with a 1-mm hole spacing (the fractional laser can make holes of smaller dimensions). Although the skin is completely removed within the 1-mm hole, the surrounding intact skin prevents scarring and therefore the full thickness excision model is invoked within each hole.

In some embodiments, the integumental perturbation by laser is non-fractional and ablative. In one such embodiment, the non-fractional, ablative integumental perturbation is by full bulk ablation, wherein the tissue of the entire area of treatment is ablated. In one embodiment, the non-fractional, ablative integumental perturbation by bulk ablation is over an area of 1.5 cm×1.5 cm to 15 cm×15 cm. In one embodiment, the non-fractional, ablative integumental perturbation by bulk ablation is accomplished at 10,600 nm using a carbon dioxide laser. In one embodiment, the non-fractional, ablative integumental perturbation by bulk ablation is accomplished at 2940 nm using a Erbium-YAG laser.

In some embodiments, the laser treatment is fractional and ablative. For example, fractional tissue ablation can be achieved using a $CO_2$ laser at 10,600 nm or an erbium-YAG laser at 2940 nm (e.g., the Lux 2940 laser, Pixel laser, or Profractional laser). In some such embodiments, the lasing beam creates micro-columns of thermal injury into the skin, at depths up to 4 mm and vaporizes the tissue in the process. Ablative treatment with a fractional laser leads to ablation of a fraction of the skin leaving intervening regions of normal skin intact to rapidly repopulate the epidermis. Approximately 15%-25% of the skin is treated per session. The density of micro thermal zones (MTZ) can be varied to create a dense "grid" of injury columns surrounded by intact skin and viable cells. The density of the grid on the treatment area plays an important role. The denser the grid, the more the thermal injury and the type of injury begins to approximate full ablation. Therefore, it is appreciated that there may be an "optimum" MTZ density that is appropriate for use in the methods disclosed herein. In one embodiment, one or more hair growth-promoting agents is delivered into the dermis immediately after wounding, or after initial re-epithelialization has occurred.

In one embodiment, the fractional, ablative integumental perturbation results in fractional ablation of the skin at a depth between 100 microns and 4000 microns into the skin, or results in fractional ablation of the skin at a depth approximating the depth of a full-thickness excision wound. In one such embodiment, the fractional, ablative integumental perturbation results in fractional ablation of the skin over an area of 1.5 cm×1.5 cm to 15 cm×15 cm. In another such embodiment, the fractional, ablative integumental perturbation results in fractional ablation of the skin at a depth density of the micro-thermal zones of the fractional ablation approximates that of a full bulk ablation of the entire area of treatment.

In one embodiment, the fractional, ablative integumental perturbation is by full bulk ablation, wherein the tissue of the entire area of treatment is ablated. In one such embodiment, the fractional, ablative integumental perturbation by bulk ablation is over an area of 1.5 cm×1.5 cm to 15 cm×15 cm. In one such embodiment, the fractional, ablative integumental perturbation by bulk ablation is accomplished at 10,600 nm using a carbon dioxide laser. In one such embodiment, the fractional, ablative integumental perturbation by bulk ablation is accomplished at 2940 nm using a Erbium-YAG laser.

In another embodiment, the mode of laser treatment is non-ablative, wherein the stratum corneum and the epidermis are intact after treatment, with the dermis selected for the deep thermal treatment required for the requisite injury to tissue. This can be accomplished by cooling the epidermis during the laser treatment. For example, one could use the timed cooling of the epidermis with a cryogen spray while the laser delivers deep thermal damage to the dermis. In this application, the depth of treatment may be 1 mm to 3 mm into the skin. One could also use contact cooling, such as a copper or sapphire tip. Lasers that are non-ablative have emission wavelengths between 1000-1600 nm, with energy fluences that will cause thermal injury, but do not vaporize the tissue. The non-ablative lasers can be bulk, wherein a single spot beam can be used to treat a homogenous section of tissue. In some embodiments, multiple treatments are required to achieve the desired effect. In one embodiment, one or more hair growth-promoting agents is delivered deep into the dermis in polymeric micro-depots and released in a sustained fashion. Lasers that are non-ablative include the pulsed dye laser (vascular), the 1064 Nd:YAG laser, or the erbium-YAG laser at 1540 nm or 1550 nm (e.g., the Fraxel® laser). Use of an erbium-YAG laser at around 1540 nm or around 1550 nm, as opposed to its use at 2940 nm, "coagulates" zones of dermis and epidermis (forming a "coagulum") and leaves the stratum corneum essentially intact.

In another embodiment, the mode of laser treatment is fractional and non-ablative. Treatment with a fractional, non-ablative laser leads to perturbation of a fraction of the skin, leaving intervening regions of normal skin intact to rapidly repopulate the epidermis. Approximately 15%-25% of the skin is treated per session. As in any non-ablative process, the skin barrier function is maintained, while deep thermal heating of dermis can occur. Thus, zones of dermis and epidermis are coagulated and the stratum corneum is left essentially intact. This process has been coined "fractional photothermolysis" and can be accomplished, e.g., using the Erbium-YAG laser with an emission at or around 1540 nm or 1550 nm. In one embodiment, one or more hair growth-promoting agents is delivered immediately after the tissue injury, deep into the dermis. In another embodiment, a combination of bulk and fractional ablation modes of tissue injury are used.

In a particular embodiment, the fractional, non-ablative integumental perturbation by laser is performed by use of an Erbium-YAG laser at 1500-1590 nm.

In a specific embodiment, the mode of laser treatment for, e.g., a Caucasian male 30-50 years old, is fractional and non-ablative using an erbium-YAG laser at 1550 nm, with the following settings: 50-70 $J/cm^2$, treatment level 8-10 (density of the "dots"), with 8 passes. In this regard, the laser device can be equipped with a touch pad screen that offers the operator a menu of options for setting the parameters for operating the laser to promote hair growth. For example, the device can be programmed to offer the operator selections for hair growth vs. removal, choice of skin color, hair follicle density, power settings, etc.

In another embodiment, a treatment comprising use of a laser includes administration to the skin of a compound absorbing light at wavelengths between 1000-1600 nm for the purpose of efficient channeling of light to heat energy. This method of channeling energy may cause micro-zones of thermal injury within the skin. The compound may be delivered to the skin homogenously in the treatment zone, then subsequently irradiated with a non-ablative laser to efficiently capture the vibrational energy of the infrared beam. This method may result in evenly distributed and deep thermal injury, without causing tissue vaporization.

In another embodiment, a treatment comprising use of a laser includes administration of one or more hair growth-promoting agents that is encapsulated in matrices that are highly hydrophilic and charged, for example, linked to the dermis by covalent or ionic bonding to prevent the matrices from being cleared by phagocytosis, as part of the wound healing process.

In another embodiment, a treatment comprising use of a laser includes the step of placing a biocompatible, synthetic skin substitute on the newly created wound, especially if the wound is deep, covers large area and is bulk ablated. This process can help minimize or prevent the rapid wound contraction that occurs after loss of a large area of tissue, frequently culminating in scar tissue formation and loss of skin function. In one embodiment, the biocompatible synthetic skin substitute is be impregnated with depots of a slow releasing hair growth-promoting agent formulation described herein. This method of treatment may enable treating a large bald area on the scalp in one session at the treatment clinic. In some embodiments, other molecules are also co-eluted at the site through the skin substitute, such as, e.g., anesthetics and antibiotics, to prevent further pain and minimization of infection, or any other compound described herein. The skin substitute, in the presence or absence of one or more hair growth-promoting agents and/or other compounds described herein, may also be pre-cooled and applied to the wound to provide a feeling of comfort to the patient. This mode of treatment may prevent the one or more hair growth-promoting agents or other compound from being cleared away from the wound site as the wound heals.

5.1.3 Controlled Integumental Perturbation

The aforementioned methods of integumental perturbation can be carried out in a fashion that exerts control over the extent of perturbation and/or control over the way in which the integumentally perturbed skin heals. In one embodiment, the integumental perturbation method causes only superficial wounding to the area of skin on which hair growth is desired. In a particular embodiment, the extent of wounding is minimized by controlling the depth of perturbation. For example, the integumental perturbation procedures described herein can be controlled to limit perturbation to part or all of the epidermis, to part or all of the stratum corneum, or deeper into the papillary dermis, reticular dermis, and/or hypodermis. The occurrence of pinpoint bleeding would indicate removal of the stratum corneum, epidermis (or part thereof) and portions of the upper layer of the dermis, such as the superficial papillary dermis. The occurrence of increased bleeding would indicate deeper penetration (and thus perturbation) into the deeper papillary dermis and reticular dermis layer.

In one embodiment, the integumental perturbation does not remove the epidermis. In some embodiments, the integumental perturbation achieves removal of part of the epidermis. In some embodiments, integumental perturbation removes the entire epidermis. In some embodiments, the integumental perturbation removes all of the epidermis and part of the dermis. In some embodiments, integumental perturbation removes part of the stratum corneum. In some embodiments, integumental perturbation removes the stratum corneum. In some embodiments, integumental perturbation removes part of the papillary dermis. In some embodiments, integumental perturbation removes part of the more superficial papillary dermis. In some embodiments, integumental perturbation removes part of the deeper papillary dermis. In some embodiments, integumental perturbation removes the papillary dermis. In some embodiments, integumental perturbation removes the reticular dermis, or part of the reticular dermis. The depth of integumental perturbation depends on the thickness of the skin at a particular treatment area. For example, the skin of the eyelid is significantly thinner than that of the scalp. The occurrence of pinpoint bleeding indicates that the epidermis and portions of the dermis have been removed. Deeper penetration can results in much more bleeding, and the perturbation can go as deep as the hypodermis.

In particular embodiments, integumental perturbation is done to a clinical endpoint of pinpoint bleeding. In some embodiments, the depth reaches the level of blood vessels of the follicular papilla. In some embodiments, the depth does not go deeper than the level of blood vessels of the capillary loops in the dermal papilla, e.g., the area of papillary dermis in between rete pegs (see FIG. 23). In some embodiments, the integumental perturbation does not penetrate the dermis. In some embodiments, the integumental perturbation does not completely remove all, or in some embodiments, most, of the hair follicles in an area of treated skin. In one embodiment, the integumental perturbation does not penetrate the reticular dermis. In one embodiment, the integumental perturbation does not penetrate more than halfway through the papillary dermis.

In some embodiments, integumental perturbation by one or more of the aforementioned methods is to a skin depth of between 5 and 40 µm, 40 and 100 µm, 30 and 200 µm, 50 and 150 µm, 70 and 130 µm, 80 and 120 µm, 90 and 110 µm, 95 and 105 µm or 100 and 150 µm.

In some embodiments, integumental perturbation by one or more of the aforementioned methods is to a skin depth of at least 30 µm. In some embodiments, integumental perturbation by one or more of the aforementioned methods is to a skin depth of 30 µm. In some embodiments, integumental perturbation is to a skin depth of 50 µm. In some embodiments, integumental perturbation by one or more of the aforementioned methods is to a skin depth of 60 µm. In some embodiments, integumental perturbation is to a skin depth of 30-100 µm. In some embodiments, integumental perturbation is to a skin depth of 60-100 µm. In some embodiments, integumental perturbation is to a skin depth of 60-200 µm. In some embodiments, integumental perturbation is to a skin depth of 100 µm. In some embodiments, integumental perturbation is to a skin depth of 100-150 µm. In some embodiments, integumental perturbation is to a skin depth of 150 µm. In some embodiments, integumental perturbation is to a skin depth of 100-200 µm. In some embodiments, integumental perturbation is to a skin depth of 30-200 µm. In some embodiments, integumental perturbation is to a skin depth of 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 µm. In some embodiments, the maximum depth of integumental perturbation is to, e.g., 30, 40, 50, 60, 70, 80, 85, 90, 95, 100, 105, 110, 120, 130, 140, 150, 160, 170, 180, 190 or 200 µm.

In some embodiments, integumental perturbation is to a skin depth of 100-500 µm. In some embodiments, integumental perturbation is to a skin depth of less than 500 µm. In some embodiments, integumental perturbation is to a skin depth of 500-1000 µm. In some embodiments, integumental perturbation is to a maximum skin depth of about 1 mm. In some embodiments, integumental perturbation is to a skin depth of about 1 mm or more. In some embodiments, integumental perturbation is to a maximum skin depth of about 2 mm. In some embodiments, integumental perturbation is to a skin depth of about 2 mm or more. In some embodiments, integumental perturbation is to a skin depth of 1 mm to 3 mm. In some embodiments, integumental perturbation is to a skin depth of 1 mm to 5 mm. In a particular embodiment, the depth of integumental perturbation does not exceed 500 µm. In a particular embodiment, the depth of integumental perturbation does not exceed 1 mm. In a particular embodiment, the depth of integumental perturbation does not exceed 2 mm.

In particular embodiments, integumental perturbation is not by microdermabrasion. In some embodiments, integumental perturbation is not by full thickness excision. In some embodiments, integumental perturbation is by partial thickness excision. In some embodiments, integumental perturbation is not partial thickness excision.

Any of the above-described methods may be used to remove a precise amount of epidermal tissue. For example, the methods of controlled integumental perturbation described herein may be used to achieve:

Removal of the stratum corneum, through removal of the first 10-30 µm of these dead skin cells.

Removal of the stratum corneum and part or all of the epidermis by removing the first 30-100 µm of the skin. This is not deep enough to remove the sebaceous gland, bulge, or hair papilla of existing follicle structures. The removal of the epidermis can be detected by the appearance of a shiny, smooth, whiteish layer of skin.

Removal of the stratum corneum, all of the epidermis, and disruption of the papillary dermis (e.g., between 100 µm and 150 µm of the skin). Disruption of the papillary dermis can be detected by the appearance of small pinpoints of blood in the treated area.

Removal of the stratum corneum, the full epidermis, and part of the dermis down to approximately 200 µm.

In another embodiment, the extent of integumental perturbation and, in some cases, the resultant wounding, is reduced by controlling the size of the perturbed area of skin; for example, by making a series of small wounds to effect wounding of a large area rather than a single large wound. Thus, in certain embodiments, the area of integumental perturbation can be of any desired size, for example, between 0-3 mm in width (e.g., 1 mm, 2 mm, 3 mm, or greater), 0-2 cm in width (e.g., 1 cm, 1.5 cm, and 2.0 cm), or greater (for example, up to 10%, 30%, 50%, 70%, 90%, or 100% of a subject's scalp or other area of hair growth, such as the eyebrow area). Optionally, the area of integumental perturbation can be interfollicular.

In some embodiments, a method of integumental perturbation described herein induces a wound in the skin. In some such embodiments, the wounded skin is healed by primary intention. In other embodiments, the wounded skin is healed by secondary intention. In yet other embodiments, the wounded skin is healed by tertiary intention. In certain embodiments, the wounded skin is healed more slowly than usually indicated for that kind of wound. This may enhance scarless wound healing and/or prolong the period during which hair growth in the wounded area of skin is promoted.

5.2 Post-Perturbation Treatments

Provided herein are pharmaceutical compositions for administration to skin following (and optionally before or during) integumental perturbation. Such pharmaceutical compositions may be used in the post-perturbation treatment steps described herein. In certain embodiments, the post-perturbation pharmaceutical composition is formulated for topical administration to skin. In a particular embodiment, the post-perturbation treatment is administered to an area of the skin that will be, is being, or that has been subjected to integumental perturbation in accordance with a method described herein. In some embodiments, a post-perturbation treatment is a non-occlusive wound covering. In some such embodiments, a post-perturbation treatment is administered in order to heal the integumentally perturbed skin by primary intention. In some such embodiments, a post-perturbation treatment is administered in order to heal the integumentally perturbed skin by secondary intention. In some such embodiments, a post-perturbation treatment is administered in order to heal the integumentally perturbed skin by tertiary intention. In some such embodiments, a post-perturbation treatment is administered in order to heal the integumentally perturbed skin more slowly than usually indicated for that kind of wound. This may enhance scarless wound healing and/or prolong the period during which hair growth in the wounded area of skin is promoted. In some such embodiments, a post-perturbation treatment promotes wound healing with no or minimal scarring.

In non-limiting embodiments, a pharmaceutical composition for post-perturbation treatment is formulated for topical administration as a gel, hydrogel, emulsion, solution, suspension, cream, ointment, dusting powder, dressing, elixir, lotion, suspension, tincture, paste, powder, crystal, foams film, aerosol, irrigation, spray, suppository, stick, bar, ointment, bandage, wound dressing, microdermabrasion or dermabrasion particle, drop, transdermal patch, or dermal patch. In particular embodiments, the post-perturbation pharmaceutical composition is an aqueous formulation (e.g., hydrogel), a non-aqueous formulation, ointment, or cream (e.g., emulsion). In one embodiment, the composition is a hydrogel. In some embodiments, the composition is occlusive. In other embodiments, the composition is non-occlusive. The compositions may be administered via any topical means of delivery known in the art. In particular embodiments, the composition is administered as part of an article of manufacture, such as a bandage or other wound dressing, such as described in Section 5.5.2.1 infra. In particular embodiments, the composition is administered using a drug delivery system, such as described in Section 5.5.4.3 infra.

In some embodiments, the pharmaceutical composition for post-perturbation treatment contains an active ingredient or active ingredients, such as described in Sections 5.3 or 5.4 below.

In some embodiments, the formulation of the pharmaceutical composition for post-perturbation treatment is varied in order to control the rate of release of active ingredients (where present) in the composition. This may be accomplished by, for example, varying the molecular fluidity of the carrier, without changing its hydrophobicity, such as by varying the petrolatum to mineral oil ratio. In one embodiment, the pharmaceutical formulation is an ointment, comprising petrolatum, mineral oil, and lanolin alcohol. Exemplary formulations prepared in accordance with such embodiments are provided in the Examples below. In another embodiment, release of active ingredients can be modulated by varying the hydrophobic/hydrophilic ratio of the formulation, for example, by preparing a petrolatum/water emulsion. Exemplary formulations prepared in accordance with such embodiments are provided in the Examples below.

In certain embodiments, a composition for post-perturbation treatment provided herein is a hydrogel comprising the following components at the listed concentrations Citric Acid at 6% to 10%, 7% to 9%; or at 8%; CMC at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Allantoin at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

In certain embodiments, a composition for post-perturbation treatment provided herein comprises the following components at the listed concentrations: Citric Acid at 6% to 10%, 7% to 9%; or at 8%; Sodium Hyaluronate at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Allantoin at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

In certain embodiments, a composition for post-perturbation treatment provided herein comprises the following components at the listed concentrations: Citric Acid at 6% to 10%, 7% to 9%; or at 8%; Collagen at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Aloe Vera Gel at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

In certain embodiments, a composition for post-perturbation treatment provided herein is an emollient cream which is comprised of a Phase I and a Phase II, Citric Acid at 10% to 20%, 12% to 18%, 14% to 16%, 15% to 17%, or at 16%; Hyaluronic Acid at 1% to 3%, 1.5% to 2.5%, or at 2%; Glycerin at 5% to 15%, 7% to 12%, or at 10%; Allantoin at 0.1% to 1%, 0.2% to 0.8%, 0.3% to 0.6%, 0.35% to 0.5%, at 0.4%, or at 0.32%; Sodium Chloride at 0.1% to 1%, 0.3% to 0.7%, or at 0.5%; Methyl Paraben at 0.1% to 0.3%, 0.15% to 0.25%, or at 0.2%; Propyl Paraben at 0.05 to 0.15%, 0.075 to 0.125% or at 0.1% or at 0.096%; 10% NaOH to adjust the pH; and Water to 100%; and wherein Phase II comprises Soybean Oil at 10% to 30%, 15% to 25%, 18% to 22% or at 20%; Hydrogenated Cottonseed Oil at 5% to 15%, 7.5% to 12.5%, at 9% to 11%, or at 10%; Polyglyceryl-10 decaoleate at 4% to 12%, 6% to 10%, 7% to 9% or at 8%; Polyglyceryl-6-octastearate at 1% to 7%, 2% to 6%, 3% to 5%, or at 4%; Jojoba Seed Oil at 2% to 8%, 3% to 7%, 4% to 6%, or at 5%; Shea Butter at 0.5% to 8%, 1% to 6%, 2% to 4%, 2.5% to 3.5% or at 3%; Olive Oil at 5% to 15%, 7% to 12%, or at 10%. In certain embodiments, the emollient cream further comprises Citric Acid at 6% to 10%, 7% to 9%; or at 8%; Hyaluronic Acid at 0.25% to 2.5%, 0.5% to 2%, 0.75% to 1.5%, or at 1%, Glycerin at 1% to 9%, 2% to 8%, 3% to 8%, 4% to 6%, or at 5%; Allantoin 0.05% to 0.3%, at 0.1% to 0.2%, or at 0.16%; Sodium Chloride at 0.05% to 0.5%, 0.1% to 0.4%, 0.2% to 0.3%, or at 0.25%; Methyl Paraben at 0.05% to 0.15%, or at 0.1%; Propyl Paraben at 0.01 to 0.1%, 0.02 to 0.08%; 0.03% to 0.06%, or 0.05%; 10% NaOH to adjust the pH; Water to 100%; Soybean Oil at 5% to 15%, 7% to 12%, or at 10%; Hydrogenated Cottonseed Oil 5% to 15%, 7% to 12%, or at 10%; Polyglyceryl-10 decaoleate at 1% to 6%, 2% to 5%, 3% to 5%, or at 4%; Polyglyceryl-6-octastearate at 1% to 3%, 1.5% to 2.5%, or at 2%; Jojoba Seed Oil 1% to 5%, 1.5% to 4%, 2% to 3%, or at 2.5%; Shea Butter at 0.5% to 4%, 1% to 3%, 1.25% to 2%, or at 1.5%; and Olive Oil at 5% to 15%, 7% to 12%, or at 10%.

In certain embodiments, a composition for post-perturbation treatment provided herein comprises the following components at the listed concentrations: Citric Acid at 6% to 10%, 7% to 9%; or at 8%; CMC at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Allantoin at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

In certain embodiments, a composition for post-perturbation treatment provided herein comprises the following components at the listed concentrations: Citric Acid at 6% to 10%, 7% to 9%; or at 8%; Sodium Hyaluronate at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Allantoin at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

In certain embodiments, a composition for post-perturbation treatment provided herein comprises the following components at the listed concentrations: Citric Acid at 6% to 10%, 7% to 9%; or at 8%; Collagen at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Aloe Vera Gel at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

In certain embodiments, a composition for post-perturbation treatment provided herein is an emollient cream which is comprised of a Phase I and a Phase II, wherein Phase I comprises Citric Acid at 10% to 20%, 12% to 18%, 14% to 16%, 15% to 17%, or at 16%; Hyaluronic Acid at 1% to 3%, 1.5% to 2.5%, or at 2%; Glycerin at 5% to 15%, 7% to 12%, or at 10%; Allantoin at 0.1% to 1%, 0.2% to 0.8%, 0.3% to 0.6%, 0.35% to 0.5%, at 0.4%, or at 0.32%; Sodium Chloride at 0.1% to 1%, 0.3% to 0.7%, or at 0.5%; Methyl Paraben at 0.1% to 0.3%, 0.15% to 0.25%, or at 0.2%; Propyl Paraben at 0.05 to 0.15%, 0.075 to 0.125% or at 0.1% or at 0.096%; 10% NaOH to adjust the pH; and Water to 100%; and wherein Phase II comprises Soybean Oil at 10% to 30%, 15% to 25%, 18% to 22% or at 20%; Hydrogenated Cottonseed Oil at 5% to 15%, 7.5% to 12.5%, at 9% to 11%, or at 10%; Polyglyceryl-10 decaoleate at 4% to 12%, 6% to 10%, 7% to 9% or at 8%; Polyglyceryl-6-octastearate at 1% to 7%, 2% to 6%, 3% to 5%, or at 4%; Jojoba Seed Oil at 2% to 8%, 3% to 7%, 4% to 6%, or at 5%; Shea Butter at 0.5% to 8%, 1% to 6%, 2% to 4%, 2.5% to 3.5% or at 3%; Olive Oil at 5% to 15%, 7% to 12%, or at 10%. In certain embodiments, the emollient cream further comprises Citric Acid at 6% to 10%, 7% to 9%; or at 8%; Hyaluronic Acid at 0.25% to 2.5%, 0.5% to 2%, 0.75% to 1.5%, or at 1%, Glycerin at 1% to 9%, 2% to 8%, 3% to 8%, 4% to 6%, or at 5%; Allantoin 0.05% to 0.3%, at 0.1% to 0.2%, or at 0.16%; Sodium Chloride at 0.05% to 0.5%, 0.1% to 0.4%, 0.2% to 0.3%, or at 0.25%; Methyl Paraben at 0.05% to 0.15%, or at 0.1%; Propyl Paraben at 0.01 to 0.1%, 0.02 to 0.08%; 0.03% to 0.06%, or 0.05%; 10% NaOH to adjust the pH; Water to 100%; Soybean Oil at 5% to 15%, 7% to 12%, or at 10%; Hydrogenated Cottonseed Oil 5% to 15%, 7% to 12%, or at 10%; Polyglyceryl-10 decaoleate at 1% to 6%, 2% to 5%, 3% to 5%, or at 4%; Polyglyceryl-6-octastearate at 1% to 3%, 1.5% to 2.5%, or at 2%; Jojoba Seed Oil 1% to 5%, 1.5% to 4%, 2% to 3%, or at 2.5%; Shea Butter at 0.5% to 4%, 1% to 3%, 1.25% to 2%, or at 1.5%; and Olive Oil at 5% to 15%, 7% to 12%, or at 10%.

Additional examples of compositions for use in the post-perturbation treatments follow:

A composition comprising menthol at 0.1% to 0.5%, 0.1% to 0.3%, 0.15% to 0.25%, at about 0.2%, or at 0.206%; Citric Acid at 6% to 10%, 7% to 9%; or at 8%; CMC at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Allantoin at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

A composition comprising Menthol at 0.1% to 0.5%, 0.1% to 0.3%, 0.15% to 0.25%, at about 0.2%, or at 0.206%; Citric Acid at 6% to 10%, 7% to 9%; or at 8%; Sodium Hyaluronate at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Allantoin at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

A composition comprising menthol at 0.1% to 0.5%, 0.1% to 0.3%, 0.15% to 0.25%, at about 0.2%, or at 0.206%; Citric Acid at 6% to 10%, 7% to 9%; or at 8%; Collagen at 1% to 3%, 1.5% to 2.5%, or at 2%; Methyl Paraben at 0.05% to 0.15%, or at 0.1%; Propyl Paraben at 0.01 to 0.1%, 0.02 to 0.08%; 0.03% to 0.06%, or 0.05%; distilled Water to 100%; 10% NaOH to adjust pH; Aloe Vera Gel at 0.05% to 0.3%, at 0.1% to 0.2%, or at 0.16%; Alginate at 0.05% to 0.2%, 0.08% to 0.14%, or at 0.12%; and Glycerin at 5% to 15%, 7% to 12%, or at 10%.

An emollient cream which is comprised of a Phase I and a Phase II, wherein Phase I comprises Menthol at 0.1% to 1%, 0.2% to 0.8%, 0.3% to 0.6%, 0.35% to 0.5% or at 0.4%; Citric Acid at 10% to 20%, 12% to 18%, 14% to 16%, 15% to 17%, or at 16%; Hyaluronic Acid at 1% to 3%, 1.5% to 2.5%, or at 2%; Glycerin at 5% to 15%, 7% to 12%, or at 10%; Allantoin at 0.1% to 1%, 0.2% to 0.8%, 0.3% to 0.6%, 0.35% to 0.5%, at 0.4%, or at 0.32%; Sodium Chloride at 0.1% to 1%, 0.3% to 0.7%, or at 0.5%; Methyl Paraben at 0.1% to 0.3%, 0.15% to 0.25%, or at 0.2%, Propyl Paraben at 0.05 to 0.15%, 0.075 to 0.125% or at 0.1% or at 0.096%; 10% NaOH to adjust the pH; and Water to 100%; and wherein Phase II comprises Soybean Oil at 10% to 30%, 15% to 25%, 18% to 22% or at 20%; Hydrogenated Cottonseed Oil at 5% to 15%, 7.5% to 12.5%, at 9% to 11%, or at 10%; Polyglyceryl-10 decaoleate at 4% to 12%, 6% to 10%, 7% to 9% or at 8%; Polyglyceryl-6-octastearate at 1% to 7%, 2% to 6%, 3% to 5%, or at 4%; Jojoba Seed Oil at 2% to 8%, 3% to 7%, 4% to 6%, or at 5%; Shea Butter at 0.5% to 8%, 1% to 6%, 2% to 4%, 2.5% to 3.5% or at 3%; Olive Oil at 5% to 15%, 7% to 12%, or at 10%. In certain embodiments, the emollient cream further comprises Menthol at 0.1% to 0.5%, 0.1% to 0.3%, 0.15% to 0.25%, at about 0.2%; Citric Acid at 6% to 10%, 7% to 9%; or at 8%; Hyaluronic Acid at 0.25% to 2.5%, 0.5% to 2%, 0.75% to 1.5%, or at 1%, Glycerin at 1% to 9%, 2% to 8%, 3% to 8%, 4% to 6%, or at 5%; Allantoin 0.05% to 0.3%, at 0.1% to 0.2%, or at 0.16%; Sodium Chloride at 0.05% to 0.5%, 0.1% to 0.4%, 0.2% to 0.3%, or at 0.25%; Methyl Paraben at 0.05% to 0.15%, or at 0.1%; Propyl Paraben at 0.01 to 0.1%, 0.02 to 0.08%; 0.03% to 0.06%, or 0.05%; 10% NaOH to adjust the pH; Water to 100%; Soybean Oil at 5% to 15%, 7% to 12%, or at 10%; Hydrogenated Cottonseed Oil 5% to 15%, 7% to 12%, or at 10%; Polyglyceryl-10 decaoleate at 1% to 6%, 2% to 5%, 3% to 5%, or at 4%; Polyglyceryl-6-octastearate at 1% to 3%, 1.5% to 2.5%, or at 2%; Jojoba Seed Oil 1% to 5%, 1.5% to 4%, 2% to 3%, or at 2.5%; Shea Butter at 0.5% to 4%, 1% to 3%, 1.25% to 2%, or at 1.5%; and Olive Oil at 5% to 15%, 7% to 12%, or at 10%.

5.2.1 Hydrogels

In one embodiment, the post-perturbation pharmaceutical composition is formulated as an aqueous hydrogel. In one embodiment, the aqueous hydrogel comprises Carbopol 980, methyl paraben, propyl paraben, propylene glycol, glycerine, and water. In one embodiment, a hydrogel formulation comprises citric acid, CMC, methyl paraben, propyl paraben, allantoin, alginate, and water. Exemplary formulations prepared in accordance with such embodiments are provided in the Examples below. In one embodiment, a hydrogel has the following composition: glycerol, carboxymethyl cellulose, allantoin, sodium alginate, methyl paraben, propyl paraben, water (Q.S.), and sodium hydroxide (pH adjusted to 6.5-7.5). Methods for formulating hydrogels are described in detail in the Examples below. These methods may be adapted to generate other hydrogel formulations using methods known in the art and described herein.

In certain embodiments, a hydrogel contains approximately 75%, 80%, 85%, 90%, or 95% water. In a particular embodiment, the hydrogel contains 90% water. Preferably, the hydrogel has one or more or all of the following characteristics: is transparent, odorless, colorless, has a viscosity (at 25° C.) of, e.g., 2,000-10,000 cP, 2,000-8,000 cP, or 6,000-10,000 cP (measured using, for example, a rheometer), has assay and dose uniformity (which can be measured by, e.g., flame photometry or atomic adsorption spectrometry (AAS)), has an emollient "smooth-feel" texture, could be easily applied to skin, readily spreads over a surface, has minimal migration to surrounding sites, has minimal run off, has a neutral pH (e.g., pH 6.5-7.5), is sterile, is stable for an extended period (e.g., 1 week or more, 2 weeks or more, 4 weeks or more, 8 weeks or more, 12 weeks or more, 4 months or more, 6 months or more, 1 year or more, or 2 years or more) at one or more temperature conditions (e.g., 4° C., 25° C. and 40° C.) with respect to, for example, strength, viscosity, and homogeneity. In one embodiment, the hydrogel is stable at room temperature for up to 4 weeks or more. In one embodiment, the hydrogel is stable at room temperature for up to 8 weeks or more. In one embodiment, the hydrogel is stable at 4° C. for up to 6 months or more. In one embodiment, the hydrogel is stable at 4° C. for up to 1 year or more. In certain embodiments, a hydrogel is prepared with the excipients and an amount of active ingredient chosen to contribute to one or more of the foregoing or following attributes, which may be desirable for a topical formulation for use in the methods described herein: viscosity (e.g., imparted by carboxymethyl cellulose), surface wetting ability and prevention of "dry-out" (e.g., imparted by glycerol), preservative effectiveness (e.g., imparted by parabens, such as methyl or propyl parabens, although in certain embodiments, a paraben-free formulation may also be generated), maintenance of pH, stability (e.g., imparted by altering the strength of surfactants used in the hydrogel) and pharmacokinetic properties (such as rate of release of active ingredient from the formulation, and peak and trough concentrations of active ingredient in skin and blood). In embodiments where the formulation is for administration to skin that is wounded or that may be wounded, excipients that are wound compatible, contribute to sterility, wound healing, and/or aid in cell attachment and/or proliferation may be included, such as, e.g., allantoin or sodium alginate.

In some embodiments, the hydrogel is formulated so that it releases active ingredients, where present, at varying rates. Release rate may be modified by one or more of the following: incorporating the formulation into different scaffolds, such as described in Section 5.5.5 infra, modifying the concentration of components, including any active ingredients, of the formulation, or modifying the types and concentrations of excipients. In some embodiments, most or all of the active ingredient is released from the formulation within 2 hours, within 4 hours, within 8 hours, within 10 hours, within 12 hours, within 16 hours, within 24 hours, within 36 hours, within 48 hours, within 3 days, within 5 days, within 7 days, within 10 days, within 14 days, within 30 days, or within 2 months or more. In a specific embodiment, most or all of any active ingredient is released from a hydrogel described herein within 12 hours. In one embodiment, all of the active ingredient is released from the hydrogel within 12 hours. In another embodiment, most or all of the active ingredient is released from a hydrogel described herein within 24 hours. In one embodiment, the formulation is an "immediate release" formulation, i.e., releases 90-100% of active ingredient within the first day of administration. In another embodiment, the formulation is an "Intermediate Release" formulation, i.e., releases 90-100% of active ingredient within 1 to 3 days of administration. In another embodiment, the formulation is a "Sustained Release" formulation, i.e., releases 90-100% of active ingredient within 3 to 7 days of administration.

5.2.2 Creams

In another particular embodiment, the post-perturbation composition formulated for topical administration is in the form of an emulsion, e.g., a cream. In one embodiment, the cream is an oil/water emulsion.

In certain embodiments, a cream contains approximately 75%, 80%, 85%, 90%, or 95% water. In certain embodiments, the cream (e.g., dispersion, suspension, colloid or emulsion) has one or more or all of the following characteristics: is odorless, colorless upon application to the skin, has a viscosity (at 25° C.) of, e.g., 2,000-10,000 cP, 2,000-8,000 cP, or 6,000-10,000 cP (measured using, for example, a rheometer), has assay and dose uniformity (which can be measured by, e.g., flame photometry or atomic adsorption spectrometry (AAS)), has an emollient "smooth-feel" texture, could be easily applied to skin, readily spreads over a surface, has minimal migration to surrounding sites, has minimal run off, has a neutral pH (e.g., pH 6.5-7.5), is sterile, is stable for an extended period (e.g., 1 week or more, 2 weeks or more, 4 weeks or more, 8 weeks or more, 12 weeks or more, 4 months or more, 6 months or more, 1 year or more, or 2 years or more) at one or more temperature conditions (e.g., 4° C., 25° C. and 40° C.) with respect to, for example, strength, viscosity, and homogeneity. In one embodiment, the cream is stable at room temperature for up to 4 weeks or more. In one embodiment, the cream is stable at room temperature for up to 8 weeks or more. In one embodiment, the cream is stable at 4° C. for up to 6 months or more. In one embodiment, the cream is stable at 4° C. for up to 1 year or more. In certain embodiments, a cream is prepared with the excipients and an amount of active ingredient chosen to contribute to one or more of the foregoing or following attributes, which may be desirable for a topical formulation for use in the methods described herein: viscosity, surface wetting ability and prevention of "dry-out," preservative effectiveness, maintenance of pH, stability (e.g., imparted by altering the strength of surfactants used in the cream), and pharmacokinetic properties (such as rate of release of any active ingredients from the formulation, and peak and trough concentrations in skin and blood). In embodiments where the formulation is for administration to skin that is wounded or that may be wounded, excipients that are wound compatible, contribute to wound healing, and/or aid in cell attachment and/or proliferation may be included, such as, e.g., allantoin or sodium alginate.

The rate of release of active ingredients, where present, from the cream may be modified by one or more of the following: incorporating the formulation into different scaffolds, such as described in Section 5.5.5 infra, modifying the concentration of active ingredients in the formulation, or modifying the types and concentrations of excipients. For example, in one embodiment, the rate of release of active ingredients from the cream may be decreased by decreasing the concentration of hydrophilic polymers in the cream. In some embodiments, the rate of release of active ingredients from the cream may be altered by varying the concentration of cetearyl alcohol, lanolin alcohol, or by varying the types of aqueous or non-aqueous carrier(s), and preferably non-aqueous carrier(s) (e.g., silicone, mineral oil, petrolatum, etc.), used.

In some embodiments, most or all of the active ingredient is released from the formulation within 2 hours, within 4 hours, within 8 hours, within 10 hours, within 12 hours, within 16 hours, within 24 hours, within 36 hours, within 48 hours, within 3 days, within 5 days, within 7 days, within 10 days, within 14 days, within 30 days, or within 2 months or more. In a specific embodiment, most or all of the active ingredient is released from a cream described herein within 10 hours. In one embodiment, all of the active ingredient is released from the cream within 10 hours. In another embodiment, most or all of the active ingredient is released from a cream described herein within 24 hours. In one embodiment, the formulation is an "immediate release" formulation, i.e., releases 90-100% of active ingredient within the first day of administration. In another embodiment, the formulation is an "Intermediate Release" formulation, i.e., releases 90-100% of active ingredient within 1 to 3 days of administration. In another embodiment, the formulation is a "Sustained Release" formulation, i.e., releases 90-100% of active ingredient within 3 to 7 days of administration.

In a specific embodiment, the cream is an immediate release formulation. Such a formulation may be generated using a two-phase system: (i) an aqueous phase for dissolving any active ingredients and hydrophilic excipients and (ii) a non-aqueous phase for dissolving hydrophobic polymers. In an exemplary embodiment, the cream is a water-in-oil emulsion, which acts not only act as a biocompatible skin emollient, but also as a delivery system for any active ingredients.

In another embodiment, the cream is an intermediate release formulation. In one embodiment, the intermediate release cream formulation is an emulsion prepared by homogenization of two phases, as described, e.g., for the immediate release cream formulation above.

In another embodiment, the cream is a sustained release formulation. In one embodiment, the sustained release cream formulation is prepared by homogenization of two phases (an aqueous phase and a non-aqueous phase), as described, e.g., for the immediate and intermediate release cream formulations above, but by decreasing the concentration of hydrophilic polymers in the non-aqueous phase.

The foregoing formulations for post-perturbation topical administration may be administered in accordance with any embodiments described herein. For example, in specific embodiments, a 50 kg patient is administered a single droplet of a hydrogel described herein at 3 sites, twice daily. In some embodiments, the hydrogel is administered once daily. In some embodiments, the hydrogel is administered twice daily. In some embodiments of a twice daily treatment regimen, doses are administered 6 hours apart, or 7 hours apart, or 8 hours apart, or 9 hours apart, or 10 hours apart, or 11 hours apart, or 12 hours apart. In a particular embodiment, the doses are administered 7 to 8 hours apart.

5.3 Hair Growth-Promoting Agents

Most drugs for hair loss aim to retain the existing hair follicles in their active cycling states, or to rejuvenate telogen hair follicles to actively cycling anagen states. Other drugs encourage the conversion of vellus hair to terminal hair. In contrast, an integumental perturbation treatment (that may encourage the growth of "new" hair follicles or activation of existing follicles) combined with a drug treatment that may retain hair follicles in their actively cycling states, offers significant value to the individual who is balding. Such treatments may be more effective, efficient, cost-effective, and user friendly. For example, fewer treatments may be required. The hair that results may be more cosmetically satisfactory, longer lasting, thicker, more uniform, longer, and properly pigmented hair. Such characteristics are associated with terminal hair rather than vellus hair.

The integumental perturbation methods described in Section 5.1 supra, alone or in combination with a post-perturbation treatment described in Section 5.2 supra, may be used in combination treatments with hair growth-promoting agents, and optionally in combination with the treatments described in Section 5.4 below. In some embodiments, a hair growth-promoting agent described herein promotes hair follicle development and growth, resulting in the transition of vellus hair on an area of the skin to nonvellus, e.g., intermediate or terminal, hair. In some embodiments, a hair growth-promoting agent described herein acts synergistically with the integumental perturbation method to promote hair growth. The effect that each treatment offers could be an additive or synergistic improvement, or a combination of two different biologically defined effects, to achieve the desired end result.

In some embodiments, the hair growth-promoting agent is a treatment that promotes hair growth and/or treats a disease or condition associated with excessive hair loss. Any treatment that promotes hair growth and/or treats a disease or condition associated with excessive hair loss that is known in the art or yet to be developed is contemplated for use in accordance with these embodiments.

In some embodiments, the hair growth-promoting agent treatment comprises treatment with one or more channel openers (e.g., potassium channel opener, e.g., an ATP-sensitive potassium channel (KATP opener), or an activator of such a channel), such as, e.g., minoxidil (e.g., marketed as Rogaine™ or Regaine™), diazoxide, or phenytoin. In a particular embodiment, the hair growth-promoting agent treatment comprises treatment with minoxidil. Commonly used dosage forms of minoxidil that may be used in accordance with these embodiments are topical solutions comprising 2% minoxidil or 5% minoxidil, for example, topical minoxidil foam 5%.

In some embodiments, the hair growth-promoting agent treatment comprises treatment with one or more 5α-reductase inhibitors. Non-limiting examples of 5α-reductase inhibitors include finasteride, dutasteride (e.g., Avodart™), turosteride, bexlosteride, izonsteride, epristeride, epigallocatechin, MK-386, azelaic acid, FCE 28260, and SKF 105,111. Commonly used dosage forms of finasteride that may be used in such treatments are, for example, oral finasteride at 1 mg/day. See, e.g., *Physicians' Desk Reference*, 2009, 63rd ed., Montvale, N.J.: Physicians' Desk Reference Inc., entries for Propecia® and Proscar® at pages 2095-2099 and 2102-2106, respectively, which are incorporated herein by reference in their entireties.

In some embodiments, the hair growth-promoting agent treatment comprises treatment with one or more antiandrogens, such as, e.g., finasteride (e.g., marketed as Propecia™ or Proscar™), ketoconazole, fluconazole, spironolactone, flutamide, diazoxide, 17-alpha-hydroxyprogesterone, 11-alpha-hydroxyprogesterone, ketoconazole, RU58841, dutasteride (marketed as Avodart™), fluridil, or QLT-7704, an antiandrogen oligonucleotide, or others described in Poulos & Mirmirani, 2005, Expert Opin. Investig. Drugs 14:177-184, the contents of which is incorporated herein by reference.

In some embodiments, the hair growth-promoting agent treatment comprises treatment with one or more prostaglandin F2α analogs, prostaglandin analogs, or prostaglandins. Non-limiting examples of prostaglandin F2α analogs include bimatoprost (e.g., Latisse™, Lumigan™), latanoprost (trade name Xalatan™), travoprost (trade name Travatan™), tafluprost, unoprostone, dinoprost (trade name Prostin F2 Alpha™), AS604872, BOL303259X, PF3187207, carboprost (trade name Hemabate™). For exemplary prostaglandin F2α analogs, as well as formulations, dosages, and treatment regimens, for use in accordance with the methods described herein, see, e.g., U.S. Pat. Nos. 8,017,655, 5,688,819, 6,403,649, 5,510,383, 5,631,287, 5,849,792, 5,889,052, 6,011,062, 7,163,959, 5,296,504, 5,422,368, 6,429,226, and 6,946,120, the entire contents of each of which is incorporated herein by reference in its entirety. See also, with respect to latanoprost, Uno et al., 2002, *Acta Derm Venereol* 82:7-12, the contents of which is incorporated herein by reference in its entirety.

In some embodiments, the hair growth-promoting agent treatment comprises treatment with one or more of the following hair growth-promoting agents: kopexil (for example, the product Keranique™), $CaCl_2$, botilinum toxin A, adenosine, ketoconazole, DoxoRx, docetaxel, FK506, GP11046, GP11511, LGD 1331, ICX-TRC, MTS-01, NEOSH101, HYG-102440, HYG-410, HYG-420, HYG-430, HYG-440, spironolactone, CB-03-01, RK-023, abatacept, Viviscal®, MorrF, ASC-J9, NP-619, AS101, Metron-F-1, PSK 3841, Targretin™ (bexrotene, e.g., 1% gel), MedinGel, PF3187207, BOL303259X, AS604872, THG11331, PF-277343, PF-3004459, Raptiva™ (efalizumab), caffeine, an coffee. In some embodiments, the hair growth-promoting agent treatment comprises drugs for alopecia being developed by SWITCH Biotech LLC.

In some embodiments, the hair growth-promoting agent treatment comprises treatment with one or more of the following: herbs (such as, e.g., saw palmetto, glycine soja, Panax ginseng, Castanea Sativa, Arnica Montana, Hedera Helix Geranium Maculatum), triamcinolone acetonide (e.g., suspension of 2.5 to 5 mg/ml for injection), a topical irritant (e.g., anthralin) or sensitizer (e.g., squaric acid dibutyl ester [SADBE] or diphenyl cyclopropenone [DPCP]), clomipramine, unsaturated fatty acids (e.g., gamma linolenic acid), a fatty acid derivative, thickeners (such as, e.g., carbomer, glycol distearate, cetearyl alcohol), a hair loss concealer, niacin, nicotinate esters and salts, adenosine, and methionine. In some embodiments, the hair growth-promoting agent treatment comprises treatment with nitroxide spin labels (e.g., TEMPO and TEMPOL). See U.S. Pat. No. 5,714,482, which is incorporated herein by reference.

In some embodiments, the hair growth-promoting agent treatment comprises treatment with an androgen receptor inhibitor, which have been shown to be useful for stimulating scalp hair growth (Hu L Y, et al., 2007, Bioorg Med Chem Lett. 2007 17:5983-5988).

In some embodiments, the hair growth-promoting agent treatment comprises treatment with a copper peptide(s), preferably applied topically, or another compound with superoxide dismutation activity. In some embodiments, the hair growth-promoting agent treatment comprises treatment with an agent that increases nitric oxide production (e.g., arginine, citrulline, nitroglycerin, amyl nitrite, or sildenafil (Viagra)). In preferred embodiments, such compounds are administered further in combination with a catalase or catalase mimetic, or other antioxidant or free radical scavenger.

In some embodiments, the hair growth-promoting agent treatment comprises treatment with a compound that mobilizes bone marrow-derived stem cells (e.g., growth factors such as G-CSF and/or chemical agents such as plerixafor (Mozobil®)); and/or that regulates the differentiation of these stem cells into gender-specific specialized human hair follicles (e.g., using agents such as finasteride, fluconazole, spironolactone, flutamide, diazoxide, 11-alpha-hydroxyprogesterone, ketoconazole, RU58841, dutasteride, fluridil, or QLT-7704, an antiandrogen oligonucleotide, cyoctol, topical progesterone, topical estrogen, cyproterone acetate, ru58841, combination 5α-reductase inhibitors, oral contraceptive pills, and others in Poulos & Mirmirani, 2005, Expert Opin. Investig. Drugs 14:177-184, incorporated herein by reference, or any other antiestrogen, an estrogen, or estrogen-like drug (alone or in combination with agents that increase stem cell plasticity; e.g., such as valproate), etc., known in the art), that can result in, e.g., the appearance of specialized follicles having features that are different from natural follicles in the target location of skin.

In some embodiments, the hair growth-promoting agent treatment comprises treatment with one or more agents that counteract age-related hair thinning and/or hair follicle cell senescence (also referred to herein as "anti-senescence agents") for example, anti-oxidants such as glutathione, ascorbic acid, tocopherol, uric acid, or polyphenol antioxidants); inhibitors of reactive oxygen species (ROS) generation, such as superoxide dismutase inhibitors; stimulators of ROS breakdown, such as selenium; mTOR inhibitors, such as rapamycin; or sirtuins or activators thereof, such as resveratrol, or other SIRT1, SIRT3 activators, or nicotinamide inhibitors.

In some embodiments, the hair growth-promoting agent treatment comprises treatment with one or more agents that induce an immune response or cause inflammation, such as, e.g., tetanus toxoid, topical non-specific irritants (anthralin), or sensitizers (squaric acid dibutyl ester [SADBE] and diphenyl cyclopropenone [DPCP]). While not intending to be bound by any theory, it is thought that by contacting these agents to the skin, lymphocytes and hair follicle stem cells may be recruited to skin. In some embodiments, the hair growth-promoting agent treatment comprises treatment with a chemical or mechanical (such as those discussed infra) treatment that induces an inflammatory process in the skin. While not intending to be bound by any theory, inducing inflammation in the site where hair growth is desired helps to recruit stem cells to the tissues that drive the formation of new follicles.

In some embodiments, the hair growth-promoting agent treatment comprises treatment with an antiapoptotic compound. In one embodiment, the antiapoptotic compound is not a Wnt or a Wnt agonist.

In some embodiments, the hair growth-promoting agent treatment comprises treatment with stem cell therapy, hair cloning, hair transplantation, scalp massage, a skin graft, hair plugs, follicular unit extraction, or any surgical procedure aimed at hair restoration.

In certain embodiments, a hair growth-promoting agent described herein may be used at a dosage or in a range of dosages known in the art for that agent (e.g., as made available on a package insert or in the *Physicians' Desk Reference*). In other embodiments the regular dosage of the hair growth-promoting agent is adjusted to optimize a combination treatment (e.g., integumental perturbation or treatment with another active ingredient) described herein. For example, the regular dosage may be increased or decreased as directed by the physician. For example, a lower dosage may be used over a shorter duration owing to the synergistic effect of combination with another treatment described herein.

In certain embodiments, the hair growth-promoting agent may be used in its commercially available form. In other embodiments, the form of the hair growth-promoting agent is adjusted to optimize a combination treatment (e.g., integumental perturbation or treatment with another active ingredient) described herein. In a particular embodiment, the hair growth-promoting agent is formulated as a different salt form than that which is commercially available. In a particular embodiment, the hair growth-promoting agent is formulated for topical administration, e.g., by incorporation into a pharmaceutical composition for post-perturbation treatment described in Section 5.2 infra.

In some embodiments, the hair growth-promoting agent enhances conversion of vellus hair to nonvellus hair. In a particular embodiment, the hair growth-promoting agent enhances conversion of vellus hair to terminal hair. Exemplary hair growth-promoting agents that promote conversion of vellus to nonvellus hair that may be used in accordance with these embodiments are prostaglandin F2α analogs (in one aspect, latanoprost), minoxidil, etc. In some embodiments, the hair growth-promoting agent enhances conversion of telogen hair to anagen hair. In a particular embodiment, the hair growth-promoting agent enhances conversion of telogen hair to anagen hair. Exemplary hair growth-promoting agents that promote conversion of telogen to anagen hair that may be used in accordance with these embodiments are prostaglandin F2α analogs (in one aspect, latanoprost), minoxidil, etc.

In some embodiments, the hair growth-promoting agent treatment comprises treatment with an antiandrogen (e.g., a 5α-reductase inhibitor) and a channel opener (e.g., minoxidil). In one such embodiment, a 5α-reductase inhibitor is administered in combination with minoxidil. In one such embodiment, finasteride is administered in combination with minoxidil. In some embodiments, the hair growth-promoting agent treatment comprises treatment with a prostaglandin F2α or prostamide analog (e.g., latanoprost, bimatoprost, etc.) in combination with a channel opener (e.g., minoxidil). In one such embodiment, a prostaglandin F2α or prostamide analog is administered in combination with minoxidil. In one such embodiment, latanoprost is administered in combination with minoxidil. In another such embodiment, bimatoprost is administered in combination with minoxidil.

In some embodiments, a treatment described herein for promoting hair growth in a female subject does not comprise finasteride or ketoconazole. In some embodiments, a treatment described herein for promoting hair growth in a pregnant female subject is not finasteride or ketoconazole.

In some embodiments a treatment described herein for promoting hair growth does not comprise minoxidil. In some embodiments a treatment described herein for promoting hair growth does not comprise finasteride. In some embodiments a treatment described herein for promoting hair growth does not comprise dutasteride. In some embodiments a treatment described herein for promoting hair growth does not comprise fluridil. In some embodiments a treatment described herein for promoting hair growth does not comprise spironolactone. In some embodiments a treatment described herein for promoting hair growth does not comprise cyproterone acetate. In some embodiments a treatment described herein for promoting hair growth does not comprise bicalutamide. In some embodiments a treatment described herein for promoting hair growth does not comprise flutamide. In some embodiments a treatment described herein for promoting hair growth does not comprise nilutamide. In some embodiments a treatment described herein for promoting hair growth does not comprise an inhibitor of an androgen receptor. In some embodiments a treatment described herein for promoting hair growth does not comprise an androgen antagonist. In some embodiments a treatment described herein for promoting hair growth does not comprise an anti-androgen.

5.3.1 Hair Growth-Promoting Agent Dosage Forms

In the embodiments described herein, the hair growth-promoting agent or formulation thereof can be administered topically, subcutaneously, intravenously, orally, etc. Regardless of the route of administration used for hair growth-promoting agent delivery, the dosing regimen should be adjusted so that maximum benefit is achieved while reducing potential side effects.

In some embodiments, the target concentration of hair growth-promoting agent should be maintained in the skin or blood, and preferably the skin, for at least 1 day; at least 2 days; at least 3 days; at least 4 days; at least 5 days; at least 6 days; at least 7 days; at least 8 days; at least 9 days; at least 10 days; at least 11 days; at least 12 days; at least 13 days; at least 14 days; at least 15 days; at least 16 days; at least 19 days; or at least 21 days; and, in certain embodiments, not more than 28 days. In certain embodiments, the target concentration of hair growth-promoting agent is maintained in skin or blood, and preferably the skin, for 1 month or more, 2 months or more, 3 months or more, 3 to 6 months or more, or 6 to 12 months or more. This can be accomplished using, e.g., repeated applications of the hair growth-promoting agent or a single application of a sustained release or extended release hair growth-promoting agent formulation. For example, a modified release form can be used to achieve the target concentration of hair growth-promoting agent for shorter maintenance periods (i.e., for at least 1, 2 or 3 days). Maintenance periods longer than 3 days may require repeated application of the hair growth-promoting agent treatments. In some embodiments, it is preferable to allow the concentration of hair growth-promoting agent to decline between dosages.

In some embodiments, topical administration of a hair growth-promoting agent is preferred over oral or subcutaneous administration. Depending on the formulation used, a topically administered hair growth-promoting agent may achieve a higher concentration of hair growth-promoting agent in skin than in the blood, thereby reducing the risk of toxicity that may be associated with elevated blood levels of hair growth-promoting agent. Conversely, and depending on the formulation used, a subcutaneously or orally administered hair growth-promoting agent may be preferred in order to achieve a controlled release of hair growth-promoting agent from the blood to the skin.

Regardless of the route of administration, care should be taken to avoid toxicity. In this regard, a dosage should be chosen that maximizes efficacy while minimizing toxicity. Such a dosage may be chosen using the assays described in Section 5.3. Patients should be monitored for toxic side effects according to standard clinical practice. In some embodiments, hair growth-promoting agent doses should be adjusted on the basis of the blood concentration (serum or plasma) drawn (by convention) 12 or 24 hours after the last dose of the hair growth-promoting agent. It may be possible to predict dosage requirements for an individual patient based on the results of administration of a single test dose, followed by a skin and/or blood sample assay (plasma or serum) at the peak concentration time; followed by blood sample assays to monitor toxicity at the 12 hour or 24 hour trough concentration; and 24 or 48 or 96 hours later (when hair growth-promoting agent is generally eliminated) which serves as the control value. Once the dose is established for a patient, routine monitoring for toxicity is recommended. It may also be possible to predict who will respond better to minoxidil by checking levels of minoxidil sulfotransferase (Buhl et al., J Invest Dermatol. 1990; 95(5):553-557).

In some embodiments, an effective amount of hair growth-promoting agent is administered such that the target concentration of hair growth-promoting agent in plasma or serum, as measured 30 minutes to 1 hour after the hair growth-promoting agent treatment, is less than 0.1 nM, 0.1-1.0 nM, 1.0-10 nM, 10-50 nM, 50-100 nM, 100-500 nM, 0.5-1.0 µM, 1.0 µM-2.0 µM, 2.0-2.5 µM, 2.5-3.0 µM, or 3.0 µM or greater. In some embodiments, an effective amount of hair growth-promoting agent is administered such that the plasma or serum hair growth-promoting agent concentration measured either 8 hours, 16 hours, 1 day, 2 days, 3 days, 1 week, 2 weeks, or 1 month after the hair growth-promoting agent treatment is less than 0.1 nM, 0.1 to 1 nM, 0.5 to 1.5 nM, 1 to 10 nM, 10 to 50 nM, 50 to 100 nM, 100 to 150 nM, 150 to 200 nM, 250 to 300 nM, 100 to 250 nM, 100 to 500 nM, 200 to 400 nM, 500 to 1000 nM; or 1000 to less than 100000 nM. In one embodiment, the plasma or serum hair growth-promoting agent concentration reaches at least 1 nM. In another embodiment, the peak plasma level never reaches greater than 1 µM. Serum hair growth-promoting agent concentration may be measured using methods of liquid chromatography and/or mass spectrometry, which are well known in the art.

In some embodiments, an amount of hair growth-promoting agent is administered such that the target concentration of hair growth-promoting agent in the skin is 0.1 nM to 1 nM, 1 nM to 10 nM, 10-100 nM, 100-500 nM, 500-1000 nM, 1 to 1.5 µM, 1 to 2.5 µM, 1 to 5 µM, 5 to 10 µM, 10 to 50 µM, 50 to 100 µM, 100 to 150 µM, 150 to 200 µM, 250 to 300 µM, 100 to 250 µM, 100 to 500 µM, 200 to 400 µM, 500 to 1000 µM, 1 to 10 mM, 10 to 100 mM, 100 to 200 mM, or 500 to 1000 mM. In some embodiments, the concentration of hair growth-promoting agent achieved in the skin is greater than 0.1 nM. In some embodiments, the concentration of hair growth-promoting agent achieved in the skin is greater than 1 nM. In some embodiments, the concentration of hair growth-promoting agent achieved in the skin is greater than 100 nM. In some embodiments, the concentration of hair growth-promoting agent achieved in the skin is greater than 500 nM. In one embodiment, the concentration of hair growth-promoting agent achieved in the skin is approximately 10-100 nM. In one embodiment, the concentration of hair growth-promoting agent achieved in the skin is approximately 100-1000 nM. In one embodiment, the concentration of hair growth-promoting agent achieved in the skin is approximately 1 µm to 10 µm. In one embodiment, the concentration of hair growth-promoting agent achieved in the skin is approximately 10-100 In other embodiments, an amount of hair growth-promoting agent is administered such that the concentration of hair growth-promoting agent delivered to the skin is 0.0000001 mg/ml to 0.000001 mg/ml, 0.000001 mg/ml to 0.00001 mg/ml, 0.00001 mg/ml to 0.0001 mg/ml, 0.0001 mg/ml to 0.001 mg/ml, 0.001 mg/ml to 0.01 mg/ml, 0.01 mg/ml to 0.1 mg/ml, 0.1 mg/ml to 1 mg/ml, 1 mg/ml to 10 mg/ml. In some embodiments, the concentration of hair growth-promoting agent delivered to the stratum corneum is 0.0000001 mg/ml to 0.000001 mg/ml, 0.000001 mg/ml to 0.00001 mg/ml, 0.00001 mg/ml to 0.0001 mg/ml, 0.0001 mg/ml to 0.001 mg/ml, 0.001 mg/ml to 0.01 mg/ml, 0.01 mg/ml to 0.1 mg/ml, 0.1 mg/ml to 1 mg/ml, 1 mg/ml to 10 mg/ml. One of skill in the art would be able to measure hair growth-promoting agent concentrations in skin using techniques known in the art, for example, mass spectroscopy, e.g., inductively coupled plasma mass spectroscopy (ICP-MS), of the LC/MS/MS assay used herein.

In other embodiments, the hair growth-promoting agent concentration is measured in the hair shaft using techniques known in the art, e.g., Tsanaclis & Wicks, 2007, Forensic Science Intl. 176: 19-22, which is incorporated by reference herein in its entirety.

5.3.1.1 Topical Dosage Forms

In the embodiments described in the subsections that follow, the hair growth-promoting agent can be applied topically, e.g., as a cream, gel, ointment, suspension, or other form for topical administration as described in Section 5.3 supra. The hair growth-promoting agent can be formulated as a pharmaceutical composition for topical administration.

In some embodiments, topical hair growth-promoting agent is administered twice daily. In some embodiments, topical hair growth-promoting agent is administered once daily. In some embodiments, the form of the hair growth-promoting agent for topical administration (e.g., gel, cream, ointment, salve, etc.) comprises, w/w, 0.000001%, 0.00001%, 0.0001% hair growth-promoting agent, 0.001% hair growth-promoting agent, 0.01% hair growth-promoting agent, 0.1% hair growth-promoting agent, 0.5% hair growth-promoting agent, 1% hair growth-promoting agent, and 10% hair growth-promoting agent. In some embodiments, the form of the hair growth-promoting agent for topical administration comprises, w/w, 0.000001% to 0.00001% hair growth-promoting agent, 0.00001% to 0.0001% hair growth-promoting agent, 0.0001% to 0.001% hair growth-promoting agent, 0.001% to 0.01% hair growth-promoting agent, 0.01% to 0.1% hair growth-promoting agent, 0.1% to 1.0% hair growth-promoting agent, 1.0% to 5% hair growth-promoting agent, 5% to 10% hair growth-promoting agent, or 10% to 15% hair growth-promoting agent. In one embodiment, the form of the hair growth-promoting agent for topical administration is 0.00001% to 1.0% w/w hair growth-promoting agent.

In some embodiments, a topical formulation is formulated such that 0.01 mg hair growth-promoting agent per kg of patient weight (mg/kg) is administered, or 0.02 mg/kg, 0.05 mg/kg, 0.1 mg/kg, 0.2 mg/kg, 0.5 mg/kg, 1.0 mg/kg, 2 mg/kg, 5.0 mg/kg, 10 mg/kg, 15 mg/kg, 20 mg/kg, 25 mg/kg, 30 mg/kg, 35 mg/kg, 40 mg/kg, 50 mg/kg, 75 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or 1500 mg/kg is administered. In some embodiments, the topical formulation contains a dose in the range of about 0.01 mg/kg to about 0.1 mg/kg, 0.02 mg/kg to about 0.2 mg/kg, 0.1 mg/kg to about 1 mg/kg, 0.2 mg/kg to about 2 mg/kg, 0.01 mg/kg to about 2 mg/kg, 0.1 mg/kg to about 100 mg/kg, about 1 mg/kg to about 20 mg/kg, about 2 mg/kg to about 10 mg/kg, about 100 mg/kg to about 1 g/kg, about 125 mg/kg to about 500 mg/kg, or about 150 mg/kg to about 300 mg/kg of hair growth-promoting agent. In some embodiments, the topical formulation contains a dose in the range of about 0.01 mg/kg to about 1 mg/kg. In some embodiments, the topical formulation contains a dose in the range of about 0.02 mg/kg to about 2 mg/kg.

The concentration of hair growth-promoting agent in a particular topical formulation to deliver the intended dose of hair growth-promoting agent will depend on the release properties of the hair growth-promoting agent, the hydrophobicity of the hair growth-promoting agent, the partition coefficient of the hair growth-promoting agent, etc. The amount of hair growth-promoting agent to generate a topical formulation with one of the aforementioned concentrations of hair growth-promoting agent is readily deducible by one of ordinary skill in the art, and depends upon several factors including, e.g., its salt form, stability, release properties, its hydrophobicity or hydrophilicity, etc.

5.3.2 Discussion

Most drugs for hair loss aim to retain the existing hair follicles in their active cycling states, or to rejuvenate telogen hair follicles to actively cycling anagen states. Other drugs encourage the conversion of vellus hair to terminal hair. However, a treatment that encourages the growth of new hair follicles and/or growth of vellus hair toward terminal hair (such as integumental perturbation) combined with one that retains the hair follicles in their actively cycling states or promotes conversion of vellus to nonvellus hair, or maintains new terminal hairs or enhances further growth of new terminal hairs, offers significant value to the individual who is balding. The combined modality of treatment could involve alternating treatment of each dosage form or concurrent or simultaneous treatment.

The hair growth-promoting agent treatments described herein potentiate new hair growth. Moreover, integumental perturbation in the affected skin tissue can stimulate, activate, or reorganize pre-existing hair follicles, such that resident hair follicles may be reprogrammed. Accordingly, and without being bound by any theory for how the invention works, integumental perturbation in combination with one or more hair growth-promoting agents provides an environment for hair growth and follicles with desired properties.

New hair follicles originate from Hair Follicle Stem Cells (FSCs), oligopotent cells whose progeny can differentiate into the highly differentiated specialized cells of the hair follicle (see Amoh Y, et al. Human hair follicle pluripotent stem (hfPS) cells promote regeneration of peripheral-nerve injury: an advantageous alternative to ES and iPS cells. J Cell Biochem, 2009, 107:1016-1020; and Amoh Y, et al. Nascent blood vessels in the skin arise from nestin-expressing hair-follicle cells. Proc Natl Acad Sci USA. 2004 Sep. 7; 101(36):13291-5. Epub 2004 Aug. 26).). A dermal stem cell population has been identified for hair follicles in mouse (see Biernaskie J, Paris M, Morozova O, et al. SKPs derive from hair follicle precursors and exhibit properties of adult dermal stem cells. Cell Stem Cell. 2009; 5(6):610-623).

FSCs originate from one or more of the following: (i) existing follicles ("follicle derived follicle stem cells" or "FDFSC") (see, e.g., Toscani et al., 2009, Dermatol Surg. 2009; (ii) the skin ("tissue derived follicle stem cells" or "TDFSC") (see, e.g., Ito M, 2007, Nature 447:316-320); (iii) bone marrow ("bone marrow derived follicle stem cells" or "BMDFSC") (see, e.g., Fathke et al., 2004, Stem Cells 22:812-822; and Rove) et al., 2005, Exp Hematol. 33:909-911); and/or (iv) from mesenchymal stem cells such as adipocyte stem cells.

FSCs generate new hair follicles that preserve the type of hair follicle that is typical for each location of skin or scalp. For example, FSCs from the coronal scalp of a male with MPHL typically generate atrophic follicles with vellus or club hairs. In contrast, FSCs from the occipital scalp of the same male typically generate follicles with terminal hair that are not subject to involution in response to DHT.

However, if external signals are provided that interfere with this "default" program, the FSCs responsible for follicle formation may be reprogrammed. FSCs in the process of asymmetric division and subsequent differentiation are susceptible to signals (such as estrogen or testosterone) that alter their differentiation program. For example, FSCs from the coronal scalp of a male with MPHL, under the influence of estrogen, can generate follicles with terminal hair that are not subject to involution in response to DHT. Such follicles have characteristics usually associated with: (i) pre-alopecia follicles in the coronal scalp; (ii) female-type follicles on the coronal scalp; or (iii) occipital scalp type follicles. Alternatively, by antagonizing estrogen or testosterone, the assumption of the default hair pattern in a particular skin area may be prevented. For example, a female's unwanted moustache hair may be reduced by perturbing the skin of the upper lip and administering a testosterone antagonist.

Thus, treatment with one or more hair growth-promoting agents in combination with integumental perturbation provides a window during which a third treatment that alters the follicle development program may be administered in order to significantly change the number or quality of follicles in a particular area of skin. In some embodiments, the third treatment (e.g., estrogen or testosterone modulator, such as those described in Poulos & Mirmirani, 2005, Expert Opin. Investig. Drugs 14:177-184 (incorporated herein by reference) is administered simultaneously with integumental perturbation. In some embodiments, the third treatment is administered after integumental perturbation. In some embodiments, the third treatment is administered 1 day, 2 days, 3 days, 5 days, 7 days, 10 days, or 2 weeks after integumental perturbation. In one embodiment, the third treatment is administered at the time of integumental perturbation and then daily for 5 days thereafter (in some embodiments, a scab forms during this time). In some embodiments, the third treatment is administered daily for 5 days beginning as soon as the scab falls off. In some embodiments, the third treatment is administered in order to modulate the neoepidermis that forms underneath the scab. In some such embodiments, the third treatment is administered at the time of integumental perturbation and up to some time after scab falls off, for example, between 5-14 days following integumental perturbation. In some embodiments, the course of treatment with the third treatment is short, for example, limited to a few days just following scab detachment, or even continued only for as long as the scab is still attached. The timing of the integumental perturbation, hair growth-promoting agent administration, and the third treatment can be monitored and adjusted so that optimal results are achieved.

5.4 Additional Active Ingredients

In some embodiments, a method of the invention comprising integumental perturbation (Section 5.1) and/or post-perturbation treatment (Section 5.2) and/or administration of a pharmaceutical composition comprising one or more hair growth-promoting agents (Section 5.3) may be combined with one or more additional treatments with an active ingredient. The one or more additional treatments with an active ingredient can be administered before, during, or after one or more of the steps of integumental perturbation, post-perturbation treatment, and/or administration of a hair growth-promoting agent. In certain embodiments, the active ingredient is administered together with, optionally in the same formulation, a post-perturbation pharmaceutical composition. In certain embodiments, the active ingredient is administered together with, optionally in the same formulation, a hair growth-promoting agent.

In accordance with these embodiments, an active ingredient for formulation into a pharmaceutical composition for an additional treatment can be selected from, e.g., cell therapy (such as a stem cell), a formulation for gene therapy (such as, e.g., a virus, virus-like particle, virosome), an antibody or antigen-binding fragment thereof, an herb, a vitamin (e.g., a form of vitamin E, a vitamin A derivative, such as, e.g., all-trans retinoic acid (ATRA), a B vitamin, such as, e.g., inositol, panthenol, or biotin, or a vitamin D3 analog), a mineral, essential oils, an antioxidant or free radical scavenger, amino acids or amino acid derivatives, a shampoo ingredient (e.g., caffeine, ammonium chloride, ammonium lauryl sulfate, glycol, sodium laureth sulfate, sodium lauryl sulfate, ketoconazole, zinc pyrithione, selenium sulfide, coal tar, a salicylate derivative, dimethicone, or plant extracts or oils), a conditioning agent, a soap product, a moisturizer, a sunscreen, a waterproofing agent, a powder, talc, or silica, an oil-control agent, alpha-hydroxy acids, beta-hydroxy acids (e.g., salicylic acid), poly-hydroxy acids, benzoyl peroxide, antiperspirant ingredients, such as astringent salts (e.g., zinc salts, such as zinc pyrithione, inorganic or organic salts of aluminum, zirconium, zinc, and mixtures thereof, aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY (abbreviation for glycine), aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY, potassium aluminum sulphate, (also known as alum ($KAl(SO_4)_2 12H_2O$)), aluminum undecylenoyl collagen amino acid, sodium aluminum lactate+ aluminum sulphate ($Na_2HAl(OOCCHOHCH_3)_2$—$(OH)_6)+Al_2(SO_4)_3$), sodium aluminum chlorohydroxylactate, aluminum bromohydrate ($Al_2Br(OH)_5 nH_2O$), aluminum chloride ($AlCl_3 6H_2O$), complexes of zinc salt and of sodium salt, complexes of lanthanum and cerium, and the aluminum salt of lipoamino acids (R—CO—NH—CHR'—CO—OAl—$(OH)_2$ with R=$C_{6-11}$ and R'=amino acid), retinoids (e.g., retinoic acid, retinol, retinal, or retinyl esters), sunscreens (e.g., derivatives of para-aminobenzoic acid (PABA), cinnamate and salicylate, avobenzophenone (Parsol 1789®), octyl methoxycinnamate (Parsol™ MCX) and 2-hydroxy-4-methoxy benzophenone (also known as oxybenzone and available as Benzophenone™, and preservatives), an anti-age agent, a sebum production inhibitor and/or pore size reducing agent (e.g., carboxyalkylates of branched alcohols and/or alkoxylates thereof, e.g., tridecyl carboxy alkylates, cerulenin or a cerulenin analog, including pharmaceutically acceptable salts or solvates thereof, another fatty acid synthase inhibitor, such as triclosan or analogs thereof, a polyphenol extracted from green tea (EGCG), available from Sigma Corporation (St. Louis, Mo.), or α-methylene-γ-butyrolactone), a massage agent, an exfoliant, an anti-itch agent, a pro-inflammatory agent, an immunostimulant (e.g., cytokines, agonists or antagonists of various ligands, receptors and signal transduction molecules of the immune system, immunostimulatory nucleic acids, an adjuvant that stimulates the immune response and/or which causes a depot effect), a cell cycle regulator, a hormonal agonist, hormonal antagonist (e.g., flutamide, bicalutamide, tamoxifen, raloxifene, leuprolide acetate (LUPRON), LH-RH antagonists), an inhibitor of hormone biosynthesis and processing, a steroid (e.g., dexamethasone, retinoids, deltoids, betamethasone, cortisol, cortisone, prednisone, dehydrotestosterone, glucocorticoids, mineralocorticoids, estrogen, testosterone, progestins), antigestagens (e.g., mifepristone, onapristone), an antiandrogen (e.g., cyproterone acetate), an antiestrogen, an antihistamine (e.g., mepyramine, diphenhydramine, and antazoline), an anti-inflammatory (e.g., corticosteroids, NTHEs, and COX-2 inhibitors), a retinoid (e.g., 13-cis-retinoic acid, adapalene, all-trans-retinoic acid, and etretinate), an immunosuppressant (e.g., cyclosporine, tacrolimus, rapamycin, everolimus, and pimecrolimus), an antibiotic, an anti-cancer agent (such as, e.g., fluorouracil (5-FU or f5U) or other pyrimidine analogs, methotrexate, cyclophosphamide, vincristine), a mood stabilizer (e.g., valproic acid or carbamazepine) an antimetabolite, an anti-viral agent, and an antimicrobial (e.g., benzyl benzoate, benzalkonium chloride, benzoic acid, benzyl alcohol, butylparaben, ethylparaben, methylparaben, propylparaben, camphorated metacresol, camphorated phenol, hexylresorcinol, methylbenzethonium chloride, cetrimide, chlorhexidine, chlorobutanol, chlorocresol, cresol, glycerin, imidurea, phenol, phenoxyethanol, phenylethylalcohol, phenylmercuric acetate, phenylmercuric borate, phenylmercuric nitrate, potassium sorbate, sodium benzoate, sodium proprionate, sorbic acid, and thiomersal (thimerosal)).

In one embodiment, the drug of choice is minoxidil, minoxidil sulfate, or another salt form such as chloride, carbonate, nitrate, etc. In another embodiment, the drug of choice is a prostaglandin, or a prostaglandin analogue, a prostaglandin prodrug. In another embodiment, the drug is a 5 alpha reductase inhibitor.

In some embodiments, the drug will be formulated such it is targeted to a specific ligand present in the hair follicle. In another example, the drug will be formulated into positively charged nanospheres, that will reside within the hair follicle as drug-containing depots.

In some embodiments, the additional treatment comprises one or more antimicrobial agents or preservatives including, but not limited to, alkyl esters of p-hydroxybenzoic acid, hydantoins derivatives, propionate salts, phenols, cresols, mercurials, phenyoxyethanol, benzyl alcohol, chlorobutanol, methyl and propyl p-hydroxybenzoates, thimerosal, benzalkonium chloride (e.g., benzethonium chloride), butyl, methyl- and propyl-parabens, sorbic acid, and any of a variety of quarternary ammonium compounds.

Suitable antioxidants include ascorbate, bisulfite and sodium metabisulfite.

In some embodiments, the additional treatment comprises one or more anesthetic compounds. Anesthetic compounds can be administered topically, by injection directly to the site of the disruption, or systemically. Examples of anesthetic compounds for use in the methods and compositions described herein include lidocaine, prilocaine, bupivicaine, levobupivacaine, ropivacaine, mepivacaine, dibucaine, isoflurane, desflurane, sevoflurane, and nitrous oxide. Suitable local anesthetics include, but are not limited to, procaine hydrochloride, lidocaine and salts thereof, benzocaine and salts thereof and novacaine and salts thereof.

In some embodiments, the additional treatment comprises one or more pain relievers, e.g., non-steroidal anti-inflammatory drugs or acetaminophen. In some embodiments, the additional treatment comprises one or more narcotic analgesics, selected from the group of, e.g., alfentanil, benzylmorphine, codeine, codeine methyl bromide; codeine phosphate, codeine sulfate, desomorphine, dihydrocodeine, dihydrocodeinone enol acetate, dihydromorphine, ethylmorphine, hydrocodone, hydromorphone, methadone hydrochloride, morphine, morphine hydrochloride, morphine sulfate, nicomorphine, normethadone, normorphine, opium, oxycodone, oxymorphone, phenoperidine, and propiram. In some embodiments, the additional treatment comprises one or more non-narcotic analgesics, selected from the group of, e.g., aceclofenac, acetaminophen, acetanilide, acetyl salicyl salicylic acid; aspirin, carbamazepine, dihydroxyaluminum acetylsalicylate, fenoprofen, fluproquazone, ibufenac, indomethacin, ketorolac, magnesium acetylsalicylate, morpholine salicylate, naproxen, phenacetin, phenyl salicylate, salacetamide, salicin, salicylamide, sodium salicylate, and tolfenamic acid. Other pain treatments that may be used include nerve blocks or non-traditional pain medications, such as, e.g., Lyrica (pregabalin) or Neurontin (gabapentin).

Soothing preparations, e.g., for topical administration, may contain sodium bicarbonate (baking soda), and coal tar based products. Formulations may also optionally contain a sunscreen or other skin protectant, or a waterproofing agent.

5.5 Pharmaceutical Formulations and Modes of Administration 5.5.1 Formulations The pharmaceutical compositions described in Sections 5.2, 5.3, and 5.4 supra may be formulated with a pharmaceutically acceptable carrier (also referred to as a pharmaceutically acceptable excipients), i.e., a pharmaceutically-acceptable material, composition, or vehicle, such as a liquid or solid filler, diluent, solvent, an encapsulating material, or a complexation agent. In one embodiment, each component is "pharmaceutically acceptable" in the sense of being chemically compatible with the other ingredients of a pharmaceutical formulation, and biocompatible, when in contact with the biological tissues or organs of humans and animals without excessive toxicity, irritation, allergic response, immunogenicity, or other problems or complications, commensurate with a reasonable benefit/risk ratio. See, *Remington: The Science and Practice of Pharmacy*, 2005, 21st ed., Philadelphia, Pa.: Lippincott Williams & Wilkins; Rowe et al., eds., 2005, *Handbook of Pharmaceutical Excipients*, 5th ed., The Pharmaceutical Press and the American Pharmaceutical Association; Ash & Ash eds., 2007, *Handbook of Pharmaceutical Additives*, 3rd ed., Gower Publishing Company; Gibson ed., 2009, *Pharmaceutical Preformulation and Formulation*, 2nd ed., Boca Raton, Fla.: CRC Press LLC, each of which is incorporated herein by reference.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, forms for topical administration such as a cream may contain excipients not suited for use in transdermal or intravenous administration. The suitability of a particular excipient depends on the specific active ingredients in the dosage form. Exemplary, non-limiting, pharmaceutically acceptable carriers for use in the hair growth-promoting agent formulations described herein are the cosmetically acceptable vehicles provided in International Patent Application Publication No. WO 2005/120451, which is incorporated herein by reference in its entirety.

The pharmaceutical compositions disclosed herein may be formulated to include an appropriate aqueous vehicle, including, but not limited to, water, saline, physiological saline or buffered saline (e.g., phosphate buffered saline (PBS)), sodium chloride for injection, Ringers for injection, isotonic dextrose for injection, sterile water for injection, dextrose lactated Ringers for injection, sodium bicarbonate, or albumin for injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, lanolin oil, lanolin alcohol, linoleic acid, linolenic acid and palm seed oil. Suitable water-miscible vehicles include, but are not limited to, ethanol, wool alcohol, 1,3-butanediol, liquid polyethylene glycol (e.g., polyethylene glycol 300 and polyethylene glycol 400), propylene glycol, glycerin, N-methyl-2-pyrrolidone (NMP), N,N-dimethylacetamide (DMA), and dimethyl sulfoxide (DMSO). In one embodiment, the water-miscible vehicle is not DMSO.

Suitable isotonic agents include, but are not limited to, sodium chloride, glycerin, and dextrose. Suitable buffering agents include, but are not limited to, phosphate, glutamate and citrate. Suitable suspending and dispersing agents include but are not limited to sodium carboxymethylcelluose (CMC), hydroxypropyl methylcellulose (HPMC), polyvinyl alcohol (PVA), and polyvinylpyrrolidone (PVP). Suitable emulsifying agents include but are not limited to, including polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

A product for application to the scalp or face may additionally be formulated so that it has easy rinsing, minimal skin/eye irritation, no damage to existing hair, has a thick and/or creamy feel, pleasant fragrance, low toxicity, good biodegradability, and a slightly acidic pH (pH less than 7), since a basic environment weakens the hair by breaking the disulfide bonds in hair keratin.

5.5.2 Modes of Administration

The pharmaceutical compositions disclosed herein, for example, the pharmaceutical compositions used in post-perturbation treatments described in Section 5.2, the hair growth-promoting agents described in Section 5.3, or the pharmaceutical agents described in Section 5.4, can be formulated in forms suitable for topical (e.g., applied directly to the skin, transdermal, or intradermal), subcutaneous, intramuscular, intravenous or by other parenteral means, oral administration, sublingual administration, or bucchal administration. For example, the pharmaceutical compositions for use in the methods and uses disclosed herein can be administered in forms suitable for topical (e.g., applied directly to the skin, transdermal, or intradermal), subcutaneous, intramuscular, intravenous or by other parenteral means, oral administration, sublingual administration, or bucchal administration. In some embodiments, the topical (e.g., applied directly to the skin, transdermal, or intradermal) administration is accomplished with the use of a mechanical device, such as, e.g., an iontophoretic device. The pharmaceutical compositions described herein can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, Rathbone et al., eds., 2008, *Remington: The Science and Practice of Pharmacy, supra; Modified-Release Drug Delivery Technology*, 2nd ed., New York, N.Y.: Marcel Dekker, Inc.). The pharmaceutical compositions described herein can be administered by a health care practitioner or, where appropriate, by the subject. In some embodiments, the subject administers the a post-perturbation treatment as described in Section 5.2 or a growth-promoting agent as described in Section 5.3 to him or herself.

5.5.2.1 Topical Administration

In a preferred embodiment, topical administration is to the skin, either to the skin surface, transdermally, or intradermally. Topical administration can be with or without occlusion with a bandage or other type of dressing. In some embodiments, topical administration is to orifices or mucosa, or conjunctival, intracorneal, intraocular, ophthalmic, auricular, nasal, vaginal, urethral, respiratory, and rectal administration. The formulation used for topical administration can be designed to retain the hair growth-promoting agent (or other active ingredient) in the skin or to deliver a dose of the hair growth-promoting agent systematically. In some embodiments, topical administration of a hair growth-promoting agent is combined with another treatment described herein, such as, but not limited to, a technique of integumental perturbation described in Section 5.1 supra.

Dosage forms that are suitable for topical administration for preferably local but also possible systemic effect, include emulsions, solutions, suspensions, creams, gels, hydrogels, ointments, dusting powders, dressings, elixirs, lotions, suspensions, tinctures, pastes, powders, crystals, foams, films, aerosols, irrigations, sprays, suppositories, sticks, bars, ointments, bandages, wound dressings, microdermabrasion or dermabrasion particles, drops, and transdermal or dermal patches. The topical formulations can also comprise micro- and nano-sized capsules, liposomes, micelles, microspheres, microparticles, nanosystems, e.g., nanoparticles, nanocoacervates and mixtures thereof. See, e.g., International Patent Application Publication Nos. WO 2005/107710, published Nov. 17, 2005, and WO 2005/020940, published Mar. 10, 2005, each of which is incorporated herein by reference in its entirety. In one embodiment, the nano-sized delivery matrix is fabricated through a well-defined process, such as a process to produce the hair growth-promoting agent encapsulated in a polymer. In another embodiment, the hair growth-promoting agent is spontaneously assembled in aqueous solutions, such as in liposomes and micelles. In some embodiments, the formulation for topical administration is a shampoo or other hair product, tanning product or sun protectant, skin lotion, or cosmetic.

The selected formulation will penetrate into the skin and reach the hair follicle. Thus, in some embodiments, the stratum corneum and/or epidermis are removed by a method of integumental perturbation described herein (including by wounding or scar revision, by laser, or by dermabrasion or microdermabrasion, which is a less vigorous form of dermabrasion), permitting application of the dosage form for topical administration directly into the exposed dermis. In some embodiments, the formulation for topical administration will be lipid-based, so that it will penetrate the stratum corneum. In some embodiments, the formulation for topical administration will contain a skin penetrant substance, such as, e.g., propylene glycol or transcutol. See, e.g., International Patent Application Publication No. WO 2004/103353, published Dec. 2, 2004, which is incorporated herein by reference in its entirety. The ability to penetrate into the skin can be tested using any method known in the art, such as, e.g., the method described in International Patent Application Publication No. WO 2005/107710, which is incorporated herein by reference in its entirety. In one embodiment, a formulation in ointment form comprises one or more of the following ingredients: wool alcohol (acetylated lanolin alcohol), hard paraffin, white soft paraffin, liquid paraffin, and water. See, e.g., Langtry et al., supra. In some embodiments, the selected formulation is inconspicuous when applied to the skin, for example, is colorless, odorless, quickly-absorbing, etc. In some embodiments, the selected formulation is applied on the skin surface as a solution, which can crosslink into a hydrogel within a few minutes, thus creating a biocompatible dressing. In one application, the hydrogel may be biodegradable. In another embodiment, the solution will absorb into the skin and crosslink into depots releasing drug. In another embodiment, the hair growth-promoting agent will be used to crosslink the polymer, with release of the hair growth-promoting agent controlled by the rate of degradation of the hydrogel.

In an exemplary embodiment, the drug is encapsulated in microspheres, e.g., of sizes between 0.10 microns and 200 microns, or between 0.20 microns and 50 microns. In another embodiment, the drug is encapsulated in liposomes, e.g., of sizes between 10 nm and 50 microns, or between 500 nm and 20 microns.

In another embodiment, the drug is applied in the form of liposomes or self-ordered vesicles such as multi-micellar aggregates of size ranges 0.1-100 nm, 100-1000 nm, 1-10 microns, 10-100 microns.

In an exemplary embodiment, the drug (or, e.g., the post-perturbation treatment) is administered as a cold liquid, which gels at a temperature of 32° C.-37° C. For example, the drug may be administered as a liquid, which then hardens into a depot that delivers drug over time. In another embodiment the drug, or post-permeation treatment, is administered as a hydrogel. In a particular embodiment, the post-perturbation treatment or drug-containing composition comprises propylene glycol, polyethylene glycol or ethanol.

In another embodiment, the drug-containing composition comprises one or more excipients that complex to the drug. In a particular embodiment, the excipient comprises hyaluronic acid, polyacrylic acid or alginic acid. In another embodiment, the composition comprises one or more permeation enhancing agents or carriers that solubilize the drug in skin.

Pharmaceutically acceptable carriers and excipients suitable for use in topical formulations include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

Forms for topical administration can also be in the form of ointments, creams, and gels. Suitable ointment vehicles include oleaginous or hydrocarbon vehicles, including lard, benzoinated lard, olive oil, cottonseed oil, mineral oil and other oils, white petrolatum, paraffins; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, wool alcohol (acetylated lanolin alcohol), and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

(i) Other Means of Topical Administration, Including Mechanical Means

Other means of topical administration of pharmaceutical compositions disclosed herein (see, e.g., Sections 5.2, 5.3, and 5.4 supra) are also contemplated. Each of these methods of topical administration may be used alone to administer hair growth-promoting agents or in combination with one or more other treatments described herein.

In some embodiments, topical administration is by electrical current, ultrasound, laser light, or mechanical disruption or integumental perturbation. These include electroporation, RF ablation, laserporation, laser ablation (fractional or non-fractional), non-ablative use of a laser, iontophoresis, phonophoresis, sonophoresis, ultrasound poration, or using a device that accomplishes skin abrasion, or microneedle or needle-free injection, such as topical spray or POWDERJECT™ (Chiron Corp., Emeryville, Calif.), BIOJECT™ (Bioject Medical Technologies Inc., Tualatin, Oreg.), or JetPeel™ (from TavTech, Tel Aviv, Israel), which uses supersonically accelerated saline to remove epidermis. Means of topical administration that can be used in accordance with the methods described herein are known in the art and are described in, e.g., U.S. Pat. Nos. 5,957,895, 5,250,023, 6,306,119, 6,726,693, and 6,764,493, and International Patent Application Publication Nos. WO 2009/061349, WO 1999/003521, WO 1996/017648, and WO 1998/011937, each of which is incorporated herein by reference in its entirety.

In some embodiments, the device for topical administration is an automatic injection device worn continuously but delivers the hair growth-promoting agent or other active ingredients in a pulse fashion or intermittently. In some embodiments, the device for topical administration is an automatic injection device that is inconspicuous, for example, can be worn without undue discomfort under clothes, in the hair, under a hairpiece, etc. In some embodiments, the delivers the hair growth-promoting agent or other active ingredient at a controlled depth in the skin so that it reaches hair follicles, but entry into the circulation is minimized.

Other methods for administration of the pharmaceutical compositions described herein include use of a transdermal particle injection system, such as, e.g., a "gene gun." Such systems typically accelerate drug or drug particles to supersonic velocities and "shoot" a narrow stream of drug through the stratum corneum. In some embodiments, the stratum corneum and epidermis is previously removed using a method of integumental perturbation described herein, and thus the required delivery pressures and velocities can be reduced. This reduction reduces the required complexity of the firing mechanisms. In some embodiments, a narrow firing stream is used, particularly to accomplish systemic delivery. In other embodiments, the particle injection system administers the pharmaceutical composition over a broad area of skin. An exemplary particle delivery device compatible with broad-based skin delivery (in some embodiments, for use in conjunction with integumental perturbation, wherein the surface of skin to which drug is administered corresponds to the perturbed area) includes a low pressure/low velocity firing mechanism with a spray nozzle designed to deliver to a broad area. For example, a single-shot device that delivers to a 25-cm$^2$ area could be fired or used multiple times on the scalp or other skin surface until the entire area is treated.

In another embodiment, a dry particle spraying mechanism similar to an airbrush or miniature grit-blaster can be used to "paint" drug or drug particles onto the perturbed area. In some embodiments, the stratum corneum and epidermis are already removed, e.g., by a method of integumental perturbation described herein, and thus permits effective use of the mechanism using lowered pressure and velocity requirements to achieve dermal delivery.

In another embodiment, the hair growth-promoting agent (and/or additional drug) is present in an aqueous suspension, permitting use of standard aerosol spray can technology to deliver the hair growth-promoting agent to the desired skin area.

In another embodiment, the pharmaceutical composition can be administered using a two-chamber sprayer device, wherein the hair growth-promoting agent or other active ingredient is dispersed, solubilized, or emulsified in a liquid contained in one of the chambers. The other chamber of the device would contain a liquid that is capable of reacting with the drug-containing liquid in the first chamber, to form a physically crosslinked hydrogel or a covalently linked hydrogel. When co-eluted/or sprayed together, the liquids can react and form a drug-containing bioadhesive hydrogel to deliver the pharmaceutical composition to the desired area. In an embodiment, the drug-containing hydrogel will have additional features of supporting cell attachment and proliferation.

In another embodiment, the pharmaceutical composition will be sprayed as a dry powder that is adherent to the underlying tissue.

Specific embodiments of modes of administration using a device that combines integumental perturbation and pharmaceutical composition delivery follow. An advantage of using such a device is that it offers a convenient one step process for administration of the pharmaceutical composition.

In one embodiment, dermabrasion (e.g., using a mechanical device, including microdermabrasion devices that can be used to dermabrade, or alumina-, silica- or ice-based dermabrasion (as described by Weber, U.S. Pat. Nos. 6,764,493; 6,726,693; and 6,306,119)) is customized to include a drug particle delivery feature using methods readily known in the art. As the device fires ablation particles at the skin, it could also fire smaller drug particles that would simultaneously embed in the exposed dermis. Alternatively, via an internal valve control, the device could switch over to firing drug particles once it is determined that adequate skin disruption has occurred. See, International Patent Application Publication No. WO 2009/061349, which is incorporated herein by reference in its entirety.

In another embodiment, a standard dermabrasion device can be modified to incorporate any of the devices described herein, e.g., a spraying/painting device. In one embodiment, a spray nozzle is located behind the dermabrasion wheel such that drug is sprayed into the dermis as it is exposed by the wheel. Alternatively, the dermabrasion device, via internal controls, could turn off the abrasion wheel once it is determined that adequate skin disruption has occurred, and switch on the drug spray to convert to drug painting mode. For example, the dermabrasion tip, dermabrader, and/or kit for dermabrasion described in Section 5.1 supra may be modified in accordance with these embodiments.

In another embodiment, a non-fractional $CO_2$ or erbium-YAG laser is combined with drug spraying either without skin disruption, in conjunction with skin disruption, or following skin disruption.

In one embodiment, a pulsed dye laser (585-595 nm) is combined with drug spraying either before or without skin perturbation, in conjunction with skin perturbation, or following skin perturbation.

In another embodiment, a fractional non-ablative laser (e.g., an Erbium-YAG laser used at 1540-1550 nm) is combined with drug spraying either without skin perturbation, in conjunction with skin perturbation, or following skin perturbation. In another embodiment, a fractional ablative laser (e.g., an erbium-YAG laser used at 2940 nm or a $CO_2$ laser used at 10,600 nm) is combined with drug spraying either without skin perturbation, in conjunction with skin perturbation, or following skin perturbation.

In another embodiment, fractional ablative laser treatment of the skin (e.g., an erbium-YAG laser used at 2940 nm or a $CO_2$ laser used at 10,600 nm) is combined with drug delivery. For example, by invoking inkjet technology, a fractional laser could be combined with a precise delivery means such that as the laser forms a hole in the skin, the inkjet-like delivery component could fill that same hole with drug. One of skill in the art would appreciate that adequate integrated hardware and software controls are required such that the laser ablation and drug delivery are properly timed resulting in each newly formed hole being properly filled with drug. In another embodiment, fractional ablative laser treatment of the skin (e.g., an Erbium-YAG laser used at 2940 nm or a $CO_2$ laser used at 10,600 nm) is combined with drug delivery. For example, by invoking inkjet technology, use of a non-ablative, fractional laser could be combined with a precise delivery means such that as the laser forms a hole in the skin, the inkjet-like delivery component could fill that same hole with drug. One of skill in the art would appreciate that adequate integrated hardware and software controls are required such that the laser treatment and drug delivery are properly timed resulting in each newly formed hole being properly filled with drug.

In some embodiments, topical administration comprises administration of drug-containing particles. The particles can be delivered to the skin in combination with any of the means described herein. In one embodiment, particles with different release properties are delivered simultaneously to achieve controlled delivery of drug.

In another embodiment, topical administration comprises administration of a hair growth-promoting agent-containing formulation that is delivered through channels that are created by the use of micro-needle technology. The formulation can be, e.g., a liquid, a gel or a dry spray. In another variation, topical administration may be through delivery of a hair growth-promoting agent-containing formulation through hollow needles.

In another embodiment, topical administration comprises administration of a drug-containing formulation that is delivered into the skin by an iontophoretic patch. In one example of this embodiment, a patch can be developed in which the drug-containing formulation is incorporated.

In another embodiment, topical administration comprises administration of a drug-containing formulation that is incorporated into micro-needle shaped biodegradable polymers. In one such embodiment, the biodegradable microneedles penetrate the targeted skin tissue, and are optionally left in place to deliver the drug in a sustained fashion over time.

An example of a device that can be used to deliver the therapeutic compound to the skin site is depicted in FIGS. 17A-21E. The device or drug sprayer 2 includes a control unit or generator 4, a foot switch 6, a hand piece 8, and a power module 10.

The control unit 4 is the interface between the foot switch 6, the hand piece 8, and the power module 10. It serves as the central point of connectivity and provides a user with a means to power the system on or off, load/eject a drug cartridge into/from the hand piece 8, and select the drug delivery speed. To control all of this functionality, the control unit 4 includes at least one circuit board that controls operation of the hand piece 8 via embedded software.

Figure 18:
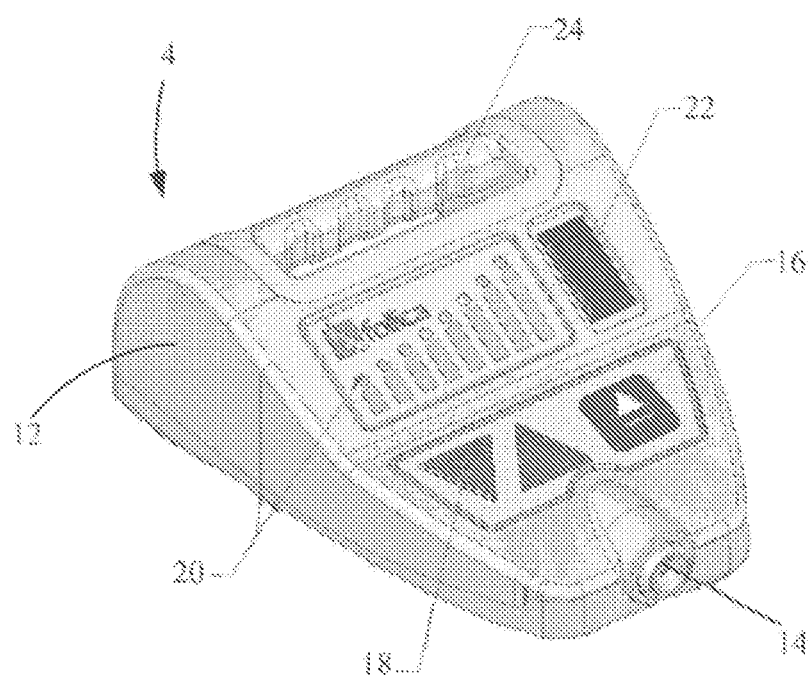

As can be seen in FIG. 18, the control unit 4 comprises a housing 12 that includes a hand piece connection port 14, a load/eject button 16, a means 18 to control the drug delivery or spray speed, a means 20 to display the drug delivery speed, an on/off switch 22, and a handle 24. In the embodiment depicted in FIG. 18, the means 18 to control the drug delivery speed includes a pair of up/down buttons and the means 20 to display the drug delivery speed comprises 8 discreet LEDs (light-emitting diodes) that light up to indicate the drug delivery speed. Examples of materials that can be used for the load/eject button 16, the up/down buttons 18, and the on/off switch 22 include, but are not limited to, elastomeric materials such as silicon rubber, plastics, and metals. The housing 12 can be made from an injection molded thermoplastic material such as, for example, acrylonitrile butadiene styrene.

Figure 19A:
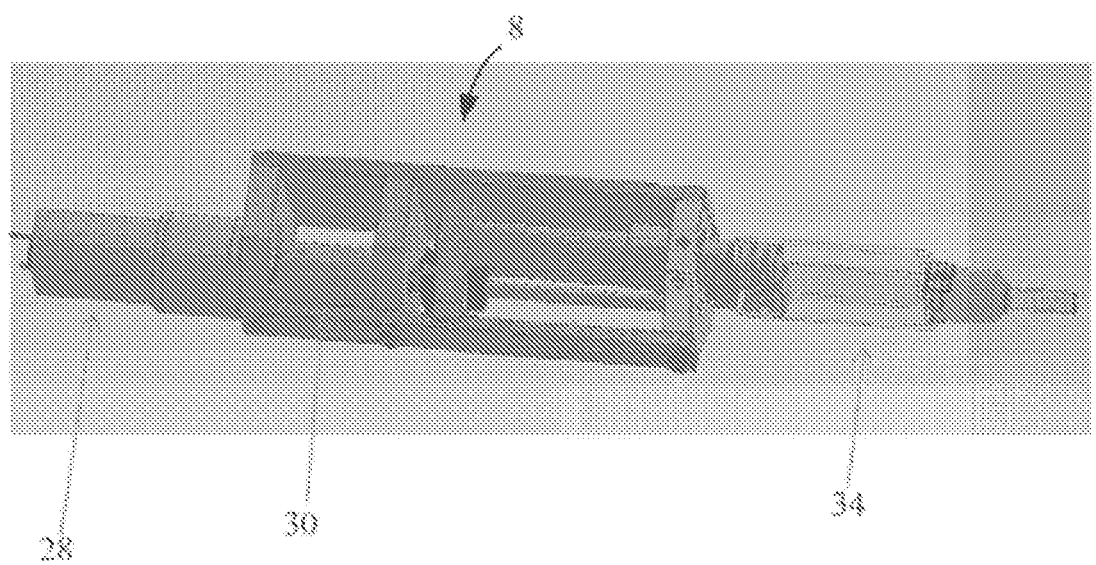
Figure 19B:
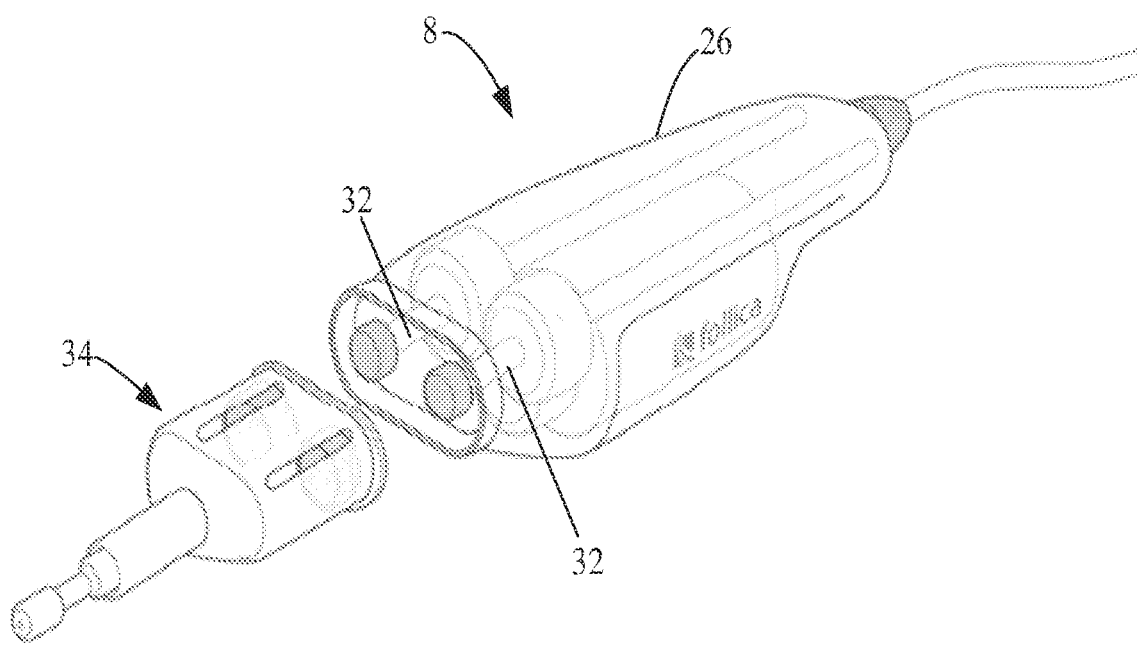

FIGS. 19A and 19B depict an embodiment of the drug sprayer's hand piece 8. The hand piece 8 comprises a housing 26, a drive motor 28, a universal joint 30 and at least one plunger 32. Attached to the end of the hand piece 8 is a drug cartridge 34 that can either be disposable or reusable. The hand piece's housing 26 can be made from an injection molded thermoplastic material such as, for example, acrylonitrile butadiene styrene. It will be readily apparent to those skilled in the art that other materials may be used to construct the hand piece's housing 26.

Some therapeutic compounds may quickly become unstable after their components are mixed or some may have a short shelf life unless they are refrigerated. Thus, in order to keep these compounds stable and increase shelf life, the components of the compounds are isolated from each other until the compounds are ready to be administered when they are mixed together forming, for example, a gel, controlled release, drug delivery matrix. Prior devices, such as those described in U.S. Pat. Nos. 4,381,778, 4,689,042, 5,122,117, and 5,423,752, the entirety of each are expressly incorporated herein by reference thereto, have been developed to store drug components separately and then mix the components prior to being dispensed.

FIGS. 20A-21E depict embodiments of a drug cartridge having two separate chambers that keep the drug components isolated until the therapeutic compound is to be dispensed. FIGS. 20A-20D depict a drug cartridge 40 that contains two liquid components and its associated hand piece 42. The drug cartridge 40 includes a housing 44 having a front end 46, a back end 48, a nozzle 50, a static mixer 52 having a mixing chamber 54 and two piercing elements 56 that extend from the back end 48 thereof and which are in fluid communication with the mixing chamber 54, two liquid component chambers 58, 60, a first liquid component 62 stored in the first component chamber 58, a second liquid component 64 stored in the second component chamber 60, and a piston 66 inserted into the back end 48 of each component chamber 58, 60 to rearwardly confine each liquid component 62, 64 within its respective component chamber 58, 60. The pistons 66 form an airtight seal with the interior walls of their respective component chambers 58, 60. To seal off the front end of each chamber 58, 60, a pierceable seal 68 is included. Thus, when the drug cartridge 40 is attached to the hand piece 42, the piercing elements 56 penetrate the pierceable seals 68 of the first and second component chambers 58, 60, thereby forming a fluid connection between the static mixer 52 and the first and second component chambers 58, 60. In order to promote mixing of the two liquid components 62, 64, the mixing chamber 54 includes mixing elements 70 therein. For example, these mixing elements 70 can be pathways or channels formed in the interior walls of the mixing chamber 54 or can be mixing vanes that cause the liquid components 62, 64 to swirl as they travel through the mixing chamber 54 resulting in turbulent fluid flow, thereby mixing the liquid components 62, 64 together.

Figure 20A:
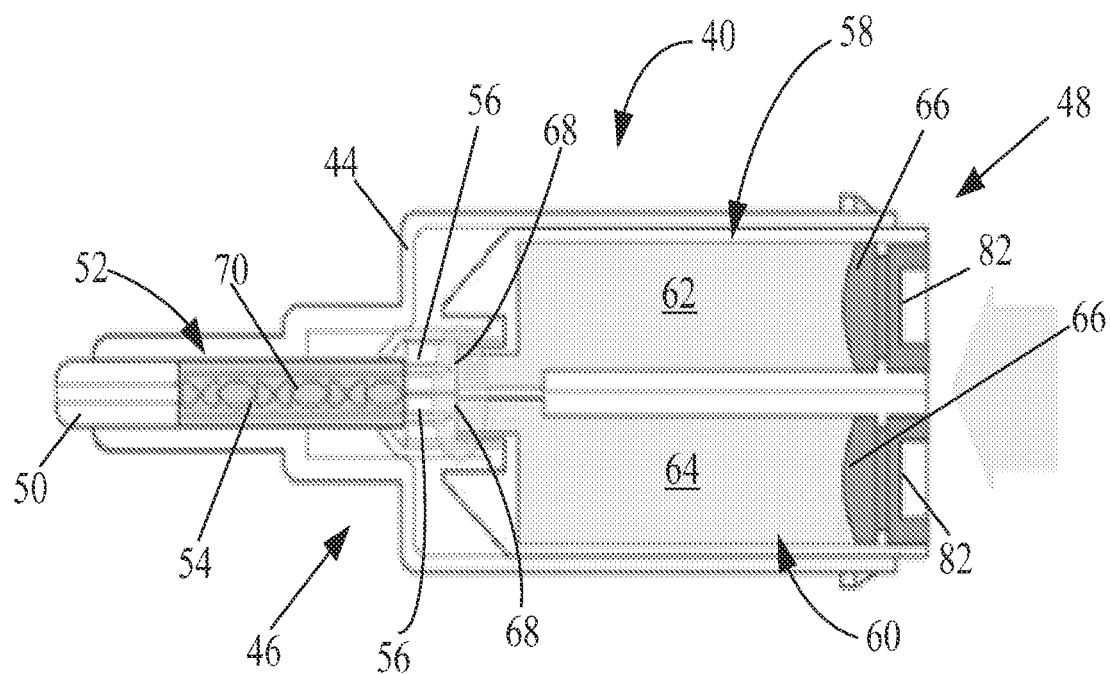
Figure 20B:
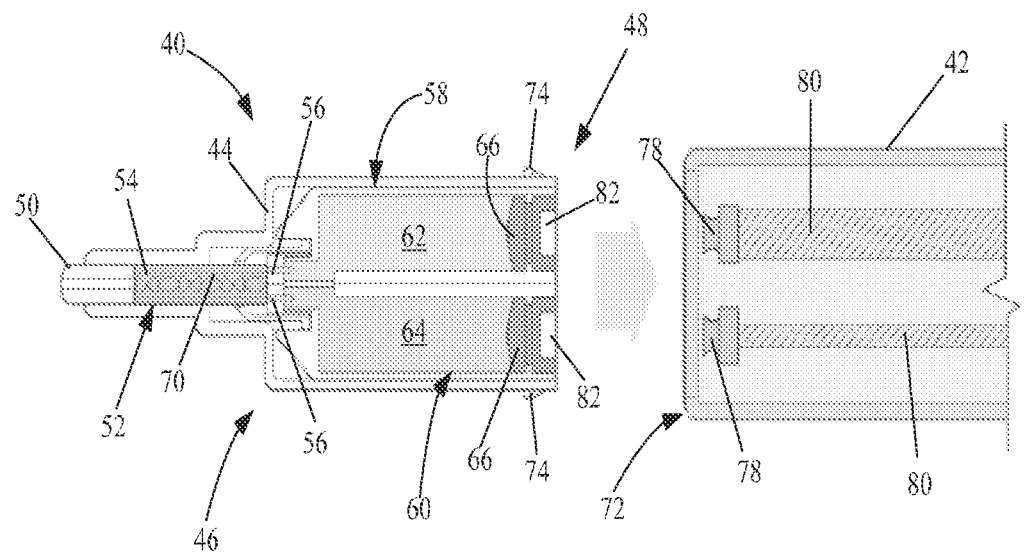
Figure 20C:
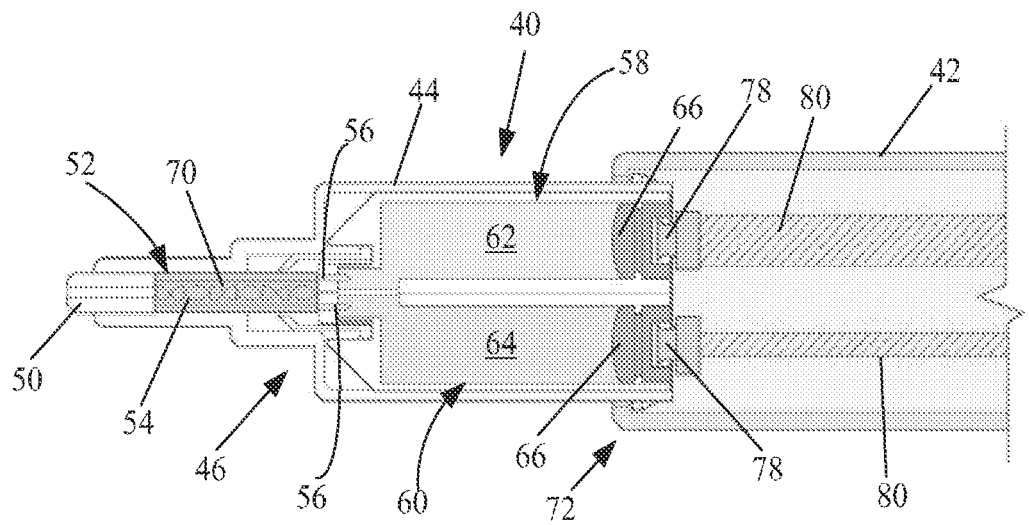
Figure 20D:
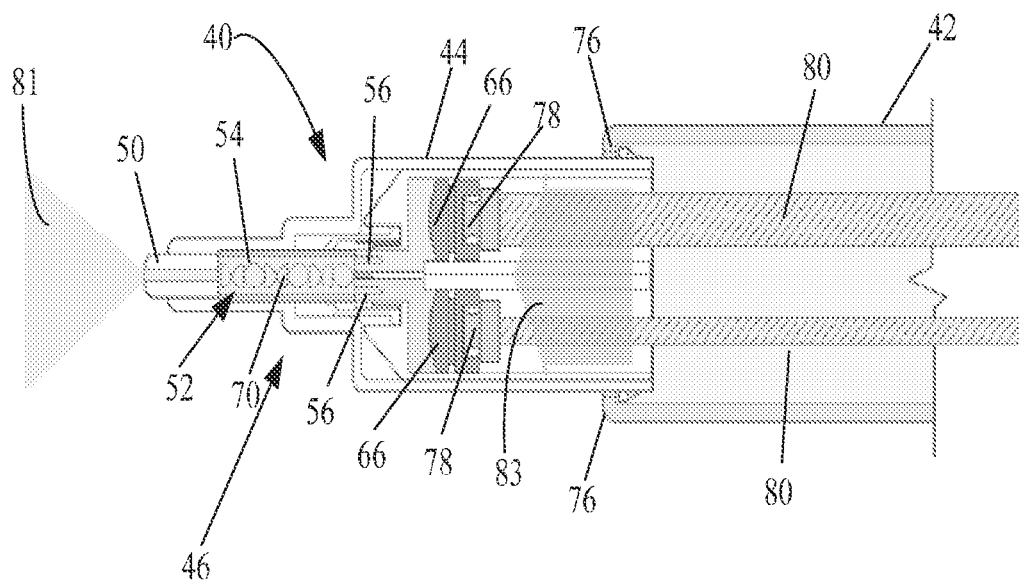

To use the two liquid component drug cartridge 40 with the drug sprayer 2, as can be seen in FIGS. 20B-20D, a user inserts the drug cartridge 40 into the front end 72 of the hand piece 42. When inserted, detents 74 on the drug cartridge 40 engage detents 76 on the hand piece 42 and lock the drug cartridge 40 and the hand piece 42 together. As shown in FIGS. 20C and 20D, when the drug cartridge 40 is fully inserted into the hand piece 42, the connecting portions 78 of each plunger 80 engage a corresponding cavity 82 in the pistons 66, forming a press-fit connection between the two. Thus, when the plungers 80 move, the pistons 66 move in a corresponding manner.

When a user desires to dispense the therapeutic compound, the user activates the hand piece 42 via the control unit 4. Activation of the hand piece 42 in turn energizes the drive motor 28, which acts through a universal joint (see FIGS. 19A and 19B) to move or drive the plungers 80 towards the front end 46 of the drug cartridge 40. Thus, as can be seen in FIG. 20D, as the plungers 80 move in the direction indicated by arrow 83, the pistons 66 move into the component chambers 58, 60 in a corresponding manner, forcing each separate liquid component 62, 64 through the piercing elements 56 and into the mixing chamber 54. As the liquid components 62, 64 travel through the mixing chamber 54, the turbulent flow created therein causes the liquid components 62, 64 to mix with each other. The newly mixed components then exit the nozzle 50 as the mixed therapeutic compound 81.

In another embodiment, the drug sprayer 2 can be used with a drug cartridge 84 that contains a liquid component 86 and a solid component 88. As depicted in FIGS. 21A-21E, the drug cartridge 84 includes a housing 90 having a front end 92, a back end 94, a lower chamber 96, a nozzle 98, a liquid component chamber 100 that houses the liquid component 86, a solid component chamber 102 that houses the solid component 88, a first piston 104 inserted into the back end of the liquid component chamber 100 to rearwardly confine the liquid component 86 therein, and a second piston 106 inserted into the back end of the solid component chamber 102 to rearwardly confine the solid component 88 therein. The first and second pistons 104, 106 form an airtight seal with the interior walls of the liquid and solid component chambers 100, 102.

The front end 92 of the liquid component chamber 100 includes a first one-way or check valve 108 that confines the liquid component 86. The front end 92 of the solid component chamber 102 does not include a check valve. Instead, a second check valve 110 is included at the back end of the of the lower chamber 96. An example of such a one-way valve that can be used with the present drug cartridge 84 is a duck bill valve. This configuration of the first and second check valves 108, 110 allows the liquid component 86 and the solid component 88 to be stored separate from each other and also closes the front ends of the liquid and solid component chambers 100, 102 forming a sealed volume of air between the first and second pistons 104, 106 and the first and second check valves 108, 110.

To use the drug cartridge 84 containing a liquid component 86 and a solid component 88 with the drug sprayer 2, as can be seen in FIGS. 21A-21E, a user inserts the drug cartridge 84 into the front end 112 of the hand piece 114. When inserted, detents 116 on the drug cartridge 84 engage detents 118 on the hand piece 114 and thereby lock the drug cartridge 84 and the hand piece 114 together. In contrast to the liquid-liquid drug cartridge 40 discussed above, the hand piece 114 for use with the liquid-solid drug cartridge 84 includes a single plunger 120, which is inserted into the solid component chamber 102. As can be seen in FIGS. 21B-21E, when the drug cartridge 84 is fully inserted into the hand piece 114, the connecting portion 122 of the plunger 120, engages a corresponding cavity 124 in the second piston 106 forming a press-fit connection between the two. Thus, when the plunger 120 moves, the second piston 106 moves in a corresponding manner.

Figure 21A:
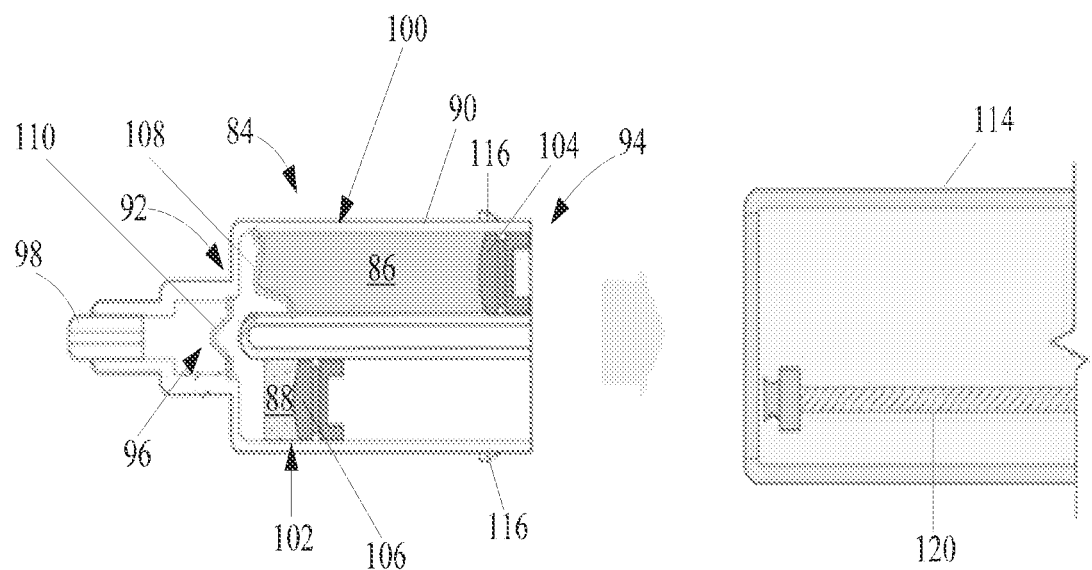
Figure 21B:
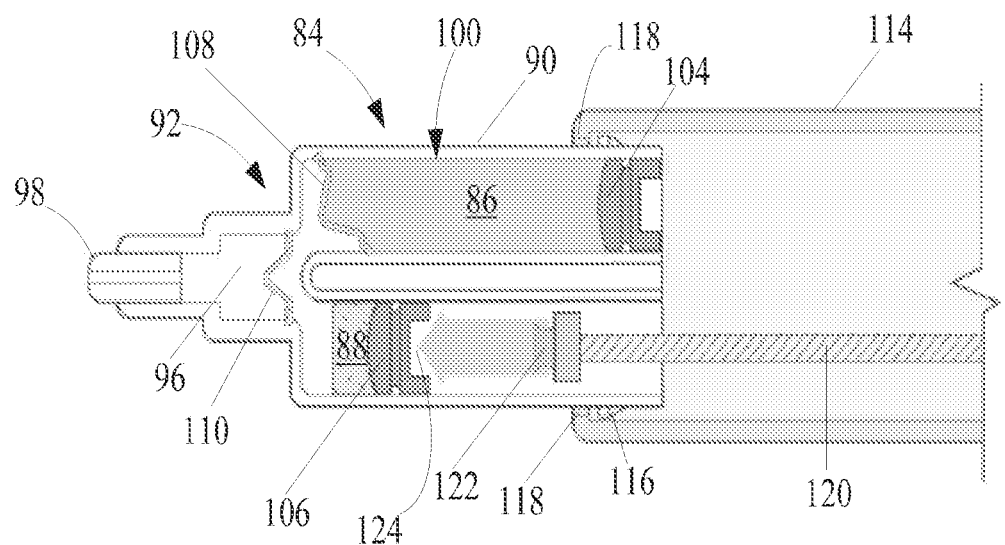
Figure 21C:
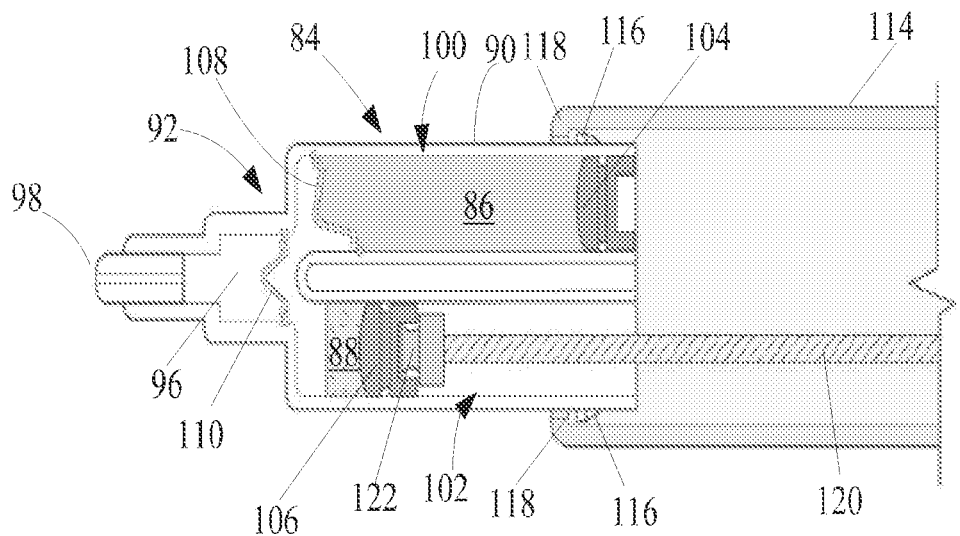
Figure 21D:
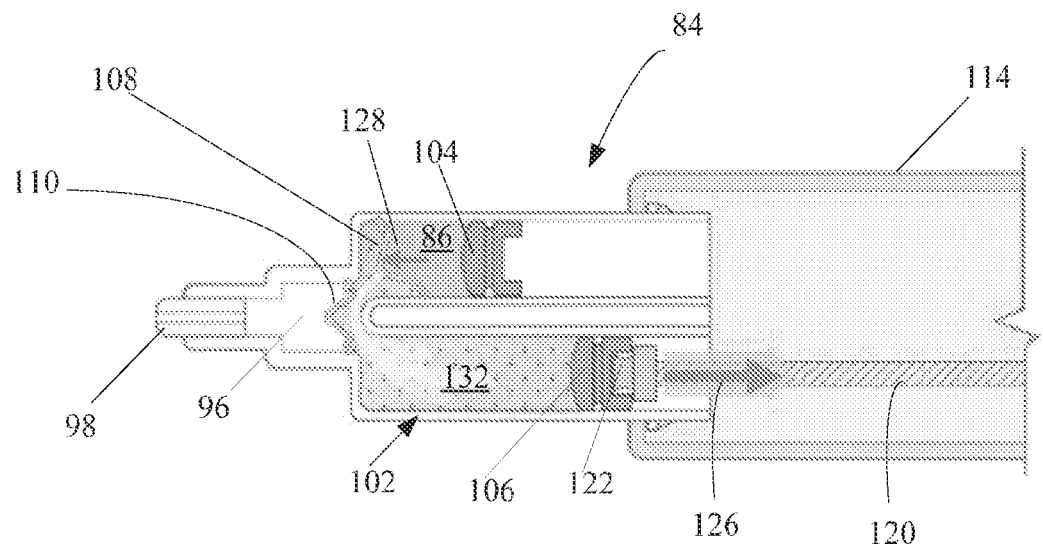

When a user desires to dispense the therapeutic compound, the user activates the hand piece 114 via the control unit 4. Activation of the hand piece 114 in turn energizes the drive motor 28, which acts through a universal joint 30 (see FIGS. 19A and 19B) to move the plunger 120. Initially, the plunger 120 is retracted in the direction shown by arrow 126 in FIG. 21D causing the second piston 106 to move in a corresponding manner. Because of the air tight seals created by the first and second pistons 104, 106 and the first and second check valves 108, 110, as can be seen in FIG. 21D, as the second piston 106 retracts, negative pressure or suction is created in the solid component chamber 102. This negative pressure or suction causes the first piston 104 to move in the direction of arrow 128 forcing the liquid component 86 through the first check valve 108 and into the liquid component chamber 102. As the liquid component 86 enters the solid component chamber 102, turbulent fluid flow is created, which operates to mix the liquid and solid components 86, 88 together. The negative pressure within the closed system acts to keep the second check valve 110 closed.

Figure 21E:
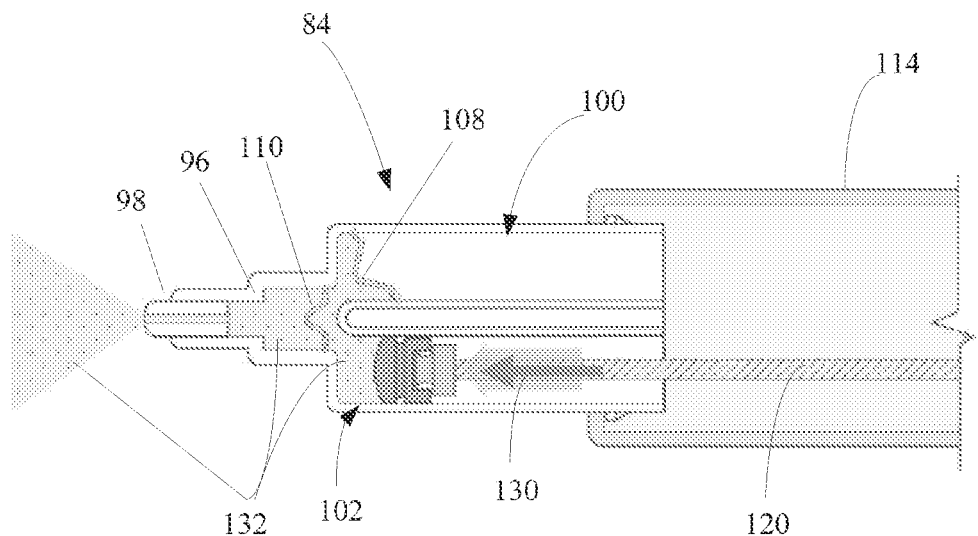
Figure 22A:
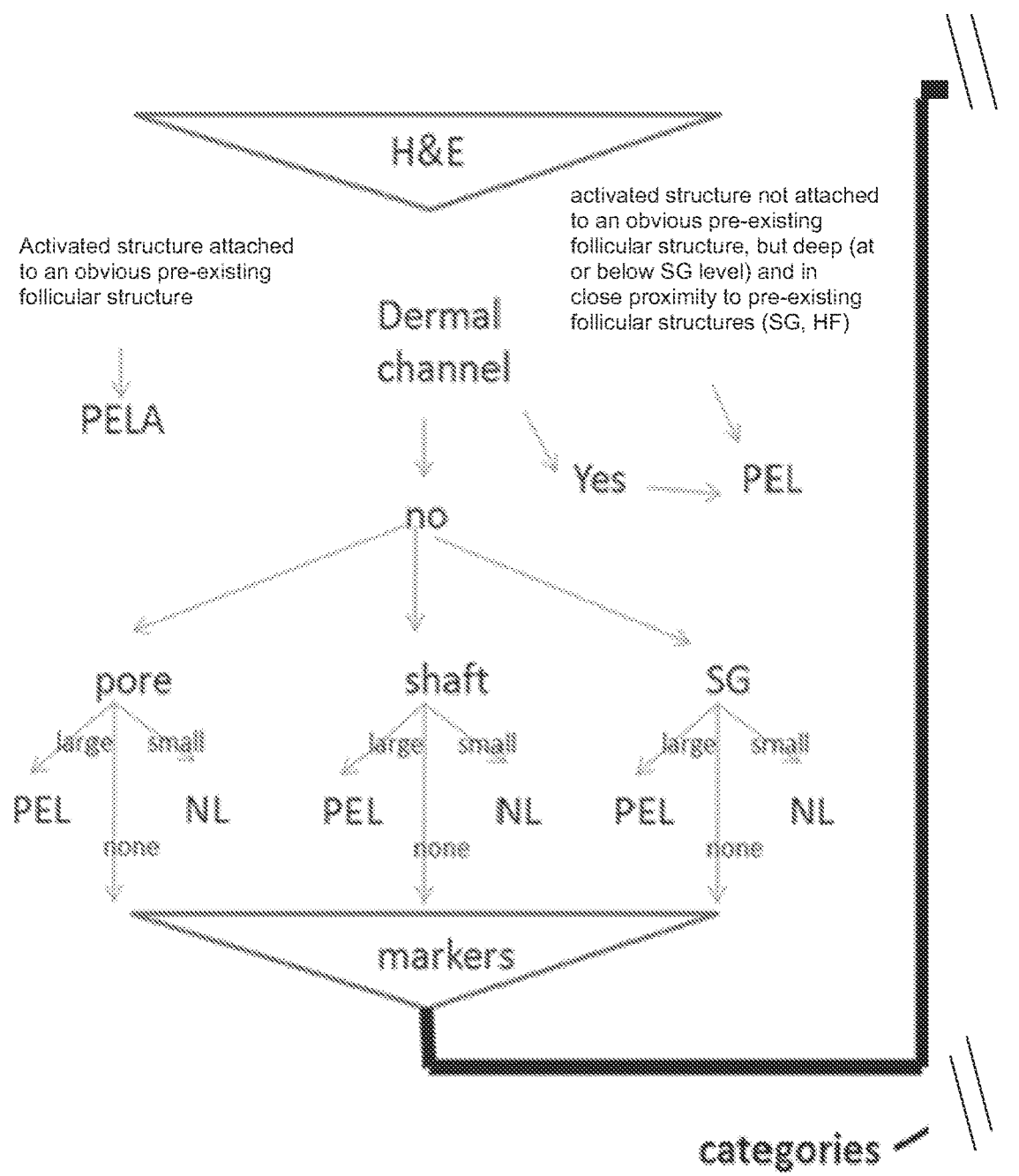
Figure 22B:
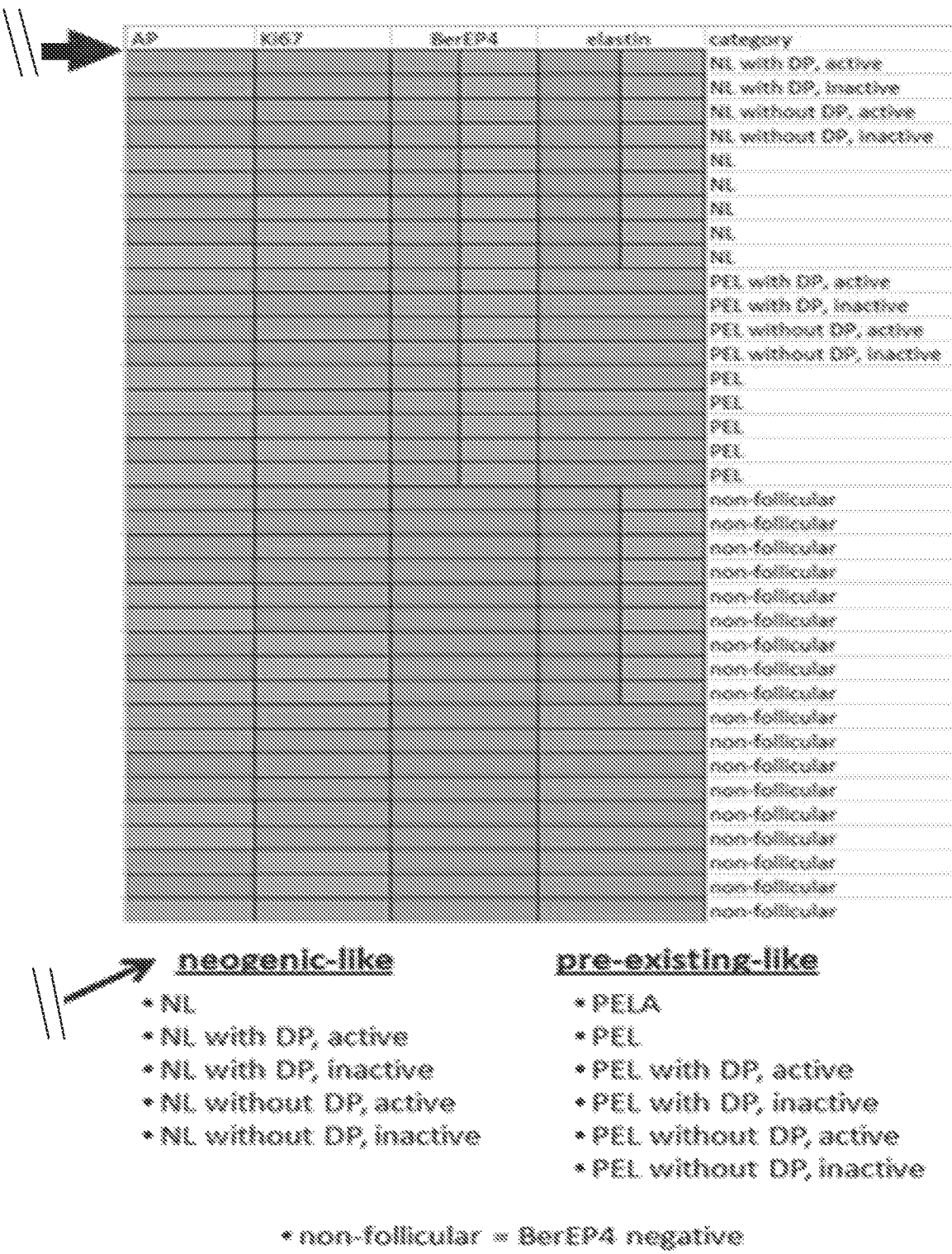

After the liquid and solid components 86, 88 are mixed together in the solid component chamber 102, a user can dispense the mixed drug by reversing the direction of travel of the plunger 120 as shown by arrow 130 in FIG. 21E. This forces the mixed therapeutic compound 132 through the second check valve 110, into the lower chamber 96, and out through the nozzle 98. Pressure acting on the front end of the first check valve 108, forces the first check valve 108 to remain closed during the dispensing operation.

It will be readily apparent to those skilled in the art that the amount of the liquid component 86 that is added to the solid component 88 and, hence, the concentration of the mixed drug, can be controlled by adjusting the distance that the plunger 120 is retracted before reversing the direction of travel of the plunger 120 and dispensing the mixed drug. Therefore, for example, the further back that the plunger 120 is retracted, the more liquid component 86 enters into the solid component chamber 102 and thus, the more dilute the therapeutic compound becomes.

In certain embodiments, the first liquid component 62 is a solution comprising a hair growth-promoting agent salt and the second liquid component 64 is a polymeric solution that comprises a water-soluble polymer that is a solution at room temperature (20-25° C.) and below, but gels at physiological temperatures of 32-37° C. The hair growth-promoting agent concentration in the hair growth-promoting agent solution can be at least 1.2 times, 1.4 times, 1.6 times, 1.8 times, 2 times, 2.2 times, 2.4 times, 2.6 times, 2.8 times, 3 times, 4 times, or at least 5 times the concentration of the final concentration. The hair growth-promoting agent solution can be a water-based solution.

In certain embodiments, the liquid component 86 is a polymeric solution that comprises a water-soluble polymer that is a solution at room temperature (20-25° C.) and below, but gels at physiological temperatures of 32-37° C. and the solid component 88 comprises a hair growth-promoting agent as described herein (see, e.g., Section 5.1).

In certain embodiments, either the drug spraying device, the drug cartridge, or both may be manufactured as a disposable. In certain embodiments, the drug spraying device may be altered so that it is battery powered.

As will be readily apparent to those skilled in the art, the components of the present device can be modified to dispense a therapeutic compound that comprises more than two components that need to be mixed together prior to dispensing.

In certain embodiments, a device for spraying a therapeutic compound comprises:
(A) a control unit;
(B) a foot piece,
(C) a power module;
(D) a hand piece comprising:
  (i) a housing;
  (ii) a first plunger having a first connecting portion; and
  (iii) a second plunger having a second connecting portion; and
(E) a drug cartridge comprising:
  (i) a housing;
  (ii) a first chamber containing a first liquid component, wherein the first liquid component is rearwardly confined by a first piston having a first cavity formed in an end thereof;
  (iii) a second chamber containing a second liquid component, wherein the second liquid component is rearwardly confined by a second piston having a second cavity formed in an end thereof;
  (iv) a static mixer; and
  (v) a nozzle;
(F) wherein the first connecting portion engages the first cavity such that movement of the first plunger moves the first piston within the first chamber in a corresponding manner, and
(G) wherein the second connecting portion engages the second cavity such that movement of the second plunger moves the second piston within the second chamber in a corresponding manner.

In certain embodiments, a device for spraying a therapeutic compound comprises:
(A) a control unit;
(B) a foot piece,
(C) a power module;
(D) a hand piece including a housing and a plunger having a connecting portion; and
(E) a drug cartridge comprising:
  (i) a drug cartridge housing having a front end and a back end;
  (ii) a first chamber containing a liquid component, wherein the liquid component is confined at a first end by a first piston and at a second end by a first one-way valve;
  (iii) a second chamber containing a solid component, wherein the solid component is confined at a first end by a second piston having a cavity formed in an end thereof and at a second end by the first one-way valve and a second one-way valve;
  (iv) a bottom chamber; and
  (v) a nozzle;
(F) wherein the connecting portion engages the cavity in the second piston such that movement of the plunger moves the second piston within the second chamber in a corresponding manner, and
(G) wherein movement of the piston away from the front end of the drug cartridge housing creates negative pressure within the second chamber, and
(H) wherein the negative pressure created in the second chamber pulls the liquid component through the first one-way valve into second chamber.

In certain embodiments, a drug cartridge for use in a device for spraying a therapeutic compound comprises:
(A) a housing having a front end and a back end;
(B) a first chamber containing a liquid component, wherein the liquid component is confined at a first end by a first piston and at a second end by a first one-way valve;
(C) a second chamber containing a solid component, wherein the solid component is confined at a first end by a second piston having a cavity formed in an end thereof and at a second end by the first one-way valve and a second one-way valve;
(D) a bottom chamber; and
(E) a nozzle;
(F) wherein movement of the second piston away from the front end of the housing creates negative pressure within the second chamber, and
(G) wherein the negative pressure created in the second chamber pulls the liquid component through the first one-way valve into second chamber.

(ii) Delivery of Cross-Linked Microspheres

In certain embodiments, the drug spraying device disclosed herein enables the sustained release of drug, e.g., hair growth-promoting agent or other active ingredient, without the use of highly hydrophobic, occlusive matrices. In particular, the drug spraying device enables the delivery of drug in microspheres (e.g., PLG microspheres) such that the microspheres stay at the wound site for a prolonged period of time and are not cleared rapidly by phagocytosis. A prolonged period of time can be at least 1, 2, 3, 4, 5, 6, 7, 8, 9, 10, 11, 12, 13, 14, 15, 16, 17, 18, 19, or at least 20 days.

Without being bound by theory, the drug spraying device enables the administration of drug-containing microspheres to the tissue such that the microspheres are sequestered to the wound surface by an in-situ crosslinking hydrogel that will form molecular bonds with the tissue surface. An in-situ crosslinking hydrogel cannot be "rubbed" off like an ointment or a cream. The microspheres will be sequestered in the hydrogel, releasing drug in a sustained manner. Thus, the issue of phagocytosis of the microspheres is overcome.

In certain embodiments, to deliver cross-linked microspheres, the solid component 88 comprises a polymer macromonomer (Polymer 1) (a polymer that can further crosslink with another component) and microspheres containing a hair growth-promoting agent. The liquid component 86 comprises another polymer macromonomer (Polymer 2) that is capable of reacting with Polymer 1. Polymer 2 does not contain hydrolytically labile linkages and is stable in water.

Illustrative embodiments of the use of the presently disclosed drug spraying device to deliver cross-linked microspheres to a wound site are set forth in the Examples below.

(iii) Delivery of Cross-Linked Biodegradable Scaffold

In certain embodiments, the drug spraying device disclosed herein enables the sustained release of drug, e.g., hair growth-promoting agent or other active ingredient, and uptake by the skin through a scab. In particular, the drug spraying device enables the delivery of hair growth-promoting agent such that the delivery system is incorporated into the scab. This can be accomplished by placing a hair growth-promoting agent containing thin, gauze-like, pliable biodegradable scaffold on the fresh wound. The material properties of the scaffold will be adjusted such the gauze is able to absorb the blood and other exudates from the wound. In certain, more specific embodiments, the biodegradable scaffold has high content of void space, to absorb blood, fibrin and fibrinogen. Without being bound by theory, this incorporation of the scaffold into the fibrin clot during its formation, results in its incorporation into the fibrous network, also called a scab, after it solidifies. After placement of the drug-containing biodegradable scaffold into the wound, an in-situ crosslinking hydrogel may be applied on top to cover the entire site as a wound dressing.

In certain embodiments, the solid component 88 comprises a polymer macromonomer (Polymer 1) (a polymer that can further crosslink with another component) and the liquid component 86 comprises another polymer macromonomer (Polymer 2) that is capable of reacting with Polymer 1. Polymer 2 does not contain hydrolytically labile linkages and is stable in water. Mixing of these two components yields a cross-linking hydrogel that is applied to the wound. The cross-linking hydrogel is applied together with a biodegradable scaffold that comprises hair growth-promoting agent. The biodegradable scaffold can be in the form a pliable, gauze-like material that is a blend of PLG polymers. Other polymers may be added to the main component (PLG) to impart attributes such as biodegradability, pliability, etc.

In a specific embodiment, hair growth-promoting agent can be incorporated in the biodegradable scaffold. In certain embodiments, the cross-linking hydrogel is applied to the wound before the scaffold is applied; the cross-linking hydrogel is applied to the wound at the same time when the scaffold is applied; the cross-linking hydrogel is applied to the wound after the scaffold is applied.

In certain embodiments, the biodegradable scaffold has an "open-cell" structure that would allow cells to attach themselves, differentiate and proliferate. The scaffold can have other components such as RGD peptides, etc. incorporated to encourage cell attachment. The scaffold can have bioadhesive attributes to keep it "in place."

Illustrative embodiments of the use of the presently disclosed drug spraying device to deliver cross-linked biodegradable scaffold to a wound site are set forth in the Examples below.

(iv) Delivery of Drug Combinations

In certain embodiments, the drug spraying device disclosed herein enables the concurrent delivery of two or more drugs with different solubility properties and/or physical/chemical incompatibilities (such as different excipient requirements; binding and/or reaction of the two or more drugs with each other).

In certain embodiments, the first liquid component 62 is a first formulated drug and the second liquid component 64 is a second formulated drug. In certain other embodiments, the presently disclosed drug spray device can be engaged for spraying each drug separately. For example, an alcoholic solution (±drug) can be used to first "prepare" the wound by thorough cleansing, followed by spraying a hair growth-promoting agent formulation as disclosed herein. In even other embodiments, both chambers could contain the same drug, but in different forms and formulated differently to achieve different release profiles. For example, the first liquid component 62 could contain micronized hair growth-promoting agent suspended in a FDA-approved liquid excipient and the second liquid component 64 can be a dissolved hair growth-promoting agent in an aqueous sprayable gel. Co-spraying both forms of hair growth-promoting agent provides instantly-bioavailable, hair growth-promoting agent and a sustained form of hair growth-promoting agent made available as the micronized hair growth-promoting agent dissolves.

Illustrative embodiments of the use of the presently disclosed drug spraying device to deliver cross-linked biodegradable scaffold to a wound site are set forth in the Examples below.

(v) Cleansing and Drug Delivery

In certain embodiments, the drug spraying device disclosed herein enables the cleansing and administration of one or more drugs with one single device. In these embodiments, the contents of each chamber could be sprayed separately. Once chamber can contain the cleansing solution; the liquid in the other chamber contains a hair growth-promoting agent. Any wound-cleansing solution known to the skilled artisan can be used with these embodiments.

Illustrative embodiments of the use of the presently disclosed drug spraying device to deliver cross-linked biodegradable scaffold to a wound site are set forth in the Examples below.

It will be evident to the skilled artisan that while the drug delivery devices described above may be preferred for delivery of the cross-linked microspheres, cross-linked biodegradable scaffold, drug combinations, and drug delivery with a cleansing solution described above, their delivery—to wounded or unwounded skin—may be accomplished using any method or device described herein or known in the art.

(vi) Specific Examples

In one embodiment, provided herein is a device for spraying a therapeutic compound comprising:
(A) a control unit;
(B) a foot piece,
(C) a power module;
(D) a hand piece comprising:
  (i) a housing;
  (ii) a first plunger having a first connecting portion; and
  (iii) a second plunger having a second connecting portion; and
(E) a drug cartridge comprising:
  (i) a housing;
  (ii) a first chamber containing a first liquid component, wherein the first liquid component is rearwardly confined by a first piston having a first cavity formed in an end thereof;
  (iii) a second chamber containing a second liquid component, wherein the second liquid component is rearwardly confined by a second piston having a second cavity formed in an end thereof;
  (iv) a static mixer; and
  (v) a nozzle;
(F) wherein the first connecting portion engages the first cavity such that movement of the first plunger moves the first piston within the first chamber in a corresponding manner, and
(G) wherein the second connecting portion engages the second cavity such that movement of the second plunger moves the second piston within the second chamber in a corresponding manner.

In another embodiment, a device for spraying a therapeutic compound comprises:
(A) a control unit;
(B) a foot piece,
(C) a power module;
(D) a hand piece including a housing and a plunger having a connecting portion; and
(E) a drug cartridge comprising:
  (i) a drug cartridge housing having a front end and a back end;
  (ii) a first chamber containing a liquid component, wherein the liquid component is confined at a first end by a first piston and at a second end by a first one-way valve;
  (iii) a second chamber containing a solid component, wherein the solid component is confined at a first end by a second piston having a cavity formed in an end thereof and at a second end by the first one-way valve and a second one-way valve;
  (iv) a bottom chamber; and
  (v) a nozzle;
(F) wherein the connecting portion engages the cavity in the second piston such that movement of the plunger moves the second piston within the second chamber in a corresponding manner, and
(G) wherein movement of the piston away from the front end of the drug cartridge housing creates negative pressure within the second chamber, and
(H) wherein the negative pressure created in the second chamber pulls the liquid component through the first one-way valve into second chamber.

In certain embodiments, a drug cartridge for use in a device for spraying a therapeutic compound comprises:
(A) a housing having a front end and a back end;
(B) a first chamber containing a liquid component, wherein the liquid component is confined at a first end by a first piston and at a second end by a first one-way valve;
(C) a second chamber containing a solid component, wherein the solid component is confined at a first end by a second piston having a cavity formed in an end thereof and at a second end by the first one-way valve and a second one-way valve;
(D) a bottom chamber; and
(E) a nozzle;
(F) wherein movement of the second piston away from the front end of the housing creates negative pressure within the second chamber, and
(G) wherein the negative pressure created in the second chamber pulls the liquid component through the first one-way valve into second chamber.

In certain embodiments, the drug spraying device disclosed herein enables the sustained release of a hair growth-promoting agent, without the use of highly hydrophobic, occlusive matrices. In particular, the drug spraying device enables the delivery of a hair growth-promoting agent in microspheres (e.g., PLG microspheres) such that the microspheres stay at the wound site for a prolonged period of time and are not cleared rapidly by phagocytosis. A prolonged period of time can be at least 1, 2, 3, 4, 5, 6, 7, 8, 9, 10, 11, 12, 13, 14, 15, 16, 17, 18, 19, or at least 20 days.

In certain embodiments, the drug spraying device disclosed herein enables the sustained release of a hair growth-promoting agent and uptake by the skin through a scab. In particular, the drug spraying device enables the delivery of a hair growth-promoting agent such that the delivery system is incorporated into the scab. This can be accomplished by placing a hair growth-promoting agent-containing, thin, gauze-like, pliable biodegradable scaffold on the fresh wound. The material properties of the scaffold will be adjusted such the gauze is able to absorb the blood and other exudates from the wound. In certain, more specific embodiments, the biodegradable scaffold has high content of void space, to absorb blood, fibrin and fibrinogen. In some embodiments, after placement of the drug-containing biodegradable scaffold into the wound, an in-situ crosslinking hydrogel is applied on top to cover the entire site as a wound dressing.

In certain embodiments, the drug spraying device disclosed herein enables the concurrent delivery of two or more drugs with different solubility properties and/or physical/chemical incompatibilities (such as different excipient requirements; binding and/or reaction of the two or more drugs with each other).

In certain embodiments, the drug spraying device disclosed herein enables the cleansing and administration of one or more drugs with one single device. In these embodiments, the contents of each chamber could be sprayed separately. Once chamber can contain the cleansing solution; the liquid in the other chamber contains a hair growth-promoting agent. Any wound-cleansing solution known to the skilled artisan can be used with these embodiments.

5.5.2.2 Parenteral Administration

Administration of the pharmaceutical compositions described herein, for example, in Sections 5.2, 5.3, and 5.4 supra can be parenteral by injection, infusion, or implantation, for local or systemic administration. Parenteral administration, as used herein, includes intravenous, intraarterial, intraperitoneal, intrathecal, intraventricular, intraurethral, intrasternal, intracranial, intramuscular, intrasynovial, intravesical, and subcutaneous administration. Compositions for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra). Compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases. All such compositions must be sterile, as known in the art. The compositions for parenteral administration can be formulated as a suspension, solid, semi-solid, or thixotropic liquid, for administration as an implanted depot. In one embodiment, the compositions are dispersed in a solid inner matrix, which is surrounded by an outer polymeric membrane that is insoluble in body fluids but allows the active ingredient in the pharmaceutical compositions diffuse through. Suitable inner matrixes include, but are not limited to, polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate. Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

5.5.2.3 Oral Administration

Pharmaceutical compositions described herein, e.g., for use in post-perturbation treatments described in Section 5.2, or comprising hair growth-promoting agents (Section 5.3) and/or other active ingredients (Section 5.4) disclosed herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide. Compositions for oral administration can be also provided in the forms of liposomes, micelles, microspheres, or nanosystems. Micellar dosage forms can be prepared as described in U.S. Pat. No. 6,350,458.

5.5.3 Ex Vivo Delivery

The pharmaceutical compositions described herein may also be administered to skin-derived cells or skin tissue ex vivo. For example, a hair growth-promoting agent treatment may be used to enhance the re-association of dissociated hair follicle cells into follicles and their growth and expansion in culture for their implantation into fresh wounds and scar revisions. Thus, in some embodiments, hair follicles promoted by a hair growth-promoting agent treatment are added to an area of skin before, at the time of, and/or subsequent to, integumental perturbation. With these methods, traditional approaches to scar revision, such as human skin transplantation, can be efficiently replaced with transplantation of follicular units or other smaller appendage structures from skin. Thus, hair follicles can be introduced to the wound by migration, reorganization, stimulation, or activation, or de novo hair follicle neogenesis, or by transplanting one or more of the following skin elements: full skin (xeno-; autologous human), follicular units, dissociated cells (donor dominance; recipient effects), ex vivo-expanded skin and/or follicular units, or human skin equivalents in vivo (universal donors). Engineered human skin, or human skin equivalents, can also be used for hair follicle formation and activation and scar revision platforms.

Human skin equivalents can be grown and assembled in vitro, with the advantage that they can be grown to theoretically to any size/shape; can be comprised of different types of cells, including keratinocytes (hair follicle derived and non-hair follicle derived), dermal cells (hair follicle derived and non-hair follicle derived), other cell types (e.g., mesenchymal stem cells); can contain cells that are genetically modified to include, e.g., markers or "inducible" signaling molecules; provide an unlimited and uniform source of human cells; from normal skin based on histology and marker studies; are generally devoid of skin appendages; and can be wounded and show similar wound healing events as in vivo.

5.5.4 Modified Release Forms

The hair growth-promoting agents and other active ingredients disclosed herein can be formulated as modified release dosage forms. As used herein, the term "modified release" refers to a dosage form in which the rate or place of release of the hair growth-promoting agent or other active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The compositions in modified release dosage forms can be prepared using a variety of modified release devices and methods known to those skilled in the art, including, but not limited to, matrix controlled release devices, osmotic controlled release devices, multiparticulate controlled release devices, ionexchange resins, enteric coatings, multilayered coatings, microspheres, liposomes, and combinations thereof. The release rate of the active ingredient(s) can also be modified by varying the particle sizes and polymorphism of the active ingredient(s). In some embodiments, the controlled release is achieved by using an adjuvant that causes a depot effect, i.e., that causes an active agent or antigen to be released slowly, leading to prolonged exposure to a target cell or tissue (e.g., cells of the follicle, or, in the case of immunostimulatory adjuvants, prolonged exposure to the immune system).

Examples of formulations for modified release to skin or hair include those described in International Patent Application Publication No. WO 2008/115961, published Sep. 25, 2008, which is incorporated herein by reference in its entirety. Other examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80, each of which is incorporated by reference herein in its entirety.

5.5.4.1 Matrix Controlled Release Devices

The modified release dosage form can be fabricated using a matrix controlled release device known to those skilled in the art. See, Takada et al., 1999, in *Encyclopedia of Controlled Drug Delivery*, Mathiowitz E, ed., Vol. 2, Wiley.

In certain embodiments, the modified release dosage form is formulated using an erodible matrix device, which is water-swellable, erodible, or soluble polymers, including, but not limited to, synthetic polymers, and naturally occurring polymers and derivatives, such as polysaccharides and proteins. Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the compositions are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The modified release dosage forms can be prepared by methods known to those skilled in the art, including direct compression, dry or wet granulation followed by compression, and melt-granulation followed by compression.

5.5.4.2 Osmotic Controlled Release Devices

The modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

A semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

An osmotic controlled-release dosage form can further comprise additional conventional excipients or carriers as described herein to promote performance or processing of the formulation. The osmotic controlled-release dosage forms can be prepared according to conventional methods and techniques known to those skilled in the art. See *Remington: The Science and Practice of Pharmacy, supra*; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the compositions are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Publication No. WO 2002/17918. The AMT controlled-release dosage forms can be prepared according to conventional methods and techniques known to those skilled in the art, including direct compression, dry granulation, wet granulation, and a dip-coating method. In certain embodiments, the compositions are formulated as ESC controlled-release dosage form, which comprises an osmotic membrane that coats a core comprising the active ingredient(s), a hydroxylethyl cellulose, and other pharmaceutically acceptable excipients or carriers.

5.5.4.3 In Situ Gelling Drug Delivery Systems

In one embodiment, a pharmaceutical composition described in Section 5.2, Section 5.3, and/or Section 5.4 supra can be formulated as a polymeric solution that consists of a water-soluble polymer that is a solution at room temperature (20-25° C.) and below, but gels at physiological temperatures of 32-37° C. In one application the solution can be cooled to 2-8° C. to impart a soothing effect, while being sprayed as a liquid spray on the tissue surface. Once sprayed on, the solution will thicken into a gel, releasing the any drug contained therein slowly over time. Examples of these thermo-gelling polymers are poly(isopropyl acrylamide), poly(EO)x-(PO)y-(EO)x and poly(PO)x-(EO)y-(PO)x, wherein EO=ethylene oxide and PO=propylene oxide. Other examples include, but are not limited to, PLA-PEO-PLA polymers, wherein PLA=polylactic acid, PEO=polyethylene oxide, poly(sebacic anhydride)-poly(ethylene oxide)-poly (sebacic anhydride) and poly(stearate)-poly(ethylene oxide)-poly(stearate). In a variation of the idea, the solution can be injected as a liquid, to form an in situ depot within the tissue. In another variation of the concept, the solution can be delivered as a solution, which can flow into orifices of the tissue, such as hair follicles and then form a gel to release the hair growth-promoting agent for follicle-associated conditions, such as MPHL, folliculitis, or another condition described herein. The temperature and time of gelation can be correlated to the concentration of the polymers and the length of the polymer blocks that constitute the polymers.

5.5.4.4 Multiparticulate Controlled Release Devices

The a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including microfluidization, membrane-controlled emulsification, oil-in-water, water-oil-water and oil-in oil emulsification and homogenization processes, complex coacervation, wet- and dry-granulation, extrusion/spheronization, roller-compaction, melt-congealing, and by spray-coating seed cores. See, for example, Ghebre-Sellassie, ed., 1994, *Multiparticulate Oral Drug Delivery*, Marcel Dekke; and Ghebre-Sellassie ed., 1989, Pharmaceutical Pelletization Technology, Marcel Dekker.

Other excipients or carriers as described herein can be blended with the compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

5.5.4.5 Targeted Delivery

The pharmaceutical compositions for use herein may be formulated with a carrier that delivers the hair growth-promoting agent or other active ingredient(s) to the site of action, for example, a follicle in a particular tissue. Such targeted delivery may be preferable in formulations for systemic administration, in order to reduce side effects associated with therapy with the hair growth-promoting agent or other active ingredient(s) and/or ensure that the hair growth-promoting agent or other active ingredient(s) reaches only follicles of particular tissues. The carrier may be an aptamer targeted to a particular protein or cell type in the follicle, an antibody or antigen-binding fragment thereof, a virus, virus-like particle, virosome, liposome, micelle, microsphere, nanoparticle, or any other suitable compound.

Compositions for use in the methods provided herein can also be formulated to be targeted to a particular tissue, follicle, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

In some embodiments, targeting is accomplished by the attachment of specific targeting moieties to the delivery systems containing the drug. Targeting moieties can be in the form of antibodies, aptamers or small molecules that bind to specific proteins expressed in specific tissues. Specific or guided targeting can "channel" the drug only to the specific tissue type, thus minimizing distribution to all tissues. This concept is especially useful if the drug causes side effects. For hair follicle drug delivery, microspheres and nanospheres have been utilized, to deliver drugs into the hair follicle. Entry into the hair follicle is governed by the size of the drug-containing spheres, with microspheres of size 0.5-0.7 microns of ideal size for entry. However, out-flux of sebaceous fluid from the hair follicle can result in a short residence time of the delivery systems in the follicle. To minimize this, the surface of the microspheres can be functionalized with moieties that bind to specific surfaces in the follicular orifice to "retain" them at the site. These moieties can be non-specific, such as hydrophobic coatings, or cationic coatings, in order to be bioadhesive to cells within the follicle. The moieties can be specific and targeted to certain proteins that are expressed specifically on specific cell membranes. For example, proteins over-expressed on the follicular lymphoma cell surfaces can be targeted by delivery systems that have antibodies or aptamers designed to bind to these proteins. The surface of the delivery systems can also be functionalized with cell-penetrating moieties such as cell-permeable peptides, positively charged polymers that bind to anionic cell surfaces.

5.5.4.6 Local Delivery

In order to circumvent side effects, the dosage of any systemically administered drug is tightly controlled. Another way in which such side effects may be circumvented is to deliver the drug locally to the site where hair growth modulation is desired.

The hair growth-promoting agents or other active ingredient(s) described herein may be delivered locally to any part of the subject in which modulation of hair growth is desired, including, e.g., the head (e.g., the scalp, cheek, chin, upper lip, lower lip, ears, nose, eyelashes, or eyebrow), neck, abdomen, chest, breast, e.g., the nipples, back, arms, armpits (axillary hair), stomach, genital area, buttocks, legs, hands, or feet of a subject. In one embodiment, hair growth-promoting agent is applied or administered to wounded or scarred skin.

Such local delivery of the hair growth-promoting agent or other active ingredient(s) can be achieved by topical administration, transdermal, intradermal, subcutaneous (depot effect), or by intramuscular, intravenous and oral routes of delivery in formulations for targeting systemically delivered hair growth-promoting agent to desired follicles. Such modes of delivery are discussed supra.

5.5.5 Delivery Via Scaffolds

In some embodiments, enhancement of hair follicle formation in integumentally perturbed skin is accomplished by treatment with a pharmaceutical combination described herein in combination with a pre-designed biomaterial dressing that may serve as a substrate to encourage a step-wise attachment of keratinocytes and epithelial cells to it, such that formation of an organized extra-cellular matrix (ECM) is enhanced in order to promote wound healing. Without being bound by any theory, formation of an organized extracellular matrix leads to less granular epithelialization of the wound and, therefore, less scarring. Furthermore, and also without being bound by any theory, it is thought that the presence of a "scaffold" at the wounded or perturbed site prevents rapid wound contraction, whereupon the edges of the wound contract in a rapid, haphazard manner to produce granular collagen-rich skin devoid of any adnexal structures such as follicles or sweat glands, and rapid wound contraction by secondary intention almost always results in fibrous tissue that is sub-optimal in temperature regulation, tensile and compressive strength and barrier function.

The scaffold for use in combination with treatment with a pharmaceutical composition described herein may be comprised of a mesh of a biocompatible, bioabsorbable material that cells recognize and attach to, preferably with ease. For example, these materials can be collagen type VIII, hyaluronic acid, chitosan, alginates, or combinations and derivatives thereof or any other such material described herein or known in the art. The mesh scaffold may be neutral, or charged. If the mesh is positively charged, it may permit cells (which are negatively charged) to adhere to it more effectively. If the mesh scaffold is negatively charged, it may contain signaling moieties that the cells will recognize and attach to. For example, polymers such as hyaluronic acid are present already in skin, and thus a mesh comprised of this material is thought to be compatible with cells.

In some embodiments, the scaffold is pre-fabricated with a fine microstructure that is of the dimension of cells, for example, red blood cells that will initially diffuse throughout the scaffold, or epithelial cells and keratinocytes from surrounding tissue. Moreover, it is envisioned that the "epithelial tongue" can move with greater ease and organization by crawling on the scaffold mesh.

In some embodiments, the mesh scaffold has an "open-cell" structure, with the pores inter-connected, much like an open-celled foam. The open, interconnecting nature of the scaffold may allow free diffusion of oxygen and cells, so that optimal organized wound healing can occur.

In some embodiments, the mesh scaffold has the capacity to hydrate and remain hydrated throughout the wound healing period. This is useful because, without being bound by any theory, drying out of the wound results in an impermeable granular structure that the keratinocytes cannot "crawl upon."

In some embodiments, the mesh scaffold has moieties that act as molecular signals to the cells, for example, to aid their proliferation. These moieties include, but are not limited to, peptidoglycans and RGD integrin recognition sequences that encourage cell attachment and subsequent proliferation.

In some embodiments, the mesh scaffold has incorporated within it one or more active agents, for example, a small molecule, or a nucleic acid, or a protein. In some embodiments, the additional active agent is a protein, such as noggin or WNT, or is a nucleic acid that encodes noggin or WNT. In some embodiments, a small molecule is incorporated into the scaffold, such as, e.g., a hair growth-promoting agent (such as one or more hair growth-promoting agents described herein, or another hair growth-promoting agent), BMP inhibitor, or PPAR antagonist.

In some embodiments, the compound incorporated in the mesh scaffold is a compound considered for use in the combination therapies described herein, for example, in Sections 5.2-5.4. For example, the scaffold may incorporate superoxide dismutase, a free radical quenching molecule that functions in the reduction of inflammation. In other embodiments, compounds are included in the mesh scaffold that alter the kinetics of wound healing, for example, that slow wound healing. Such compounds are known in the art and described elsewhere herein. Other compounds that may be incorporated in the mesh scaffold include growth factors that aid in cell proliferation and tissue regeneration. In some embodiments, the compounds aid in hair follicle migration or the formation of new or activated follicular structures in the integumentally perturbed or wounded site.

In some embodiments, a hair growth-promoting agent is incorporated within the mesh scaffold. In some embodiments, the hair growth-promoting agent is incorporated within one or more layers of a multilayered mesh scaffold. For example, in one embodiment the mesh scaffold contains the hair growth-promoting agent in alternating layers, which may achieve a pulsatile delivery of hair growth-promoting agent. In some embodiments, the hair growth-promoting agent is incorporated in microspheres in the scaffold, enabling a controlled release of hair growth-promoting agent from the scaffold.

In another embodiment, the mesh scaffold can be fibrin gels that additionally contain hair growth-promoting agent. A fibrin network is the first scaffold that a cell encounters as it performs its role in healing wounds due to trauma or other insults to tissue. Unlike the extracellular matrices and basement membranes that are formed by collagen, laminin and proteoglycans, which assemble slowly in an ordered manner, the fibrin network (the "scab") assemble rapidly by a modified polycondensation reaction from fibrinogen, an abundant constituent of blood plasma, as soon as the protease thrombin is activated in the clotting cascade—the result is a three-dimensional network of branching fibers, What is envisioned is a fibrin delivery matrix containing hair growth-promoting agent, fibrinogen and thrombin, that "gels" in situ. One issue that is encountered is the ability of hair growth-promoting agent to diffuse through the fibrin "scab"—making the drug part of the scab solves this issue.

In another embodiment, the mesh scaffold is a synthetic biodegradable dressing and hair growth-promoting agent delivery system that also acts as a "sponge" and absorbs the exudates/bloods from a wound or otherwise integumentally perturbed site. These exudates intercalating with the synthetic scaffold contain an abundance of fibrinogen, thrombin, fibronectin, cell adhesion proteins, growth factors and hyaluronic acid, all of which create an integrated structure that is an attractive matrix for cell attachment/differentiation and delivery of hair growth-promoting agent. The release rate of hair growth-promoting agent can be modulated by varying the composition of polymers that comprise the synthetic scaffold, or sponge. For example, a synthetic scaffold fabricated out of poly(lactide)-co-(glycolide) (PLG) and poly(lactide) (PLA) can be developed to have varied release profiles of hair growth-promoting agent. Changing the ratio of PLA to PLG will change the release profile of the hair growth-promoting agent from the scaffold. Other polymers that can utilized to generate synthetic scaffolds are chitosan, carrageenan, alginate, poly(vinyl alcohol), poly(ethylene oxide) (PEO), poly(ethylene oxide)-co-poly(propylene oxide)-co-poly(ethylene oxide) (PEO-PPO-PEO), poly(acrylates) and poly(vinyl pyrrolidone) (PVP). By varying the composition of polymers, the rate of hair growth-promoting agent release from the formulation (e.g., scaffold or sponge) can be controlled, so that it takes anywhere from 2 hours to 30 days for most (e.g., 80% or more, 85% or more, 90% or more, 95% or more, 98% or more, or 100%) of the hair growth-promoting agent to be released. In some embodiments, most of the hair growth-promoting agent is released from the formulation within 2 hours, within 4 hours, within 8 hours, within 16 hours, within 24 hours, within 36 hours, within 48 hours, within 3 days, within 5 days, within 7 days, within 10 days, within 14 days, within 30 days, or within 2 months or more.

In some embodiments, the mesh scaffold releases the aforementioned compounds in a timed release manner, acting as a controlled release formulation such as described in Section 5.3.1 above. For example, the compounds may be bound to the mesh scaffold, and are then released at a sustained release manner as a result of de-binding kinetics from the mesh. In some embodiments, the compound may be bound to a polymer, which is then incorporated to the mesh scaffold, and which may allow the compound to diffuse from the mesh at a slow rate, resulting in sustained release.

In some embodiments, the mesh scaffold is extruded as a gel, with certain components of the gel precipitating out to form a mesh in situ. Alternatively, in some embodiments, the in situ mesh can be sprayed on the wounded or otherwise perturbed surface, such as tissue that has been extensively burned. A large area can be covered in this manner.

In some embodiments, the mesh scaffold is pre-fabricated as a dressing or a wrap, to cover large areas of wounded or otherwise perturbed tissue. In some such embodiments, the mesh scaffold can be cut to size to fit the size of the wound or perturbed site to present a compatible surface for favorable movement of the epithelial tongue.

In some embodiments, the scaffold is prepared by melt spinning, electrospinning, micromachining, weaving, or other methods known in the art in which open cell foams are fabricated. Using starting materials that are United States Pharmacopeia (USP)-approved, the mesh scaffold can be fabricated by these methods, with the optional incorporation of additional compound(s) (which are optionally sterilized), then sterilized by gentle ethylene oxide sterilization. In some embodiments, the additional compounds are sterilized, and then added to the sterile mesh scaffold.

In a particular embodiment, a combinatorial strategy that uses a biodegradable scaffold combined with integumental perturbation and, optionally, administration of a hair growth-promoting agent formulation or other pharmaceutical composition described herein is applied, which may result in the in situ generation of embryonic stem cells or recruitment of cells required for healing following wounding or other form of integumental perturbation. This approach may be used together with a form of integumental perturbation described in Section 5.1 (e.g., dermabrasion accomplished by a standard dermabrader or a laser, deep full-thickness excision (as for deep burns) accomplished by a bulk ablative laser) or integumental perturbation by acute wounds, chronic wounds, or wounds generated for the purpose of scar revision. While not being bound by any theory of how the invention works, such integumental perturbation in combination with a scaffold that administers drug results in the in situ generation of stem cells or recruitment of other cells required for the wound healing process and may facilitate more effective wound healing with little or no scarring.

5.5.5.1 Biodegradable Properties of the Scaffold

In one embodiment, the scaffold is biodegradable. Placement of a 3-dimensional biodegradable scaffold in the wound assists the attachment, growth and differentiation of cells. Historically, tissue repair has been by autologous cell/tissue transplantation—however, autografts are associated with donor site morbidity and limited availability. An alternative is allografts, but these are susceptible to immune responses and also carry the risk of disease transfer. Thus, tissue engineering has emerged as an interdisciplinary field that makes use of biomaterials, cells and factors either alone, or in combination to restore tissues. The tissue engineering strategy generally involves isolation of healthy cells from a patient, followed by their expansion in vitro. These expanded cells are then seeded onto three-dimensional biodegradable frameworks that provide structural support for the cells and allow cellular infiltration, attachment, proliferation and growth ultimately leading to new tissue. In a sense, natural wound healing utilizes a "scaffold" as well—the fibrin clot. A fibrin network is the natural network that forms rapidly due to a polycondensation reaction from fibrinogen, an abundant constituent of blood plasma, as soon as the protease thrombin is activated in the clotting cascade. The fibrin clot then forms a three-dimensional network for cells to attach, for re-epithelialization.

In some embodiments, the biodegradability of the scaffold is modulated. Ideally, the biodegradability of the scaffold should be matched to the formation of the new epithelium due to wound healing or other form of integumental perturbation. One skilled in the art would know how to measure whether a synthetic matrix is biodegradable. For example, biodegradability can be measured ex vivo in implants or using rats or another animal model, by histological and HPLC analysis. In one embodiment, biodegradability by hydrolysis can be assessed. In such an embodiment, the scaffold structure of choice is incubated in phosphate buffered saline, pH 7.4 and 37° C. For degradation by enzymolysis, the incubation buffer includes enzymes. The scaffolds are weighed prior to incubation. The scaffolds are retrieved two-at-a-time at predetermined time points and dried in a vacuum oven. The scaffolds are weighed at each time point and a plot of weight versus time is generated to develop the rate of biodegradability. In one embodiment, the biodegradability of the scaffold matrix is modulated to coincide with the healing process, and can be modulated by changing the composition of polymers utilized to fabricate the mesh. For example, a percentage of polyethylene glycol (PEG) can be included in a composition with PLG to increase biodegradation (for example, see ASTM E1279-89, 2008, Standard Test Method for Biodegradation By a Shake-Flask Die-Away Method).

5.5.5.2 Biomimetic Properties of the Scaffold

Biodegradable synthetic matrices can be created to mimic the extra-cellular micro-environment for the enhanced cellular attachment necessary for tissue regeneration. In some embodiments, cell-recognition motifs such as RGD peptides may be incorporated to encourage cells to attach themselves to the scaffold.

One skilled in the art would know how to measure whether the biodegradable synthetic matrix has biomimetic properties. For example, in one embodiment, the biomimetic nature of the scaffold is judged on the basis of the content of the mesh and resultant intercalating fibrin.

5.5.5.3 Physical Properties of the Scaffold

The properties of the synthetic scaffold are dependent upon the three-dimensional geometry, matching of the modulus of the matrix with the tissue type and the porosity. It has been shown that the differentiation process can be modulated if the modulus of the tissue type is matched with the modulus of the scaffold.

One skilled in the art would know how to measure whether the biodegradable synthetic matrix has optimal physical properties. For example, in one embodiment, the modulus of the scaffold is matched with the modulus of the tissue type. In general, the compressive modulus of a scaffold or hydrogel can be measured by a standard Instron instrument (e.g., using the TA Instruments DMA Q800).

5.5.5.4 Biocompatibility of the Scaffold

Further, the micro-environment created by the cells is optimally highly biocompatible to the cells present at the site, namely keratinocytes and stem cells derived from the dermal papilla. In one embodiment, this can be accomplished through the use of hydrophilic components that can absorb water. Use of hydrophobic components such as petrolatum is likely to be occlusive and prevent rapid cell proliferation.

One skilled in the art would know how to measure whether the biodegradable synthetic matrix is biocompatible. For example, in one embodiment, the scaffold is incubated with human foreskin fibroblasts (HFF) in vitro and the scaffold is considered to be biocompatible if the cells maintain their shape and attach appropriately. See, e.g., the following reference for studies on the biocompatibility of materials: Altankov et al., 1996, Journal of Biomedical Materials Research Part A; 30:385-391, which is incorporated by reference herein in its entirety.

5.5.5.5 Oxygen Permeability of the Scaffold

In some embodiments, the biodegradable scaffold is permeable to water, nutrients, oxygen and growth factors, enabling easy exchange of nutrients between tissues and cells (see, e.g., ASTM D39857). In some embodiments, a non-occlusive, non-permeable barrier is avoided.

5.5.5.6 Utility of the Scaffold in Deep Wounds

In one embodiment, the scaffold is used to "fill" a deep wound, as is common in a deep burn, to provide a matrix for the cells to attach, grow and differentiate—existence of the scaffold will likely minimize the scar formation normally observed in deep, large-area wounds.

5.5.5.7 Combined Biological/Synthetic Mesh

In another embodiment, a loose, dry, highly porous network or scaffold or mesh is placed in the bleeding site of the wound or otherwise integumentally perturbed site to gently absorb the blood and the cell adhesion proteins released at the site. This will result in creation of a highly rich environment that consists of a combination of a 3-dimensional scaffold combined with fibrinogen and thrombin, which will ultimately result in a highly biocompatible hydrogel suitable for cell attachment and growth. In some embodiment, inclusion of blood components and cell adhesion proteins into the network is critical for establishment of the ECM (extracellular matrix) necessary to form continuous tissue in-growth, particularly in the case of large-area and deep wounds.

A dry scaffold has the added advantage of absorbing the blood at the wound or otherwise integumentally perturbed site. Thus, a person's own blood components can be used to create a combined synthetic/natural ECM. In practical terms, the scaffold has an added advantage of serving as a blood absorbing gauze.

In another embodiment, the scaffold has cell-recognition motifs, such as RGD peptides, to recruit cells to the site and attachment, thereof. Once attached, cells will proliferate. Without being bound by any theory, it is hypothesized that the primary attachment of cells to the scaffold is a critical step to prevent premature cell death.

In one embodiment, a dry, sterile biodegradable scaffold is placed onto the freshly formed wound or perturbed skin site. The properties of the scaffold will be such that it will transform into an adherent hydrogel upon water absorption.

5.5.5.8 Fabricating and Applying the Scaffold

Methods that may be employed to fabricate the scaffold are known in the art, and include electrospinning, micromachining, and others. Nano-fiber meshes fabricated by electrospinning, hydrogel imprint technologies have been utilized to create three-dimensional microstructures that match the supramolecular architecture of the tissue type. In situ forming scaffolds are also contemplated.

In some embodiments, the active agents (e.g., hair growth-promoting agent alone or in a combination described herein) are administered using an active agent-containing spray-on hydrogel. In one such embodiment, after placement of the biodegradable scaffold, the active agent is sprayed on the tissue. The active agent (or combination of active agents, e.g., a hair growth-promoting agent and a stem cell signaling agent) may be incorporated into a spray-on hydrogel that will be sprayed on as a liquid, but which transforms into a hydrogel after it is sprayed on the tissue. This will be especially useful if the area of the wound or integumental perturbation is large and uniform coverage is needed.

In some embodiments, the active agent-containing spray-on hydrogel is applied on the wound or otherwise integumentally perturbed site, forming a cross-linked hydrogel that releases active agent over the time period of healing or a shorter or longer time period, as necessary. Depending upon the release characteristics that are required, the active agent will either be incorporated in micro-encapsulates or nano-encapsulates and suspended into the pre-hydrogel solution. The active agent can also be dissolved into the pre-hydrogel solution. The "pre-hydrogel" solution is defined as the solution that will be sprayed on the tissue and which also contains the active agent.

In some embodiments, the active agent is contained within microspheres that can be positively charged to rapidly bind themselves to the negatively charged collagen present in the dermis. Binding the microspheres to the dermis renders the active agent-releasing moiety immobile at the site.

In a variation of the foregoing embodiments, the wound or otherwise integumentally perturbed site may be covered with a breathable, non-occlusive spray-on hydrogel to cover the site from infection during healing.

5.6 Treatment Regimens

For any of the treatments described infra, in specific embodiments, a particular treatment can be administered prior to, concurrently with, or subsequent to the administration of a second (or third, or more) treatment. In certain embodiments, the second or third or later treatment comprises treatment with the same active agent, albeit at a different (e.g., in one embodiment, higher) dose.

In one embodiment, one treatment is administered to a subject at reasonably the same time as the other treatment. This method provides that the two administrations are performed within a time frame of less than one minute to about five minutes, or up to about sixty minutes from each other, for example, at the same doctor's visit.

In another embodiment, one treatment and another treatment are administered at exactly the same time.

In yet another embodiment, one treatment and the other treatment are administered in a sequence and within a time interval such that the one treatment and the other treatment can act together to provide an increased benefit than if they were administered alone. In another embodiment, the one treatment and the other treatment are administered sufficiently close in time so as to provide the desired outcome. Each can be administered simultaneously or separately, in any appropriate form and by any suitable route. In one embodiment, the one treatment and the other treatment are administered by different routes of administration. In an alternate embodiment, each is administered by the same route of administration. In certain embodiments, the one treatment and the other treatment can be administered at the same or different sites of the subject's body. When administered simultaneously, the one treatment and the other treatment may or may not be administered in a single formulation, a mixture of formulations, or at the same site of administration, or by the same route of administration.

In various embodiments, the one treatment and the other treatment are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In other embodiments, the one treatment and the other treatment are administered 2 to 4 days apart, 4 to 6 days apart, 1 week a part, 1 to 2 weeks apart, 2 to 4 weeks apart, one month apart, 1 to 2 months apart, 2 to 3 months apart, 3 to 4 months apart, 4 to 5 months apart, 6 months apart, 6 months to one year apart, or one year or more apart. In some embodiments, the one treatment and the other treatment are administered in a time frame where both are still active. One skilled in the art would be able to determine such a time frame by determining the half life of each administered component.

In one embodiment, the one treatment and the other treatment are administered within the same patient visit. In one embodiment, the one treatment is administered prior to the administration of the other treatment. In an alternate embodiment, the one treatment is administered subsequent to the administration of the other treatment.

In certain embodiments, the one treatment and the other treatment are cyclically administered to a subject. Cycling treatment involves the administration of one or more treatments once or for a period of time, followed by the administration of the other treatment once or for a period of time, and repeating this sequential administration. The first treatment may be with the one treatment or with the other treatment, depending on the subject's prior treatment history and the intended outcome. Not only does such cycling treatment have the advantages described herein, cycling treatment can also reduce the development of resistance to one or more of the treatments, avoid or reduce the side effects of one of the treatments, and/or improve the efficacy of the treatment. In such embodiments, alternating administration of the one or more treatments may be followed by the administration of another treatment (or vice versa) 1 year later, 6 months later, 3 months later, 1 month later, 3 weeks later, 2 weeks later, 1 week later, 4 to 6 days later, 2 to 4 days later, or 1 to 2 days later, wherein such a cycle may be repeated as many times as desired. In certain embodiments, the one (or more) treatments and the other treatment are alternately administered in a cycle of 3 weeks or less, once every two weeks, once every 10 days or once every week. Such time frames can be extended or reduced depending on properties of the treatment, e.g., whether a controlled release formulation is used, and/or depending on the progress of the treatment course.

In particular embodiments, subjects discontinue their current treatment (e.g., topical minoxidil or finasteride), the area to be treated is integumentally perturbed, and the post-perturbation treatment is applied for 12 days. After 12 days, the post-perturbation treatment is discontinued, and treatment with the current treatment (or another hair growth-promoting agent, or a combination of hair growth-promoting agents) is re-started. In some embodiments, the subject is treated with 10 cycles of the protocol: integumental perturbation followed by post-perturbation treatment (e.g., for 3 months, 4 months, 5 months, 6 months, 7 months, 8 months, 9 months, 10 months, 11 months, or 12 months) alternating with the other treatment, e.g., with hair growth-promoting agent (e.g., for 3 months, 4 months, 5 months, 6 months, 7 months, 8 months, 9 months, 10 months, 11 months, or 12 months).

In certain embodiments, the timing of treatment or a combination of treatments can be coordinated with the presence or absence of indicators of hair growth in a treated area of skin. For example, the timing of repeated treatments with integumental perturbation (optionally in combination with a post-perturbation treatment) or a treatment with integumental perturbation (optionally in combination with a post-perturbation treatment) preceded or followed by one or more hair growth-promoting agent treatments may be adjusted based on the appearance, or anticipated appearance, of one or more of the following indicators in a treated skin site: NL, PEL, and/or PELA follicular structures, pre-existing vellus hair, new vellus hair, vellus-to-terminal hair switch, terminal hair, terminal-to-vellus hair switch, etc.

In an exemplary embodiment in which integumental perturbation involving hair transplantation (e.g., follicular unit extraction) accompanies treatment with one or more hair growth-promoting agents, an area of scalp that was pre-treated with one or more hair growth-promoting agents, e.g., minoxidil or finasteride, is used as a source for transplanted follicles. Before hair follicle removal, a perturbation treatment is administered to the sites from which transplanted tissue will be obtained. This site undergoes post-perturbation treatment for one week, and then discontinued and followed by treatment with, e.g., minoxidil or finasteride for three months. In another exemplary embodiment in which integumental perturbation involving hair transplantation (e.g., follicular unit extraction) accompanies treatment with one or more hair growth-promoting agents, an area of scalp that was formerly a donor area in a previous hair transplant is treated before a subsequent hair transplant. The former donor site is pre-treated with one or more hair growth-promoting agents, e.g., minoxidil or finasteride, and this site will be used as a source for transplanted follicles. Before hair follicle removal, a perturbation treatment is administered to the sites from which transplanted tissue will be obtained. This site is integumentally perturbed, and the post-perturbation treatment is applied for one week, and then discontinued and followed by treatment with, e.g., minoxidil or finasteride for three months or more. In another exemplary embodiment in which integumental perturbation involving hair transplantation (e.g., follicular unit extraction) accompanies treatment with one or more hair growth-promoting agents, an area of scalp that was formerly a donor area in a previous hair transplant is treated before a subsequent hair transplant. Before hair follicle removal, a perturbation treatment is administered to the sites from which transplanted tissue will be obtained without any pre-treatment with a hair growth-promoting drug, e.g. minoxidil or finasteride. This site is integumentally perturbed, and the post-perturbation treatment is applied for one week, and then discontinued and followed by treatment with, e.g., minoxidil or finasteride for three months or more. In another exemplary embodiment in which integumental perturbation involving hair transplantation (e.g., follicular unit extraction) accompanies treatment with one or more hair growth-promoting agents, an area of scalp that has not been a donor area in a previous hair transplant but will be used in the future is treated before a subsequent hair transplant. This site is pre-treated with one or more hair growth-promoting agents, e.g., minoxidil or finasteride, and this site will be used as a source for transplanted follicles. Before hair follicle removal, a perturbation treatment is administered to the sites from which transplanted tissue will be obtained. This site is integumentally perturbed, and the post-perturbation treatment is applied for one week, and then discontinued and followed by treatment with, e.g., minoxidil or finasteride for three months or more. In another exemplary embodiment in which integumental perturbation involving hair transplantation (e.g., follicular unit extraction) accompanies treatment with one or more hair growth-promoting agents, an area of scalp that has not been a donor area in a previous hair transplant but will be used in the future is treated before a subsequent hair transplant. Before hair follicle removal, a perturbation treatment is administered to the sites from which transplanted tissue will be obtained without pre-treatment with a hair growth-promoting drug, e.g. minoxidil or finasteride and the post-perturbation treatment is applied for one week, and then discontinued and followed by treatment with, e.g., minoxidil or finasteride for three months or more.

Specific exemplary regimens pertaining to the treatment steps described in Section 5.1, 5.2, and 5.3, respectively, follow.

5.6.1 Integumental Perturbation Treatment Regimens

In some embodiments, integumental perturbation is performed in combination with one or more techniques of depilation (removal of the part of the hair above the surface of the skin) or epilation (removal of the entire hair, including the part below the skin) on a part of the skin to be treated. Any form of epilation or depilation known in the art can be used. Methods of depilation that can be used include, but are not limited to, shaving, the use of abrasive materials, a mechanical device, and the use of chemical depilatories (e.g., Nair® or thioglycolic acid), which work by breaking the disulfide bonds that link the protein chains that give hair its strength, making the hair disintegrate. Methods of epilation that can be used include, but are not limited to, plucking with tweezers, waxing, sugaring, epilation devices, threading, home pulsed light, laser, electrolysis, and can include the use of hair growth retardants (e.g., Vaniqa® (eflornithine)). Prior to disruption, the skin can depilated or epilated.

In some embodiments, depilation is performed prior to integumental perturbation. In some embodiments, depilation is performed immediately prior to integumental perturbation. In some embodiments, depilation is performed 5 minutes, 10 minutes, 15 minutes, 20 minutes, 30 minutes, 1 hour, 2 hours, 3 hours, 4 hours, or 5 hours, 6 hours, 7 hours, 8 hours, 9 hours, 10 hours, 12 hours, 24 hours, or 2 days prior to integumental perturbation.

In some embodiments, epilation is performed prior to integumental perturbation. In some embodiments, epilation is performed immediately prior to integumental perturbation. In some embodiments, epilation is performed 5 minutes, 10 minutes, 15 minutes, 20 minutes, 30 minutes, 1 hour, 2 hours, 3 hours, 4 hours, or 5 hours, 6 hours, 7 hours, 8 hours, 9 hours, 10 hours, 12 hours, 24 hours, or 2 days prior to integumental perturbation.

In some embodiments, depilation is not performed prior to integumental perturbation. In some embodiments, epilation is not performed prior to integumental perturbation. In some embodiments, both depilation and epilation is not performed prior to integumental perturbation. In a particular embodiment, a method of integumental perturbation described herein can be carried out without epilation or depilation. In one such embodiment, dermabrasion (e.g., using a device with the dermabrasion tip described in Section 5.1.1 herein) is carried out without epilation or depilation.

In certain embodiments, the skin, following integumental perturbation, is not contacted for a period of time with any substance (e.g., wound dressing, ointment, a bandage, or a device) that is normally administered to an abrasion or wound to promote speed of healing. In one embodiment, the skin is not contacted with any substance until, for example, the integumental perturbation has healed (e.g., any time between 1 day and 3 weeks). Alternatively, the skin can be contacted with a cast or bandage, e.g., resulting in increased blood flow to the disrupted skin or decreased transdermal water loss or decreased mass transfer of gases (e.g. oxygen, carbon dioxide, water vapor) into the skin and/or from the skin, decreased heat transfer from the skin (e.g. resulting in an increased temperature of the skin surface), or increased pressure on the skin.

In some embodiments, the integumental perturbation is administered in combination with a treatment that reduces scarring, e.g., surgical scarring, which may be accomplished by placement of elective incisions parallel to the natural lines of skin tension (Langer's lines) or by applying sutures in a "zigzag" pattern, or other methods known in the art. In some embodiments, the integumental perturbation is administered in combination with a treatment of wounds (e.g., surgical wounds) that minimizes scarring, by, for example, administering physical therapy to a subject, reducing infection, reducing separation of wound edges, minimizing collagen synthesis, deposition, or accumulation or otherwise causing the process of healing by secondary intention to better resemble healing by primary intention. Other interventions that reduce scarring and which may be used in combination with the methods described herein include meticulous hemostasis of wound healing (including control of bleeding by coagulation, desiccation, or ligation techniques), which decreases amount of hematoma to be cleared and thus decreases the inflammatory phase of wound healing, exercising care during dermal closure (e.g., avoiding forceps crush-injury of the epidermis and dermis), avoidance of necrotic tissue at the wound edge, which reduces inflammation, cleansing of the wound, and applying skin grafts where needed. These interventions may be administered prior to, concurrent with, or following the integumental perturbation, and can be used with a treatment of integumental perturbation or as part of or in combination with another treatment described in Section 5.2-5.4 or elsewhere herein or otherwise known in the art.

5.6.2 Post-Perturbation Treatment Regimens

A post-perturbation treatment can be administered one time, or multiple times at intervals of time. For example, in one embodiment, the post-perturbation treatment is administered one time per day, or two times per day, or three times per day, or one time or more per week. It is understood that the precise dosage and duration of treatment may vary with the type of treatment, and the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In some embodiments, a post-perturbation treatment is administered to an area of the skin that has not yet been subjected to integumental perturbation. In some embodiments, a post-perturbation treatment is administered prior to integumental perturbation. In some embodiments, a post-perturbation treatment is administered prior to integumental perturbation and administration of the post-perturbation treatment is stopped during integumental perturbation treatment. In a specific embodiment, administration of the post-perturbation treatment is resumed after integumental perturbation treatment. In some embodiments, a post-perturbation treatment is administered prior to integumental perturbation and administration of the post-perturbation treatment is continued during and after integumental perturbation treatment. In some embodiments, a post-perturbation treatment is administered concurrently with integumental perturbation. In some embodiments, a post-perturbation treatment is administered to an area of the skin that has already been subjected to integumental perturbation. In some embodiments, a post-perturbation treatment is administered immediately after integumental perturbation.

In some embodiments, a post-perturbation treatment is administered immediately prior to integumental perturbation. In some embodiments, a post-perturbation treatment is administered within 5 minutes, 10 minutes, 15 minutes, 20 minutes, 30 minutes, 1 hour, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 8 days, 9 days, 10 days, 11 days, 12 days, 13 days, 14 days, or 1 month prior to integumental perturbation.

In some embodiments, a post-perturbation treatment is administered within 5 minutes of integumental perturbation, or 5 minutes, 10 minutes, 15 minutes, 20 minutes, 30 minutes, 1 hour, 2 hours, 3 hours, 4 hours, or 5 hours, 6 hours, 7 hours, 8 hours, 9 hours, 10 hours, 12 hours, 24 hours, or 2 days, 3 days, 4 days, 5 days, 6 days, 7 days, 8 days, 9 days, 10 days, 11 days, 12 days, 13 days, 14 days, or 1 month or more after integumental.

In some embodiments, following commencement of the post-perturbation treatment, the treatment is continued for 1 day, or for 2, 3, 4, 5, 6, 7, 8, 9, 10, 11, 12, 13, or 14 days or more following integumental perturbation. In some embodiments, following commencement of the post-perturbation treatment, the treatment is continued for 3 weeks, 4 weeks, 1 month, or 2, 3, 4, 5, or 6 months, or more following integumental perturbation. In some embodiments, following commencement of the post-perturbation treatment, the treatment is continued for 1 year or more following integumental perturbation.

In some embodiments, integumental perturbation is followed by a period of 5 minutes, 10 minutes, 15 minutes, 20 minutes, 30 minutes, 1 hour, 2 hours, 3 hours, 4 hours, or 5 hours, 6 hours, 7 hours, 8 hours, 9 hours, 10 hours, 12 hours, 1 day, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days without the post-perturbation treatment.

In various embodiments, the integumental perturbation and the post-perturbation treatment are administered less than 1 day apart, at about 1 day apart, 2 days apart, 3 days apart, 4 days apart, 5 days apart, 6 days apart, 7 days apart, 8 days apart 9 days apart, 10 days apart, 11, days apart, 12 days apart, 13 days apart, 14 days apart, or no more than 2 weeks apart. In other embodiments, the integumental perturbation and the post-perturbation treatment are administered 2 to 4 days apart, 4 to 6 days apart, 1 week apart, 1 to 2 weeks apart, 2 to 4 weeks apart, one month apart, 1 to 2 months apart, 2 to 3 months apart, 3 to 4 months apart, 6 months apart, or one year or more apart.

In one embodiment, the integumental perturbation and the post-perturbation treatment are administered within the same patient visit. In certain embodiments, the integumental perturbation and the post-perturbation treatment are cyclically administered to a subject. Cycling treatment involves the administration of the integumental perturbation one time or for a period of time, followed by the administration of the post-perturbation treatment one time or for a period of time and repeating this sequential administration. The first treatment may be with the integumental perturbation or with the post-perturbation treatment, depending on the subject's prior treatment history and the intended outcome. In certain embodiments, the integumental perturbation and the post-perturbation treatment are alternately administered in a cycle of 2 years or less, once every 1 year, once every 6 months, once every 3 months, once every 2 months, or once every month.

In one embodiment, the post-perturbation treatment is administered at the time of integumental perturbation and then maintained for 1 or 2 or 3 or 4 or 5 or 6 or 7 or 8 or 9 or 10 or 11 or 12 or 13 or 14 days or longer thereafter (in some embodiments, a scab forms during this time). In some embodiments, a post-perturbation treatment is administered as soon as the scab falls off and maintained for 3 or 4 or 5 days or longer. In one embodiment, the post-perturbation treatment is administered at the time of integumental perturbation and then maintained for 7 or 10 or 12 or 14 days thereafter (in some embodiments, a scab forms during this time). In some embodiments, a post-perturbation treatment is administered as soon as the scab falls off and maintained for 7 or 10 or 12 or 14 days. In one embodiment, the post-perturbation treatment is administered at the time of integumental perturbation and then maintained for 19 or 21 days thereafter (in some embodiments, a scab forms during this time). In some embodiments, a post-perturbation treatment is administered as soon as the scab falls off and maintained for 19 or 21 days. In one embodiment, the post-perturbation treatment is administered at the time of integumental perturbation and then maintained for 1 month, 2 months, 3 months, up to 6 months, or up to 1 year or longer thereafter. In some embodiments, a post-perturbation treatment is administered as soon as the scab falls off and maintained 1 month, 2 months, 3 months, up to 6 months, or up to 1 year or longer thereafter.

In some embodiments, a post-perturbation treatment is combined with a form of integumental perturbation that does not lead to formation of a scab. In one such embodiment, the post-perturbation treatment is administered before integumental perturbation. In another such embodiment, the post-perturbation treatment is administered at the time of integumental perturbation. In some embodiments, post-perturbation treatment is administered following integumental perturbation. In some embodiments, in which a post-perturbation treatment is administered following integumental perturbation that does not lead to formation of a scab, the post-perturbation treatment is administered within 15 minutes of, or 15 minutes, 30 minutes, 45 minutes, 1 hour, 2 hours, 4 hours, 6 hours, 8 hours, 12 hours, 18 hours, 1 day, 2 days, 3 days, 5 days, 7 days, 10 days, 2 weeks, or 3 weeks after integumental perturbation. In other embodiments, in which a post-perturbation treatment is administered following integumental perturbation that does not lead to formation of a scab, the post-perturbation treatment is administered within 1 month, 2 months, 3 months, 4 months, 5 months, 6 months, or 1 year or more after integumental perturbation.

In one embodiment, in which a post-perturbation treatment is administered following a form of integumental perturbation that leads to formation of a scab, the post-perturbation treatment is administered before scab formation. In one embodiment, in which a post-perturbation treatment is administered following a form of integumental perturbation that leads to formation of a scab, the post-perturbation treatment is administered during scab formation. In one embodiment, in which post-perturbation treatment is administered following a form of integumental perturbation that leads to formation of a scab, the post-perturbation treatment is administered periscab detachment. In one embodiment, in which a post-perturbation treatment is administered following a form of integumental perturbation that leads to formation of a scab, the post-perturbation treatment is administered immediately after scab detachment. In one embodiment, in which post-perturbation treatment is administered following a form of integumental perturbation that leads to formation of a scab, the post-perturbation treatment is administered 1 hour after scab detachment. In one embodiment, in which a post-perturbation treatment is administered following a form of integumental perturbation that leads to formation of a scab, the post-perturbation treatment is administered up to 6 hours after scab detachment. In one embodiment, in which a post-perturbation treatment is administered following a form of integumental perturbation that leads to formation of a scab, the post-perturbation treatment is administered 6-12 hours after scab detachment. In one embodiment, in which a post-perturbation treatment is administered following a form of integumental perturbation that leads to formation of a scab, the post-perturbation treatment is administered 12-18 hours after scab detachment. In one embodiment, in which a post-perturbation treatment is administered following a form of integumental perturbation that leads to formation of a scab, the post-perturbation treatment is administered 18-24 hours after scab detachment. In one embodiment, in which post-perturbation treatment is administered following a form of integumental perturbation that leads to formation of a scab, the post-perturbation treatment is administered 1 day, 2 days, 3 days, 4 days 5 days, 6 days, 7 days, 8 days, 9 days, 10 days, 11 days, 12 days, 13 days, 2 weeks, 3 weeks, or 4 weeks, one month, 2 months, 3 months, 4 months, 5 months, 6 months, 7 months, 8 months, 9 months, 10 months, 11 months, or 12 months after integumental perturbation. In one embodiment, in which a post-perturbation treatment is administered following a form of integumental perturbation that leads to formation of a scab, the post-perturbation treatment is administered 2 months, 3 months, 4 months, 5 months, 6 months, or 1 year or more after integumental perturbation.

A post-perturbation treatment can be administered one time, or repeatedly, in combination with integumental perturbation. In certain aspects, a post-perturbation treatment does not include an active pharmaceutical ingredient. In certain aspects, a post-perturbation treatment is a hydrogel that does not include an active pharmaceutical ingredient. In some embodiments, a post-perturbation treatment is administered at intervals of time, optionally alternating with integumental perturbation treatments also administered at intervals of time. In a variation, the post-perturbation treatment can be administered one or more times in a controlled release form, which can deliver drug (e.g., as described in Section 5.4 supra) in a regimen similar to multiple separate administrations.. In certain aspects, the present invention comprises integumental perturbation in combination with an additional treatment, wherein the additional treatment may or may not include an active pharmaceutical ingredient For example, in some embodiments, the period of time between treatments is at least 1 day, at least 2 days, at least 3 days, at least 4 days, at least 5 days, at least 7 days; and in some embodiments not more than 14 days. In one embodiment, the time between treatments is one week. In some embodiments, the time between treatments with post-perturbation treatment is at least 14 days, 21 days, 28 days, or longer.

In some embodiments, the post-perturbation treatment is administered in order to modulate the neoepidermis that forms underneath the scab. In some such embodiments, the post-perturbation treatment is administered at the time of integumental perturbation and is maintained up to some time after scab falls off, for example, between 5-14 days following integumental perturbation. In some embodiments, the course of treatment with post-perturbation treatment is short, for example, limited to one or a few days just following scab detachment, or even continued only for as long as the scab is still attached. The timing of integumental perturbation and post-perturbation treatment administration is preferably monitored and adjusted so that optimal results are achieved.

In some embodiments, the timing of integumental perturbation (e.g., using a method described in Section 5.1 or otherwise known in the art) and administration of post-perturbation treatment is adjusted in order to optimize hair growth. Thus, in one embodiment, a post-perturbation treatment is administered some time before integumental perturbation, and post-perturbation treatment is resumed again after integumental perturbation (optionally in combination with one of the treatments described in Sections 5.3, 5.4 or elsewhere herein or known in the art). In one embodiment, a post-perturbation treatment is administered (optionally in combination with one of the treatments described in Sections 5.3, 5.4 or elsewhere herein or known in the art) together with or shortly after integumental perturbation, for example, is administered directly to integumentally perturbed skin.

In some embodiments, following commencement of the post-perturbation treatment, the treatment is continued even as a treatment with a hair growth-promoting agent is begun. For example, this may be accomplished by administering the two treatments concurrently. This may also be accomplished by administering the hair growth-promoting agent in a formulation that is identical to the pharmaceutical composition for post-perturbation treatment, the only difference being the presence or absence, respectively, of hair growth-promoting agent and/or any required excipients, stabilizers, etc.

5.6.3 Treatment Regimens with Hair Growth-Promoting Agents

Treatment with a hair growth-promoting agent (also referred to as "hair growth-promoting agent treatment") can be administered one time, or multiple times at intervals of time. For example, in one embodiment, the hair growth-promoting agent treatment is administered one time per day, or two times per day, or three times per day, or one time or more per week. It is understood that the precise dosage and duration of treatment may vary with the type of treatment, and the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the embodiments described herein, treatment with a hair growth-promoting agents is in combination with integumental perturbation, or is administered to a subject who has undergone treatment with integumental perturbation. These treatments may optionally be combined with a post-perturbation treatment described in Section 5.2 supra, and/or a post-perturbation treatment regimen described in Section 5.6.2 supra.

In some embodiments, a hair growth-promoting agent is administered prior to integumental perturbation. In some embodiment, a hair growth-promoting agent is administered prior to integumental perturbation and administration of the hair growth-promoting agent is continued during and after integumental perturbation treatment. In some embodiments, a hair growth-promoting agent is administered prior to integumental perturbation and administration of the hair growth-promoting agent is stopped during integumental perturbation treatment. In a specific embodiment, administration of the hair growth-promoting agent is resumed after integumental perturbation treatment.

In some embodiments, one or more hair growth-promoting agents is administered prior to integumental perturbation. In some embodiments, one or more hair growth-promoting agents is administered within 6 months, 1 year, 2 years, 3 years, 4 years, 5 years, or 6 years prior to integumental perturbation. In some embodiments, one or more hair growth-promoting agents is administered continuously prior to integumental perturbation. In some embodiments, one or more hair growth-promoting agents is administered intermittently prior to integumental perturbation. In some embodiments, two or more hair growth-promoting agents are administered serially prior to integumental perturbation. In some embodiments, two or more hair growth-promoting agents are administered concurrently prior to integumental perturbation.

In some embodiments, one or more hair growth-promoting agents is administered immediately prior to integumental perturbation. In some embodiments, a hair growth-promoting agent is administered within 5 minutes, 10 minutes, 15 minutes, 20 minutes, 30 minutes, 1 hour, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 8 days, 9 days, 10 days, 11 days, 12 days, 13 days, 14 days, or 1 month prior to integumental perturbation.

In some embodiments, the hair growth-promoting agent is administered after integumental perturbation. In some embodiments, the hair growth-promoting agent is administered immediately after integumental perturbation. In particular embodiments for topical administration of hair growth-promoting agent(s) to wounded skin, the hair growth-promoting agent is formulated to reduce burning or irritation of the wound site. In some embodiments, a hair growth-promoting agent is administered 5 minutes, 10 minutes, 15 minutes, 20 minutes, 30 minutes, 1 hour, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 8 days, 9 days, 10 days, 11 days, 12 days, 13 days, 14 days, or 1 month after integumental perturbation. In some embodiments, a hair growth-promoting agent is administered about 1, 1.5, 2, 2.5, 3, 3.5, 4, 4.5, 5, 5.5, or 6 months or more after integumental perturbation. In some embodiments, integumental perturbation is followed by a period of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days or more without the hair growth-promoting agent.

In other embodiments, the timing of treatment with one or more hair growth-promoting agents can be coordinated with the presence or absence of indicators of hair growth in the skin of an area that was treated with integumental perturbation (optionally in combination with a post-perturbation treatment described herein). For example, in some embodiments, the one or more hair growth-promoting agents are administered prior to the appearance of vellus hair in a skin site that was treated with integumental perturbation. For example, in some embodiments, the one or more hair growth-promoting agents are administered prior to the appearance of new vellus hair in a skin site that was treated with integumental perturbation. In some embodiments, the one or more hair growth-promoting agents are administered following the appearance of new vellus hair in a skin site that was treated with integumental perturbation. In some embodiments, the one or more hair growth-promoting agents are administered following the appearance of vellus hair in a skin site that was treated with integumental perturbation. In some embodiments, the one or more hair growth-promoting agents are administered prior to the appearance of terminal hair in a skin site that was treated with integumental perturbation. In some embodiments, the one or more hair growth-promoting agents are administered following the appearance of terminal hair in a skin site that was treated with integumental perturbation. In some embodiments, the one or more hair growth-promoting agents are administered following the appearance of terminal hair, and before the terminal-to-vellus hair transition, in a skin site that was treated with integumental perturbation. In some embodiments, the one or more hair growth-promoting agents are administered prior to the appearance of NL, PEL, and/or PELA follicular structures in a skin site that was treated with integumental perturbation. In some embodiments, the one or more hair growth-promoting agents are administered after the appearance of NL, PEL, and/or PELA follicular structures in a skin site that was treated with integumental perturbation.

In various embodiments, the integumental perturbation and the hair growth-promoting agent are administered less than 1 day apart, at about 1 day apart, 2 days apart, 3 days apart, 4 days apart, 5 days apart, 6 days apart, 7 days apart, 8 days apart 9 days apart, 10 days apart, 11, days apart, 12 days apart, 13 days apart, 14 days apart, no more than 2 weeks apart. In other embodiments, the integumental perturbation and the hair growth-promoting agent are administered 2 to 4 days apart, 4 to 6 days apart, 1 week apart, 1 to 2 weeks apart, 2 to 4 weeks apart, one month apart, 1 to 2 months apart, 2 to 3 months apart, 3 to 4 months apart, 6 months apart, or one year or more apart.

In one embodiment, the integumental perturbation and the hair growth-promoting agent are administered within the same patient visit. In certain embodiments, the integumental perturbation and the hair growth-promoting agent treatment are cyclically administered to a subject. Cycling treatment involves the administration of the integumental perturbation for a period of time, followed by the administration of the hair growth-promoting agent for a period of time and repeating this sequential administration. The first treatment may be with the integumental perturbation or with the hair growth-promoting agent, depending on the subject's prior treatment history and the intended outcome. In certain embodiments, the integumental perturbation and the hair growth-promoting agent treatment are alternately administered in a cycle of 3 weeks or less, once every two weeks, once every 10 days or once every week. In certain embodiments, the integumental perturbation and the post-perturbation treatment are alternately administered in a cycle of 2 years or less, once every 1 year, once every 6 months, once every 3 months, once every 2 months, or once every month.

In one embodiment, the hair growth-promoting agent treatment is administered at the time of integumental perturbation and then maintained for 1 or 2 or 3 or 4 or 5 days or longer thereafter (in some embodiments, a scab forms during this time). In some embodiments, a hair growth-promoting agent treatment is administered as soon as the scab falls off and maintained for 3 or 4 or 5 days or longer. In one embodiment, the hair growth-promoting agent treatment is administered at the time of integumental perturbation and then maintained for 7 or 10 or 12 or 14 days or longer thereafter (in some embodiments, a scab forms during this time). In some embodiments, a hair growth-promoting agent treatment is administered as soon as the scab falls off and maintained for 7 or 10 or 12 or 14 days or longer. In one embodiment, the hair growth-promoting agent treatment is administered at the time of integumental perturbation and then maintained for 19 or 21 days or longer thereafter (in some embodiments, a scab forms during this time). In some embodiments, a hair growth-promoting agent treatment is administered as soon as the scab falls off and maintained for 19 or 21 days or longer. In one embodiment, the hair growth-promoting agent treatment is administered at the time of integumental perturbation and then maintained for 1 month, 2 months, 3 months, up to 6 months, or up to 1 year or longer thereafter. In some embodiments, a hair growth-promoting agent treatment is administered as soon as the scab falls off and maintained 1 month, 2 months, 3 months, up to 6 months, or up to 1 year or longer thereafter.

In some embodiments, a hair growth-promoting agent treatment is combined with a form of integumental perturbation that does not lead to formation of a scab. In one such embodiment, the hair growth-promoting agent treatment is administered before integumental perturbation. In another such embodiment, the hair growth-promoting agent treatment is administered at the time of integumental perturbation. In some embodiments, a hair growth-promoting agent treatment is administered following integumental perturbation. In some embodiments, in which a hair growth-promoting agent treatment is administered following integumental perturbation that does not lead to formation of a scab, the hair growth-promoting agent treatment is administered within 15 minutes of, or 15 minutes, 30 minutes, 45 minutes, 1 hour, 2 hours, 4 hours, 6 hours, 8 hours, 12 hours, 18 hours, 1 day, 2 days, 3 days, 5 days, 7 days, 10 days, 2 weeks, or 3 weeks after integumental perturbation. In other embodiments, in which a hair growth-promoting agent treatment is administered following integumental perturbation that does not lead to formation of a scab, the hair growth-promoting agent treatment is administered within 1 month, 2 months, 3 months, 4 months, 5 months, 6 months, or 1 year or more after integumental perturbation.

In one embodiment, in which a hair growth-promoting agent treatment is administered following a form of integumental perturbation that leads to formation of a scab, the hair growth-promoting agent treatment is administered before scab formation. In one embodiment, in which a hair growth-promoting agent treatment is administered following a form of integumental perturbation that leads to formation of a scab, the hair growth-promoting agent treatment is administered during scab formation. In one embodiment, in which a hair growth-promoting agent treatment is administered following a form of integumental perturbation that leads to formation of a scab, the hair growth-promoting agent treatment is administered periscab detachment. In one embodiment, in which a hair growth-promoting agent treatment is administered following a form of integumental perturbation that leads to formation of a scab, the hair growth-promoting agent treatment is administered immediately after scab detachment. In one embodiment, in which a hair growth-promoting agent treatment is administered following a form of integumental perturbation that leads to formation of a scab, the hair growth-promoting agent treatment is administered 1 hour after scab detachment. In one embodiment, in which a hair growth-promoting agent treatment is administered following a form of integumental perturbation that leads to formation of a scab, the hair growth-promoting agent treatment is administered up to 6 hours after scab detachment. In one embodiment, in which a hair growth-promoting agent treatment is administered following a form of integumental perturbation that leads to formation of a scab, the hair growth-promoting agent treatment is administered 6-12 hours after scab detachment. In one embodiment, in which a hair growth-promoting agent treatment is administered following a form of integumental perturbation that leads to formation of a scab, the hair growth-promoting agent treatment is administered 12-18 hours after scab detachment. In one embodiment, in which a hair growth-promoting agent treatment is administered following a form of integumental perturbation that leads to formation of a scab, the hair growth-promoting agent treatment is administered 18-24 hours after scab detachment. In one embodiment, in which a hair growth-promoting agent treatment is administered following a form of integumental perturbation that leads to formation of a scab, the hair growth-promoting agent treatment is administered 1 day, 2 days, 3 days, 5 days, 7 days, 10 days, 2 weeks, 3 weeks, or 4 weeks after integumental perturbation. In one embodiment, in which a hair growth-promoting agent treatment is administered following a form of integumental perturbation that leads to formation of a scab, the hair growth-promoting agent treatment is administered 2 months, 3 months, 4 months, 5 months, 6 months, or 1 year or more after integumental perturbation.

A hair growth-promoting agent treatment can be administered one time, or repeatedly, in combination with integumental perturbation. In some embodiments, a hair growth-promoting agent treatment is administered at intervals of time, optionally alternating with integumental perturbation treatments also administered at intervals of time. In a variation, the hair growth-promoting agent can be administered one or more time in a controlled release form, which can deliver drug in a regimen similar to multiple separate administrations.

For example, in some embodiments, the period of time between treatments is at least 1 day, at least 2 days, at least 3 days, at least 4 days, at least 5 days, at least 7 days; and in some embodiments not more than 14 days. In one embodiment, the time between treatments is one week. In some embodiments, the time between treatments with hair growth-promoting agent is least 14 days, 21 days, 28 days, or longer. In certain embodiments, the period of time between treatments is at least one month, 3 months, 6 months, 9 months, 12 months, 2 years, 3 years, 4, years, 5 years, 6 years, 7 years or longer.

In some embodiments, the hair growth-promoting agent treatment is administered in order to modulate the neoepidermis that forms underneath the scab. In some such embodiments, the hair growth-promoting agent treatment is administered at the time of integumental perturbation and is maintained up to some time after scab falls off, for example, between 5-14 days following integumental perturbation. In some embodiments, the course of treatment with hair growth-promoting agent is short, for example, limited to one or a few days just following scab detachment, or even continued only for as long as the scab is still attached. The timing of integumental perturbation and hair growth-promoting agent administration is preferably monitored and adjusted so that optimal results are achieved.

In some embodiments, the timing of integumental perturbation (e.g., using a method described in Section 5.1 or otherwise known in the art) and administration of hair growth-promoting agent is adjusted in order to optimize hair growth. Thus, in one embodiment, a hair growth-promoting agent is administered some time before integumental perturbation, and treatment with the hair growth promoting agent is resumed again after integumental perturbation (optionally in combination with one of the treatments described in Sections 5.2, 5.4 or elsewhere herein or known in the art). In one embodiment, a hair growth-promoting agent is administered (optionally in combination with one of the treatments described in Sections 5.2, 5.4 or elsewhere herein or known in the art) together with or shortly after integumental perturbation, for example, is administered directly to integumentally perturbed skin. In one embodiment, a hair growth-promoting agent is administered (optionally in combination with one of the treatments described in Sections 5.2, 5.4 or elsewhere herein or known in the art) following the new appearance of vellus hair on an area of skin that has been subjected to integumental perturbation. In one embodiment, a hair growth-promoting agent is administered (optionally in combination with one of the treatments described in Sections 5.2, 5.4 or elsewhere herein or known in the art) following the appearance of new visually-detectable hair on an area of skin that has been subjected to integumental perturbation. In one embodiment, a hair growth-promoting agent is administered (optionally in combination with one of the treatments described in Sections 5.2, 5.4 or elsewhere herein or known in the art) following the appearance of new photographically-detectable hair on an area of skin that has been subjected to integumental perturbation. In one embodiment, a hair growth-promoting agent is administered (optionally in combination with one of the treatments described in Sections 5.2, 5.4 or elsewhere herein or known in the art) following the appearance of new terminal hair on an area of skin that has been subjected to integumental perturbation.

In other embodiments, treatment with hair growth-promoting agent is performed using a formulation as described in Section 5.2 above.

In certain embodiments, treatment with hair growth-promoting agent is commenced on the same day as the integumental perturbation and is continued once, twice, three times, four times, or five times daily for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days. In certain embodiments, upon commencement with treatment with the hair growth-promoting agent, the treatment is continued once, twice, three times, four times, or five times daily for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days. In certain embodiments, upon commencement with treatment with the hair growth-promoting agent, the treatment is continued once, twice, three times, four times, or five times daily for one month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 year, 12 years, 13 years, or indefinitely.

Moreover, the one or more hair growth-promoting agents may be administered in combination with any additional treatment(s) described or incorporated by reference herein (see, e.g., Section 5.4 above) or determined to be appropriate by the medical practitioner. The amount of an additional treatment(s) will depend on the desired effect and the additional compound that is selected. Dosages and regimens for administering such additional treatment(s) are the dosages and regimens commonly in use, which can be easily determined by consulting, for example, product labels or physicians' guides, such as the Physicians' Desk Reference ("PDR") (e.g., 63rd edition, 2009, Montvale, N.J.: Physicians' Desk Reference).

The one or more hair growth-promoting agents may be administered concurrently with or separately from the additional compound(s), or may be administered and/or delivered to the tissue site with different pharmacokinetics. In one embodiment, the combination treatment comprises one or more hair growth-promoting agents and an additional compound(s) formulated together. The hair growth-promoting agent in such formulations may be released concurrently with or separately from the additional compound(s), or may be released and/or delivered to the tissue site with different pharmacokinetics. For example, in some embodiments, one or more of the compounds in the formulation undergoes controlled release, whereas one or more of the other compounds does not. For example, one or more of the compounds in the formulation undergoes sustained release whereas one or more of the other compounds undergoes delayed release.

In another embodiment, the combination treatment comprises one or more hair growth-promoting agents and an additional compound(s) formulated separately. The separate formulations may be administered concurrently, sequentially, or in alternating sequence. For example, the one or more hair growth-promoting agents may be administered sequentially, or concurrently with another compound such as finasteride or minoxidil, to achieve the desired effect of hair retention and growth.

In certain embodiments, treatment with one or more hair growth-promoting agents in combination with integumental perturbation (with or without a post-perturbation treatment) prevents, delays, or reverses scalp hair loss in MPHL, FPHL, and/or diffuse hair thinning associated with aging.

In certain embodiments, treatment with integumental perturbation (with or without a post-perturbation treatment) prior to treatment with one or more hair growth-promoting agents improves the effectiveness of the hair growth-promoting agent, making the treatment more effective, efficient, cost-effective, and/or user friendly. For example, the efficacy of the agent may be increased. In certain embodiments, one of the treatments on its own is not cosmetically satisfactory, the benefits are too short-lived, or the hair that results from the treatment is vellus hair, or other thin or patchy hair, or has inadequate pigmentation. When one of these treatments is combined with treatment with one or more of the other treatments, the hair that results may be more cosmetically satisfactory, longer lasting, thicker, more uniform, and properly pigmented hair, terminal hair or scalp hair as opposed to vellus hair inferior in such attributes. In certain embodiments, more than one hair will emerge from each follicle, leading to the appearance of thicker hair.

The following embodiment is illustrative of the methods described herein. Integumental perturbation is achieved by either treatment with a fractional erbium-YAG laser to epidermal or dermal depth, a fractional $CO_2$ laser to epidermal or dermal depth, or dermabrasion to epidermal or dermal depth as described herein. This is followed by treatment with one or more of the following hair growth-promoting agents: estrogen, finasteride, or dutasteride (Avodart™). This treatment causes follicles (or Follicle Stem Cells) to be stimulated, activated, or reprogrammed, e.g., a miniaturizing male temporal scalp follicle (or Follicle Stem Cell) is changed to a non-miniaturizing female-type temporal scalp follicle (or Follicle Stem Cell). Then, optionally, terminal hair growth is further stimulated by the application of minoxidil, bimatoprost, or latanoprost. Alternatively, in this embodiment the follicle type can be stimulated, activated, or reprogrammed, e.g., a miniaturizing male temporal scalp follicle can be changed to a non-miniaturizing male occipital scalp-type follicle. Then, optionally, terminal hair growth is stimulated by the application of finasteride, dutasteride, minoxidil, bimatoprost, or latanoprost. In another illustrative embodiment, integumental perturbation is achieved by either treatment with a fractional erbium-YAG laser to epidermal or dermal depth, a fractional $CO_2$ laser to epidermal or dermal depth, or dermabrasion to epidermal or dermal depth as described herein. This treatment causes follicles to be stimulated, activated, or reorganized and/or or Follicle Stem Cells to form new follicles, which are receptive to the effects of hair growth-promoting agents, such as finasteride, dutasteride, minoxidil, bimatoprost, or latanoprost. Stimulation of the reorganized and/or new follicles by such agents then results in increased numbers of terminal hairs.

In some embodiments, the combination of integumental perturbation and treatment with one or more hair growth-promoting agents of an area of skin that already contains hair-producing follicles (e.g., vellus or terminal hair) increases production of hair in that area of skin. In some embodiments, the combination of integumental perturbation and hair growth-promoting agent treatment is administered to skin that has been damaged and which no longer contains follicles. In such embodiments, the combination of integumental perturbation and hair growth-promoting agent treatment may restore follicle production in that area of skin. In one such embodiment, an area of skin containing a wound that has not healed correctly, such as a scar (e.g., a keloid scar), is administered a combination treatment of integumental perturbation and one or more hair growth-promoting agents in order to restore hair follicles and/or growth to that area of skin. These effects may be accomplished by modulating the dosage of the one or more hair growth-promoting agents.

Synergism occurs when the combination has an effect that is more than would be expected from merely the additive effect of each element in the combination, for example, if branched hair follicles or multiple shafts per pore were produced by the combination and not by either alone.

5.6.3.1 Integumental Perturbation and Minoxidil Treatment

This section provides an exemplary method to induce hair growth on the scalp. More specifically, provided herein is a method to induce hair growth on the scalp of a male or female subject with androgenetic alopecia. Even more specifically, provided herein is a method to induce hair growth on the scalp of a male or female subject having androgenetic alopecia with the presence of a vertex transition zone defined as an area possessing both terminal and miniaturized hairs, Hamilton-Norwood type 3V, 4, 5, 5A, or 5V, and Fitzpatrick skin type 1-4. In certain embodiments, the method for inducing hair growth comprises: (a) integumental perturbation; (b) an optional period of treatment with a post-perturbation treatment described in Section 5.2 supra; and (c) an optional period of treatment with minoxidil. More specifically, the method for inducing hair growth comprises in the following order: (a) integumental perturbation; (b) a period of treatment with a post-perturbation treatment described in Section 5.2 supra; (c) a period without treatment; and (d) a period of treatment with minoxidil. Without being bound by theory, in areas of hair loss in male or female subjects with androgenetic alopecia, controlled integumental perturbation using dermabrasion results in neogenic-like hair follicles, and/or stimulated, activated or reorganized pre-existing hair follicles; and the subsequent treatment of the induced neogenic-like follicles, and/or stimulated, activated or reorganized pre-existing hair follicles, with minoxidil or other hair growth-promoting agent(s) results in more numerous, longer lasting, and/or thicker hair shafts. In some embodiments, in areas of hair loss in male or female subjects with androgenetic alopecia, treatment with minoxidil or other hair growth-promoting agent(s) prior to controlled integumental perturbation results in more numerous, longer lasting, and/or thicker hair shafts.

In a specific embodiment, treatment with the optional post-perturbation treatment is commenced on the same day as the integumental perturbation and is continued once, twice, three times, four times, or five times daily for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days.

In some embodiments, integumental perturbation is followed by a period of zero, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days without topical treatment (e.g., perturbation without treatment with the post-perturbation pharmaceutical composition and without treatment with minoxidil; or perturbation followed by treatments with a post-perturbation pharmaceutical composition, then a period with no topical agent, followed by minoxidil; or perturbation followed by a treatment with a post-perturbation pharmaceutical composition for a period of time, and then followed by topical minoxidil, starting the day after the topical application of post-perturbation treatment has ended).

In some embodiments, subsequent to the period without topical treatment, treatment with minoxidil is commenced wherein minoxidil is applied once, twice, three times, four times, or five times daily for at least 2 weeks, 1 month, 2 months, 3 months, 4 months, 5 months, 6 month, 7 months, 8 months, 9 months or at least 10 months. In specific embodiments, 0.1%, 0.5%, 1%, 2%, 3%, 4%, 5%, 6%, 7%, or 8% topical minoxidil can be used (e.g., ROGAINE™).

In certain embodiments, treatment with minoxidil can be combined with another treatment as described elsewhere in Section 5.3 above and in Section 5.4 below, or administered with a drug delivery device, for example, described in Section 5.3.1.

In certain embodiments, the method for inducing hair growth further comprises administration of finasteride (PROPECIA™). For example, finasteride can be administered orally at a dose of 1 mg/day. In certain embodiments, administration of finasteride commences concurrently with the topical treatment with minoxidil.

In certain embodiments, the method for inducing hair growth further comprises administration of dutasteride or any other 5-alpha-reductase inhibitor known to the skilled artisan. For example, dutasteride can be administered orally at a dose of 0.05 mg/day, 0.1 mg/day, 0.5 mg/day, or 2.5 mg/day. In certain embodiments, administration of dutasteride commences concurrently with the topical treatment with minoxidil.

In certain embodiments, a method for inducing hair growth on the scalp of a male or female subject with androgenetic alopecia comprises:
 (a) Dermabrasion (estimated depth 100 microns) at Day 0;
 (b) Topical administration of a hydrogel described in Section 5.2 supra twice daily from Day 0 to Day 11;
 (c) Period without topical treatment from Day 12 to Day 14;

(d) Topical administration of 5% topical minoxidil commencing at Day 15 for at least 5.5 months.

In certain embodiments, a method for inducing hair growth on the scalp of a male or female subject with androgenetic alopecia comprises:
(a) Dermabrasion (estimated depth 100 microns) at Day 0;
(b) Commencing at Day 0, topical administration of a hydrogel described in Section 5.2 supra twice daily for about 14 days;
(c) Period without topical treatment overnight;
(d) Immediately following step (c), topical administration of 5% topical minoxidil for at least 5.5 months.

In certain embodiments, a method for inducing hair growth on the scalp of a male or female subject with androgenetic alopecia comprises:
(a) Dermabrasion (estimated depth 100 microns) at Day 0;
(b) Commencing at Day 0, topical administration of a hydrogel described in Section 5.2 supra twice daily for about 14 days;
(c) Period without topical treatment for 2 weeks;
(d) Commencing at Day 28, topical administration of 5% topical minoxidil for at least 5.5 months.

In certain embodiments, the present invention provides a kit comprising in separate containers hydrogel and topical minoxidil. The minoxidil can be 0.1%, 0.5%, 1%, 2%, 3%, 4%, 5%, 6%, 7%, or 8% topical minoxidil (e.g., ROGAINE™). In certain embodiments, the kit further comprises means for integumental perturbation (e.g., a handheld dermabrasion device).

Any method known to the skilled artisan can be used to demonstrate that hair growth has been induced. For example, detectable hairs can be quantified by photography, e.g., by global photographic recording or phototrichographic analysis (as described in, e.g., Uno et al., 2002, *Acta Venereol* 82:7-12, incorporated herein by reference) or assessed visually e.g. by a rating scale (as described in Kaufman et al. J Amer Acad Dermatol 1998; 39: 578-89. Further, changes in the hair shaft thickness of photographically detectable hairs can be determined. Further, the permanence of the hair growth is monitored over a time period of at least 3 months, 6 months, 9 months, 1 year, 1.5 years, 2 years, 2.5 years, 3 years, 4 years, or at least 5 years.

In specific embodiments, 0.005%, 0.01%, 0.05%, 0.1%, 0.15%, or 0.2% topical latanoprost can be used. In specific embodiments, 0.01%, 0.03%, 0.05% or 0.1% topical bimatoprost can be used. In specific embodiments, 0.0005%, 0.0015%, 0.005%, or 0.05% topical tafluprost can be used. In specific embodiments, 0.00013%, 0.00033%, 0.001%, 0. 0.00267%, 0.004%, or 0.01% topical travoprost can be used.

Other regimens for combination treatments for use in the methods described herein include those described elsewhere in this section.

5.7 Indications and Patient Populations

Human hair patterning consists of gender specific changes that occur over the life of subjects and vary in degree between individuals and more generally between humans of different racial and ethnic backgrounds. Before puberty, males and females have similar patterns of scalp hair and the rest of their bodies are covered with largely invisible vellus hair. The forearms and legs grow thin, fine terminal hair gradually even before puberty. In males and females puberty is associated with terminal hair growth in the axilla, and anogenital regions. During puberty, both males and females grow terminal hair over forearms and legs, but males have quantitatively more growth in these regions. Males after puberty grow terminal hair over the moustache/beard, chest, and back regions. Later, males manifest varying degrees of loss of terminal hair on the scalp (vertex/corona and frontal/temporal/parietal regions) in a process called "MPHL alopecia." Both males and females with genetic susceptibilities manifest diffuse scalp terminal hair thinning that is called "androgenetic alopecia." Males manifest various degrees of terminal hair growth on ears, in the nose (nares) and of eyebrows. After menopause, females manifest moustache/beard hair growth. Both males and females manifest diffuse scalp hair thinning with age. Both females and males with genetic susceptibility manifest hair color changes with age.

The sex hormones, androgens and estrogens, play important roles in much of human hair patterning. A high ratio of androgen to estrogen activity drives both the process of transforming vellus hair to terminal hair (in puberty, e.g. axilla and anogenital regions; male moustache and beard) and in transforming terminal hair (and large terminal follicles) to vellus hair (and miniaturized follicles) in MPHL alopecia. Sex hormones are synthesized by the skin locally where they exert intracrine or paracrine actions. (Reviewed in, Zouboulis C C, Chen W C, Thornton M J, Qin K, Rosenfield, 2007, "Sexual hormones in human skin" Horm Metab Res 39:85-95) The local level and activity of each sex steroid depends upon the activity of androgen- and estrogen-synthesizing enzymes and of appropriate androgen- and estrogen receptors in specific cell types. Androgens are regulated by five major enzymes and changes in the expression of isoenzymes; or changes in the expression of androgen receptor and androgen receptor transactivating factors regulate hair patterning. Estrogens are produced in sebaceous glands which express cytochrome P450 aromatase ("aromatase") that converts androgen to 17-beta-estradiol (E2). Estrogens act on Estrogen Receptor alpha (ERalpha) and Estrogen Receptor alpha (ERbeta) in human skin are expressed in site specific localizations. In addition to regulating hair patterning and growth, androgens have effects in sebaceous gland growth and differentiation, epidermal barrier homeostasis and wound healing; and estrogens regulate skin aging, pigmentation, hair growth, sebum production and skin cancer. (Ohnemus et al., 2006, Endocr Rev. 27(6): 677-706, "The hair follicle as an estrogen target and source.")

The location of specialized human hair follicles allow us to introduce a classification (Table 1 and FIG. 1) of those follicles that produce terminal hair which highlights the distinctive features including type of hair produced (length, curl); appearance/disappearance during life and regulation by sex steroids. This classification makes several assumptions in grouping together as similar types certain male and female follicles that may not be justified by future study. For example, except for scalp hair, humans have only small amounts of visible hair until puberty, when specialized hair follicles in the pubic (anogenital) and armpit (axillary) regions begin producing terminal hair. Some believe that pubic and axillary specialized follicles change their activity in response to only androgens in both males and females and that the hair follicles in the female pubic and axillary regions are extremely sensitive to androgens. The classification system is useful to show the variety and unique characteristics of specialized hair follicles in humans that can be modified using the methods described herein.

TABLE 1

Types of Human Hair Follicles Producing Terminal Hair

Pubic (anogenital)—puberty driven, not androgen or estrogen specific, curly intermediate length
Armpit (axillary)—puberty driven, not androgen or estrogen specific, curly intermediate length
Scalp—throughout life, thins with aging
Vertex—induced by androgens in males in genetically susceptible males to miniaturize and involute
Crown—induced by androgens in genetically susceptible males to miniaturize and involute
Temples—induced by androgens in genetically susceptible males to miniaturize and involute
Beard/Moustache—induced by androgens to at puberty, suppressed by estrogens, curly intermediate length
Chest/back—induced by androgens to at puberty, suppressed by estrogens, short length
Eyebrow—throughout life, thickens/grows with aging in men, straight short length
Nose surface—on the surface of the nose; thickens/grows with aging in males, short length
Nose/nostrils (nares)—in the lumen; increases at puberty, thickens/grows with aging in males, short length
Ear (auricle)—appears with aging in males, short length
Leg—induced by androgens in males at puberty, suppressed by estrogens but not as completely as beard, short length
Arm—induced by androgens in males & females at puberty, suppressed by estrogens but not as completely as beard, short length
Eyelid/eyelashes—throughout life, single units After puberty, males begin to lose the scalp hair over the vertex, crown and frontal/parietal areas in a relatively characteristic pattern that is a continuum (described by the Hamilton Norwood scale; see FIG. 8). The different stages of Hamilton-Norwood scale that can be treated in accordance with the methods described herein are as follows:

Class I represents an adolescent or juvenile hairline and it not actually balding. The adolescent hairline generally rests on the upper brow crease.

Class II indicates a progression to the adult or mature hairline which sits a finger breath (1.5 cm) above the upper brow crease, with some temporal recession. This also does not represent balding.

Class III is the earliest stage of male hair loss. It is characterized by a deepening temporal recession.

Class III Vertex represents early hair loss in the crown (vertex).

Class IV is characterized by further frontal hair loss and enlargement of vertex, but there is still a solid band of hair across top separating front and vertex.

Class V: the bald areas in the front and crown continue to enlarge and the bridge of hair separating the two areas begins to break down.

Class VI occurs when the connecting bridge of hair disappears leaving a single large bald area on the front and top of the scalp. The hair on the sides of the scalp remains relatively high.

Class VII patients have extensive hair loss with only a wreath of hair remaining in the back and sides of the scalp.

Class A patterns are less common than the regular pattern (<10%), but are significant because of the fact that, since the hair loss is most dramatic in the front, the patients look very bald even when the hair loss is minimal.

In some embodiments, any stage of the Ludwig classification for female pattern hair loss can be treated by the methods and treatments described herein. The Ludwig Classification uses three stages to describe female pattern genetic hair loss: Type I (mild), Type II (moderate), Type III (extensive). In all three Ludwig stages, there is hair loss on the front and top of the scalp with relative preservation of the frontal hairline. The back and sides may or may not be involved. Regardless of the extent of hair loss, only women with stable hair on the back and sides of the scalp are candidates for hair transplant surgery. In some embodiments, the treatments described herein can be used to treat Type 1, Type II and/or Type III stages of the Ludwig classification for female pattern genetic hair loss.

In some embodiments, any stage of the Savin scale for female pattern hair loss can be treated by the methods and treatments described herein. In stage I-1, there is no hair loss. In stages I-2, I-3, I-4 of the Savin scale, the width of the parting gets progressively wider indicating thinner hair along the center of the scalp. In stages II-1 and II-2 of the Savin scale, there is diffuse thinning of the hair over the top of the scalp. In stage III of the Savin scale, there is extensive diffuse hair loss on top of the scalp, but some hair does survive. In the "advanced" stage of the Savin scale, there is extensive hair loss and little to no surviving hair in the alopecia affected area. Very few women ever reach the advanced stage and if they do it is usually because they have a condition that causes significant, abnormally excessive androgen hormone production. In the "frontally accentuated" stage of the Savin scale, there is more hair loss at the front and center of the hair parting instead of just in the top middle of the scalp.

In some embodiments, any stage of the Savin scale for female pattern hair loss can be treated by the methods and treatments described herein. The Olsen scale grades female hair loss into 3 stages based on a frontal accentuation pattern in which the hair loss is more profound in the frontal region that gradually tapers back toward less hair loss in the occipital when viewed with a central hair part. In stage 1 of the Olsen scale, there is mild to moderate frontal accentuation loss. In stage 2 of the Olsen scale, there is both frontal accentuation that can be more severe than in stage 1 and mixed with diffuse hair loss. In stage 3 of the Olsen scale, the loss is so severe that only diffuse thinning is principally noted.

5.7.1 Patient Populations for Baldness, Alopecia and Hair Growth

A candidate subject for treatment with one or more methods described herein is any subject suffering from hair loss, hair thinning, balding, or who has or has had a disease or condition associated therewith, or who wishes to enhance the growth or thickness of hair.

The subject may be any subject, preferably a human subject, including male, female, intermediate/ambiguous (e.g., XO), and transsexual subjects. In certain embodiments, the subject is a human adolescent. In certain embodiments, the subject is undergoing puberty. In certain embodiments, the subject is a middle-aged adult. In certain embodiments, the subject is a premenopausal adult. In certain embodiments, the subject is undergoing menopause. In certain embodiments, the subject is elderly. In certain embodiments, the subject is a human of 1 year old or less, 2 years old or less, 2 years old, 5 years old, 5 to 10 years old, 10 to 15 years old, e.g., 12 years old, 15 to 20 years old, 20 to 25 years old, 25 to 30 years old, 30 years old or older, 30 to 35 years old, 35 years old or older, 35 to 40 years old, 40 years old or older, 40 to 45 years old, 45 to 50 years old, 50 years old or older, 50 to 55 years old, 55 to 60 years old, 60 years old or older, 60 to 65 years old, e.g., 65 years old, 65 to 70 years old, 70 to 75 years old, 75 to 80 years old, 80 to 85 years old, 85 to 90 years old, 90 to 95 years old or 95 years old or older. In some embodiments, the subject is a male 20 to 50 years old. In some embodiments, the subject is a male 20 to 60 years old. In some embodiments, the subject is a male 30 to 60 years old. In some embodiments, the subject is a male 40 to 60 years old. In some embodiments, the subject is a male or female 12 to 40 years old. In some embodiments, the subject is not a female subject. In some embodiments, the subject is not pregnant or expecting to become pregnant. In some embodiments, the subject is not a pregnant female in the first trimester of pregnancy. In some embodiments, the subject is not breastfeeding.

In one embodiment, the treatment is delivered to an area in which hair growth is desired, for example, the scalp, the face (e.g., the eyebrow, eyelashes, upper lip, lower lip, chin, cheeks, beard area, or mustache area), or another part of the body, such as, e.g., the chest, abdomen, arms, armpits (site of axillary hair), legs, or genitals. In some embodiments, treatment is delivered to the head. In some embodiments, treatment is delivered to the scalp. In some embodiments, treatment is delivered to a balding scalp. In one embodiment, treatment is not delivered to the face. In one embodiment, treatment is not delivered to an area of the skin that is normally covered with only, or mostly, vellus hair. In some embodiments, hair restoration to a wounded or scarred part of the skin is desired. In one embodiment, the scar is caused by surgery, such as a face lift, skin graft, or hair transplant.

The subject may have a disease or disorder of balding or hair loss (including hair thinning), such as forms of nonscarring (noncicatricial) alopecia, such as androgenetic alopecia (AGA), including MPHL or FPHL (e.g., thinning of the hair, i.e., diffuse hair loss in the frontal/parietal scalp), or any other form of hair loss caused by androgens, toxic alopecia, alopecia areata (including alopecia universalis), scarring (cicatricial) alopecia, pathologic alopecia (caused by, e.g., medication, trauma stress, autoimmune diseases, malnutrition, or endocrine dysfunction), trichotillomania, a form of hypotrichosis, such as congenital hypotrichosis, or lichen planopilaris, or any other condition of hair loss or balding known in the art or described infra.

In some embodiments, the subject has hair loss caused by a genetic or hereditary disease or disorder, such as androgenetic alopecia.

In some embodiments, the subject has hair loss caused by anagen effluvium, such as occurs during chemotherapy (with, e.g., 5-fluorouracil, methotrexate, cyclophosphamide, vincristine). In addition to chemotherapy drugs, Anagen effluvium can be caused by other toxins, radiation exposure (including radiation overdose), endocrine diseases, trauma, pressure, and certain diseases, such as alopecia areata (an autoimmune disease that attacks anagen follicles.)

In some embodiments, the subject has hair loss caused by telogen effluvium. Telogen effluvium is caused frequently by drugs like lithium and other drugs like valproic acid and carbamazepine. In addition to psychiatric drugs, telogen effluvium can be induced by childbirth, traction, febrile illnesses, surgery, stress, or poor nutrition. (See, Mercke et al., 2000, Ann. Clin. Psych. 12:35-42).

In some embodiments, the subject has hair loss caused by or associated with medication, such as chemotherapy (e.g., anti-cancer therapy or cytotoxic drugs), thallium compounds, vitamins (e.g., vitamin A), retinoids, anti-viral therapy, or psychological therapy, radiation (such as the banding pattern of scalp hair loss that may be caused by radiation overdose), trauma, endocrine dysfunction, surgery, physical trauma, x-ray atrophy, burning or other injury or wound, stress, aging, an autoimmune disease or disorder, malnutrition, an infection (such as, e.g., a fungal, viral, or bacterial infection, including chronic deep bacterial or fungal infections), dermatitis, psoriasis, eczema, pregnancy, allergy, a severe illness (e.g., scarlet fever), myxedema, hypopituitarism, early syphilis, discoid lupus erythematosus, cutaneous lupus erythematosus, lichen planus, deep factitial ulcer, granuloma (e.g., sarcoidosis, syphilitic gummas, TB), inflamed tinea capitis (kerion, favus), a slow-growing tumor of the scalp or other skin tumor, or any other disease or disorder associated with or that causes balding or hair loss known in the art or described infra.

In some embodiments, the subject has hair thinning, or "shock loss," or a bald patch caused by prior use as a source of tissue or follicles for hair transplantation or follicular unit transplantation.

In some embodiments, a candidate subject is a subject who wishes to enhance hair growth, for example, to have more hair, faster-growing hair, longer hair, and/or thicker hair. In some embodiments, the candidate is a subject who wishes to increase hair pigmentation. In some embodiments, the subject is not affected by a condition of excessive hair loss.

5.7.2 Scarring Alopecia

In some embodiments, the subject has scarring (cicatricial) alopecia. Forms of cicatricial alopecia that may be treated in accordance with the methods described herein include primary cicatricial alopecia (PCA) and secondary cicatricial alopecia. Primary cicatricial alopecias that may be treated in accordance with the methods described herein include lymphocyte-mediated PCAs, such as lichen planopilaris (LPP), frontal fibrosing alopecia (FFA), central centrifugal cicatricial alopecia (CCCA), and pseudopelade (Brocq); neutrophil-mediated PCAs, such as folliculitis decalvans and tufted folliculitis; and PCAs involving a mixed inflammatory infiltrate, such as occurs in dissecting cellulitis and folliculitis keloidalis.

In some embodiments, in a candidate subject for treatment, the area affected by the scarring alopecia is no longer increasing. In some embodiments, in a candidate subject for treatment, hair loss has in the affected area has ceased. In some embodiments, a candidate subject for treatment is clinically quiescent with respect to the inflammatory activity that may be associated with the condition. In one embodiment with respect to a subject having a lymphocyte-mediated PCA, inflammation is measured as the number of T lymphocytes and/or T lymphocyte subsets as detected in lesional skin, e.g., by immunoperoxidase cell surface staining using monoclonal antibodies. In another embodiment with respect to a subject having a lymphocyte-mediated PCA, lymphocytic inflammation (which may be found along with necrotic keratinocytes) is detected by histologic examination of the scalp. In another embodiment, direct immunofluorescence staining techniques are employed to detect antibody deposits in the affected tissue. In certain embodiments, clinical evaluation of the scalp is performed to determine clinical quiescence of the inflammation. Symptoms of itching, burning, pain, or tenderness usually signal ongoing activity. Signs of scalp inflammation include redness, scaling, and pustules. In certain embodiments, a scalp biopsy can be performed to demonstrate active inflammation or its absence. In certain embodiments, a hair "pull test" is performed to identify areas of active disease in which follicles are easily pulled out, and thus, inflammation is still ongoing. The pulled hairs can be mounted on a slide and the hair bulbs are viewed with a microscope to determine how many are growing hairs and how many are resting hairs. In addition, if pustules are present, cultures may be performed to identify which microbes, if any, may be contributing to the inflammation. In certain embodiments, a subject is clinically quiescent if hairs cannot be easily pulled out, if itching, burning, pain, tenderness, redness, scaling, and/or pustules are absent from the affected area.

In some embodiments, a method described herein is used to enhance hair growth in a patient with scarring alopecia. In some embodiments, the patient has a secondary cicatricial alopecia. In some embodiments, the patient has a form of primary cicatricial alopecia, such as lymphocyte-mediated PCAs, such as lichen planopilaris (LPP), frontal fibrosing alopecia (FFA), central centrifugal cicatricial alopecia (CCCA), and pseudopelade (Brocq); neutrophil-mediated PCAs, such as folliculitis decalvans and tufted folliculitis; and PCAs involving a mixed inflammatory infiltrate, such as occurs in dissecting cellulitis and folliculitis keloidalis.

Cicatricial alopecias affect both men and women, most commonly adults, although all ages may be affected. In general, they are rare. There have been a few reports of cicatricial alopecia occurring in a family. However, the majority of patients with cicatricial alopecia have no family history of a similar condition. Lichen planopilaris may affect middle-aged women most commonly. Central centrifugal alopecia may affect black women most commonly. Frontal fibrosing alopecia is seen most commonly in post-menopausal women. Thus, in certain embodiments, in addition to the subjects described herein, a candidate subject for treatment for scarring alopecia is a black woman (e.g., of African-American descent), a middle-aged woman, or a post-menopausal woman.

In some embodiments, the invention provides a method for enhancing hair growth in a patient with scarring alopecia comprising controlled integumental perturbation using a fractional ablative laser, followed by twice daily topical administration of hair growth-promoting agent for 14 days. In certain embodiments, the hair growth-promoting agent treatment is begun on the same day as the laser treatment. In certain embodiments, treatment with hair growth-promoting agent is commenced on the same day as the integumental perturbation and is continued once, twice, three times, four times, or five times daily for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days.

In a specific embodiment, the invention provides a method for enhancing hair growth in a patient with lichen planopilaris comprising controlled integumental perturbation using a fractional ablative laser, followed by twice daily topical administration of hair growth-promoting agent for 14 days. In certain embodiments, the hair growth-promoting agent treatment is begun on the same day as the laser treatment. In certain embodiments, treatment with hair growth-promoting agent is commenced on the same day as the integumental perturbation and is continued once, twice, three times, four times, or five times daily for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days.

In another specific embodiment, the invention provides a method for enhancing hair growth in a patient with frontal fibrosing alopecia comprising controlled integumental perturbation using a fractional ablative laser, followed by twice daily topical administration of hair growth-promoting agent for 14 days. In certain embodiments, the hair growth-promoting agent treatment is begun on the same day as the laser treatment. In certain embodiments, treatment with hair growth-promoting agent is commenced on the same day as the integumental perturbation and is continued once, twice, three times, four times, or five times daily for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days.

5.7.2.1 Integumental Perturbation and Hair Growth—Promoting Agent Treatments for Scarring Alopecia In addition to the combination treatments for enhancing hair growth described herein, the following are exemplary combination treatments comprising integumental perturbation and hair growth-promoting agent treatment for enhancing hair growth in a patient having scarring alopecia. In certain embodiments, the combination treatment is specific for a particular subtype of scarring alopecia.

In some embodiments, the combination treatment for enhancing hair growth in a patient with scarring alopecia comprises a form of integumental perturbation, such as described in Section 5.1, optionally in combination with a post-perturbation treatment described in Section 5.2, a hair growth-promoting agent treatment such as described in Section 5.3, and/or one or more additional treatments described in Section 5.4 or elsewhere herein or otherwise known in the art.

For example, in some embodiments, an affected area of the skin is transplanted with hair follicles from an unaffected area. In some embodiments, surgical techniques for replacing tissue comprising scarred hair follicles with tissue from another area of the skin (e.g., scalp) comprising unaffected hair follicles are used. Surgical treatment for cosmetic benefit is an option in, for example, some cases after the disease has been inactive for one to two or more years. Hair restoration surgery or scalp reduction may be considered in these instances. Thus, in some embodiments, the integumental perturbation is a form of scar revision, such as skin graft, serial expansion of surrounding skin, or laser treatment. In some embodiments, the integumental perturbation is a form of scar re-excision with subsequent healing by primary intention, treatment with steroids (e.g., corticosteroid injection), silicone scar treatments (e.g., dimethicone silicone gel or silicone sheeting), use of porcine fillers or other cosmetic fillers (e.g., inserted under atrophic scars), ribosomal 6 kinase (RSK) antagonists, antagonists of pro-inflammatory cytokines, such as TGFβ2 or TNF, osteopontin antagonists, the use of pressure garments, needling, dermabrasion, collagen injections, low-dose radiotherapy, or vitamins (e.g., vitamin E or vitamin C or its esters).

In some embodiments, the integumental perturbation for the treatment of scarring alopecia is administered with a procedure that promotes wound healing with reduced scarring, as described in, e.g., Section 5.1 supra. In a specific embodiment, the combination treatment for a patient with scarring alopecia comprises controlled integumental perturbation using a fractional ablative laser, followed by twice daily topical administration of hair growth-promoting agent for 14 days. In certain embodiments, the hair growth-promoting agent treatment is begun on the same day as the laser treatment. In one embodiment, the patient has primary cicatricial alopecia. In a specific embodiment, the patient has lichen planopilaris or frontal fibrosing alopecia.

In some embodiments, the combination treatment for enhancing hair growth in a patient having scarring alopecia comprises integumental perturbation, optionally with hair growth-promoting agent treatment, in combination with one or more anti-inflammatory medications and antimalarial drugs. Medications that may be administered orally include hydroxychloroquine, doxycycline, mycophenolate mofetil, cyclosporine, or corticosteroids. Medications that may be administered topically include corticosteroids (such as, e.g., betamethasone, e.g., Luxiq®), tacrolimus, pimecrolimus, or Derma-Smoothe/FS scalp oil. Medications that may be administered by injection include triamcinolone acetonide (a corticosteroid), which may be injected into inflamed, symptomatic areas of the scalp. In particular, non-limiting, embodiments, such combinations are used in the treatment of a patient with the lymphocytic group of cicatricial alopecias, including lichen planopilaris, frontal fibrosing alopecia, central centrifugal alopecia, and pseudopelade (Brocq).

In some embodiments, the combination treatment for enhancing hair growth in a patient having scarring alopecia comprises integumental perturbation, optionally in combination with a hair growth-promoting agent treatment, in combination with one or more antibiotics, such as oral or topical antibiotics. In some embodiments, the combination treatment comprises one or more retinoids, such as isotretinoin, or methotrexate, tacrolimus, cyclosporin, or thalidomide. In particular, non-limiting embodiments, such combinations are used in enhancing hair growth in a patient with the neutrophilic group of cicatricial alopecias (e.g., folliculitis decalvans, tufted folliculitis, and dissecting cellulitis), and successful treatment enhances hair growth while reducing or eliminating microbes that are involved in the inflammatory process.

In some embodiments, a combination treatment for a patient with the mixed group of cicatricial alopecias (e.g., folliculitis keloidalis) may include antimicrobials, isotretinoin, and anti-inflammatory medications.

5.7.3 Androgenetic Alopecia

Both males and females develop diffuse hair loss in the frontal/parietal scalp called "thinning," which begins between 12 and 40 years of age. In females, thinning is known as "Female Pattern Hair Loss (FPHL)" and is caused or exacerbated by androgens. (Price V H, 2003, J Investig Dermatol Symp Proc. 8(1):24-7, Androgenetic alopecia in women).

5.7.4 Male Pattern Hair Loss (MPHL)

After puberty, males begin to lose the scalp hair over the vertex, crown and frontal/parietal areas in a relatively characteristic pattern that is a continuum (described by Hamilton Norwood scale). The loss of scalp hair in men is called MPHL and is known to be a process driven by the androgen, dihydrotestosterone (DHT), which can be inhibited and to some extent reversed by finasteride which inhibits the conversion of testosterone to DHT. Minoxidil can also delay or reverse MPHL.

5.7.5 Aging

Aging of humans results in programmed hair patterning. Diffuse hair loss, including thinning of the occipital scalp occurs in aging. This can either be an extension of androgenetic alopecia (MPHL or FPHL) from the earlier years or even start in the latter decades of life when amounts of testosterone and DHT in the body are decreasing.

It is believed that hair loss in postmenopausal women is related to the loss of estrogens (and/or a decrease in the estrogen/androgen ratio). Accordingly, in some embodiments, the combination treatments disclosed herein for age-related hair loss comprise a combination of treatment with one or more hair growth-promoting agents and estrogen replacement therapy or androgen inhibition therapy.

Aging also results in change of follicle cycle control. In males, eyebrows grow longer and nares hair grow longer suggesting that the lengths of telogen and anagen are no longer regulated as closely. In other words, with aging there is a loss of the function of suppressing terminal hair growth.

5.7.6 Hair Color Changes

Hair color changes in both males and females becoming progressively grayer (mixture of gray hair; white hair and black hair) and whiter. Color change is patterned, since scalp hair changes earlier than body beard hair or body hair. Beard hair may also change color in a pattern that follow a moustache line, before ultimately turning uniformly gray (typically a mixture of white and black hair). This is due to decreased melanin content in the hair shaft (supplied by melanocytes associated with hair follicles).

5.7.7 Factors that Regulate Sex Hormone Sensitivity of Hair Follicle Cells

Cytokines regulate the activity of Dermal Papillae, which is believed to be the target of androgen regulation of hair growth. Interleukin-1 alpha decreases responses to androgen in cultured dermal papilla cells (Boivin et al., 2006, Exp Dermatol. 15:784-793). TGF-beta1 may mediate androgen-induced hair growth suppression, since in culture, human dermal papilla cells (DPCs) from androgenetic alopecia (AGA) subjects that transiently expressing androgen receptor were co-cultured with keratinocytes (KCs), and secreted TGF-beta1 that inhibited KC growth (Inui et al., 2003, J Investig Dermatol Symp Proc. 8:69-71).

In certain embodiments, adjuvants and/or other stimulators of local cytokines are used in conjunction with the treatment with one or more hair growth-promoting agents. Without being bound by any theory, one rationale for administering adjuvants and/or other stimulators of local cytokines in conjunction with the treatment with one or more hair growth-promoting agents is that the production of local cytokines may induce changes in the follicle cell cycle and recruit new FSCs to follicles.

Melatonin is a protein hormone secreted by the pineal gland modulates hair growth, pigmentation and/or molting in many species. Human scalp hair follicles in anagen are important sites of extra-pineal melatonin synthesis. Melatonin may also regulate hair Follicle Cycle control, since it inhibits estrogen receptor-alpha expression (Fischer et al., 2008, Pineal Res. 44:1-15). These treatments can be administered in combination with the methods described herein.

5.7.8 Treatments for Delaying or Reversing Human Hair Patterning

Given the regulation of human hair patterning by sex steroids, it is believed that humans evolved hair patterning to provide social signals in interactions such as mating and dominance. However, current fashion motivates many men to prevent, delay or reverse male MPHL.

Women also suffer from hair thinning and hair loss due to a variety of factors; for example, certain conditions, such as, e.g., polycystic ovary, result in male-pattern facial and body hair on females, which motivates them to remove or reduce hair. Many women also desire the prevention, delay or reversal of "female-pattern baldness," which may result from a variety of factors, for example, the aging process.

5.8 Methods for Evaluating Efficacy of Treatment 5.8.1 Toxicity and Efficacy Assays The toxicity and/or efficacy of compositions comprising a hair growth-promoting agent or other drug described herein—alone or in combination with integumental perturbation—can be determined by standard pharmaceutical procedures in cell culture or experimental animals, e.g., for determining the $LD_{50}$ (the dose lethal to 50% of the population) and the $ED_{50}$ (the dose therapeutically effective in 50% of the population). The dose ratio between toxic and therapeutic effects is known as the therapeutic index and it can be expressed as the ratio $LD_{50}/ED_{50}$. Dosage regimens that exhibit large therapeutic indices are preferred. While dosage regimens that exhibit toxic side effects may be used, care should be taken to design a delivery system that targets the hair growth-promoting agent or other drug described herein to the preferred site on the skin (e.g., using a topical formulation) in order to minimize potential damage to other tissue, thereby reducing side effects.

Data obtained from the in vitro assays and animal studies described herein can be used in formulating a dosage range of the hair growth-promoting agent or other drug described herein for use in human subjects. The dosage of the hair growth-promoting agent or other drug described herein lies preferably within a range of skin concentrations, and possibly circulating concentrations, that include the $ED_{50}$ with little or no toxicity. The dosage may vary within this range depending upon the dosage form employed and the route of administration utilized. For any treatment according to the methods described herein, the therapeutically effective dose can be estimated initially from in vitro (e.g., cell culture) assays or animal assays. Such information can be used to more accurately determine useful doses in human subjects. Levels in whole blood or plasma may be measured, for example, by high performance liquid chromatography or any other method described herein. Levels in skin may be measured, for example, by an LC/MS/MS assay described herein.

Further, any assays known to those skilled in the art can be used to evaluate the efficacy of treatment with a hair growth-promoting agent or other drug described herein, either alone or in a combination treatment described herein.

5.8.2 In Vitro Models

Skin explant model. The efficacy of the treatments described herein may be tested using skin explants, for example, prepared from skin biopsies or other surgical procedures. See, e.g., Ballanger et al., supra.

Human skin equivalents can be grown and assembled in vitro, with the advantage that they can be grown to theoretically to any size/shape; can be comprised of different types of cells, including keratinocytes (hair follicle derived and non-hair follicle derived), dermal cells (hair follicle derived and non-hair follicle derived), other cell types (e.g., mesenchymal stem cells); can contain cells that are genetically modified to include, e.g., markers or "inducible" signaling molecules; provide an unlimited and uniform source of human cells; from normal skin based on histology and marker studies; are generally devoid of skin appendages; and can be integumentally perturbed as in vivo.

5.8.3 Animal Models

Human skin and hair have features that are relatively unique among terrestrial mammals. First, the great majority of human skin appears hairless to the naked eye, while the vast majority of other terrestrial mammals are essentially covered with visible hair. Second, visible human hair appears and disappears in patterns that have spatial and temporal components. Third, the patterns of visible human hair are distinct in typical male and females (exhibit gender dimorphism). Accordingly, it is evident that relative to other mammals, humans have distinct hair patterning and humans have correspondingly distinct molecular, cellular and tissue mechanisms that regulate hair growth and that control human hair patterning. Modulating human hair follicle neogenesis, formation of activated or reorganized follicular structures, and other processes involved in hair growth require considerations that are unique to humans and for which other animals can be insufficient models. However, it is noted that the treatments described herein may be evaluated for their potential use in humans using the animal models described in this section and known in the art. See, e.g., International Patent Application Publication No. WO 2011/031990, published Mar. 17, 2011, for examples of rodent dermabrasion and full thickness excision models.

It should be noted that certain non-human primates share features of hair patterning with humans. The most prominent and greatest incidence of hair loss occurs in the Stump-tailed Macaque as frontal-scalp alopecia in post-adolescent males and females. The pathogenesis of baldness in the Stump-tailed Macaque monkey and human appears to be similar and partially reversible in both species by chronic topical administration of hair growth-promoting agents (see Diani et al, 1992, J Clin Endocrinol Metab, 74:345-350). Old World Apes (gorillas and chimpanzees) have areas of skin that lack visible hair; on the face surrounding the eyes, nose and mouth; on ears; and the plantar surfaces of hands and feet. In addition, Rhesus Macaque has patterned alopecia in males and females. Gorillas have hair patterning with respect to color on dominant males: i.e., the "Silverback." While certain of these mechanisms share similarities to humans, the extent and degree of hair patterning in human remains relatively unique.

Another animal model for use in evaluating treatment that may more closely mimic the biology of human skin and hair is a guinea pig model (see, Stenn & Paus, 2001, Physiol. Revs. 81: 449-494). The methods for evaluating treatment described herein may be applied to guinea pigs according to methods known in the art. See also, e.g., Kramer et al., 1990, Dermatol Monatsschr 176:417-20; and Simon et al., 1987, Ann Plast Surg 19:519-23. Other animal models that may be of use in evaluating the treatments described herein include pig (e.g., Red Duroc), or cat models.

Success of treatment aimed at improving hair growth in an animal model can be measured by: improved overall cosmetic outcome; increased hair count; increased hair density; increased thickness of hair or hair shaft (diameter); increased hair weight; hair cuttings; longer hair; increase in the amount of terminal hair; increase in the amount of vellus hair; an increase in the ratio of terminal-to-vellus hair; increase in the amount of nonvellus, e.g., intermediary or terminal, hair; increased number of hair follicles; increased number of hair follicles at a more mature stage of development; increased numbers of follicular units with 3 or more hair follicles; increased hair follicle branching; formation of new hair follicles ("hair follicle neogenesis"); formation of new hair follicles with vellus-sized hair shafts (i.e., hair shafts with diameters less than 30 microns in diameter); hair follicle regeneration; increased stimulation or activation of existing hair follicles; increased number of stimulated or activated hair follicles; increased number of stimulated or activated pre-existing hair follicles; increased number of pre-existing hair follicles with vellus-sized hair shafts in a treated area of skin of a subject; the presence and/or increased numbers of NL, PEL, and PELA follicular structures; hair follicle synchronization so that the overall hair density appears to be greater compared to previous asynchronous hair growth; increased proportion of hair follicles in anagen or decreased proportion of hair follicles in telogen; increased proliferation of dermal papilla; increased recruitment or proliferation of stem cells to the follicle; etc.

Any method known in the art may be used to evaluate the safety and efficacy of a treatment described herein. In one embodiment, a human skin xenograft model is used. For example, one or more hair growth-promoting agents may be administered with a full thickness excision, laser, inflammatory stimulus, or dermabrasion procedure for integumental perturbation described herein. A synergistic effect of an integumental perturbation treatment and treatment with one or more hair growth-promoting agents or another treatment described herein may be measured as an improvement over a control subject receiving only one of the two or more treatments (e.g., the treatment with integumental perturbation alone, with or without a post-perturbation treatment, with or without one or more hair growth-promoting agents alone).

5.8.3.1 Human Skin Xenograft Models

Preliminary evidence of hair follicle neogenesis has been demonstrated in human skin (obtained from the hair line during a face lift procedure) grafted onto the back of an immunodeficient SCID mouse. Such human skin xenograft models are useful for testing the safety and efficacy of the treatments described herein.

Any method for producing human skin xenografts known in the art may be used, for example, the method described in Section 26 starting at page 127 of International Patent Application Publication No. WO 2011/031990, published Mar. 17, 2011, which is incorporated by reference herein in its entirety, may be adapted for testing the treatment methods described herein.

Alternatively, a human skin xenograft (without skin appendages) can be considered as similar to a scar, and can be wounded and then treated pharmacologically to induce hair growth. Xenografts can also be combined with inducible genetically modified cells to activate pathways know to form hair follicles.

In some embodiments, the safety and efficacy of a treatment described herein, is tested in a full thickness or a split thickness human skin xenograft (e.g., obtained surgically from scar revisions; from foreskin; or cadaveric), or may be tested in a three-dimensional organotypic human skin culture on SCID mice.

5.8.4 Methods for Evaluating Treatment in Humans

The safety and efficacy of a treatment described herein may also be measured in human subjects according to methods known in the art. See, e.g., International Patent Application Publication No. WO 2005/084621, published Sep. 15, 2005, the contents of which is incorporated by reference herein in its entirety.

Any method known to the skilled artisan can be used to demonstrate success of a treatment described herein. In various embodiments, success of treatment aimed at treating alopecia, treating baldness, or promoting hair growth can be measured according to one or more of the following methods:

improved overall cosmetic outcome (e.g., using the Visual Analogue Scale (VAS))
patient assessment of his/her hair growth (e.g., based on questionnaire)
investigator assessment of hair growth in a patient (e.g., based on a rating scale)
patient assessment of his/her hair growth in photographs
investigator assessments of hair growth in patient photographs
increased hair count (e.g., by measuring new hair growth as an increased number of fibers in an affected area of the skin)
increased hair density
increased thickness of hair or hair shaft (e.g., based on diameter)
increased hair weight
hair cuttings
longer hair
an increase in the number of photographically detected hairs
increase in the amount of terminal hair (by, e.g., measuring new hair growth as an increased number of fibers in an affected area of the skin, or increased thickness (e.g., diameter) or length of hair fibers (e.g., as measured photographically))
increase in the amount of vellus hair (by, e.g., measuring new hair growth as an increased number of fibers in an affected area of the skin) (e.g., as measured photographically)
increase in the amount of nonvellus hair, e.g., intermediate or terminal hair (e.g., as measured photographically)
an increase in the ratio of terminal-to-vellus hair
increased number of hair germs
increased number of hair follicles (e.g., as evaluated by a skin biopsy)
increased number of hair follicles at a more mature stage of development
increased numbers of follicular units with 3 or more hair follicles
increased hair follicle branching
formation of new hair follicles ("hair follicle neogenesis")
formation of new hair follicles with vellus-sized hair shafts (i.e., hair shafts with diameters less than 30 microns in diameter)
formation of new hair follicles with nonvellus-sized hair shafts (i.e., hair shafts with diameters 30 microns or greater in diameter)
hair follicle regeneration
increased activation of existing hair follicles
increased number of hair follicles
increased number of activated or stimulated hair follicles
increased number of activated or stimulated pre-existing hair follicles
presence or increased numbers of neogenic-like (NL) hair follicles (based on, e.g., examination of a biopsy or by confocal microscope, by assessing number of hair follicles, and/or by assessing morphology of hair follicles compared to baseline or a negative control)
presence or increased numbers of pre-existing hair follicles (based on, e.g., examination of a biopsy or by confocal microscope, by assessing number of hair follicles, and/or by assessing morphology of hair follicles compared to baseline or a negative control)
presence or increased numbers of NL, PEL, and/or PELA follicular structures (based on, e.g., examination of a biopsy or by confocal microscope, by assessing number of hair follicles, and/or by assessing morphology of hair follicles compared to baseline or a negative control, as described for example in Sections 5.8.4.1 and 5.8.4.2)
increased number of pre-existing hair follicles with vellus-sized hair shafts in a treated area of skin of a subject
increased number of neogenic-like hair follicles with vellus-sized hair shafts in a treated area of skin of a subject
increase in the amount of anagen hair
increase in the amount of telogen hair
increased proportion of hair follicles in anagen or decreased proportion of hair follicles in telogen (i.e., an increase in the ratio of anagen-to-telogen hair) (e.g., based on examination of a biopsy or phototrichograms)
increased proliferation of dermal papilla (based on, e.g., examination of a biopsy)
increased recruitment or proliferation of stem cells to the follicle (e.g., based on examination of a biopsy).

For example, in certain embodiments, success of treatment is assessed by examination of hair follicles in a treated area of the subject's skin. In certain embodiments, hair follicles are examined histologically, or by determination of the presence or absence of certain markers of hair follicle development or morphology. The area of skin for examination may be obtained by biopsy, such as a punch biopsy; alternatively or in addition, in a less invasive method, the skin may be analyzed directly by, e.g., confocal microscopy or other technique that permits imaging beneath the surface of the skin. In one embodiment, success of a treatment method described herein is determined by an increase in the number of hair follicles in a treated area, for example, compared to an untreated control (or compared to baseline before treatment). In one embodiment, success of a treatment method described herein is determined by the presence or increased numbers of neogenic-like (NL) follicles, for example, compared to an untreated control (or compared to baseline before treatment). In one embodiment, success of a treatment method described herein is determined by the presence or increased numbers of activated or stimulated pre-existing follicles, such as pre-existing like (PEL) or pre-existing-like, attached (PELA) follicular structures, for example, compared to an untreated control (or compared to baseline before treatment). In one embodiment, success of a treatment method described herein is determined by the presence or increased numbers of NL, PEL, and/or PELA follicular structures, for example, compared to an untreated control (or compared to baseline before treatment).

In some such embodiments, a treatment regimen described herein increases the number of hair follicles by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein increases the number of hair follicles by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases the number of hair follicles by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein increases the number of hair follicles by 5% or more, by 10% or more, by 15% or more, by 20% or more, by 25% or more, by 30% or more, by 40% or more, by 50% or more, by 75% or more, or by 100% or more.

In some such embodiments, a treatment regimen described herein increases the number of activated or stimulated hair follicles (e.g., NL, PEL or PELA follicular structures) by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein increases the number of activated or stimulated hair follicles (e.g., NL, PEL or PELA follicular structures) by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases the number of activated or stimulated hair follicles (e.g., NL, PEL or PELA follicular structures) by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein increases the number of activated or stimulated hair follicles (e.g., NL, PEL or PELA follicular structures) by 5% or more, by 10% or more, by 15% or more, by 20% or more, by 25% or more, by 30% or more, by 40% or more, by 50% or more, by 75% or more, or by 100% or more.

In certain of the foregoing embodiments, the increase in number of hair follicles, activated or stimulated hair follicles, and/or NL, PEL, or PELA structures is observed in the treated area, for example, in an area of skin that was treated with integumental perturbation. In other embodiments, the increase in number of hair follicles, activated or stimulated hair follicles, and/or NL, PEL, or PELA structures is observed adjacent to the treated area. In other embodiments, the increase in number of hair follicles, activated or stimulated hair follicles, and/or NL, PEL, or PELA structures is observed in and adjacent to the treated area.

In certain embodiments, measurement of hair follicles in accordance with the foregoing is within 3 days, or 4 days, 5 days, 6 days, 7 days, 8 days, 9 days, 10 days, 11 days, 12 days, 13 days, 14 days, 15 days, 16 days, 17 days, 18 days, 3 weeks, 4 weeks, or 1 month or longer after initiation of the treatment regimen. In one embodiment, measurement of hair follicles in accordance with the foregoing is based on a skin biopsy taken within 3 days, or 4 days, 5 days, 6 days, 7 days, 8 days, 9 days, 10 days, 11 days, 12 days, 13 days, 14 days, 15 days, 16 days, 17 days, 18 days, 3 weeks, 4 weeks, or 1 month or longer after initiation of the treatment regimen. In a particular embodiment, measurement of hair follicles in accordance with the foregoing is 11 days, 12 days, 13 days, 14 days, or 15 days, after initiation of the treatment regimen. In a particular embodiment, measurement of hair follicles in accordance with the foregoing is based on a skin biopsy taken 11 days, 12 days, 13 days, 14 days, or 15 days, after initiation of the treatment regimen.

In a particular embodiment, measurement of hair follicles in accordance with the foregoing provides a means for evaluating success of a method of integumental perturbation (optionally in combination with post-perturbation treatment). In an exemplary, non-limiting embodiment, success of a method of integumental perturbation is determined based on a measured increase in total hair follicles in an area of skin subjected to integumental perturbation, for example, compared to an area of skin that was not subjected to the integumental perturbation step. In another embodiment, success of a method of integumental perturbation is determined based on a measured increase in activated or stimulated hair follicles, such as NL, PEL, or PELA follicular structures, in an area of skin subjected to integumental perturbation, for example, compared to an area of skin that was not subjected to the integumental perturbation step. In one embodiment, where a desired increase in hair follicles (or activated or stimulated hair follicles) is not observed, the treatment is discontinued. In another embodiment, where a desired increase in hair follicles (or activated or stimulated hair follicles) is not observed, integumental perturbation is repeated. In another embodiment, where a desired increase in hair follicles (or activated or stimulated hair follicles) is not observed, integumental perturbation is repeated using a different method (for example, switching from a nonmechanical to a mechanical means or vice versa, or switching from laser to dermabrasion or vice versa, or switching to chemical perturbation using an inflammatory agent). In one embodiment, where a desired increase in hair follicles (or activated or stimulated hair follicles) is not observed, integumental perturbation is repeated but to a greater skin depth, for example, increasing the depth by 10, 20, 30, 40, 50, 60, 70, 80, 90, or 100 microns or more.

In another particular embodiment, measurement of hair follicles in accordance with the foregoing provides a means for evaluating whether a subject is a candidate for treatment, or continued treatment, with the methods described herein. In an exemplary, non-limiting embodiment, candidacy is established based on a measured increase in total hair follicles in an area of skin subjected to integumental perturbation (optionally in combination with post-perturbation treatment), for example, compared to an area of skin that was not subjected to the integumental perturbation step. In another embodiment, candidacy is established based on a measured increase in activated hair follicles, such as NL, PEL, or PELA follicular structures, in an area of skin subjected to integumental perturbation (optionally in combination with post-perturbation treatment), for example, compared to an area of skin that was not subjected to the integumental perturbation step. In one embodiment, where a desired increase in hair follicles (or activated hair follicles) is not observed, treatment of that particular subject is discontinued. In another embodiment, where a desired increase in hair follicles (or activated hair follicles) is not observed, integumental perturbation is repeated. In another embodiment, where a desired increase in hair follicles (or activated hair follicles) is not observed, integumental perturbation is repeated using a different method (for example, switching from a nonmechanical to a mechanical means or vice versa, or switching from laser to dermabrasion or vice versa, or switching to chemical perturbation using an inflammatory agent). In one embodiment, where a desired increase in hair follicles (or activated hair follicles) is not observed, integumental perturbation is repeated but to a greater skin depth, for example, increasing the depth by 10, 20, 30, 40, 50, 60, 70, 80, 90, or 100 microns or more. In one embodiment, a method of treatment is carried out over a small area of skin (e.g., 1×1 cm, or 1.5×1.5 cm, or 2×2 cm, or 2.5×2.5 cm, or 3×3 cm or more), hair follicles are measured in accordance with these methods, and if candidacy is established, the method of treatment is carried out over a larger area of skin, such as, e.g, an entire balding area of scalp.

In some embodiments, a treatment regimen described herein increases the anagen-to-telogen ratio by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein increases the anagen-to-telogen ratio by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases the anagen-to-telogen ratio by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein increases the anagen-to-telogen ratio by 5% or more, by 10% or more, by 15% or more, by 20% or more, by 25% or more, by 30% or more, by 40% or more, by 50% or more, by 75% or more, or by 100% or more. Such an increase in the anagen-to-telogen ratio may be measured within or after 1 month, 2 months, 3 months, 4 months, 5 months, 6 months, 7 months, 8 months, 9 months, 10 months, 11 months, or one year or longer after initiation of the treatment regimen.

In certain embodiments, success of treatment is assessed by measuring hair count in a treated area of skin. For example, detectable hairs can be quantified by photography, e.g., by global photographic recording or phototrichographic analysis (as described in, e.g., Uno et al., 2002, *Acta Venereol* 82:7-12, incorporated herein by reference). Further, changes in the hair shaft thickness of photographically detectable hairs can be determined. In certain embodiments, the permanence of the hair growth is monitored over a time period of at least 2 months, 3 months, 4 months, 5 months, 6 months, 7 months, 8 months, 9 months, 10 months, 11 months, 1 year, 1.5 years, 2 years, 2.5 years, 3 years, 4 years, or at least 5 years or more.

In some embodiments, a treatment regimen described herein increases hair count by 5% or more, by 10% or more, by 15% or more, by 20% or more, by 25% or more, by 30% or more, by 40% or more, by 50% or more, by 75% or more, or by 100% or more. In some embodiments, a treatment regimen described herein increases vellus hair by 5% or more, by 10% or more, by 15% or more, by 20% or more, by 25% or more, by 30% or more, by 40% or more, by 50% or more, by 75% or more, or by 100% or more. In some embodiments, a treatment regimen described herein increases terminal hair by 5% or more, by 10% or more, by 15% or more, by 20% or more, by 25% or more, by 30% or more, by 40% or more, by 50% or more, by 75% or more, or by 100% or more. In some embodiments, a treatment regimen described herein results in 1-5%, 5-10%, 10-15%, 15-20%, 20-25%, 25-30%, 30-35%, 35-40%, 40-45%, 45-50%, 50-75%, or 75-100% conversion of vellus hair to nonvellus (i.e., intermediary or terminal hair). In some embodiments, a treatment regimen described herein increases hair thickness by 5% or more, by 10% or more, by 15% or more, by 20% or more, by 25% or more, by 30% or more, by 40% or more, by 50% or more, by 75% or more, or by 100% or more. In some embodiments, a treatment regimen described herein increases hair shaft diameter by approximately 1, 2, 2.5, 3, 3.5, 4, 4.5, 5, 5.5, 6, 6.5, 7, 7.5, 8, 8.5, 9, 10, 15, 20, 25, or 30 microns or more. In some embodiments, a treatment regimen described herein increases mean hair shaft diameter by 5% or more, by 10% or more, by 15% or more, by 20% or more, by 25% or more, by 30% or more, by 40% or more, by 50% or more, by 75% or more, or by 100% or more. In some embodiments, a treatment regimen described herein results in 1-5%, 5-10%, 10-15%, 15-20%, 20-25%, 25-30%, 30-35%, 35-40%, 40-45%, 45-50%, 50-75%, or 75-100% increase in mean hair shaft diameter. In some embodiments, a treatment regimen described herein increases the ratio of terminal to vellus hair follicles by 5% or more, by 10% or more, by 15% or more, by 20% or more, by 25% or more, by 30% or more, by 40% or more, by 50% or more, by 75% or more, or by 100% or more. Such an improvement in hair count, vellus hair, terminal hair, conversion of vellus hair to nonvellus (e.g., intermediate or terminal) hair, hair thickness, hair shaft diameter, or the ratio of terminal to vellus hair may be measured within or after 1 month, 2 months, 3 months, 4 months, 5 months, 6 months, 7 months, 8 months, 9 months, 10 months, 11 months, or one year or longer after initiation of the treatment regimen.

In some embodiments, an integumental perturbation treatment described herein increases hair count by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein increases vellus hair by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein increases terminal hair by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein results in 1-5%, 5-10%, 10-15%, 15-20%, 20-25%, 25-30%, 30-35%, 35-40%, 40-45%, 45-50%, 50-75%, or 75-100% conversion of vellus hair to nonvellus (i.e., intermediary or terminal hair). In some embodiments, an integumental perturbation treatment described herein increases hair thickness by 5% or more, by 10% or more, by 15% or more, by 20% or more, by 25% or more, by 30% or more, by 40% or more, by 50% or more, by 75% or more, or by 100% or more. In some embodiments, an integumental perturbation treatment herein increases hair shaft diameter by approximately 1, 2, 2.5, 3, 3.5, 4, 4.5, 5, 5.5, 6, 6.5, 7, 7.5, 8, 8.5, 9, 10, 15, 20, 25, or 30 microns or more. In some embodiments, an integumental perturbation treatment described herein increases hair shaft diameter by 5% or more, by 10% or more, by 15% or more, by 20% or more, by 25% or more, by 30% or more, by 40% or more, by 50% or more, by 75% or more, or by 100% or more. In some embodiments, an integumental perturbation treatment described herein increases the ratio of terminal to vellus hair follicles by 5% or more, by 10% or more, by 15% or more, by 20% or more, by 25% or more, by 30% or more, by 40% or more, by 50% or more, by 75% or more, or by 100% or more. Such an improvement in hair count, vellus hair, terminal hair, conversion of vellus hair to nonvellus (e.g., intermediate or terminal) hair, hair thickness, hair shaft diameter, or the ratio of terminal to vellus hair may be measured within or after 1 month, 2 months, 3 months, 4 months, 5 months, 6 months, 7 months, 8 months, 9 months, 10 months, 11 months, or one year or longer after initiation of the treatment regimen.

In some embodiments, an integumental perturbation treatment in combination with a post-perturbation treatment described herein increases hair count by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases vellus hair by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases terminal hair by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein results in 1-5%, 5-10%, 10-15%, 15-20%, 20-25%, 25-30%, 30-35%, 35-40%, 40-45%, 45-50%, 50-75%, or 75-100% conversion of vellus hair to nonvellus (i.e., intermediary or terminal hair). In some embodiments, an integumental perturbation treatment in combination with a post-perturbation treatment described herein increases hair thickness by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases hair shaft diameter by approximately 1, 2, 2.5, 3, 3.5, 4, 4.5, 5, 5.5, 6, 6.5, 7, 7.5, 8, 8.5, 9, 10, 15, 20, 25, or 30 microns or more. In some embodiments, an integumental perturbation treatment in combination with a post-perturbation treatment described herein increases hair shaft diameter by 5% or more, by 10% or more, by 15% or more, by 20% or more, by 25% or more, by 30% or more, by 40% or more, by 50% or more, by 75% or more, or by 100% or more. In some embodiments, an integumental perturbation treatment in combination with a post-perturbation treatment described herein increases the ratio of terminal to vellus hair follicles by 5% or more, by 10% or more, by 15% or more, by 20% or more, by 25% or more, by 30% or more, by 40% or more, by 50% or more, by 75% or more, or by 100% or more. Such an improvement in hair count, vellus hair, terminal hair, conversion of vellus hair to nonvellus (e.g., intermediate or terminal) hair, hair thickness, hair shaft diameter, or the ratio of terminal to vellus hair may be measured within or after 1 month, 2 months, 3 months, 4 months, 5 months, 6 months, 7 months, 8 months, 9 months, 10 months, 11 months, or one year or longer after initiation of the treatment regimen.

In some embodiments, an integumental perturbation treatment (optionally with a post-perturbation treatment described herein) in combination with a treatment with one or more hair growth-promoting agents described herein increases hair count by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein increases vellus hair by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein increases terminal hair by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein results in 1-5%, 5-10%, 10-15%, 15-20%, 20-25%, 25-30%, 30-35%, 35-40%, 40-45%, 45-50%, 50-75%, or 75-100% conversion of vellus hair to nonvellus (i.e., intermediary or terminal hair). In some embodiments, an integumental perturbation treatment (optionally with a post-perturbation treatment described herein) in combination with a treatment with one or more hair growth-promoting agents described herein increases hair thickness by 5% or more, by 10% or more, by 15% or more, by 20% or more, by 25% or more, by 30% or more, by 40% or more, by 50% or more, by 75% or more, or by 100% or more. In some embodiments, a treatment regimen described herein increases hair shaft diameter by approximately 1, 2, 2.5, 3, 3.5, 4, 4.5, 5, 5.5, 6, 6.5, 7, 7.5, 8, 8.5, 9, 10, 15, 20, 25, or 30 microns or more. In some embodiments, an integumental perturbation treatment (optionally with a post-perturbation treatment described herein) in combination with a treatment with one or more hair growth-promoting agents described herein increases hair shaft diameter by 5% or more, by 10% or more, by 15% or more, by 20% or more, by 25% or more, by 30% or more, by 40% or more, by 50% or more, by 75% or more, or by 100% or more. In some embodiments, an integumental perturbation treatment (optionally with a post-perturbation treatment described herein) in combination with a treatment with one or more hair growth-promoting agents described herein increases the ratio of terminal to vellus hair follicles by 5% or more, by 10% or more, by 15% or more, by 20% or more, by 25% or more, by 30% or more, by 40% or more, by 50% or more, by 75% or more, or by 100% or more. Such an improvement in hair count, vellus hair, terminal hair, conversion of vellus hair to nonvellus (e.g., intermediate or terminal) hair, hair thickness, hair shaft diameter, or the ratio of terminal to vellus hair may be measured within or after 1 month, 2 months, 3 months, 4 months, 5 months, 6 months, 7 months, 8 months, 9 months, 10 months, 11 months, or one year or longer after initiation of the treatment regimen.

In certain of the foregoing embodiments, the increase in hair count, vellus hair, terminal hair, conversion of vellus hair to nonvellus (e.g., intermediate or terminal) hair, hair thickness, hair shaft diameter, and/or the ratio of terminal to vellus hair is observed in the treated area, for example, in an area of skin that was treated with integumental perturbation. In other embodiments, the increase in hair count, vellus hair, terminal hair, conversion of vellus hair to nonvellus (e.g., intermediate or terminal) hair, hair thickness, hair shaft diameter, and/or the ratio of terminal to vellus hair is observed adjacent to the treated area. In other embodiments, the increase in hair count, vellus hair, terminal hair, conversion of vellus hair to nonvellus (e.g., intermediate or terminal) hair, hair thickness, hair shaft diameter, and/or the ratio of terminal to vellus hair is observed in and adjacent to the treated area.

A synergistic effect of a combination of one or two or three or four or more treatments described herein (e.g., as described in Section 5.1, Section 5.2, Section 5.3, and/or Section 5.4) may be measured as an improvement over a control subject (or a control skin site on the same subject) receiving fewer of the treatments. In certain embodiments, treatment with a hair growth-promoting agent for 1 year or more, 8 months, 6 months, 3 months, 2 months, 1 month, 3 weeks, 2 weeks, 1 week or for a lesser period prior to integumental perturbation enhances the efficacy of the integumental perturbation treatment (either alone or in combination with other treatments described herein). In certain embodiments, treatment with a hair growth-promoting agent for 1 year or more, 8 months, 6 months, 3 months, 2 months, 1 month, 3 weeks, 2 weeks, 1 week or for a lesser period or longer period following integumental perturbation enhances the efficacy of the integumental perturbation treatment (either alone or in combination with other treatments described herein). In a particular embodiment, enhanced efficacy of treatment with integumental perturbation (either alone or in combination with other treatments described herein) followed by treatment with a hair growth-promoting agent described herein, compared to treatment with integumental perturbation alone (or in combination with other treatments described herein) is measured as an increase in counts of nonvellus hairs and vellus hairs. In a more particular embodiment, enhanced efficacy of treatment with integumental perturbation (either alone or in combination with other treatments described herein) followed by treatment with a hair growth-promoting agent described herein, compared to treatment with integumental perturbation alone (or in combination with other treatments described herein) is measured as an increase in counts of nonvellus hairs and vellus hairs.

In a particular embodiment, measurement of hair in accordance with the foregoing provides a means for evaluating whether a subject is a candidate for treatment, or continued treatment, with the methods described herein. Such measurement may be at 1, 2, 3, 4, 5, 6, 7, 8, 9, 10, 11, or 12 months or more after initiation of the treatment regimen, or after initiation of a particular step of the treatment regimen. In one embodiment, such measurement is 2, 3, or 4 months after the integumental perturbation step. In an exemplary, non-limiting embodiment, candidacy is established based on a measured increase in hair (e.g., total hair, or vellus hair, or nonvellus hair) in an area of skin subjected to integumental perturbation (optionally in combination with post-perturbation treatment, optionally in combination with hair growth-promoting agent(s) treatment), for example, compared to an area of skin that was not subjected to the treatment step(s). In another embodiment, candidacy is established based on a measured increase in hair (e.g., total hair, or vellus hair, or nonvellus hair) in an area of skin subjected to integumental perturbation (optionally in combination with post-perturbation treatment, optionally in combination with hair growth-promoting agent(s) treatment), for example, compared to an area of skin that was not subjected to the integumental perturbation step. In one embodiment, where a desired increase in hair is not observed, treatment of that particular subject is discontinued. In another embodiment, where a desired increase in hair is not observed, integumental perturbation and/or the post-perturbation treatment and/or treatment with hair growth-promoting agent(s) is repeated. In another embodiment, where a desired increase in hair is not observed, integumental perturbation is repeated using a different method (for example, switching from a nonmechanical to a mechanical means or vice versa, or switching from laser to dermabrasion or vice versa, or switching to chemical perturbation using an inflammatory agent). In one embodiment, where a desired increase in hair is not observed, integumental perturbation is repeated but to a greater skin depth, for example, increasing the depth by 10, 20, 30, 40, 50, 60, 70, 80, 90, or 100 microns or more. In one embodiment, where a desired increase in hair is not observed, the subject is switched to a different post-perturbation treatment, for example, a topical composition comprising an inflammatory agent or pharmacologic modulator of hair follicle development. In one embodiment, where a desired increase in hair is not observed, the subject is switched to a different hair growth-promoting agent treatment, for example, an increased dose of agent, or treatment with a different agent (for example, switching from minoxidil to finasteride or vice versa, or switching from minoxidil to latanoprost or vice versa, or switching from minoxidil alone to a combination of minoxidil and finasteride or a combination of minoxidil and latanoprost, etc.).

In one embodiment, a method of treatment is carried out over a small area of skin (e.g., 1×1 cm, or 1.5×1.5 cm, or 2×2 cm, or 2.5×2.5 cm, or 3×3 cm or more), hair is measured in accordance with a foregoing methods, and if candidacy is established, the method of treatment is carried out over a larger area of skin, such as, e.g., an entire balding area of scalp.

5.8.4.1 Methods for Evaluating Hair Follicles

In certain embodiments, hair follicles are characterized according to the following criteria for structures of interest (SOIs):

NL (neogenic-like): Unattached primitive follicular structure, with only one of the following "small" traits: shaft, sebaceous gland, or pore. Dermal channel is absent or inconclusive. Further subcategories of NL include: NL with DP (dermal papilla)/active, NL with DP/inactive, NL without DP/active, and NL without DP/inactive.

PEL (pre-existing-like): Unattached primitive follicular structure, with one or more of the following "large" traits or two or more of the following "small" traits: shaft, sebaceous gland, or pore. Dermal channel is present. Further subcategories of PEL include: PEL with DP (dermal papilla)/active, PEL with DP/inactive, PEL without DP/active, and PEL without DP/inactive.

PELA (pre-existing-like, attached): Primitive follicular structure that is attached to larger, mature, pilosebaceous unit that extends to the epidermis.

In a particular embodiment, these criteria are derived from the flow chart/algorithm for categorizing the structures of interest outlined in FIG. 31. In one embodiment, the following specific protocol for obtaining and categorizing structures of interest is used:

A biopsy is harvested from a treated (and/or control) area of skin of a subject. For example, the biopsy may be taken 14 days post-integumental perturbation. One or two or more punch biopsies each, e.g., 1 mm, 2 mm, 3 mm, 4 mm, 5 mm, or more in diameter, are harvested from a subject. In a particular embodiment, the punch biopsy is 4 mm in diameter. Biopsies are bisected longitudinally down the midline of the punch biopsy to keep epidermal-dermal orientation intact, fixed in 4% paraformaldehyde for 24 hours, transferred to 30% sucrose in 1×PBS for 24 hours, and then embedded bisected side face down in OCT (Tissue-Tek); and kept frozen on either dry ice or in a −20° C. freezer. Each cryoblock is sectioned serially. Two sections are collected onto each slide with every third slide stained with H&E.

Slides stained with H&E are analyzed for structures of interest (SOI) identified based on morphology. A SOI attached to another pilosebaceous unit that extended to the epidermis is classified as a preexisting-like attached (PELA). Unattached SOIs are then classified based on the presence of a dermal channel, shaft (small or large), sebaceous gland (small or large), and/or pore (small or large). One or more large traits or two or more small traits result in the SOI being classified as PEL, while only one small trait results in the SOI being classified as NL. SOIs that have neither a dermal channel, shaft, sebaceous gland, or pore and are not attached to another pilosebaceous unit are stained for AP, Ki67, Ber-EP4, and elastin.

SOIs are categorized based on their marker expression: presence or absence of alkaline phosphatase activity (DP marker); presence or absence of Ki67 (proliferation marker); presence or absence of Ber-EP4 (hair follicle marker); and presence or absence of dermal channels (extracellular matrix marker visualized with elastin). SOIs that do not have a dermal channel are classified as NL, while those that have a dermal channel are classified as PEL. SOIs that are Ber-EP4-negative are classified as non-follicular. NLs and PELs are refined into further categories: with or without DP (positive or negative AP staining); and active or inactive (positive or negative Ki67 staining). Inconclusive staining for Ber-EP4 is treated as a positive result for Ber-EP4, and inconclusive staining for alkaline phosphatase or Ki67 results in the SOI categorized as an NL (no dermal channel present) or a PEL (dermal channel present).

5.8.4.2 Scanning Laser Confocal Microscopy

Scanning laser confocal microscopy (CM) is a noninvasive imaging technique that uses laser light to visualize the skin in vivo. Progress of treatment, starting at day 0, may be monitored using CM alone or in combination with photography. This fluid immersion microscope requires oil/water immersion to measure changes in the index of refraction within the tissue as detected by the reflected laser light. Real-time noninvasive confocal infrared imaging of the epidermis, papillary dermis, and superficial reticular dermis to a maximum depth of 350 μm is possible with resolution comparable to conventional light microscopy. Skin can be imaged in its native state without the fixing, sectioning, and staining necessary for histology. As such, dynamic processes can be noninvasively observed over an extended period of time. As a research tool, RCM has been reported to facilitate the in vivo assessment of several pigmented (Grimes, 2005, Microdermabrasion. Dermatol Surg 31:1351-1354) and non-pigmented skin lesions. See Curiel-Lewandrowski, et al., Use of in vivo confocal microscopy in malignant melanoma: an aid in diagnosis and assessment of surgical and nonsurgical therapeutic approaches, Arch Dermatol 140 (2004), pp. 1127-1132; Gerger et al., Diagnostic applicability of in vivo confocal laser scanning microscopy in melanocytic skin tumors, J Invest Dermatol 124 (2005), pp. 493-498; Swindells et al. Reflectance confocal microscopy may differentiate acute allergic and irritant contact dermatitis in vivo, J Am Acad Dermatol 50 (2004), pp. 220-228; Aghassi, et al., Time-sequence histologic imaging of laser-treated cherry angiomas with in vivo confocal microscopy, J Am Acad Dermatol 43 (2000), pp. 37-41; and Gonzalez et al. Noninvasive (real-time) imaging of histologic margins of a proliferative skin lesion. In Vivo. J Invest Dermatol 1998 111: 538-539. This technique has been successfully used to image hair follicles, including structures associated with hair follicle neogenesis, in mice and may have similar utility in people. Incorporating CM imaging into the treatment methods described herein may also help determine the optimal timing of biopsies of treated skin areas.

In one embodiment, confocal microscopy is performed using a device (Vivascope; Lucid, Inc.) used for human studies. An exemplary protocol follows, which may be optimized as deemed necessary by the practitioner. Subjects are positioned in an inclined or sitting position to allow visualization of the treated area of the scalp. Each subject remains still in the imaging position for a minimum of 15 minutes of imaging per subject. A medical grade adhesive secures the fluid immersion ring to the surface of the skin. The ring remains attached throughout the imaging session and a new ring is applied on each test site. In one embodiment, CM is performed on Day 0, 7, and 14 (11 and 17 if punch biopsy was not taken on Day 14) following the beginning of the treatment regimen.

5.8.4.3 Methods for Evaluating Treatment of Scarring Alopecia

The safety and efficacy of a treatment described herein for scarring alopecia may be measured using the methods described in herein. In some embodiments, successful treatment is determined as an increase in the number of visually or photographically detected hairs. In other embodiments, successful treatment is evaluated by a skin biopsy for hair follicle structures and scar attributes. In other embodiments, treatment is continued until the symptoms and signs of scalp inflammation are controlled, and progression of the condition has been halted. In certain embodiments, scalp inflammation is measured by biopsy of the scalp. For example, in some embodiments, treatment is continued until, e.g., itching, burning, pain, and tenderness have cleared, scalp redness, scaling, and/or pustules are no longer present, and the hair loss has not extended. Commonly, cicatricial alopecias may reactivate after a quiet period, and treatment may have to be repeated at the reemergence of symptoms or signs of the condition.

6. EXAMPLE: CLINICAL EVALUATION OF THE EFFECTS OF DERMABRASION ON HAIR FOLLICLE STRUCTURES

The objective of the following protocol is to determine the effects of dermabrasion on inducing the formation of neogenic or neogenic-like hair follicles in human skin.

Although any patient population may be treated, patients for the following protocol may be Caucasian males 20-50 years of age, have androgenetic alopecia with the presence of a transition zone defined as an area possessing both terminal and miniaturized hairs, have a Fitzpatrick skin type 1-4 (higher Fitzpatrick skin type ratings are not preferred due to the increased risk of keloid formation and hypopigmentation in these subjects). Patients for whom treatment may be contraindicated (particularly at the clinical trial stage) are those who are currently participating in or have participated in any clinical study with an investigational drug within the thirty (30) days immediately preceding treatment, with current or recent use (<1 y) of isotretinoin (Accutane), currently taking hormone therapy, or steroids or other immunomodulators or have taken these medications within the past thirty (30) days (inhaled steroids are acceptable), currently using Rogaine™ or Propecia™ or used them in the past forty-five (45) days, immune compromised or undergoing therapy to treat an immune disorder, have a clinically significant medical condition that may interfere with the protocol described herein, have other active skin diseases (such as actinic keratosis or psoriasis) or skin infections (bacterial, fungal or viral, esp. HSV infection) in the area to be treated, have a history of keloids or hypertrophic scarring, hypersensitivity to lidocaine, poor wound healing, diabetes, or coagulopathy, undergoing current drug or alcohol abuse, psychiatric dysfunction, or other factors that would limit compliance, have sunburned skin, or who are currently taking anti-platelet agents other than aspirin.

Dermabrasion using alumina particles is performed on Day 0. Dermabrasion is performed to a depth of approximately 100 µm, which includes removal of epidermis and disruption of the papillary dermis (detectable by a shiny, whitish appearance) inducing the formation of small pinpoints of blood in the treated area. Dermabrasion is performed in two sites of the scalp skin corresponding to transitional areas (or advancing margin) of balding in the vertex region. The area is then allowed to heal without manipulation. 4 mm punch biopsies are performed either on day 11 or 14, and structures associated with hair follicles are examined in these subjects based on histological assessment. A third biopsy is optionally performed on Day 14 on an untreated area 1 cm away from the treated area to serve as histologic control. In the event that limited evidence of hair follicle structures associated with new (or neogenic-like) follicles are observed on day 14, another biopsy may be performed on day 17. Subjects scheduled for day 11 biopsies for whom the scab in the wound detaches before day 8, will have the biopsy rescheduled for 3 days afterwards. Conversely, subjects for whom the scab has not detached by day 10 will have the biopsy visit rescheduled for 3 days after the scab detaches. It is expected that the scab will detach around days 6-10.

The protocol may be amended in accordance with the findings. For example, if dermabrasion causes presence of neogenic-like hair follicles in a 4 mm punch biopsy in, for example, at least three of the first 15 patients, then additional patients will be treated in two sites: one site corresponding to the area of greatest balding on the vertex and one site corresponding to a transitional area (or advancing margin) of balding in the vertex region.

6.1 Determination of Treatment Sites

Two sites on each subject's scalp are identified for treatment, both corresponding to transitional areas (or advancing margins) of balding in the vertex region. Some patients may be treated in a site of greatest balding on the vertex region.

6.2 Dermabrasion

The procedure begins with shaving/clipping of the existing hair in the area to be treated followed by a thorough cleaning with antiseptic cleansing agent. Numbing agents, such as lidocaine HCL 2% and Epinephrine 1:100,000, are injected to anesthetize the surface to be treated. Dermabrasion is performed to a depth of approximately 100 µm, which includes removal of epidermis and disruption of the papillary dermis (detectable by a shiny, whitish appearance) inducing the formation of small pinpoints of blood in the treated area. Each dermabraded area is approximately a 1.5 cm×1.5 cm square. Suitable devices for dermabrasion are the ASEPTICO ECONO-DERMABRADER from Tiemann and Company, the DX system from Advanced Microderm (see, e.g., http://www.advancedmicroderm.com/products/tech_specs.html), or the M2-T system from Genesis Biosystems. Adhesive ocular shields are worn by the patient during the procedure to avoid complications due to aluminum crystals entering the eye (chemosis, photofobia, punctuate keratitis) and the doctor should wear safety goggles. The dermabrasion tool is carefully maneuvered over the area to carefully remove layers of skin until the desired level is reached. The procedure usually takes only a few minutes, up to about a half hour.

Pre-dermabrasion, patients should be asked to: not wear contact lenses during the procedure. discontinue use of over the counter exfoliation products such as Retinol, Glycolic or other hydroxy acids, Salicylic acid, Beta hydroxyl acids 3 days prior to treatment, discontinue use of retinoids 30 days prior to treatment, not receive Botox or collagen injections for 2 weeks prior to treatment.

Following the procedure the treated skin will be red, swollen and tender, and the wound should be cared for as follows until new skin starts to grow; this usually takes 7-10 days: 1) Keep the area clean and dry for today. Do not cover, bandage, or otherwise manipulate the treated area; 2) Avoid touching the area when washing hair; 3) Pat the area dry. Do not cover, bandage, or otherwise manipulate the treated area.

The treated are may itch as the new skin grows and may be slightly swollen, sensitive, and bright pink for several weeks after dermabrasion.

The following measures are taken to prevent any complications.

Inform your doctor of any yellow crusting or scabs—this may be the start of an infection.

Swelling and redness should subside after a few days to a month. Persistent redness of an area could be the sign of a scar forming so contact your doctor immediately.

No swimming is permitted for the first 7 days following dermabrasion.

To avoid abnormal pigmentation, once the new skin is healed, keep out of the sun and apply a broad spectrum sunscreen daily for at least 3 months after microdermabrasion. Even the sun through window-glass can promote unwanted pigmentation.

6.3 Punch Biopsy

The procedure begins with thoroughly cleaning the area to be biopsied with antiseptic cleansing agent. Lidocaine HCL 2% and Epinephrine 1:100,000 (approximately 0.5 cc to each site) are injected to anesthetize the site that will be biopsied. 4 mm punch biopsy is performed. The biopsied site is closed with 2 4.0 Ethalon sutures. Vaseline and band-aid are applied. Tissue samples are stored in formalin for histological analysis.

6.4 Primary Endpoints

Histologic analysis of structures associated with new or neogenic-like hair follicles following dermabrasion. The null hypothesis is that no (0) such structures will form, since that is the current dogma in humans. A positive response to treatment is characterized as the appearance of 3 or more neogenic-like follicles in a 4 mm punch biopsy.

Among the factors to be evaluated when determining success of treatment are the presence or absence of: crusting/scabbing; comedones; infection; pigmentary changes (e.g., absent, hypopigmentation (mild, moderate or severe), or hyperpigmentation (mild, moderate or severe)); scarring; re-epithelialization; or presence of hair follicles by gross observation.

6.5 Secondary Endpoints

1) To determine which day after integumental perturbation is new (or neogenic-like) follicle formation most active.
2) To quantify the number and characterize the morphology of follicles in each biopsy.
3) Clinical characteristics of dermabraded areas.

6.6 Results

A clinical study was carried out in accordance with the protocol described above. In particular, the goal of the clinical study was to examine whether dermabrasion involving removal of epidermis and some papillary dermis could induce hair follicles in human scalp.

In brief, on Day 0, fifteen subjects received standard particle-mediated dermabrasion ("PMDA"; DX system, Advanced Microderm™), using alumina particles. PMDA was performed to a depth of approximately 100 microns, including removal of epidermis and disruption of the papillary dermis (detectable by a shiny, whitish appearance) inducing the formation of small pinpoints of blood in the treated area.

Thirteen of the fifteen enrolled subjects had skin biopsies in each of their two dermabraded sites (right and left scalp). Two of these thirteen subjects (15%) had neogenic-like follicles present in both their left and right sites, for a total of four positive biopsies out of 26 adequate biopsies (15%). Ten of the thirteen subjects had biopsies at a third control site. One out of ten subjects (10%) had neogenic-like follicles in the biopsy, for a total of 1 positive biopsy out of 10 adequate biopsies (10%).

This study is described in more detail below.

6.6.1 Methods

Fifteen eligible subjects were recruited into the trial without randomization and received dermabrasion to two sites (left and right side of scalp). Prior to enrollment, subjects were screened for eligibility; at which time a complete medical history, including concomitant medications, a baseline assessment of the subject's scalp, and a focused physical exam, including vital signs (VS), were performed. Fifteen subjects who fulfilled the inclusion/exclusion criteria were enrolled. Evaluations to detect adverse events and changes in existing medical conditions were made throughout the study. To ensure proper post-treatment care, all subjects were given a Wound Care Instructions Form at the end of the baseline visit.

In addition, subjects were evaluated for Fitzpatrick skin type; only subjects with a Fitzpatrick skin type of 1-4 were allowed in the study. Higher Fitzpatrick skin ratings were excluded due to the increased risk of keloid formation and hypopigmentation.

Digital photography of the dermabraded areas was done at baseline, and on any of the post-PMDA days that the subject returned to clinic; e.g., on days 7, 11, 14, 17, 24, and 60 or other intervening days if subjects returned on a non-scheduled day. At Baseline (Day 0), tattooing was done with a 4 mm long 28 gauge needle at two points at diagonally opposite corners of a 1.5 cm×1.5 cm square in the scalp sites. A template of sterile (plastic) material was used to guide the tattooing. Tattoos were used to register the photographs obtained at different times throughout the study. High resolution close up digital images (Nikon™ DL series camera), using tattoos for registration, were used to record the visible aspects of the wound and the healing process.

On Day 0, fifteen subjects received particle-mediated dermabrasion (PMDA) (DX system from Advanced Microderm™), using alumina particles. All subjects were given ocular protection and anesthesia for the procedure. The procedure began with shaving/clipping of the existing hair in the area to be treated, followed by a thorough cleaning with antiseptic cleansing agent. Lidocaine HCL 2% plus Epinephrine 1:100,000 was injected to anesthetize the surface that was treated. PMDA was performed to a depth of approximately 100 that included removal of epidermis and disruption of the papillary dermis (detectable by a shiny, whitish appearance) inducing the formation of small pinpoints of blood in the treated area. Each of the two dermabraded areas (transitional areas or advancing margins of balding in the vertex region of the right and left scalp) was approximately 1.5 cm×1.5 cm square. Subjects were instructed to allow the area to heal without manipulation. The scab resulting from the PMDA generally detached six-ten days after PMDA. Locations of dermabraded areas are listed in Table 2 below.

TABLE 2

| | Location of Treatment Areas | |
|---|---|---|
| ID | Treatment Area A | Treatment Area B |
| 01 | RIGHT PARIETAL (ARROW POINTING TO INNER TATTOO) | LEFT PARIETAL |
| 02 | RIGHT ARROW: PATIENT'S LEFT | LEFT ARROW: PATIENT'S LEFT |

TABLE 2-continued

Location of Treatment Areas

| ID | Treatment Area A | Treatament Area B |
|---|---|---|
| 03 | LEFT SCALP | RIGHT |
| 04 | RIGHT SCALP | LEFT SCALP |
| 05 | RIGHT SCALP | LEFT SCALP |
| 06 | RIGHT SCALP | LEFT SCALP |
| 07 | LEFT | RIGHT |
| 08 | LEFT SCALP | RIGHT SCALP |
| 09 | LEFT SCALP | RIGHT SCALP |
| 010 | LEFT | RIGHT |
| 011 | LEFT SCALP | RIGHT SCALP |
| 012 | LEFT | RIGHT |
| 013 | LEFT | RIGHT |
| 014 | RIGHT SCALP | LEFT SCALP |
| 015 | LEFT SCALP | RIGHT SCALP |

The volume of local anesthetic used and whether contact lenses were worn during the procedure are listed in Table 3. All subjects used adhesive ocular shields to avoid complications due to aluminum crystals entering the eye.

TABLE 3

PMDA conditions

| ID | Contact lenses | Amount of Anesthesia |
|---|---|---|
| 01 | NO | 6 CC |
| 02 | NO | 3 CC |
| 03 | NO | 1.5 CC |
| 04 | YES | 2.0 |
| 05 | NO | 2.8 CC |
| 06 | NO | 2 CC |
| 07 | NO | 2 CC |
| 08 | NO | 3 |
| 09 | NO | 4.5 ML |
| 010 | NO | 2.0 |
| 011 | YES | 2.5 CC |
| 012 | YES | 3 CC |
| 013 | YES | 2 CC |
| 014 | NO | 3 CC |
| 015 | NO | 3 CC |

Scalps were visually examined on any or all of the following days: baseline, any suture removal day, days 7, 11, 14 and 60, and the following characteristics analyzed: crusting/scabbing, comedones, infection, pigmentary changes, scarring, re-epithelialization, and the presence of hair follicles by gross observation. The timing and results of the scalp examinations for each subject can be found in Table 4.

TABLE 4

Scalp examination

| ID | Visit | Scalp Examination Site | Comments |
|---|---|---|---|
| 01 | BASELINE | ERYTHEMA | LIGHT - MODERATE ERYTHEMA |
|  | SUTURE REMOVAL | EROSION | MILD 3 MM EROSION ON LEFT BX SITE |
|  | DAY 60 | ERYTHEMA | MILD ERYTHEMA AT TREATED SITES |
| 02 | DAY 7 | ERYTHEMA | MINIMAL |
|  |  | SCAB | RIGHT > LEFT |
|  | DAY 11 | EROSION | 4 (1 MM) EROSIONS ON RIGHT SITE |
|  | DAY 14 | EROSION | 4 (1 MM) EROSIONS ON RIGHT SITE |
|  | SUTURE REMOVAL | SCAB | RIGHT |
| 03 | DAY 7 | ERYTHEMA |  |
|  |  | SCAB |  |
|  | DAY 11 | ERYTHEMA |  |
|  | DAY 14 | ERYTHEMA | VERY MINIMAL |
| 04 | DAY 7 | ERYTHEMA |  |
|  |  | OTHER | MINIMAL CRUSTING |
|  | DAY 14 | ERYTHEMA | MILD PINKNESS |
|  | SUTURE REMOVAL | ERYTHEMA | MILD |
| 05 | DAY 7 | SCAB | MINIMAL |
|  | DAY 11 | SCAB | MINIMAL CRUSTING |
|  | DAY 14 | ERYTHEMA | MILD |
|  | SUTURE REMOVAL | ERYTHEMA | MILD LEFT > RIGHT |
|  | DAY 60 | ERYTHEMA | MILD |
| 06 | DAY 7 | ERYTHEMA | MINIMAL |
|  |  | SCAB | THICK ON BOTH SIDES |
| 07 | DAY 7 | ERYTHEMA | MILD (BOTH SIDES) |
|  | DAY 11 | ERYTHEMA |  |
|  | DAY 14 | ERYTHEMA | MILD |
|  | SUTURE REMOVAL | EDEMA | ONLY ON RIGHT STITCH REACTION |
|  |  | ERYTHEMA | ONLY ON RIGHT STITCH REACTION |
| 08 | DAY 7 | ERYTHEMA |  |
|  |  | EROSION |  |
|  | DAY 11 | ERYTHEMA |  |
|  | DAY 14 | ERYTHEMA |  |
|  | SUTURE REMOVAL | ERYTHEMA | MILD ON BACK |
|  | DAY 60 | ERYTHEMA | MILD |
| 09 | DAY 7 | ERYTHEMA |  |
|  |  | SCAB | SPOTTY |
|  | DAY 11 | ERYTHEMA |  |
|  | DAY 14 | EROSION |  |
|  | SUTURE REMOVAL | ERYTHEMA | MILD |
|  |  | SCAB | BIOPSY CONTROL |
|  | DAY 60 | ERYTHEMA | MILD ON BIOPSY SITE |

TABLE 4-continued

Scalp examination

| ID | Visit | Scalp Examination Site | Comments |
|---|---|---|---|
| 010 | DAY 7 | SCAB | |
| | DAY 11 | ERYTHEMA | MILD |
| | DAY 14 | ERYTHEMA | |
| | SUTURE REMOVAL | ERYTHEMA | |
| | DAY 60 | ERYTHEMA | MILD ERYTHEMA |
| 011 | DAY 7 | ERYTHEMA | MILD |
| | | SCAB | LEFT > RIGHT |
| | DAY 11 | ERYTHEMA | |
| | DAY 14 | ERYTHEMA | |
| | SUTURE REMOVAL | ERYTHEMA | |
| | DAY 60 | ERYTHEMA | |
| 013 | DAY 7 | ERYTHEMA | |
| | DAY 11 | ERYTHEMA | |
| | DAY 14 | ERYTHEMA | MILD |
| | SUTURE REMOVAL | ERYTHEMA | |
| | | SCAB | |
| | DAY 60 | ERYTHEMA | MILD L > R |
| 014 | DAY 7 | ERYTHEMA | MILD |
| | | SCAB | THIN LEPT > RIGHT |
| | DAY 11 | ERYTHEMA | |
| | | SCAB | IN SOME AREA (THIN CRUSTING) |
| | DAY 14 | ERYTHEMA | MILD |
| | SUTURE REMOVAL | ERYTHEMA | MILD |
| | DAY 60 | ERYTHEMA | FROM BIOPSY SIDE |
| 015 | DAY 7 | SCAB | WITH CONTRACTION OF TREATED AREA |
| | DAY 11 | ERYTHEMA | |
| | DAY 14 | ERYTHEMA | MILD |
| | SUTURE REMOVAL | ERYTHEMA | |
| | | SCAB | |

6.6.2 Safety Results

Safety was assessed throughout the study with clinical and photographic assessments of local reactions at the treated site and reported adverse events. Of eight reported adverse events (AEs) that occurred during the course of this study, seven were treatment emergent adverse events (TEAE) and one was a non-treatment emergent adverse event (NTEAE), Table 5, with each event occurring in a different subject. Of the seven TEAEs, five were considered to be related to the PMDA: two pain; two inflammation; one wound infection; and two were considered to be unrelated to PMDA: scalp laceration secondary to an automobile accident and a sinus polyp. The one NTEAE was sinusitis. There were no serious adverse events. All events had resolved by the time of the last study visit.

TABLE 5

Number (%) of subjects with adverse events

| Primary System Organ Class | Preferred Term | AE (N = 15) N(%) | TEAE (N = 15) N(%) |
|---|---|---|---|
| Any class | | 8 (53.3) | 7 (46.7) |
| INFECTIONS AND INFESTATIONS | POSTOPERATIVE WOUND INFECTION | 1 (6.7) | 1 (6.7) |
| INFECTIONS AND INFESTATIONS | SINUSITIS | 1 (6.7) | 0 (0.0) |
| RESPIRATORY, THORACIC AND MEDIASTINAL DISORDERS | SINUS POLYP | 1 (6.7) | 1 (6.7) |
| SKIN AND SUBCUTANEOUS TISSUE DISORDERS | ERYTHEMA | 1 (6.7) | 1 (6.7) |
| GENERAL DISORDERS AND ADMINISTRATION SITE CONDITIONS | PAIN | 1 (6.7) | 1 (6.7) |
| INJURY, POISONING AND PROCEDURAL COMPLICATIONS | POST PROCEDURAL COMPLICATION | 1 (6.7) | 1 (6.7) |
| INJURY, POISONING AND PROCEDURAL COMPLICATIONS | PROCEDURAL PAIN | 1 (6.7) | 1 (6.7) |
| INJURY, POISONING AND PROCEDURAL COMPLICATIONS | SKIN LACERATION | 1 (6.7) | 1 (6.7) |

AE = Any Adverse Event during study
TEAE = Treatment Emergent Adverse Event
N = Number of subjects treated
n(%) = Number and % of subjects with at least one AE or TEAE in each category
MedDRA version: MEDDRA V12.1

6.6.3 Hair Follicle Analysis Results

Between ten and fourteen days after PMDA, thirteen of the original fifteen subjects returned to the clinic to undergo a 4 mm punch biopsy to their right and left PMDA sites. Ten of the thirteen subjects also consented to have a third biopsy in a non-dermabraded area, 1 cm from the dermabraded areas, to act as histological controls (control).

The presence of neogenic-like hair follicles was evaluated in biopsy specimens using routine histological techniques. General morphological parameters, including presence or absence of a hair pore, presence or absence of a hair shaft, and presence or absence of a sebaceous gland, were assessed from sections stained by hematoxylin and eosin (H&E). The presence of elastin fibers was determined using the Luna stain. Immunohistochemistry was performed using antibodies against BerEP4 (a marker of embryonic hair follicles) and Ki67 (a marker of cell proliferation). Alkaline phosphatase (AP) histochemistry was used to identify the dermal papilla of the HF.

Neogenic-like hair follicles were characterized by using some or all of the following criteria: hairs that were of 1) shorter length than vellus and/or vellus-like hair follicles, 2) had lack of a connection with a pre-existing pilosebaceous unit, 3) had lack of a pore at the skin surface, 4) had lack of a well-differentiated sebaceous gland, 5) had lack of a hair shaft, 6) had lack of an elastin-negative "streamer" or "dermal channel," and 7) had positive staining for alkaline phosphatase, BerEP4 (a marker of embryonic hair follicles), and Ki67 (a marker of cell proliferation).

If the H&E stains were negative for neogenic-like hair follicles, the other staining procedures were not performed. The data from the two subjects (#3 and #5) in which neogenic-like hair follicles were detected by a variety of stains can be found in Table 6.

PMDA areas; ten left sided PMDA areas; six control areas). Biopsies on day ten (three biopsies), day eleven (one biopsy), day thirteen (one biopsy), and day 20 (one biopsy) were negative for neogenic-like hair follicles. All ten biopsies done in control areas often subjects (non-dermabraded) were negative for neogenic-like hair follicles (one on day thirteen, six on day fourteen, one on day 20, and two on unknown dates).

Two of the thirteen subjects (15%) had neogenic-like hair follicles present in both their left and right sites, for a total of four positive biopsies out of 26 adequate biopsies (15%) (Table 6). In total, as shown in Table 6, 11 neogenic-like structures were identified in the dermabraded sites. In contrast, only one such structure was identified (in one subject) in a biopsy taken from an untreated control site. In the histological analysis, there were also a small number of structures that resembled the morphology of neogenic-like hair follicles, but likely had dermal channels, suggesting that these structures derived from pre-existing hair follicles.

7. EXAMPLE: EVALUATION OF HAIR GROWTH AFTER INTEGUMENTAL PERTURBATION BY LASER OR DERMABRASION

The objective of this study is to assess the effects of three laser treatments as a method of integumental perturbation compared to dermabrasion on promoting hair growth, as evidenced, e.g., by hair follicle activation, stimulation, or reorganization, and/or neogenesis in human skin.

Although any patient population may be treated, patients selected for treatment in the study may be Caucasian males 20-50 years of age, have androgenetic alopecia with the presence of a transition zone defined as an area possessing

TABLE 6

Data from two subjects (#3 and #5) with PMDA induction of neogenic-like hair follicles

| NL HF | AP | BerEP4 | Ki67 | No elastin neg zone | No shaft | No SG | No pore | Not connected to pre-existing HF | Isolated (from nearby HF) |
|---|---|---|---|---|---|---|---|---|---|
| 003, L, a | NA-paraffin | + | + | +* | + | + | + | + | + |
| 003, L, c | NA-paraffin | + | −* | + | + | + | + | + | − |
| 003, R, a | NA-paraffin | + | + | * | + | + | + | + | + |
| 005, R, a | + | + | +* | + | − (IRS cone) | + | + | + | − |
| 005, R, b | + | + | + | + | + | − | + | + | −* |
| 005, R, c | + | + | + | + | * | + | + | + | + |
| 005, R, d | −* | + | − | Not avail | + | + | + | + | + |
| 005, L, a | + | + | −* | + | + | + | + | + | + |
| 005, L, b | + | + | −* | + | + | + | + | + | + |
| 005, L, d | + | − | −* | + | + | + | + | + | −* |
| 005, L, e | + | + | −* | + | + | + | + | + | −* |

+ = criteria fulfilled
− = criteria not fulfilled
* = lack of criteria fulfillment possibly due to false negative (lack of appropriate structures/cells in the section)
− and * = likely lack of fulfillment of criteria, but cannot rule out false negative due to lack of appropriate structures/cells in the section The time at which neogenic-like follicles can be detected after PMDA was also considered. Twenty-seven (27) of the biopsies were obtained on day fourteen (fourteen days after PMDA). The two subjects (#3 and #5) in whose biopsies evidence of neogenic-like hair follicles each had biopsies on day fourteen. There were also 23 biopsies negative for neogenic-like hair follicles on day 14 (seven right sided both terminal and miniaturized hairs, have a Fitzpatrick skin type 1-4 (higher Fitzpatrick skin type ratings are not preferred due to the increased risk of keloid formation and hypopigmentation in these subjects). Patients for whom treatment may be contraindicated (particularly at the clinical trial stage) are those who are currently participating in or have participated in any clinical study with an investigational drug within the thirty (30) days immediately preceding treatment, with current or recent use (<1 y) of isotretinoin (Accutane), currently taking hormone therapy, or steroids or other immunomodulators or have taken these medications within the past thirty (30) days (inhaled steroids are acceptable), currently using Rogaine™ or Propecia™$^{Pro}$ or used them in the past forty-five (45) days, immune compromised or undergoing therapy to treat an immune disorder, have a clinically significant medical condition that may interfere with the protocol described herein, have other active skin diseases (such as actinic keratosis or psoriasis) or skin infections (bacterial, fungal or viral, esp. HSV infection) in the area to be treated, have a history of keloids or hypertrophic scarring, hypersensitivity to lidocaine, poor wound healing, diabetes, or coagulopathy, undergoing current drug or alcohol abuse, psychiatric dysfunction, or other factors that would limit compliance, have sunburned skin, or who are currently taking anti-platelet agents other than aspirin.

Eligible subjects will be recruited into the trial without randomization. Four 1.5 cm×1.5 cm treatment sites will be selected on the left and right, of the anterior and posterior transitional area of the scalp. The sites will be designated—left anterior, left posterior, right anterior, right posterior. All four sites will correspond to transitional areas (or advancing margins) of balding in the anterior or posterior scalp. The method of integumental perturbation to be used at each site will be randomly assigned.

The four methods of integumental perturbation will be performed to a various depths that will include removal of the entire epidermis and disruption of the papillary dermis and may induce the formation of small pinpoints of blood in the treated area. The surgeon will perform each integumental perturbation according to the randomization schedule in each of the treatment sites along the transitional areas (or advancing margin) of balding scalp on Day 0. The subject will be instructed to allow the area to heal without manipulation. Subjects will be asked to come back to undergo a 4 mm punch biopsy on Day 14. A single follow visit will be made at Day 28 to document healing of the punch biopsy, suture removal, and collect any adverse events. The presence of new hair, and evidence of new, activated, or reorganized follicles, will be histologically examined. This exploratory trial design structure will provide a greater likelihood of observing meaningful hair growth or hair follicle activation, reorganization, or neogenesis after these various methods of integumental perturbation, if they exist.

7.1 Methods of Integumental Perturbation

Prior to integumental perturbation, patients should be asked to: not wear contact lenses during the procedure. discontinue use of over the counter exfoliation products such as Retinol, Glycolic or other hydroxy acids, Salicylic acid, Beta hydroxyl acids 3 days prior to treatment, discontinue use of retinoids 30 days prior to treatment, not receive Botox or collagen injections for 2 weeks prior to treatment.

Each procedure begins with shaving/clipping of the existing hair in the area to be treated followed by a thorough cleaning with antiseptic cleansing agent. Numbing agents, such as lidocaine HCL 2% and Epinephrine 1:100,000, are injected to anesthetize the surface to be treated.

Following each procedure the treated skin could be red, swollen and tender, and the wound should be cared for as follows until new skin starts to grow; this usually takes 7-10 days: 1) Keep the area clean and dry for today. Do not cover, bandage, or otherwise manipulate the treated area; 2) Avoid touching the area when washing hair; 3) Pat the area dry. Do not cover, bandage, or otherwise manipulate the treated area.

The treated area may itch as the new skin grows and may be slightly swollen, sensitive, and bright pink for several weeks after dermabrasion.

The following measures are taken to prevent any complications.

Inform your doctor of any yellow crusting or scabs—this could be the start of an infection.

Swelling and redness should subside after a few days to a month. Persistent redness of an area could be the sign of a scar forming so contact your doctor immediately.

No swimming is permitted for the first 7 days following dermabrasion.

To avoid pigmentation, once the new skin is healed, keep out of the sun and apply a broad spectrum sunscreen daily for at least 3 months after microdermabrasion. Even the sun through window-glass can promote unwanted pigmentation.

7.1.1 Dermabrasion

Standard dermabrasion is performed to a depth of approximately 100 μm, which includes removal the entire epidermis and disruption of the papillary dermis (detectable by a shiny, whitish appearance) inducing the formation of small pinpoints of blood in the treated area. Each dermabraded area is approximately a 1.5 cm×1.5 cm square. Suitable devices for dermabrasion are the ASEPTICO ECONO-DERMABRADER from Tiemann and Company, the DX system from Advanced Microderm (see, e.g., http://www.advancedmicroderm.com/products/tech_specs.html), or the M2-T system from Genesis Biosystems. Adhesive ocular shields are worn by the patient during the procedure to avoid complications due to aluminum crystals entering the eye (chemosis, photofobia, punctuate keratitis) and the doctor should wear safety goggles. The dermabrasion tool is carefully maneuvered over the area to carefully remove layers of skin until the desired level is reached. The procedure usually takes only a few minutes.

7.1.2 Ultrapulse $CO_2$ Fractional Laser

An Ultrapulse (fractional mode) $CO_2$ laser will be used to disrupt the epidermis and dermis to approximately 100 to 500 μm in depth. The Ultrapulse laser produces an effect that is similar to that of dermabrasion yet the integumental perturbation delivers a greater amount of energy deeper into the skin in a non-scaring fractional ablation. The treated area is approximately 1.5 cm×1.5 cm square. The Ultrapulse will be set to deliver up to 350 mJ, up to 52.5 Watts, using pattern size #8, density #4, and fill the square treatment site with up to 5 passes.

7.1.3 Ultrapulse $CO_2$ Ablation Laser

An Ultrapulse $CO_2$ laser (ablative mode) will be used to disrupt the epidermis and dermis to approximately 100 to 500 μm in depth. The Ultrapulse laser produces an effect that is similar to that of dermabrasion yet this method of integumental perturbation delivers a greater amount of energy deeper into the skin in a non-scaring ablation that resembles the dermabrasion. The treated area is approximately 1.5 cm×1.5 cm square. The Ultrapulse will be set to deliver up to 500 mJ in 1 msec, 1 Watts, using a spot size of 3 mm at 2 Hz to fill the square treatment site may require up to 15 passes.

7.1.4 Candela Smooth Peel Full-Ablation Erbium Laser

The ablative erbium laser will be set to deliver up to 5 Joules 240 msec in of energy at level 3 so that in up to 15 passes it will produce skin disruption up to a depth of 500 μm. The treated area is approximately 1.5 cm×1.5 cm square.

7.2 Punch Biopsy

The procedure begins with thoroughly cleaning the area to be biopsied with antiseptic cleansing agent. Lidocaine HCL 2% and Epinephrine 1:100,000 (approximately 0.5 cc to each site) are injected to anesthetize the site that will be biopsied. 4 mm punch biopsy is performed. Biopsied site is closed with 2 4.0 Ethalon sutures. Vaseline and band-aid are applied. Tissue samples are stored in formalin for histological analysis.

The treated subjects will be asked to return ten days after undergoing the biopsy. During this visit the following procedures and evaluations will be performed: suture removal, assessment of the treated areas, photography of treated areas, review of the subject's medical history and concomitant medications, documentation of adverse events, final evaluation.

7.3 Primary Endpoints

The primary endpoint is the number of neogenic-like hair follicle structures as determined by histologic analysis of the 4 mm punch biopsies on Study Day 14.

7.4 Secondary Endpoints

1) To determine the morphology of follicles in the 4 mm punch biopsies on Study Day 14.
2) To determine clinical characteristics of the disrupted areas.

7.5 Results

Figure 23A:
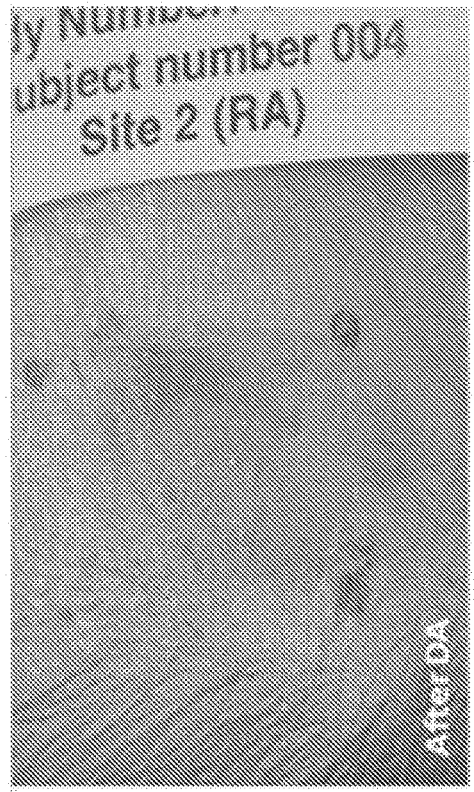
Figure 23B:
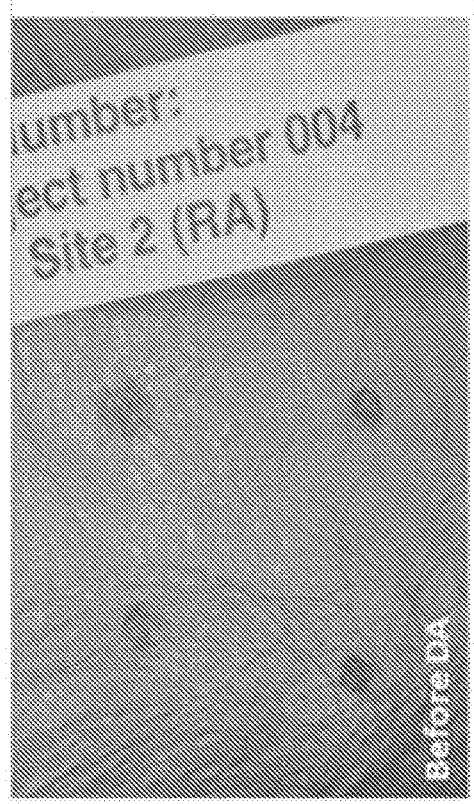
Figure 23C:
Figure 23D:
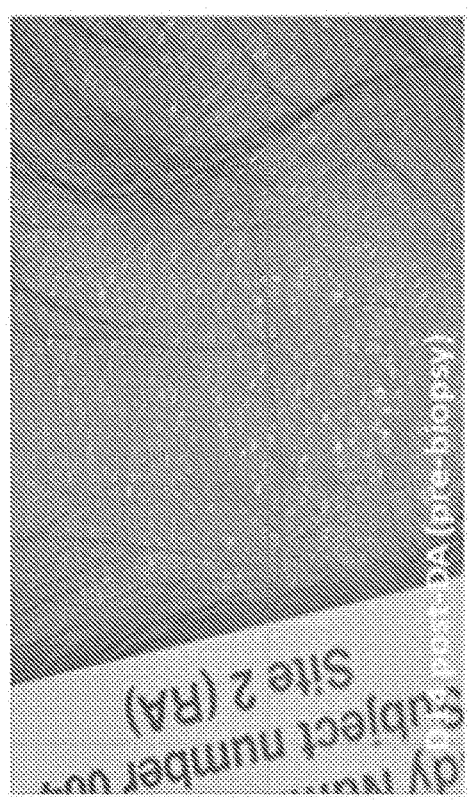
Figure 23E:
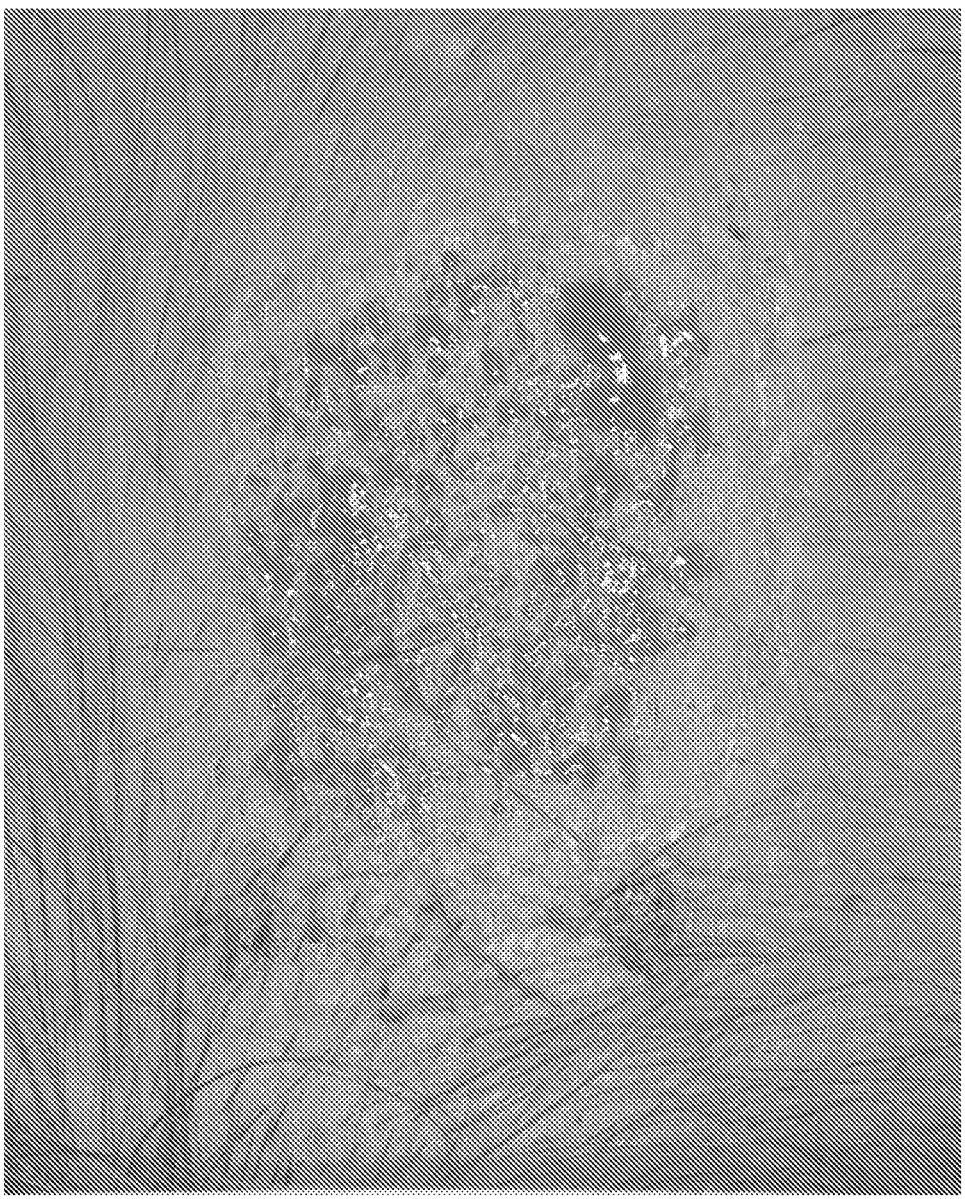
Figure 23F:
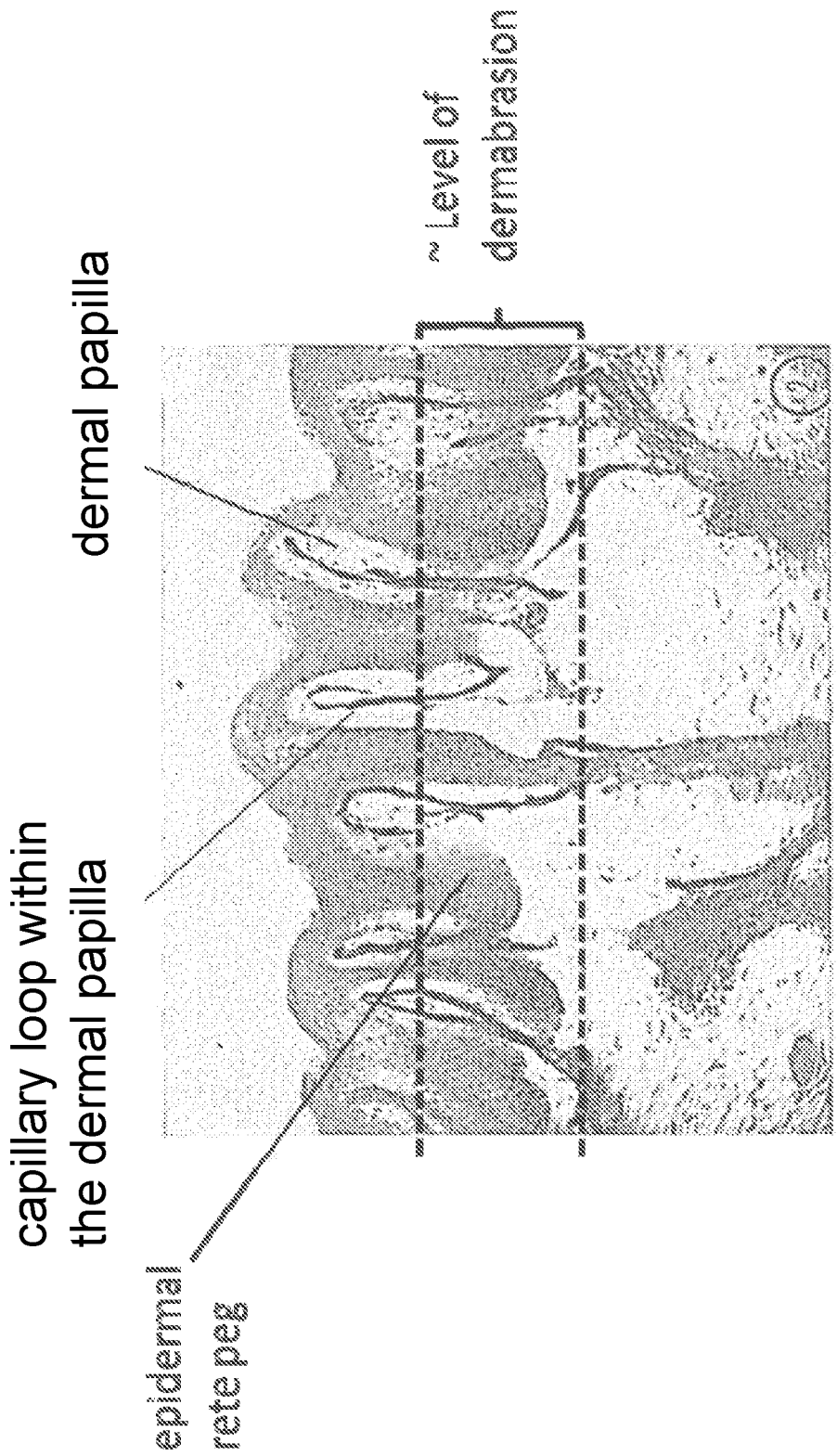

As shown in Table 7 below, all four of the modes of integumental perturbation produced activated hair follicles. Dermabrasion (using the Aseptico Econo-Dermabrader from Tiemann and Company) resulted in the highest number of activated follicles, and among the laser treatment modalities, treatment with fractional laser resulted in the highest number of activated follicles. Exemplary results from the dermabrasion study are provided in FIG. 23A-D), which demonstrates hair growth in an area of skin of a subject treated with integumental perturbation by dermabrasion ("DA"). FIG. 23E demonstrates the pinpoint bleeding achieved immediately after this modality of dermabrasion. FIG. 23F provides an image of the skin's epidermal ridges that enclose the vascularized dermal papillae and can help to illustrate how integumental perturbation, e.g., by dermabrasion to a depth of 100-150 microns, would cause pinpoint bleeding.

TABLE 7

| Treatment | Hair Follicle Type (NL or PEL) | | All Hair Follicles |
|---|---|---|---|
| | All NL | All PEL | |
| Dermabrasion | 18 | 27 | 45 |
| Fractional Laser | 12 | 16 | 28 |
| Ultrapulse Laser | 7 | 11 | 18 |
| Smoothpeel Laser | 8 | 8 | 16 |
| Totals | 45 | 62 | 107 |

8. EXAMPLE: CLINICAL EVALUATION OF INTEGUMENTAL PERTURBATION ON HAIR GROWTH

This example provides a clinical protocol to examine the use of integumental perturbation to promote hair growth, as evidenced, e.g., by hair follicle activation, stimulation, or reorganization, and/or neogenesis and/or by increased numbers of vellus and/or terminal hair counts and/or hair shaft thickness in human skin in male subjects with androgenetic alopecia. The two methods that will be used include the more superficial form of integumental perturbation with dermabrasion and the deeper (extending to the level of the subcutaneous fat) full thickness skin excision using punch biopsy.

Based on exploratory human data (see the examples of Sections 6 and 7), the clinical hypothesis underpinning the objectives of this protocol is that integumental perturbation (also referred to in this section as "controlled perturbation") will (i) increase hair follicle activation, stimulation, or reorganization, and/or neogenesis, and/or (ii) increase numbers of vellus and/or terminal hair counts, and/or (iii) increase hair shaft thickness. The controlled perturbation can be more superficial (e.g. with a dermabrasion affecting mostly the epidermis) or can be deeper (e.g. when a punch biopsy affects both the epidermis and the deeper dermis). It is possible that this type of stimulation may lead to macroscopic evidence of hair growth.

8.1 Study Protocol

The following protocol describes a Phase IIa clinical study that evaluated the effect of dermabrasion and post-perturbation treatment with a hydrogel (comprising Carbomer (Carbopol 980), glycerol, sodium hydroxide, methylparaben, propylparaben, and purified water) on (i) the formation of neogenic-like or activated or stimulated hair follicle structures (e.g., NL, PEL and PELA as described in Section 5.8.4.1 supra) and (ii) hair growth.

Diagnosis and main criteria for inclusion are Caucasian males 20-65 years of age, providing written informed consent, who have androgenetic alopecia with the presence of a vertex transition zone defined as an area possessing both terminal and miniaturized hairs, Hamilton-Norwood type 3V, 4, 5, 5A, or 5V, with a vertex area large enough to accommodate both treatment sites, and Fitzpatrick skin type 1-4.

8.1.1 Efficacy objectives

Primary. To assess changes from Baseline to Day 84 in the number of photographically detected hairs in the target analysis area of the skin of subjects treated with controlled cutaneous perturbation using dermabrasion (DA—a more superficial integumental perturbation) plus the topical application of a hydrogel.

Secondary. (i) To assess the changes from Baseline to Day 168 in the number of photographically detected hairs in the target analysis area of the skin of subjects treated with controlled cutaneous perturbation using dermabrasion (DA) plus the topical application of hydrogel; (ii) To assess the number of histologically detected neogenic-like hair follicles and other hair follicle structures of interest in biopsies taken on Day 14 from subjects treated with controlled cutaneous perturbation using dermabrasion (DA) plus topical hydrogel; (iii) To assess the number of histologically detected hair follicles in biopsies taken on Day 168 from the site of the first biopsy (allowed to heal by secondary intentions) in subjects treated with controlled cutaneous perturbation using a 4 mm punch biopsy plus topical hydrogel.

Exploratory. (i) To assess a) at Day 84 and b) at Day 168 the number of photographically detected hairs in subjects treated with controlled cutaneous perturbation using a 4 mm punch biopsy plus the topical application of hydrogel; (ii) To assess a) at Day 84 and b) at Day 168 the hair shaft thickness of photographically detected hairs induced by treatment with controlled cutaneous perturbation using a 4 mm punch biopsy plus the topical application of hydrogel; (iii) To assess changes a) from Baseline to Day 84 and b) from Baseline to Day 168 in hair shaft thickness of photographically detected hairs after treatment with controlled cutaneous perturbation with dermabrasion (DA) plus the topical application of hydrogel; (iv) the histological characteristics in a second skin punch biopsy on Day 168.

Photographic fields of measurement include the Total Analysis Area, which is a 1.13 cm$^2$ circular region in an area that is dermabraded on Day 0, treated with hydrogel, undergoes a 4 mm punch biopsy on Day 14, and then receives additional treatment with hydrogel. Within the Total Analysis Area, there is the Circular Biopsy Area, which is a 0.13 cm$^2$ circular region that undergoes a 4 mm punch biopsy, and the Target Analysis Area, which is the Total Analysis Area minus the Circular Biopsy Area, which is a 1.00 cm$^2$ circular region that has received only dermabrasion.

8.1.2 Safety Objectives

To assess the safety and tolerability of hydrogel in the setting of controlled cutaneous perturbation (dermabrasion and punch biopsy).

The safety and tolerability of hydrogel gel applied topically and epidermal disruption by dermabrasion and punch biopsies will be monitored through the collection of data from targeted examination of the treated scalp sites and the reporting of adverse events (AEs). Visits on Days 1, 2, 3, 12, 15, 17, 18, 19, 20 and 182 are safety visits to assess the sites (although visits on Days 3, 18, 19 and 20 may be replaced by calls if they fall on the weekend). Adverse events will also be reported at safety phone calls on Days 112 and 140. In addition liver and renal function, Hgb-A1C, and urinalysis will be performed at screening and on Days 182. A physical examination will also be performed at screening and Day 182. Vital signs and ECG will be performed at screening. On days 0, 14 168 (when dermabrasion and punch biopsies are performed) and 182 (end of study or at early termination), vital signs will be repeated.

8.1.3 Treatment Methods

Treatment in this study consists of two treatment modalities:

1. Physical perturbation (Dermabrasion and full thickness excision)
2. Pharmacological intervention Subjects are scheduled to receive hydrogel for 31 days: treatment period 1 (Day 0 until 2 days prior to punch biopsy 1 [Day 11]) and treatment period 2 (Day 17 until end of treatment [Day 35]). The dose of hydrogel is an approximate volume of 0.1 mL applied twice daily to two sites, for a total intended volume of 0.4 mL. Due to droplet size variability, this translates to an actual total volume range of 0.27 to 0.88 mL.

The planned duration of the study per subject is 196 days, comprising a 14 day screening period, and 182 days of treatment and follow-up. The planned total duration of the study is approximately 12 months.

Once eligibility is confirmed (Day −6/0), subjects will have Baseline photography that includes a pin-point tattoo and hair dye. Two sites will be assigned, each measuring 1.5 cm×1.5 cm and designated right (R) and left (L) with a minimal distance of 2 cm, identified in transitional areas of the balding vertex scalp, which has a very low density of terminal hairs. The hair density of the 2 sites should be as similar as is possible.

Dermabrasion of two sites per subject will be carried out using a hand-held dermabrader with a standard grit diamond fraise to achieve pinpoint capillary bleeding (estimated depth 100 microns, and therefore not anticipated to cause scarring). After dermabrasion the hydrogel will be applied to the two sites.

On Day 14, the two dermabraded sites will receive a full thickness 4 mm skin punch biopsy that is allowed to heal by secondary intention without occlusion. In addition to detecting neogenic-like follicles and possibly other activated, stimulated, or reorganized follicular structures of interest (e.g., PEL and PELA as described in Section 5.8.4.1 supra) following treatment with DA (a more superficial perturbation) and hydrogel, the 4 mm punch biopsies also provide a deeper perturbation that will be tested with hydrogel for the induction of neogenic-like follicles and other follicular structures of interest.

Subjects will return after 3 months (Day 84) and 6 months (Day 168) for repeat photographic and clinical evaluations. Monthly safety follow-up phone calls will be performed on Days 112 and 140.

On Day 168 a second skin punch biopsy will be performed over the 2 dermabraded sites where there was a first punch biopsy on Day 14. In addition to providing samples for an analysis of efficacy, any scar tissue formed from the 4 mm punch biopsies on Day 14 will be excised by this second biopsy on Day 168, which will be closed by sutures. At the discretion of the investigator and if in accordance with the subject's wish, the Day 168 punch of the dermabraded sites will be a 5 mm or 6 mm skin biopsy (or elliptical biopsy by hand, or with an excisor, of a similar size) in order to assure scar removal and photography tattoo removal. The sutures are scheduled to be removed at a safety follow-up 2 weeks later (Day 182).

8.2 Results

A clinical study was carried out in accordance with the protocol described above. A summary of the demographics and characteristics of subjects treated with integumental perturbation and a hydrogel containing no active substance is shown in Table 8.

It was found that, for subjects treated with dermabrasion plus hydrogel:

From baseline to Day 84 (3 months), target area hair counts (also referred to as "TAHC") of all hair show substantial increases that are statistically significant (see Table 9). This change in counts of all hair from baseline is maintained through the last day of measurement, Day 168 (6 months; See Table 10) and the change is statistically significant on Day 168.

From baseline to Day 84 (3 months), target area hair count of only nonvellus-sized hairs, which have hair shafts 30 microns and greater in diameter (widths measured photographically), shows substantial increases that are statistically significant (see Table 11). This change in counts of nonvellus-sized hair from baseline is not maintained through the last day of measurement, Day 168 (6 months; See Table 12).

From baseline to Day 84 (3 months), target area hair count of only vellus-sized hairs, which have hair shafts less than 30 microns in diameter (widths measured photographically), shows small increases (see Table 13). From baseline to the last day of measurement, Day 168 (6 months), target area hair count of only vellus-sized hairs shows substantial increases that are large (see Table 14).

As shown in Tables 15 and 16, the sustained positive change in all hair at the 6 month time point is comprised in large part by the striking increase in hair follicles with shafts between 10-20 microns in diameter (widths measured photographically). The increase in follicles with shafts between 20-30 microns has a small contribution to this overall positive change (see Table 14).

In dermabraded areas of skin, induction of neogenic-like hair follicles and activated, stimulated, or reorganized preexisting (including vellus-sized) follicles was measured as detected and analyzed by skin biopsy analysis at Day 14. In contrast to what is generally found in unwounded scalp skin, the controlled perturbation in this study 1) induced neogenic-like follicles and 2) placed preexisting follicles into a reorganized and activated state. The structures of interest detected and counted in the Day 14 biopsies are observed only rarely in unwounded skin. Therefore, they are comprised of neogenic-like and activated, stimulated, or reorganized structures.

TABLE 8

Subject Demographics and Characteristics

| Demographies and Baseline Characteristics | Treatment Group: Dermabrasion plus post-integumental perturbation treatment |
|---|---|
| Age (years) | |
| N | 33 |
| Mean (SD) | 43.1 (10.4) |
| Median | 43 |
| Min:Max | 22:64 |
| No. (%) ≤40 | 13 (39.4%) |
| No. (%) >40 | 20 (60.6%) |
| Fitzpatrick Skin Type, No. (%) | |
| I | 3 (9.1%) |
| II | 22 (66.7%) |
| III | 7 (21.2%) |
| IV | 1 (3.0%) |
| Hamilton-Norwood Class, No. (%) | |
| 3V | 8 (24.2%) |
| 4 | 18 (54.5%) |
| 5 | 1 (3.0%) |
| 5A | 4 (12.1%) |
| 5V | 2 (6.1%) |
| Age Noticing Hair Loss (years) | |
| N | 33 |
| Mean (SD) | 29.5 (10.2) |
| Median | 28.0 |
| Min:Max | 14:58 |
| Tried hair loss treatment in past, No. (%) | |
| Yes | 10 (30.3%) |
| No | 23 (69.7%) |

TABLE 9

Photographic hair count of all hair on Day 84 in target analysis area subjected to dermabrasion plus hydrogel treatment

| | Baseline | Day 84 | Change |
|---|---|---|---|
| N | 33 | 33 | 33 |
| Mean (SE) | 522.1 (28.82) | 575.4 (31.93) | 53.4 (11.60) |
| % Change | | | 10% |
| Min:Max | 185:885 | 280:1063 | −47:178 |
| 90% CI* | | | (33.71, 73.02) |
| P-value* | | | <0.0001 |

*CI and P-value are results for within-group mean changes.

TABLE 10

Photographic hair count of all hair on Day 168 in target analysis area subjected to dermabrasion plus hydrogel treatment

| | Baseline | Day 168 | Change |
|---|---|---|---|
| N | 33 | 33 | 33 |
| Mean (SE) | 522.1 (28.82) | 569.1 (32.38) | 47.0 (14.75) |
| % Change | | | 9% |
| Min:Max | 185:885 | 302:1026 | −99:218 |
| 90% CI* | | | (22.01, 71.99) |
| P-value* | | | <0.0016 |

*CI and P-value are results for within-group mean changes.

TABLE 11

Photographic hair count of non-vellus hair on Day 84 in target analysis area subjected to dermabrasion plus hydrogel treatment

| | Baseline | Day 84 | Change |
|---|---|---|---|
| N | 33 | 33 | 33 |
| Mean (SE) | 358.7 (25.84) | 406.3 (27.31) | 47.6 (9.71) |
| % Change | | | 13% |
| Min:Max | 106:611 | 87:752 | −39:190 |
| 90% CI* | | | (31.15, 64.06) |
| P-value* | | | <0.0001 |

*CI and P-value are results for within-group mean changes.

TABLE 12

Photographic hair count of non-vellus hair on Day 168 in target analysis area subjected to dermabrasion plus hydrogel treatment

| | Baseline | Day 168 | Change |
|---|---|---|---|
| N | 33 | 33 | 33 |
| Mean (SE) | 358.7 (25.84) | 365.2 (24.79) | 6.5 (8.85) |
| % Change | | | 2% |
| Min:Max | 106:611 | 90:635 | −99:173 |
| 90% CI* | | | (−8.51, 21.48) |
| P-value* | | | 0.2346 |

*CI and P-value are results for within-group mean changes.

TABLE 13

Photographic hair count of vellus hair on Day 84 in target analysis area subjected to dermabrasion plus hydrogel treatment

| | Baseline | Day 84 | Change |
|---|---|---|---|
| N | 33 | 33 | 33 |
| Mean* | 163.4 | 169.1 | 5.8 |
| % Change | | | 4% |

*There are two 1 cm² TAHC sites per subject; hair counts are normalized for 1 cm².

TABLE 14

Photographic hair count of vellus hair on Day 168 in target analysis area subjected to dermabrasion plus hydrogel treatment

| | Baseline | Day 168 | Change |
|---|---|---|---|
| N | 33 | 33 | 33 |
| Mean* | 163.4 | 203.9 | 40.5 |
| % Change | | | 25% |

*There are two 1 cm² TAHC sites per subject; hair counts are normalized for 1 cm².

TABLE 15

Vellus hair count and percent change from baseline by 10 micron intervals in target analysis area subjected to dermabrasion plus hydrogel treatment

| Diameter (microns) | Baseline | 3 Month Hair Count | 3 Month Percent Change | 6 Month Hair Count | 6 Month Percent Change |
|---|---|---|---|---|---|
| 20-30 | 2,962 | 2,998 | 1.22% | 3,165 | 6.85% |
| 10-20 | 2,383 | 2,554 | 7.18% | 3,506 | 47.13% |
| <10 | 45 | 28 | -37.78% | 56 | 24.44% |
| Subtotal | 5,390 | 5,580 | 3.53% | 6,727 | 24.81% |

TABLE 16

Nonvellus hair count and percent change from baseline by 10 micron intervals is target analysis area subjected to dermabrasion plus hydrogel treatment

| Diameter (microns) | Baseline | 3 Month Hair Count | 3 Month Percent Change | 6 Month Hair Count | 6 Month Percent Change |
|---|---|---|---|---|---|
| 100+ | 294 | 339 | 15.31% | 297 | 1.02% |
| 90-100 | 433 | 480 | 10.85% | 464 | 7.16% |
| 80-90 | 698 | 753 | 7.88% | 699 | 0.14% |
| 70-80 | 1,152 | 1,228 | 6.60% | 1,109 | -3.73% |
| 60-70 | 1,500 | 1,754 | 16.93 | 1,596 | 6.40 |
| 50-60 | 2,253 | 2,405 | 6.75 | 2,129 | -5.50 |
| 40-50 | 2,758 | 3,145 | 14.36 | 2,785 | 0.98 |
| 30-40 | 2,750 | 3,296 | 19.85 | 2,973 | 8.11 |
| Subtotal | 11,838 | 13,409 | 13.27 | 12,052 | 1.81 |

8.3 Discussion

These results demonstrate that dermabrasion, a non-scarring method of integumental perturbation, results in growth of vellus and terminal hair as measured by clinical hair count. Vellus-sized hairs were detected at the 6 month endpoint of the study. In addition, compared to non-dermabraded skin in other studies, skin treated with dermabrasion was found to have increased numbers of activated, stimulated, or reorganzied hair follicles, based on the observation of an increase in numbers of neogenic-like (NL), pre-existing-like (PEL), and pre-existing-like, attached (PELA) follicles in dermabraded skin samples. Such structures are generally present only rarely in unwounded skin. An increased number of terminal-sized hairs at 3 months after perturbation compared to baseline, as detected in the serial hair counts by photography, also indicates that new terminal hairs can be induced to appear by integumental perturbation.

9. EXAMPLE: DERMABRASION/HAIR GROWTH-PROMOTING AGENT ALOPECIA CLINICAL PROTOCOL

This example describes a clinical protocol for combined treatment with dermabrasion (DA) and a hair growth-promoting agent (HGPA) or agents on hair growth. The protocol may be carried out as a Phase 2a, open-label, mono-center, randomized study; in this case, subjects are randomized to have DA on the right or left side of the vertex scalp. The DA/Hydrogel site plus HGPA is the experimental site; and the non-DA/Hydrogel site plus HGPA is the control site. Thus, each subject acts as his own control. Optional steps for including these controls in the protocol are provided throughout the description below.

9.1 Protocol Design

Hair growth-promoting agents. Protocol 1: Commercially available minoxidil foam (5%); 2 ml applied twice a day; the protocol is to be supported by prior irritancy studies (DA+ minoxidil). With respect to selecting a minoxidil treatment, Olsen et al. J Am Acad Dermatol 2007; 57:767-74 and Olsen et al., J Am Acad Dermatol 2002; 47:377-85, each of which is incorporated herein by reference in its entirety, may be used as references. In a variation, a 5% solution or a 2% solution may be used. 5% minoxidil solution is approved for use in men in the US and Germany but not in women.

Follow-on Protocol 2: Latanoprost eye drops (0.005% formulation currently on the market): 1 dropper once a day. A 0.1% formulation with propylene glycol (20%) and ethanol (50%) will be used for this. Because Latanoprost can cause skin irritation, this protocol is to be supported by prior animal model studies of skin irritancy (DA and Non-DA sites). With respect to selecting a Latanoprost treatment, Blume-Peytavi et al., 2010, *American Academy of Dermatology*, doi:10.1016/j.jaad.2011.05.026, Epub Aug. 27 2011, incorporated by reference herein in its entirety and which compares latanoprost 0.1% solution to placebo, may be used as a reference.

Optional pharmacokinetic profiling of these drugs can be conducted.

Reference product(s). No reference product is required. As optional controls, subjects may receive HGPA treatment on DA and non-DA skin sites. Thus, the reference treatment with be HGPA alone (i.e., on non-DA sites).

Intended duration of treatment (per subject). Treatment consists of two modalities: (i) DA/Hydrogel; and (ii) HGPA. Subjects receive DA (or non-DA for controls), followed by application of Hydrogel (e.g., the hydrogel described in the example of Section 10 below) for 11 days. Subsequently, topical application of HGPA will begin and continue for 24 weeks to: DA sites (and non-DA sites if applicable). Subjects are treated for approximately 196 days, comprising a 14 day screening period, and 182 days of treatment and follow-up. The planned overall duration of treatment is approximately 12 months.

Diagnosis and eligibility for treatment. Caucasian males 20-65 years of age who have androgenetic alopecia with the presence of a vertex transition zone defined as an area possessing both terminal and miniaturized hairs, Hamilton-Norwood type 3V, 4, 5, 5A, or 5V, and Fitzpatrick skin type 1-4. For controls, subjects should have a vertex area large enough to accommodate both treatment sites.

Methodology and criteria for evaluation. Once eligibility for treatment is confirmed (Day −6/0), subjects receive Baseline photography. For a clinical study, this includes a pin-point tattoo and hair dye. Treatment sites measure at least 1.5 cm×1.5 cm and are preferably located in transitional areas of the balding vertex scalp, which has a very low density of terminal hairs. The two treatment sites can be designated, designated right (R) and left (L) with a minimal distance of 2 cm; the hair density of the two sites should be as similar as is possible; and in each subject, the site for DA is randomized to right or left; each subject is his own control: (i) DA/Hydrogel plus HGPA (experimental site); (ii) non-DA/Hydrogel plus HGPA (control site).

DA is performed using a hand-held dermabrader with a standard grit diamond fraise to achieve pinpoint capillary bleeding (estimated depth 100 microns, and therefore not anticipated to cause scarring).

After DA hydrogel is applied to the DA site (and, for controls, a similar sized site on the opposite side of the scalp) for 11 days. See the scheme below for more details.

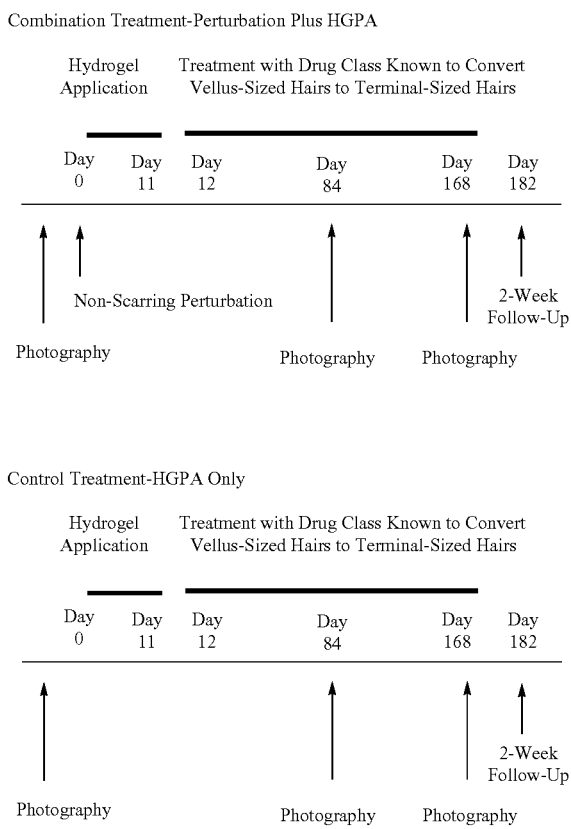

On Day 12, application of HGPA is begun on the DA treatment site (and, for controls, also on non-DA sites on the opposite side of the scalp). HGPA is applied continuously for 24 weeks; subjects return to the clinic on Day 84 and Day 168 for repeat photographic and clinical evaluations. Monthly safety follow-up phone calls may be performed on Days 28, 56, 112 and 140.

Diagnostic skin punch biopsies may be performed at the treated site (if controls are present, at both treated sites) to analyze follicular structures on, e.g., optionally on Days 84 and/or Day 168. Biopsy sites are sutured closed. The sutures are removed at a follow-up 2 weeks later.

For a clinical study, the end of the protocol is defined as the last clinical visit of the last subject.

9.2 Efficacy Objectives

Primary Objectives/Endpoints

To assess changes from Baseline to Day 168 in the number of photographically detected hairs in subjects treated with DA/Hydrogel plus HGPA (with optional comparison to non-DA/Hydrogel plus HGPA treatment).

Secondary Objectives/Endpoints (i) To assess changes from Baseline to Day 84 in the number of photographically detected hairs in subjects treated with DA/Hydrogel plus HGPA (with optional comparison to non-DA/Hydrogel plus HGPA treatment).

(ii) To assess the number of histologically detected hair follicles in biopsies of the treatment site from subjects treated with dermabrasion/Hydrogel and from subjects treated with dermabrasion/Hydrogel plus HGPA (with optional comparison to non-DA/Hydrogel plus HGPA treatment);

(iii) To assess changes (a) from Baseline to Day 84 and (b) from Baseline to Day 168 in shaft thickness of photographically detected hairs in treatment site after treatment with DA/Hydrogel plus HGPA (with optional comparison to non-DA/Hydrogel plus HGPA treatment). Hair shaft thickness can be captured by photography.

In accordance with the foregoing, a photographic field of measurement (which may extend to two Analysis Areas if controls are included) may comprise a 1.13 $cm^2$ circular region in the site that was treated with HGPA (+/−DA).

9.3 Safety Objectives

The safety and tolerability of HGPA applied topically to DA (and, if controls are present, non-DA) sites is monitored through the collection of data from targeted examination of the treated scalp sites and the reporting of adverse events.

Safety visits may be conducted on Days 1, 2, 3, 12, 15, 17, 18, 19, 20 and 182; visits on Days 3, 18, 19 and 20 may be replaced by calls if they fall on the weekend); additional or fewer days may be required depending on subject compliance. For example, subjects may be monitored for 4 weeks before letting them apply at home. Adverse events may also be reported at safety phone calls on Days 28, 56, 112 and 140. In addition liver and renal function, Hgb-A1C, and urinalysis are performed at screening and on Days 182. A physical examination is performed at screening and Day 182; vital signs and ECG are performed at screening. Vital signs are also measured on Days 0, 84 and 168 (when DA and photography are performed) and Day 182 (end of treatment protocol or at early termination).

9.4 Plan for Data Analysis/Statistics for Clinical Study

For a clinical study, if the true difference between the test (DA+minoxidil) and reference (minoxidil) treatments for the primary endpoint (changes from baseline to Day 168 in the number of hairs/$cm^2$ captured by photography) is 16 hairs/$cm^2$, then 79 subjects would provide 90% power to reject, at the 5% level of significance, the null hypothesis that the test treatment (DA+minoxidil) is no better than the reference (minoxidil). As a drop-out rate of 10% may be anticipated, an additional 8 subjects may be enrolled to ensure the primary efficacy endpoint is achieved, bringing the total number of subjects to 87.

With respect to a clinical study using latanoprost, if the true difference between the test (DA+latanoprost) and reference (latanoprost) treatments for the primary endpoint (changes from baseline to Day 168 in the number of hairs/$cm^2$ captured by photography) is 19 hairs/$cm^2$, then 57 subjects would provide 90% power to reject, at the 5% level of significance, the null hypothesis that the test treatment is no better than the reference. As a drop-out rate of 10% may be anticipated, an additional 6 subjects may be enrolled to ensure the primary efficacy endpoint is achieved, bring the total number of subjects to 63.

The primary efficacy analysis is performed for the Full Analysis Set (all subjects who were enrolled and who received at least one dose of HGPA to the DA and Non-DA sites).

Primary Endpoint. An analysis of covariance is performed on the changes from Baseline to Day 168 in the number of hairs captured by photography. Factors in the model are the fixed effects of treatment, age category, and the random effects of subjects. Subjects' Baseline (Day −6/0) hair counts are covariates.

Secondary and Exploratory Endpoints. The changes from Baseline to Day 84 in the number of hairs captured by photography are analyzed analogously to the primary endpoint (changes from Baseline to Day 168). For biopsied samples, generalized linear models are estimated for the mean number of hair follicles per biopsy. The factors in these models are the fixed effects of treatment, and age and the random effects of subjects, and the Hamilton-Norwood classifications as a covariate.

Safety and pharmacokinetic Endpoints. Descriptive statistics broken out by treatment are tabulated for each of the safety and, if applicable, pharmacokinetic endpoints.

10. EXAMPLE: GENERATION AND CHARACTERIZATION HYDROGELS

This example describes the generation and characterization of a topical hydrogel, which may be used as part of a treatment for wound healing, for administration post-integumental perturbation, for generating a topical hair growth-promoting agent formulation, etc.

10.1 Formulation i. The hydrogel was formulated with approximately 90% water, using excipients that are classified as GRAS (generally recognized as safe) in the concentration range used in the formulation and for topical use, as per the FDA Inactive Ingredients Database.

ii. Formulation Preparation Procedure—100 batch, lot #TH-003-098b

The following procedures show the steps of preparing a 100 g batch of hydrogel. There are four steps for preparing this formulation:

a) Prepare a neutralized HCl solution (Solution A): 10.58 g 10 wt % HCl was added into a beaker with stirring. 11.93 g of 10 wt % NaOH solution to neutralize this solution. pH of this solution is about 7. 0.14 g Allantoin, 0.11 g of Sodium Alginate and 8.7 g of Glycerine was added consecutively to the solution. This solution was sterile filtered.

b) 1.5 g of sterile Hyaluronic acid was gradually added into the solution. 67.04 g of water was added. The resultant dispersion was vigorously stirred until the polymer completely dissolved. The final solution is a single liquid phase of transparent appearance.

c) Add the remaining ingredients: 8.7 g glycerin was added to the solution and stirred for another 30 min.

d) Measuring pH. The pH of the mixture should be about 7.

e) Viscosity: The viscosity of the gel was measured using Brookfield Viscometry. Viscosity at RT was 4093 cP.

The hydrogel can also be prepared with methyl paraben (0.1%) and propyl paraben (0.048%) as preservatives.

A hydrogel with carboxymethyl cellulose was prepared as follows. The ingredients are described in Table 17. For a 100 g batch, 4 g citric acid was added to 59.7 g of distilled water at room temperature. The stirring was conducted at 25° C. During the process of dissolution, bubbles of carbon dioxide were generated. The solution was stirred until all the bubbles were dissipated from the system (Solution 1). Next, 0.104 g of methyl paraben and 0.049 g of propyl paraben were added to Solution 1, with vigorous stirring at room temperature. 0.165 g of allantoin, 0.12 g of sodium alginate, and 2 g of carboxymethyl cellulose were added to the solution and stirred vigorously. The temperature of the solution was raised to 80° C. and stirred. Approximately 4 hours was needed for dissolution. The clear solution was cooled down to room temperature and 10.46 g of glycerin was added to the solution. The solution was stirred at room temperature for 2 hours to achieve a homogeneous solution. An appropriate volume of 10% NaOH solution was added to the solution to adjust the pH to 6.5-7.5.

TABLE 17

| Excipient/drug | Manufacturer | Lot# |
|---|---|---|
| Alginate | FMC Biopolymer | S19626 |
| Allantoin | Spectrum | YT0711 |
| Citric acid | Roche | UJ247 |
| Carboxymethyl cellulose (MW X) | Hercules | 91157 |
| Distilled water | VWR | |
| Glycerin | Spectrum | TD0414 |
| Methyl paraben | Spectrum | TN1071 |
| Propyl paraben | Spectrum | TN1074 |
| NaOH | Alfa Aesar | F01S028 |
| HCl | Alfa Aesar | C04025 |

10.2 Characterization

Multiple 100 g batches were prepared using the process described above. The batches were characterized for the following attributes: pH (target: 7.0±0.5° C.); viscosity (cP, 25° C.) (target range 6,000-10,000 cP); and appearance (target: transparency). Characterization data is summarized in Table 18.

TABLE 18

Batch-to-Batch Characterization

| Batch # | pH | Viscosity (cP) (25° C.) (RPM 16-25, 98% torque) |
|---|---|---|
| 1 | 6.96 | 6059 |
| 2 | 6.69 | 5720 |
| 3 | 7.33 | 6120 |

Measurement of Viscosity

The shear viscosities of the formulations were measured using a Brookefield DV-III Ultra Rheometer IV, using the spindle X. Silicone oil, (12,400 cP at 25 C) was used as the standard. Samples were run at 25 C, with maximum torque (>98%).

The viscosity of the formulations at 25° C. was measured as between 2,000-8,000 centipoise (cP). Stability studies on 100 gram batches conducted under ICH temperature conditions of 4° C., 25° C., and 40° C. were stable at 8 weeks with respect to strength, viscosity and homogeneity.

Three 2.5 L batches were also prepared, using the process described above, with scaled-up measures of all ingredients, as set forth in Table 19.

TABLE 19

| Ingredient | 0 |
| --- | --- |
| Citric Acid (g) | 100 |
| Sodium Alginate (g) | 3.007 |
| Carboxymethyl Cellulose Na salt (g) | 50 |
| Allanioin (g) | 4.00 |
| Glycerin (g) | 260 |
| Methyl paraben (g) | 2.599 |
| Propyl paraben (g) | 1.199 |
| Deionized Water (g) | 1448 |
| Sodium Hydroxide 10% | 629.6 |
| Hydrochloric Acid 10% | N/A* |

*N/A = not applicable

The attributes of the scaled-up batch include a pH of 6.99 and Viscosity (at 25° C., 98% torque) of 2859 cP.

Other Properties

The hydrogel described above (hyaluronic acid-based) is a transparent, odorless, colorless formulation that readily spreads over a surface. The migration to surrounding sites and run off was minimal. The pH of the gel was adjusted to neutral (7.0±0.5° C.) for skin and wound compatibility. The hydrogel may be stored at room temperature.

11. EXAMPLE: PETROLATUM-BASED FORMULATIONS WITH MINOXIDIL

Minoxidil from different ointment formulations can be varied by varying the molecular fluidity of the carrier without changing its hydrophobicity. This is accomplished by varying the petrolatum to mineral oil ratio. Petrolatum Formulations 1-4 (Table 20) has mineral oil/petrolatum in the following ratios: (1) 8.6; (2) 2.85; (3) 0.925; and (4) 0.283. The scale of the formulations is 10 grams. Each formulation had 5% minoxidil. Each formulation has 15% lanolin alcohol as an emollient and emulsifier. Four 20 ml scintillation vials with caps and spin bars are labeled 1-4 and are each charged with 0.500 grams of minoxidil and 1.500 grams of lanolin alcohol. This mixture is heated to 80° C. until it melts into a fluid melt that stirred easily. The fluid melt is alternately sonicated and stirred until a homogeneous suspension of minoxidil is obtained. The mineral oil and petrolatum components are combined into four more vials ("Petrol. Form 1-4") and heated to 80° C. The contents of the vials labeled 1-4 are combined with the contents of the vials labeled Petrol. Form 1-4 and stirred at 80° C. for approximately 15 minutes. The vials are then removed from heat and placed on a roller and rolled at medium speed until the mixture thickened. The formulation is left to equilibrate overnight at 25° C. After 8-10 hours of stirring, a portion of the formulation is retrieved by a spatula and felt between two fingers for skin feel and "spreading ease." The formulations are placed on stability. In vitro release experiments are performed in a dissolution chamber set at 32° C. and pH 7.4 to simulate the temperature and pH of a topical wound.

TABLE 20

| Formulation | Minoxidil | Lanolin Alcohol (g) | Petrolatum (g) | Mineral Oil (Drakeol 350) (g) |
| --- | --- | --- | --- | --- |
| Petrol. Form 1 | 0.5 | 1.5 | 0.8 | 6.9 |
| Petrol. Form 2 | 0.5 | 1.5 | 2.0 | 5.7 |
| Petrol. Form 3 | 0.5 | 1.5 | 4.0 | 3.7 |
| Petrol. Form 4 | 0.5 | 1.5 | 6.0 | 1.7 |

12. EXAMPLE: PETROLATUM/WATER EMULSIONS WITH MINOXIDIL

This example demonstrates that minoxidil release can be modulated by varying the ratio of hydrophobic and hydrophilic components in an emulsion cream formulation. Petrolatum Formulation #2 from the previous Example above is selected as the most hydrophobic formulation, with 5% minoxidil, 15% lanolin alcohol and a mineral oil/petrolatum ratio of 2.85. The second formulation (60% hydrophilic/40% hydrophobic) had 60% of a water phase (containing 2% Carbopol 980) emulsified into a 40% petrolatum/mineral oil/lanolin alcohol phase. The minoxidil 5% is dissolved into the water phase. The third formulation (100% hydrophilic) is comprised of a 100% aqueous gel containing 5% minoxidil, 1.5% Carbopol 980, 10% glycerol, and water.

13. EXAMPLE: MINOXIDIL FORMULATIONS FOR SUSTAINED RELEASE DELIVERY

This example reports the generation of minoxidil cream formulations for sustained release delivery.

The formulations described in this example are all oil/water emulsions. Three types of formulations with the following drug release rates were generated by varying the formulation excipients: Immediate Release (<1 day); Intermediate Release (1-3 days); and Sustained Release (3-7 days).

13.1 Immediate Release Formulations

Immediate release formulations are generated using a two-phase system: one aqueous phase for dissolving hydrophilic excipients and another non-aqueous phase for dissolving minoxidil and hydrophobic polymers.

Formulation preparation method. Citric acid from KIC Chemicals (lot #200203) is used as a solubilizing agent and buffering agent. Carbopol from Lubrizol (lot #100655645) was used as a thickener for the aqueous phase. For the non-aqueous phase, a mixture of two silicon oils from Dow Corning Chemicals (Silicone oil 350 cts, lot #6080660, and silicone oil 12500 cts, lot #6019987, were mixed at a ratio 25:75, referred to herein as "S25") is used as a medium-viscosity carrier, and cetearyl alcohol (Croda Lot #334447) and lanolin alcohol (Croda, lot #269113) were used as thickeners/emulsifiers. Span 80 (Sigma, lot #114k0137) and tween 20 (Spectrum Chem., lot #TO0434) is used as surfactants for the non-aqueous and aqueous phases, respectively. Emulsifier 10 from Dow Corning (lot #5864667) is used as an additional emulsifier for the formulations. See Table 21.

TABLE 21

Excipients/drug used in a Minoxidil immediate release formulation

| Excipients/drug | Manufacturer | Lot# |
| --- | --- | --- |
| Brij 721 | Uniqema | 52022 |
| Carbopol | Lubrizol | 1.01E+08 |
| Citric acid | KIC chem | 200203 |
| Cetearyl alcohol | Croda | 334447 |
| Silicone oil 350 cst | Dow Corning | 6080660 |
| Silicone oil 12500 cst | Dow Corning | 6019987 |
| Ermulsifier 10 | Dow Corning | 5864667 |
| lanolin alcohol | Croda | 269113 |
| Minoxidil | Sigma | 23789 |
| Span 80 | Sigma | 114k0137 |
| Tween 20 | Spectrum Chemicals | TO0434 |

The immediate release formulation is prepared using three steps, as follows:

i) 1.2 g of citric acid is added to 21.3 g of deionized water. The mixture is vortexed and ultrasonicated until all of the citric acid went into solution. 0.72 g of Carbopol and 0.048 g of Tween 20 are added into the solution. The resultant system under vigorous stirring is heated up to 90° C. in a water bath until the Carbopol is fully swollen and dispersed into water, to yield a single liquid phase of translucent appearance.

ii) Non-aqueous phase (phase II, 16G): 50 mg/mL minoxidil, 1.6 g of cetearyl alcohol and 3.2 g of lanolin alcohol are added into a silicone oil mixture (S25, Silicone oil 350 cts, lot #6080660, and silicone oil 12500 cts, lot #6019987, are mixed at a ratio 25:75). After addition of 0.032 g of span 80 and 0.32 g of emulsifier 10, the mixture is heated up to 90° C. in a water bath until all ingredients are dissolved, resulting in a clear, single phase solution (while still hot).

c) Homogenization: All 16 g of phase II (while still hot) is added into 24 g of Phase I and the two phases are mixed together using a high speed homogenizer to obtain a single phase cream. The ratio of aqueous (Phase I) to non-aqueous (Phase II) is 60:40.

Immediate release formulation is summarized in Table 22. The aqueous phase, non-aqueous phase, and the final phase of the mixture are shown in the table, and the amount of the excipients needed in each phase are listed for a 40 g batch formulation.

The minoxidil content in the immediate release formulation is measured by HPLC.

TABLE 22

Immediate Release Formulation

| Ingredient | % | g |
|---|---|---|
| PHASE I: 24 G total | | |
| Citric Acid | 5 | 1.2 |
| Carbopol 980 | 3 | 0.72 |
| Tween 20 | 0.2 | 0.048 |
| Deionized water | 88.8 | QS |
| Total | | 24 G |
| + PHASE II: 16 G total | | |
| Minoxidil | 5 | 0.8 |
| Cetearyl Alcohol | 10 | 1.6 |
| S25 (Mixture of Silicon 350 CSt, Silicon 12,500 CSt, 25:75) | 67.8 | 10.848 |
| Span 80 | 0.2 | 0.032 |
| Lanolin Alcohol | 20 | 3.2 |
| Emulsifier 10 | 2 | 0.32 |
| Total | | 16 G |
| = FINAL PHASE: 40.1 G total | | |
| Minoxidil | 5 | 0.8 |
| Citric Acid | 3.0 | 1.2 |
| Carbopol 980 | 1.8 | 0.72 |
| Tween 20 | 0.13 | 0.05 |
| Deionized water | 53.27 | 21.37 |
| Cetearyl Alcohol | 4.03 | 1.62 |
| S25 (Mixture of Silicon 350 CSt, Silicon 12,500 CSt, 25:75) | 27.02 | 10.84 |
| Span 80 | 0.11 | 0.04 |
| Lanolin Alcohol | 8.02 | 3.22 |
| Emulsifier 10 | 0..82 | 0.33 |
| Total | 100 | 40.11 |

13.2 Intermediate Release Formulations

An intermediate release emulsion cream formulation of minoxidil is developed in the following method The emulsion was prepared by homogenization of two phases, as described above for the immediate release formulation.

Formulation preparation method. The raw materials used in this formulation were identical to those used in the immediate release formulation described above, except that mineral oil instead of silicone oil was used. The lot #s of the excipients for this intermediate release formulation are listed in Table 23 below.

TABLE 23

Excipients/drug used in intermediate release formulation

| Excipients/drug | Manufacturer | Lot# |
|---|---|---|
| Cetearyl alcohol | Croda | 334447 |
| Carbopol | Lubrizol | 100655645 |
| Citric acid | KIC chem | 200203 |
| Drakeol 350 Mineral oil | Penreco | K8061 |
| Emulsifer 10 | Dow Corning | 5864667 |
| lanolin alcohol | Croda | 269113 |
| Lecithin | Spectrum Chemicals | UK0763 |
| Span 80 | Sigma | 114k0137 |
| Tween 20 | Spectrum Chemicals | TO0434 |

For a 40 g batch, the following preparation method is used.

i) Aqueous phase (Phase I, 24G): 1.2 g of citric acid is gradually added into a solution containing and 21.32 g of water. The mixture was vortexed and ultrasonicated until all of the ingredients were dissolved. 0.72 g of Carbopol 980 and 0.05 g of Tween 20 were then added into above solution. The resultant system under vigorous stirring was heated up to 90° C. in a water bath until the Carbopol was fully swollen and dispersed into water. Phase I is a single liquid phase of translucent appearance.

ii) Non-aqueous phase (Phase II, 16G): 3.23 g of cetearyl alcohol and 2.59 g of lanolin alcohol were added into 9.89 g of Drakeol 350 mineral oil. After 0.04 g of span 80 and 0.33 g of emulsifier 10 was added into the above system, the whole mixture was heated up to 90° C. in a water bath until all polymers were dissolved. Phase II is a clear single phase solution.

ii) Homogenization: The phases were mixed together with homogenization. The ratio of aqueous to non-aqueous is 60:40.

TABLE 24

Intermediate release formulation

| Step 1 | Phase I | % | mg/g | Total wt for 24 g (g) | Actual amount (g) |
|---|---|---|---|---|---|
| | Citric Acid | 5 | 50 | 1.2 | 1.20 |
| | Carbopol 980 | 3 | 30 | 0.72 | 0.72 |
| | Tween 20 | 0.2 | 2 | 0.048 | 0.05 |
| | 10% NaOH | use to neutralize to 6.5 | | 0 | 0.00 |
| | Deionized Water | qs | qs | qs | qs |
| Step 2 | Phase II | | | 16 g batch | |
| | Minoxidil | 5 | | 0.8 | 0.8 |
| | Cetearyl alcohol | 20 | 200 | 3.2 | 3.23 |
| | Drakeol 350 Mineral Oil | 61.8 | 618 | 9.888 | 9.89 |
| | Span 80 | 0.2 | 2 | 0.032 | 0.04 |

TABLE 24-continued

| | Intermediate release formulation | | | | |
|---|---|---|---|---|---|
| | Lanolin alcohol | 16 | 160 | 2.56 | 2.59 |
| | Emulsifier 10 | 2 | 20 | 0.32 | 0.33 |
| Step 3 | Mix & Homogenize Final Composition | % | mg/g | (g) | % |
| | Citric Acid | 3 | 30 | 1.20 | 2.99 |
| | Carbopol 980 | 1.8 | 18 | 0.72 | 1.80 |
| | Tween 20 | 0.12 | 1.2 | 0.05 | 0.13 |
| | Deionized Water | QS | QS | QS | QS |
| | Cetearyl alcohol | 8 | 80 | 3.23 | 8.05 |
| | D350 Mineral Oil | 24.72 | 247.2 | 9.89 | 24.66 |
| | Span 80 | 0.08 | 0.8 | 0.04 | 0.11 |
| | Lanolin alcohol | 6.4 | 64 | 2.59 | 6.47 |
| | Emulsifier 10 | 0.8 | 8 | 0.32 | 0.82 |
| | total | | | 40.10 | 100.00 |

6.1.1 Hydrogel I

A viscous and transparent hydrogel will be applied to the skin as a hydrating gel. The hydrogel will be applied after rejuvenation treatments such as laser treatments, microdermabrasion, and chemical peels.

The hydrogel was prepared by dissolving 1.6 g of citric acid in 15.79 g of water with vigorous stirring. 0.041 g of menthol was added drop-wise. The pH of this solution was measured to ensure that the pH was in the range of 6-8. 0.024 g of sodium alginate and 0.400 g CMC was added to the solution which was then stirred vigorously. 0.032 g allantoin, 2 g glycerin, 0.021 g methyl paraben and 0.010 methyl paraben was then added to the formulation. The pH of this solution was measured and neutralized with sodium hydroxide.

TABLE 25

| Hydrogel | | |
|---|---|---|
| Ingredient | g | % |
| Menthol | 0.041 | 0.206 |
| Citric Acid | 1.600 | 8.000 |
| CMC | 0.400 | 2.000 |
| Methyl Paraben | 0.021 | 0.104 |
| Propyl Paraben | 0.010 | 0.048 |
| Distilled Water | 15.792 | 78.962 |
| 10% NaOH | PH adjust | PH adjust |
| Allantoin | 0.032 | 0.160 |
| Alginate | 0.024 | 0.120 |
| Glycerin | 2 | 10.000 |

6.1.2 Hydrogel II

Hydrogel II was prepared in the same way as Hydrogel I described in Section 6.1.1, except that sodium hyaluronate was added as an ingredient in this formulation as a moisturizer.

The hydrogel was prepared by dissolving 1.6 g of citric acid in 15.79 g of water with vigorous stirring. 0.041 g of menthol was added drop-wise. The pH of this solution was measured to ensure that the pH was in the range 6-8. 0.024 g of sodium alginate and 0.400 g sodium hyaluronate was added to the solution which was stirred vigorously. 0.032 g allantoin, 2 g glycerin, 0.021 g methyl paraben and 0.010 methyl paraben was added to the formulation. The pH was measured and the hydrogel was neutralized with sodium hydroxide.

TABLE 26

| Hydrogel II | | |
|---|---|---|
| Ingredient | g | % |
| Menthol | 0.041 | 0.206 |
| Citric Acid | 1.600 | 8.000 |
| Sodium Hyaluronate | 0.400 | 2.000 |
| Methyl Paraben | 0.021 | 0.104 |
| Propyl Paraben | 0.010 | 0.048 |
| Distilled Water | 15.792 | 78.962 |
| 10% NaOH | PH adjust | PH adjust |
| Allantoin | 0.032 | 0.160 |
| Alginate | 0.024 | 0.120 |
| Glycerin | 2 | 10.000 |

6.1.3 Hydrogel III

Hydrogel III will contain aloe vera and collagen as skin-compatible tissue regenerating agents. This gel will be applied to the skin as a rejuvenating gel.

1.6 g of citric acid will be dissolved in 15.79 g of water with vigorous stirring. 0.041 g of menthol will be added drop-wise. The pH of this solution will be measured to ensure that the pH is in the range 6-8. 0.024 g of sodium alginate, 0.400 g collagen and 1 g aloe vera will be added to the solution while stirring vigorously. 0.032 g allantoin, 1 g glycerin, 0.021 g methyl paraben and 0.010 methyl paraben will be added to the formulation. The pH will be measured and the hydrogel will be neutralized with sodium hydroxide.

TABLE 27

| Hydrogel III | | |
|---|---|---|
| Ingredient | g | % |
| Menthol | 0.041 | 0.206 |
| Citric Acid | 1.600 | 8.000 |
| Collagen | 0.400 | 2.000 |
| Methyl Paraben | 0.021 | 0.104 |
| Propyl Paraben | 0.010 | 0.048 |
| Distilled Water | 15.792 | 78.962 |
| 10% NaOH | PH adjust | PH adjust |
| *Aloe Vera* Gel | 1 | 0.160 |
| Alginate | 0.024 | 0.120 |
| Glycerin | 1 | 10.000 |

6.1.4 Emollient Cream

An emollient cream is made by mixing all the ingredients set forth in Table 28 (Phase 1) until everything was dissolved. The pH with 10% NaOH. Mixing is performed in a vessel maintained at 50° C.

All the ingredients set forth in Table 29 (Phase 2) are mixed until everything is dissolved. The mixing is performed in a vessel maintained at 80° C. The ingredients are soybean oil, hydrogenated cottonseed oil, polyglyceryl-10 decaoleate, polyglyeryl-6 octastearate, jojoba oil, shea butter, and olive oil.

The Phase 1 solution is added to the Phase 2 solution with agitation and mixing. The blend is allowed to cool to room temperature cool with mixing. The components of the resulting emollient cream are set forth in Table 30.

TABLE 28

| Phase I of Emollient Cream | |
|---|---|
| | % |
| Menthol | 0.4 |
| Citric Acid | 16 |

TABLE 28-continued

Phase I of Emollient Cream

| | % |
|---|---|
| Hyaluronic Acid | 2 |
| Glycerin | 10 |
| Allantoin | 0.32 |
| Sodium Chloride | 0.5 |
| Methyl Paraben | 0.20 |
| Propyl Paraben | 0.096 |
| 10% NaOH | pH adjust |
| Water | 70.68 |

+

TABLE 29

Phase 2 of Emollient Cream

| | % |
|---|---|
| Soybean Oil | 20 |
| Hydrogenated Cottonseed Oil | 10 |
| Polyglyceryl-10 decaoleate | 8 |
| Polyglyceryl-6-octastearate | 4 |
| Jojoba Seed Oil | 5 |
| Shea Butter | 3 |
| Olive Oil | 10 |

TABLE 30

Components of the Emollient Cream

| | % |
|---|---|
| Menthol | 0.2 |
| Citric Acid | 8 |
| Hyaluronic Acid | 1 |
| Glycerin | 5 |
| Allantoin | 0.16 |
| Sodium Chloride | 0.25 |
| Methyl Paraben | 0.10 |
| Propyl Paraben | 0.048 |
| 10% NaOH | pH adjust |
| Water | Q.S. |
| Soybean Oil | 10 |
| Hydrogenated Cottonseed Oil | 10 |
| Polyglyceryl-10 decaoleate | 4 |
| Polyglyceryl-6-octastearate | 2 |
| Jojoba Seed Oil | 2.5 |
| Shea Butter | 1.5 |
| Olive Oil | 10 |

14. EXAMPLE: GENERATION AND CHARACTERIZATION OF VESICULAR FORMULATIONS OF MINOXIDIL

Conventional topical minoxidil formulations consist of propylene glycol-water-ethanol solutions. However, twice daily applications of these formulations can cause severe adverse reactions, such as scalp irritation, burning, dryness, redness, allergic contact dermatitis, etc. To minimize these side effects and to enhance therapeutic efficacy, formulations that "deposit" the payload in the skin are advantageous. Traditional liposomal formulations, compared to conventional dosage forms, have shown in vitro enhanced cutaneous drug accumulation.

Described is a nanoliposomal formulation of minoxidil, designed for targeting to the hair follicle. Disclosed are liposomal vesicles that are prepared from soy lecithin, transcutol, dicetylphosphate, labrasol and cineole.

The structure of minoxidil (Formula $C_9H_{15}N_5O$, molecular weight 209.25 $gmol^{-1}$ is given below:

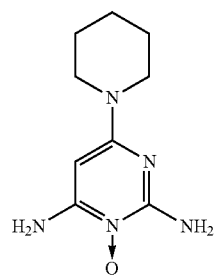 [SMILES: Nc1cc(N2CCCCC2)nc(N)[n+]1[O-]]

The raw materials are obtained from the following manufacturers: Soy Lecithin (SL) is obtained from Galeno (Potenza, Italy), minoxidil (MW 209.25) is purchased from Sigma Aldrich. Dicetylphosphate (DCP) and cineole are purchased from Aldrich. Transcutol and Labrasol are obtained from Gattefosse.

The vesicles are prepared in the following way: Soy Lecithin, CDP, minoxidil and a penetration enhancer was dissolved together in methylene chloride. Then, the lipid-drug solution is dried by rotary evaporation of the solvent. The film is analyzed by gas chromatography for traces of methylene chloride. The film is then hydrated for 1 hr at room temperature by distilled water under mechanical stirring. The suspension is sonicated using an ultrasound probe to disperse it. To achieve nanovesicles, the dispersion can be microfluidized. Liposomal dispersions are then freeze-dried at −20 degrees C. The freeze-dried vesicles are then reconstituted with water. The viscosity of the solution can be modulated by varying the viscosity of the reconstituting solution.

The nanostructures produced in the previous step are sized using a Mavern Zetasizer. The incorporation of minoxidil in the nanostructures is expressed as a percentage of the total amount of minoxidil. This is determined by high performance liquid chromatography (HPLC) after disruption of the structures by Triton X-100. The vesicles can also be characterized by transmission light microscopy (TEM) or polarized light microscopy. In vitro skin penetration and permeation studies with the formulations are performed non-occlusively using vertical diffusion Franz cells using pig skin. The various layers of the skin can be removed using tape stripping to remove the stratum corneum, and dermatoming to remove the epidermis from the dermis. The skin samples are homogenized in methanol and minoxidil extracted. The samples are quantified by HPLC to assess skin penetration of minoxidil.

15. EXAMPLE: GENERATION AND CHARACTERIZATION OF HYDROGEL FORMULATIONS OF MINOXIDIL SULFATE

This example provides a soluble hydrogel formulation of minoxidil sulfate. Minoxidil sulfate is a water soluble salt of minoxidil. 20 g/mL of minoxidil sulfate is dissolved in an aqueous solution containing 2% hyaluronic acid, 0.1% allantoin and 5% glycerol. The solution is pH neutralized using sodium hydroxide.

16. EXAMPLE: GENERATION AND CHARACTERIZATION OF NANOLIPOSOMAL FORMULATIONS OF LATANOPROST

The raw materials are obtained from the following manufacturers: Soy Lecithin (SL) is obtained from Galeno (Potenza, Italy), Latanoprost is purchased from Sigma Aldrich. Dicetylphosphate (DCP) and cineole are purchased from Aldrich. Transcutol and Labrasol are obtained from Gattefosse.

The vesicles are prepared in the following way: Soy Lecithin, CDP, Latanoprost and a penetration enhancer was dissolved together in methylene chloride. Then, the lipid-drug solution is dried by rotary evaporation of the solvent. The film is analyzed by gas chromatography for traces of methylene chloride. The film is then hydrated for 1 hr at room temperature by distilled water under mechanical stirring. The suspension is sonicated using an ultrasound probe to disperse it. To achieve nanovesicles, the dispersion can be microfluidized. Liposomal dispersions are then freeze-dried at −20 degrees C. The freeze-dried vesicles are then reconstituted with water. The viscosity of the solution can be modulated by varying the viscosity of the reconstituting solution.

The nanostructures produced in the previous step are sized using a Mavern Zetasizer. The incorporation of minoxidil in the nanostructures is expressed as a percentage of the total amount of latanoprost. This is determined by high performance liquid chromatography (HPLC) after disruption of the structures by Triton X-100. The vesicles can also be characterized by transmission light microscopy (TEM) or polarized light microscopy. In vitro skin penetration and permeation studies with the formulations are performed non-occlusively using vertical diffusion Franz cells using pig skin. The various layers of the skin can be removed using tape stripping to remove the stratum corneum, and dermatoming to remove the epidermis from the dermis. The skin samples are homogenized in methanol and latanoprost extracted. The samples are quantified by HPLC to assess skin penetration of latanoprost.

17. EXAMPLE: TREATMENT PROTOCOL WITH LASER+MINOXIDIL

A Caucasian male human subject, 30 years old, with Fitzgerald Type II skin (wherein Type I is the lightest and Type VI is the darkest (see Weller et al., 2008, *Clinical Dermatology*, 4th ed., Malden, M A: Blackwell Publishing, pp. 268)), with Hamilton-Norwood type VI male-pattern alopecia presents complaining of continued hair loss despite treatment with topical minoxidil foam 5% and/or oral finasteride 1 mg/day. The bald and transitional areas of the subject's scalp are prepared by shaving and then treated with a fractional and non-ablative Erbium-YAG laser with an emission at 1540-1550 nm (set to 50-70 $J/cm^2$, treatment level of 8-10, and 8 passes) and the subject is provided with a topical hydrogel and instructed to discontinue topical minoxidil and to apply the gel to the treated area of the scalp for one week. After approximately 11 days, treatment with the gel is discontinued and treatment with topical minoxidil foam and/or finasteride is re-started and he is evaluated after three weeks.

Response to therapy is determined by one or more of the following: measuring new hair growth (increased number of fibers in an affected area of scalp); thickness of fibers; length of hair fibers; and the patient's subjective evaluation of hair growth. The treated area of affected scalp is biopsied and studied for distribution of follicles in various stages of Follicle Cycle (anagen, catagen, etc.); distribution of follicle cells in various stages of cell cycle (e.g. G2, M, etc.); new follicle growth, bifurcating follicles; follicles undergoing follicle division; follicles growing new hair fibers, follicles with no hair fibers.

The subject is optionally treated with 10 more cycles, e.g., to increase hair density, for example: laser treatment, followed by approximately 2 weeks of topical gel followed by re-starting of minoxidil foam treatment. Response to therapy is measured by the methods described above.

The treatments described above and in foregoing example Sections 8 and 9 (or any other treatment described in Section 5 supra) may alternatively be accomplished by applying one of the following laser treatments.

17.1 Ablative Laser Treatment

In an ablative laser treatment, the application of any post-perturbation gel is sterile and, optionally, the treatment area is covered by a bandage. For example, ablative laser treatment may accomplished using an Erbium-YAG laser at 2940 nm or a $CO_2$ laser at 10,600 nm.

17.2 Ultrapulse $CO_2$ Fractional Laser

After shaving/clipping of the existing hair in the area to be treated, and followed by cleaning with antiseptic, Lidocaine HCL 2% with Epinephrine 1:100,000 are injected to anesthetize the surface of the area to be treated. An Ultrapulse (fractional mode) $CO_2$ laser is used to disrupt the epidermis and dermis to approximately 100 to 500 μm in depth. The Ultrapulse laser produces an effect that is similar to that of dermabrasion yet the disruption produced delivers a greater amount of energy deeper into the skin in a non-scaring fractional ablation. The treated area is a 1.5 cm×1.5 cm square. The Ultrapulse is set to deliver up to 350 mJ, up to 52.5 Watts, using pattern size #8, density #4, and fill the square treatment site with up to 5 passes.

17.3 Ultrapulse $CO_2$ Ablation Laser

After shaving/clipping of the existing hair in the area to be treated, and followed by cleaning with antiseptic, Lidocaine HCL 2% with Epinephrine 1:100,000 are injected to anesthetize the surface of the area to be treated. An Ultrapulse $CO_2$ laser (ablative mode) is used to disrupt the epidermis and dermis to approximately 100 to 500 μm in depth. The Ultrapulse laser produces an effect that is similar to that of dermabrasion yet the disruption produced delivers a greater amount of energy deeper into the skin in a non-scaring ablation that resembles the dermabrasion. The treated area is a 1.5 cm×1.5 cm square. The Ultrapulse is set to deliver up to 500 mJ in 1 msec, 1 Watts, using a spot size of 3 mm at 2 Hz to fill the square treatment site, which may require up to 15 passes.

17.4 Candela Smooth Peel Full-Ablation Erbium Laser

After shaving/clipping of the existing hair in the area to be treated, and followed by cleaning with antiseptic, Lidocaine HCL 2% with Epinephrine 1:100,000 are injected to anesthetize the surface of the area to be treated. The ablative erbium laser is set to deliver up to 5 Joules 240 msec in of energy at level 3 so that in up to 15 passes it will produce a disruption up to 500 μM deep. The treated area is a 1.5 cm×1.5 cm square.

18. EXAMPLE: DERMABRASION TREATMENT VARIATIONS

The treatments described in foregoing example Sections 8, 9, and 17 (or any other treatment described in Section 5 supra) may alternatively be accomplished by applying the following dermabrasion treatment in place of the laser treatment.

After shaving/clipping of the existing hair in the area to be treated, followed by cleaning with antiseptic, Lidocaine HCL 2% with Epinephrine 1:100,000 is injected to anesthetize the surface of the area to be treated. Standard dermabrasion, using the Aseptico Econo-Dermabrader from Tiemann and Company, is performed to a depth of approximately 100-150 µM, that includes removal the entire epidermis and disruption of the papillary dermis (detectable by a shiny, smooth, whitish appearance) inducing the formation of small pools of blood in the treated area. Each dermabraded area is a 1.5 cm×1.5 cm square. In an alternative example, a Bell Hand dermabrasion device may be used. In another variation, a dermabrader with the dermabrasion tip described in Section 5 supra is used, in which case the existing hair need not be shaved or clipped.

19. EXAMPLE: SOLID-LIQUID IN-SITU CROSS-LINKING SPRAY

Certain issues exist when preparing formulations that release sustained concentrations of drug, particularly highly water soluble drugs, without the use of highly hydrophobic matrices that are also occlusive. Drugs that are hydrophobic (log P>2) can be delivered to tissues in a sustained manner due to their slow dissolution in aqueous media and their subsequent extraction in cellular and tissue lipids. But drugs with high water solubility undergo rapid clearance from the tissue compartment (skin or blood). One way to slow down release of drug is with the use of highly hydrophobic matrices such as petrolatum/mineral oil ointments. These matrices can offer high stability in storage and they are easy to apply to skin or to a dermal wound. Furthermore, petrolatum-based ointment bases can provide 7-14 days of sustained release of drug. However, these ointment-based formulations are occlusive. An occlusive formulation lowers the exchange of oxygen and moisture, after application to the tissue. A "breathing" surface during the process of healing of a wound and during the process of hair growth is important. Emulsions (water-oil) can be modulated for its occlusive properties by varying its hydrophilic/hydrophobic ratio, but these result in faster release of drug.

Microsphere encapsulating drugs have been used as ways to sustain release of a molecule. Drugs can be encapsulated in poly (lactide-co-glycolide) (PLG) microspheres to modulate release. The rate of release varies as a function of L/G of the polymer. However, particulates and microspheres of sizes <10 microns are cleared rapidly by phagocytosis from a wound site in less than 3 days. Thus, a drug delivery system that deliver and maintain the microspheres at the wound site in order promote sustained delivery of the drug is needed.

One way to increase the residence time of the microspheres is to sequester the delivery system to the wound surface by an in-situ cross-linking hydrogel that forms molecular bonds with the tissue surface. An in-situ cross-linking hydrogel cannot be "rubbed" off like an ointment or a cream. The microspheres will be sequestered in the hydrogel, releasing drug in a sustained manner. Thus, the issue of phagocytosis of the microspheres can be overcome.

Additionally, sequestration can be enhanced by functionalization of the surface of the microspheres with a charge that will "bind" the microspheres to the tissue and the hydrogel. The net charge of the dermis is negative. Thus, positively charged microspheres would enhance the sequestration process of the drug-containing microspheres. PLG microspheres can be imparted a positive charge by a coating with a cationic surfactant such as cetyl pyrimidinium chloride, benkalkonium chloride, or cetyl tri-ammonium bromide (CTAB). Alternatively, the coating can be polymeric, such as a coating of chitosan, or polylysine, or poly(arginine), or poly(amidoamine) (PAMAM) or poly(ethyleneimine)(PEI).

Formation of molecular bonds of a wound dressing or topical drug formulation, such as a hydrogel described herein, with the wound surface can only be accomplished if some of the reactive groups of the hydrogel components are capable of reacting lightly with the proteins present in the dermis. The concept includes a spraying device that can deliver the hydrogel components and the microspheres onto the wound surface creating a homogeneous coating on the surface. After spraying, the liquid coating turns into a cross-linked hydrogel with the microspheres sequestered within. A solution that is sprayed has a higher energy than one that has been extruded—this assists in the mechanical interlocking of the hydrogel with the dermis as it cross-links on the tissue. The hydrogel needs to be biodegradable and needs to "slough off" the healing wound after the drug has been delivered. The characteristics of the hydrogel, such as its biodegradability, the "gel time" of its components, and its cross-link density are important characteristics that need to be optimized to arrive at the requisite delivery system.

The drug can be dissolved directly in the hydrogel components prior to formation of the cross-linked hydrogel.

Hair growth can be achieved by epidermal/dermal laser ablation. The laser can be an Erbium 2940 nm, or a 10,400 nm $CO_2$ with fractional or bulk ablative function. After ablation, the clinician mixes a first polymer (Polymer 1) with a second polymer (Polymer 2) by reconstitution of the dry solid with the liquid solution and rapidly sprays the ablated area with the in-situ cross-linking hydrogel, which acts as a biocompatible, biodegradable wound dressing and delivery system. This can be achieved using a two-chamber sprayer that contains a liquid in one chamber and a lyophilized solid (±microspheres containing a drug) in the other chamber. It should be noted that one or more drugs can be dissolved in the chamber containing the liquid. One drug or a combination of drugs can be administered in this way.

19.1 Two-Chamber Sprayer with a Lyophilized Solid in One Chamber and a Liquid in the Other Chamber The sprayer design incorporates homogeneous mixing of the liquid component with the lyophilized solid component. The sprayer design also incorporates protection of each of the components from moisture. The sprayer materials are selected from those that allow sterilization.

The lyophilized solid component contained in chamber 1, is comprised of a polymer macromonomer (Polymer 1) (a polymer that can further crosslink with another component). It is necessary for this polymer to be lyophilized due to its hydrolytic labile bonds. Thus, this component cannot be stored in water. The component in the other chamber (chamber 2) contains another polymer macromonomer (Polymer 2) that is capable of reacting with the lyophilized polymer (Polymer 1). Polymer 2 is dissolved in a phosphate buffer of pH 6-8. Polymer 2 does not contain hydrolytically labile linkages and is stable in water. Thus, Polymer 2 can be stored in water. In this concept, it is envisioned that the solution containing Polymer 2 reconstitutes the lyophilized Polymer 1 through mixing that occurs within the sprayer.

The mixed solution is then rapidly sprayed on the site of administration. Upon spraying, the solution cross-links, or forms a hydrogel. The cross-linking reaction of the mutually reacting polymers increases the viscosity of the solution to a critical point of gelation, at which time the solution is a cross-linked, solid hydrogel. The polymers need to be formulated in such a manner, that the mixed solution does not prematurely gel, or crosslink in the spraying chamber, before spraying.

Polymer 2 dissolved in phosphate buffer is the reconstitution solution for Polymer 1. In preparation of spraying, the components of chamber 2 are mixed with the solid in chamber 1, to create a homogeneous solution. The components (Polymer 1+Polymer 2) are capable of mutually reacting to form a biodegradable hydrogel. There are various means by which the "time to gelation" can be varied. The cross-linking reaction time of the polymers can be modulated by pH, since the reaction is triggered by higher pH. The pH of the reconstituting solution can be such that reaction between Polymer 1 and Polymer 2 does not cross-link instantaneously forming a gel in the sprayer, prior to spraying. The rate of cross-linking can also be modulated by the number of cross-linking groups. Thus, the two polymers at higher concentrations will crosslink faster than those at lower concentrations. The number of cross-linking groups per polymer molecule is also a factor in modulation of "gel time." Thus, 4-armed polymers with 4 reacting groups at a 3% w/w concentration will react faster than 2-armed polymers at the same concentration. The choice of buffer pH and the structure of mutually reactive polymers will control the rate of gelation.

Considering which chamber the drug-containing microspheres reside in, it becomes evident that, e.g., PLG microspheres would need to be stored in chamber 1, which is the chamber that contains the lyophilized polymer or solid component, because both the polymer and the PLG microspheres are hydrolytically labile. Also, because the drug contained in the microspheres is released only after the microspheres are hydrated, storage in a dry form is necessary. Thus, chamber 1 would contain Polymer 1 and the drug. Other excipients can be added to be part of the lyophilized solid to aid in the dispersion of the drug, minimize "clumping" of the solids, and minimize reconstitution time. Chamber 2 (the liquid chamber) would contain Polymer 2 in an aqueous solution, or a solution that is mostly aqueous. Other excipients may be added to Polymer 2, as needed, to impart additional properties to the resultant hydrogel. For example, a positively charged molecule may be added to aqueous solution in chamber 2, to impart additional bioadhesive properties to the hydrogel.

Examples of formulation compositions of Polymer 1 (chamber 1 or the solid chamber) and Polymer 2 (chamber 2 or the liquid chamber) are provided in the sub-sections below.

19.1.1 Reaction of Polyethylene Glycol 4-Armed Amine (PEG-AM) with Polyethylene Glycol 4-Armed Succinimidyl Ester (PEG-NHS)

PEG-AM/PEG-NETS hydrogels have been approved for adhesion prevention and each of the ingredients is available in pharmaceutical grade. Additionally, the hydrogels have high water content, functioning as a highly biocompatible wound dressing, while the wound heals underneath. The high water content of the hydrogels also keeps the wound environment moist. The PEG-AM and PEG-NETS are mutually reactive at pH 6-8, to form a biodegradable, covalently cross-linked, hydrogel network. Each component is 4-armed, with each arm capable of reaction. PEG-NETS is an electrophile in the reaction, activated by higher pH. Because PEG-NHS has a cleavable linkage, this ingredient must be maintained dry and in the solid state. PEG-NETS would be stored in a lyophilized, flocculated state in Chamber 1 of the sprayer. PEG-AM is the nucleophile in the reaction. The N-hydroxy succinimide groups of PEG-NETS are reactive to nucleophilic substitution by amine groups of PEG-AM. Additionally, PEG-NETS is reactive to amino groups present in the proteins in the dermis, thus enabling molecular interlocking of the hydrogel to tissue to occur. This will sequester the hydrogel with the microspheres at the site.

Because there are no cleavable linkages in PEG-AM, this component can be stored in the liquid state in Chamber 2 of the sprayer. After mixing and cross-linking into a hydrogel, ester linkages created by the reaction would render the hydrogel biodegradable by hydrolytic cleavage.

Polymer 1: Polyethylene Glycol 4-Armed Succinimidyl Ester (PEG-NETS) was purchased from Nanocs, Catalog #4APN05122010, Molecular weight 10,000 Daltons Polymer 2: Polyethylene Glycol 4-Armed Amine (PEG-AM) was purchased from Nanocs, Catalog #PEG4A-AM-10K, lot #4APM09162009, Molecular weight 10,000 Daltons Buffer Components Sodium Phosphate Dibasic, Anhydrous, Sigma, Catalog #S-0876, Lot #120K0126

Sodium Phosphate Monobasic, Anhydrous, Sigma, Catalog #S-0751, Lot #20K0228

Potassium Dihydrogen Phosphate, Alfa Aesar, Catalog #11594, Lot #B04V025

Sodium Chloride, Aldrich, Catalog #7647-14-5, Lot #12516HI

Equipment

Magnetic stirrer IKA Labortechnik, RET DVS1 with temperature/RPM control

Accument pH meter 25

Water bath

Procedures (1) Preparation of Phosphate Buffer

Stock solutions of 0.2M Sodium Phosphate Monobasic (SPM) and 0.2M Sodium Phosphate Dibasic (SPD) were prepared by dissolving 0.139 g of SPM in 5.0 mL of water and 0.284 g SPD in 10.0 mL of water. The required volumes (Table 31) of SPM and SPD were mixed and diluted by 3.0 mL water to obtain 0.1M Phosphate at pH 7.0, pH 7.5 or pH 8. The pH values were verified by pH meter and if necessary, adjusted to the required values. The recipe for preparation of the buffers is provided in Table 31.

TABLE 31

Phosphate Buffer Preparation

| pH | Sodium Phosphate Monobasic (0.2M), ml | Sodium Phosphate Dibasic (0.2M), ml |
|---|---|---|
| 7.0 | 1.17 | 1.83 |
| 7.5 | 0.48 | 2.52 |
| 8.0 | 0.159 | 2.84 |

(2) Preparation of Phosphate Buffered Saline (PBS)

The 1×PBS was prepared by dissolving 8.0 g of Sodium Chloride, 0.2 g of Potassium Chloride, 1.44 g of Sodium Phosphate Dibasic, and 0.24 g of Potassium Phosphate Monobasic in 1.0 L of water.

(3) Preparation and Characterization of PEG-AM/PEG-NHS Hydrogels (a) Preparation of PEG-AM/PEG-NHS Hydrogels In this experiment, the potential of storing the PEG-AM and PEG-NETS in water was examined, by testing gel time.

Mixing of PEG-NHS aqueous solution with a PEG-AM aqueous solution and phosphate buffer (cross-linking solution). Two stock solutions of 5% w/w PEG-NHS and 5% w/w PEG-AM were prepared by dissolution of 50.0 mg of each polymer in 1.0 mL of water. 100 μL of each stock solution was withdrawn and mixed together, followed by the addition of 200 μl of phosphate buffer. The phosphate was prepared by dissolution Sodium Phosphate Dibasic (5.678 g) and Sodium Borate (3.3401 g) in 200 ml of water. The pH of buffer solution was 8. Experiments 08-03-mix3 to 08-03-mix8 tests the cross-linking ability of PEG-AM and PEG-NETS after each of the individual solutions are stored in water for 3-120 minutes. As outlined in Table 32, the gel time increases with increased storage time in water, indicating hydrolytic instability of PEG-NETS.

TABLE 32

Effect of PEG-NHS Storage in Water on Gelation Time

| Experiment | PEG-NHS Conc., % | PEG-AM Conc., % | Gel time seconds | Time* min |
|---|---|---|---|---|
| 08-03-mix3 | 2.5 | 2.5 | 3" | 3 |
| 08-03-mix4 | 2.5 | 2.5 | 15" | 5 |
| 08-03-mix5 | 2.5 | 2.5 | 23" | 10 |
| 08-03-mix6 | 2.5 | 2.5 | 37" | 15 |
| 08-03-mix7 | 2.5 | 2.5 | 60" | 22 |
| 08-03-mix8 | 2.5 | 2.5 | no gel | 120 |

*Time passed after PEG-NHS dissolution in water and before mixing it with PEG-AM Because of instability, PEG-NETS cannot be stored in an aqueous solution at ambient temperatures and should be stored in a solid form.

(b) Mixing of Solid PEG-NHS with PEG-AM Solution.

Two Step Hydrogel Preparation. This experiment tested if PEG-AM and PEG-NHS can be formulated together in water, even to lyophilize thereafter. The experiment is testing a product concept of both PEG-AM and PEG-NETS dissolved together in water, to be lyophilized into a single chamber. The other chamber then, would only contain the phosphate buffer as the reconstitution solution. This concept can work only if PEG-NETS and PEG-AM do not react while in water (without the buffer).

In experiments 08-04-mix1 to 08-04-mix4, a solution of 2.5% PEG-AM/2.5% PEG-NHS was prepared. The final pH of the mixture was 6.4. The mixture was stored at room temperature to establish life time of the solution. Aliquots of 100 μl after each predetermined time-point were withdrawn from this mixture and added to 100 μl of 0.1M Phosphate buffer at pH 8 to induce gelation. Thus, for experiment 08-04-mix1, the buffer was added after 9 minutes and the gel time was measured. For experiment 08-04-mix4, the buffer was added after 23 minutes and gel time was measured. The results are included in Table 33.

TABLE 33

Two Step Incorporation of PEG-NHS into Hydrogel (0.1M Phosphate buffer, pH 8)

| Experiment | PEG-NHS Conc., % | PEG-AM Conc., % | Gel time | Time* Min |
|---|---|---|---|---|
| 08-04-mix1 | 2.5 | 2.5 | 3' 35" | 9 |
| 08-04-mix2 | 2.5 | 2.5 | 2' 55" | 13 |
| 08-04-mix3 | 2.5 | 2.5 | 2' 13" | 18 |
| 08-04-mix4 | 2.5 | 2.5 | 1' 47" | 23 |

*Time passed after mixing solid PEG-NHS with aqueous PEG-AM and before addition of phosphate buffer The longer contact times of PEG-NHS with PEG-AM before addition of the phosphate buffer resulted in decreasing gel times, indicating the components had started to mutually react. The time* shown in Table 33 denotes the storage of PEG-NHS and PEG-AM together prior to the addition of the buffer. After 18 minutes of storage, there was marked increase in viscosity of the mixture. After 23 minutes of contact time, it was difficult to withdraw an aliquot from this solution. After 30 minutes, the solution formed a cross-linked hydrogel plug. The PEG-NETS and PEG-AM started to react with each other immediately after mixing and formed cross-links, even though the kinetics of cross-linking was low at pH 6.4. But, the decrease in gel time indicated that cross-linking was occurring, leading to decrease of gel times and increases in viscosity (visually).

This experiment demonstrates that the cross-linking reaction between the two components in water begins prior to addition of the buffer. In practical terms, this experiment demonstrates that these two components cannot be formulated together, even it is to lyophilize. Thus, polymer 1 (PEG-NETS) would need to be formulated and lyophilized. Polymer 2 (PEG-AM) needs to be separately formulated and can be stored in a water solution.

One Step Hydrogel Preparation. This experiment demonstrates that PEG-AM formulated in phosphate buffer at pH 8 (and contained in chamber 2 of the sprayer) can be used as a reconstitution solution for PEG-NETS (contained in chamber 1 of the sprayer).

Solutions of PEG-AM in phosphate buffer were prepared, with a final pH of 8. The stock solutions of PEG-AM at concentrations 5% (50 mg/ml) or 2.5% (25 mg/ml) were prepared by dissolution of 50.0 mg in 1.0 ml or 2.0 ml of 0.1M Phosphate buffer at pH 8.0. Buffered PEG-AM was added to solid PEG-NETS. The PEG-AM buffered solutions were added to solid PEG-NETS in the amounts required to obtain equal final concentrations of both reagents. The concentrations of each of the ingredients PEG-AM or PEG-NETS were 5% w/w or 2.5% w/w (Experiment 08-05-mix, Table 34). The moment of PEG-AM addition was used as the starting point for gel time determination. The mixture was stirred using magnetic stirrer at 300 rpm. It took around 30 seconds for the PEG-AM buffer to reconstitute the PEG-NHS to be dissolved. The dissolution of PEG-NHS was included in the total gel time. Gel time was measured in triplicates for concentration of reagents at concentrations of 5% and 2.5%.

TABLE 34

One Step Incorporation of PEG-NHS into Hydrogel (0.1M Phosphate buffer, pH 8)

| Experiment | PEG-NHS Mg | PEG-AM μl | Conc. % | Gel time |
|---|---|---|---|---|
| 08-05-mix3a | 11.4 | 228 | 5 | 2' |
| 08-05-mix3b | 10.3 | 206 | 5 | 1' 56" |
| 08-05-mix3c | 11.5 | 230 | 5 | 1' 59" |
| 08-05-mix4a | 11.3 | 452 | 2.5 | 3' 15" |
| 08-05-mix4b | 11.8 | 472 | 2.5 | 3' 08" |
| 08-05-mix4c | 11.7 | 468 | 2.5 | 3' 20" |

The results of experiment 08-05-mix demonstrated that there was no interference between PEG-NETS dissolution and gelling. Therefore, the one step method was used for further studies. Gel time was faster for higher concentrations.

The experiment also demonstrates that PEG-NETS can be contained as a solid in one chamber and reconstituted easily with buffered PEG-Amine, contained as the reconstitution solution in chamber 2.

(4) Determination of Gel Time, as a Measure of Cross-Linking Kinetics

For all gel time determinations, a method was developed to standardize this test as a measure of cross-linking kinetics. Solid PEG-NETS (10-20 mg) was added to a 4.0 mL transparent glass vial with a 4 mm magnetic stir bar placed inside. The vial with solid PEG-NETS was placed in a water bath for temperature control. The stirring rate was adjusted to 300 rpm and the temperature inside the water bath was adjusted to 25-26° C. The solution of PEG-AM was prepared in a phosphate buffer at pH 7.0; 7.5 or 8.0 and added to the solid PEG-NETS. At this point, the stopwatch was started and was stopped when the solution coalesced into a solid and continued to rotate as one piece with the magnetic stir bar imbedded inside it.

(A) Effect of pH on Gel Time

The effect of pH on gel times was investigated in the experiments (Experiment 08-06-mix, Table 35), where PEG-AM solutions buffered at different pH were added to solid PEG-NETS. The solutions of PEG-AM at concentration 5% (50 mg/ml)) were prepared by dissolution of 50.0 mg in 1.0 ml of 0.1M phosphate buffer at pH 7.0, 7.5 and 8.0. PEG-AM solutions were added to solid PEG-NETS in the amounts required to obtain a 5% w/w concentration of each reagent. The mixture was stirred using magnetic stirrer at 300 rpm, leading to dissolution of PEG-NETS and gel formation. Gel time was measured in triplicates for each pH.

As discussed earlier, the pH of the reconstitution solution can be used to control the gel time, so that the cross-linking reaction does not occur prematurely before spraying. As shown in Table 35 and FIG. 24, a pH of 7.5 provides a gelation time of 3.5 minutes. This provides ample time for the clinician to spray the wound with the solution prior to gelation.

TABLE 35

Effect of pH on Gel Time (0.1M Phosphate buffer concentration, PEG-NHS and PEG-AM concentration 5%)

| Experiment | PEG-NHS mg | PEG-AM µl | pH | Gel time |
|---|---|---|---|---|
| 08-06-mix1a | 11.5 | 230 | 7 | 7' 32" |
| 08-06-mix1b | 11.1 | 222 | 7 | 7' 28" |
| 08-06-mix1c | 10.2 | 222 | 7 | 7' 20" |
| 08-06-mix2a | 11.3 | 226 | 7.5 | 3' 50" |
| 08-06-mix2b | 11.7 | 234 | 7.5 | 3' 52" |
| 08-06-mix2c | 11.7 | 234 | 7.5 | 3' 37" |
| 08-06-mix3a | 11.4 | 228 | 8 | 2' 13" |
| 08-06-mix3b | 12.1 | 242 | 8 | 2' 17" |
| 08-06-mix3c | 10.2 | 204 | 8 | 2' 17" |

Figure 24:
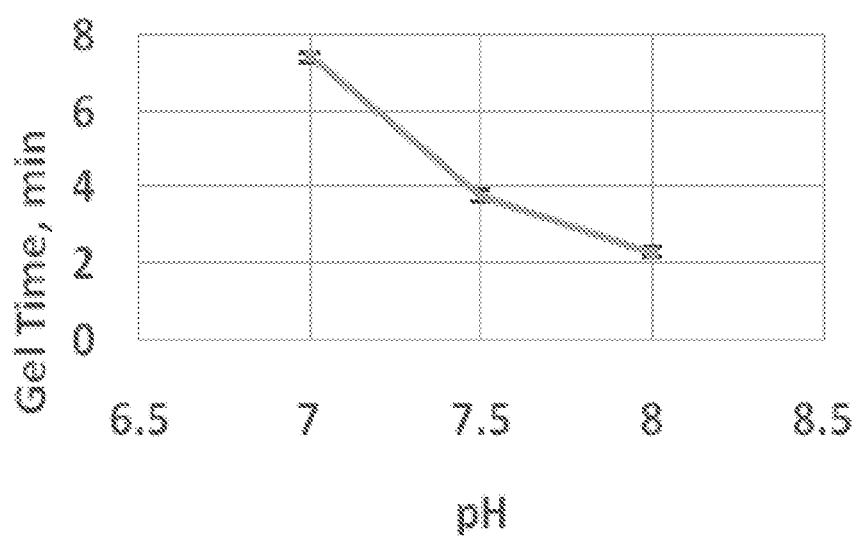

As can be seen in FIG. 24, the increasing of pH from 7 to 8 decreases the gel time from 7'32" to 2'13".

(B) Effect of PEG Concentration on Gel Time

The effect of pH on gel times was investigated in the experiments (Experiment 08-23-mix, Table 36), where PEG-AM at different concentrations was added to solid PEG-NHS. The solutions of PEG-AM at concentration 2.5% (25 mg/ml), 5.0% (50 mg/ml) and 7.5% (75.0 mg/ml) were prepared by dissolution of corresponding amounts in 0.1M Phosphate buffer at pH 7.5. The PEG-AM solutions were added to solid PEG-NETS in amounts required to obtain final concentrations of both compounds at 2.5%, 5% and 7.5%. The mixture was stirred using a magnetic stirrer at 300 rpm, resulting in a dissolution of PEG-NETS and gel formation. Gel time was measured in triplicates for each concentration.

TABLE 36

PEG-NHS/PEG-AM HYDROGEL. Effect of PEG Concentration on Gel Time (0.1M Phosphate buffer, pH 7.5)

| Experiment | PEG-NHS (mg) | PEG-AM (µl) | PEG-NHS, % | PEG-AM, % | Gel time |
|---|---|---|---|---|---|
| 08-23-mix1 | 5 | 200 | 2.5 | 2.5 | 8' 19" |
| 08-23-mix2 | 5.1 | 200 | 2.5 | 2.5 | 8' 10" |
| 08-23-mix3 | 5.1 | 200 | 2.5 | 2.5 | 8' 18" |
| 08-23-mix4 | 10 | 200 | 5 | 5 | 4' 40" |
| 08-23-mix5 | 10.1 | 200 | 5 | 5 | 4' 41" |
| 08-23-mix6 | 9.7 | 200 | 5 | 5 | 4' 24" |
| 08-23-mix7 | 15.5 | 206 | 7.5 | 7.5 | 3' 34" |
| 08-23-mix8 | 15.4 | 205 | 7.5 | 7.5 | 3' 43" |
| 08-23-mix9 | 14.3 | 190 | 7.5 | 7.5 | 3' 44" |

Figure 25A:
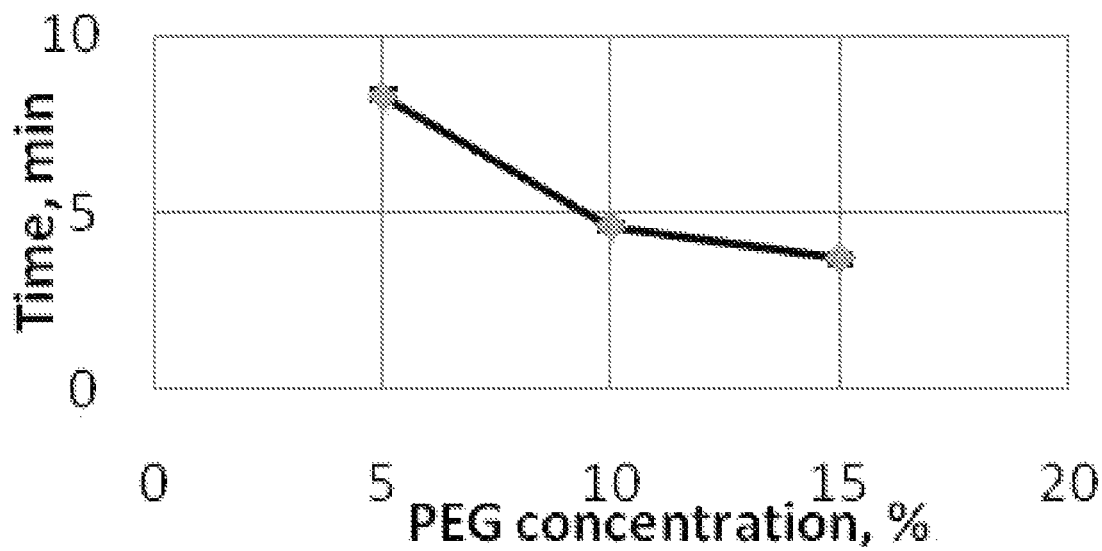
Figure 25B:
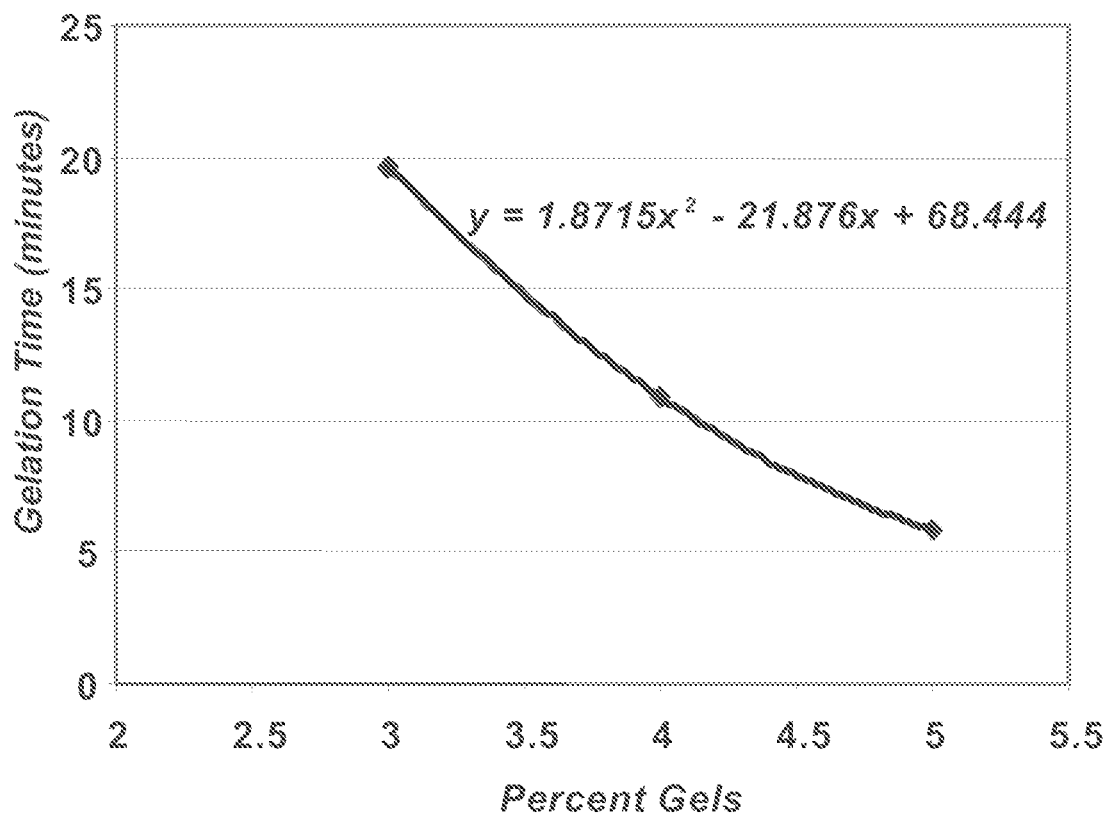
Figure 26:
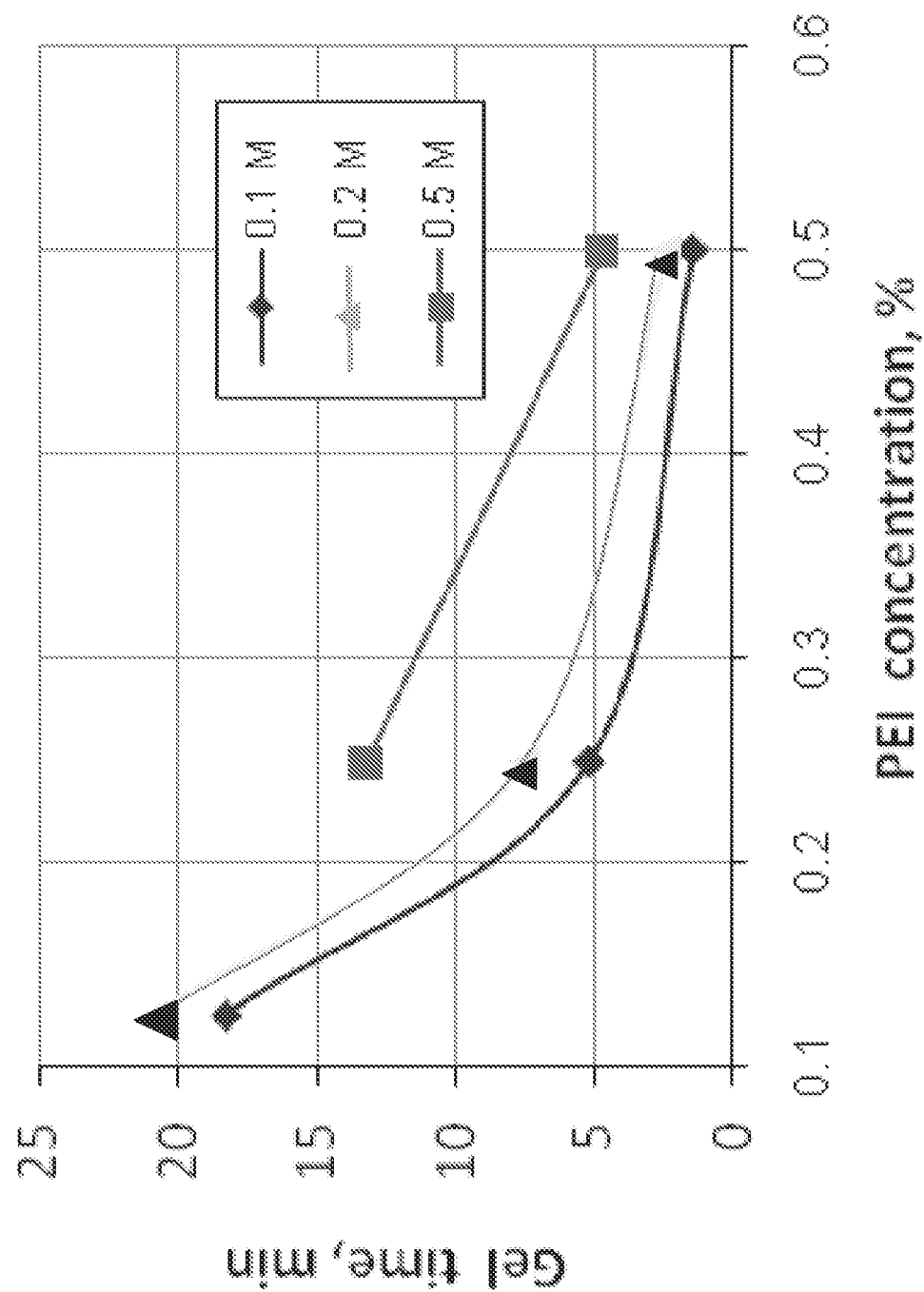
FIG. 26 is graph depicting gel time as a function of PEI concentration in Phosphate buffer (0.1M (diamonds), 0.2M (triangles) and 0.5M (squares)) for PEG-NHS/PEL hydrogels.

As can be seen in Table 36 and FIGS. 25A and B, gel times decrease when the PEG concentrations are increased. This allows modulation of PEG concentrations in each spraying chamber, so that the solution does not prematurely crosslink in the sprayer.

19.1.2 PEG-NHS/PEI Hydrogels

The following example is directed to PEG-NHS/PEI hydrogels. These hydrogels were PEG-NHS/polyethyleneimine networks and provide an alternative to PEG-AM/PEG-NHS hydrogels. Polyethyleneimine (PEI) are branched polymers with a high density of amine groups. These polymers form light molecular bonds with the dermis, preventing delamination of the hydrogel from the tissue surface. The formation of PEG-NHS/PEI hydrogels utilize identical chemistry as PEG-NHS/PEG-AM hydrogels previously described. PEI can be added in small quantities to the PEG-AM solution contained in chamber 2 of the sprayer, or it can replace PEG-AM entirely. Using PEI instead of PEG-AM, or adding this ingredient to PEG-AM introduces highly positively charged imine groups that lead to a tighter binding of the gel to the human skin.

In the examples below, the gels were prepared by the addition of PEI solutions in phosphate buffer to solid PEG-NHS. Polyethyleneimine (PEI) was purchased as a 50 wt % solution in water with a number average molecular weight of 1200 Daltons and a weight average molecular weight of 1300 from Aldrich, Catalog #485595, Lot #05329KH. The use of 5% w/w of PEI with 5% w/w PEG-NHS have led to an instantaneous precipitate formation, but 10-50 times reduction in PEI concentration resulted in an in-situ cross-linking hydrogel.

The solutions of PEI at concentrations of 0.125% w/w, 0.25% w/w and 0.5% w/w each at three concentrations of phosphate were prepared by dilution of 5% PEI stock solution with 0.1M, 0.2M and 0.5M Phosphate buffer at pH 7 (Table 37 Experiment 08-13-mix). The pH of PEI solutions was measured by pH indicator paper. The mixture was stirred using magnetic stirrer at 300 rpm, resulting in a dissolution of PEG-NHS and gel formation.

At 0.5% w/w PEI concentration, phosphate buffer capacity was not enough to maintain pH of its solution at 7.0, whish, as can be seen in Table 37, resulted in shorter gel times in experiments 08-13-mix4, 08-13-mix5 and 08-13-mix6, than would be measured at pH 7. This, however, does not change the effect of PEI concentration—as shown in FIG. 26, gel time decreased when PEI concentration increased for all three phosphate concentrations.

The concentration of phosphate appeared to have an opposite effect on gel time—gel time increased when the phosphate concentration was increased (FIG. 26). In the extreme case, 0.5M phosphate at 0.125% PEI failed to produce a gel (08-13-mix9, Table 37 (0.125% PEI in 0.5M Phosphate)).

TABLE 37

PEG-NHS/PEI Hydrogels. Effect of PEI and Phosphate Concentration on Gel Time (Phosphate buffer 0.1M, 0.2M and 0.5M at pH 7)

| Experiment | PEG-NHS conc., % | PEI conc., % | Phosphate conc., M | pH* | Gel time |
|---|---|---|---|---|---|
| 08-13-mix7 | 5 | 0.125 | 0.1 | 7.0 | 18' 18" |
| 08-13-mix1 | 5 | 0.25 | 0.1 | 7.0 | 5' 07" |
| 08-13-mix4 | 5 | 0.5 | 0.1 | 9.0 | 1' 25" |
| 08-13-mix8 | 5 | 0.125 | 0.2 | 7.0 | 20' 51" |
| 08-13-mix2 | 5 | 0.25 | 0.2 | 7.0 | 7' 31" |
| 08-13-mix5 | 5 | 0.5 | 0.2 | 8.0 | 2' 22" |
| 08-13-mix9 | 5 | 0.125 | 0.5 | 7.0 | did not gel |
| 08-13-mix3 | 5 | 0.25 | 0.5 | 7.0 | 13' 11" |
| 08-13-mix6 | 5 | 0.5 | 0.5 | 7.5 | 4' 36" |

*pH of the PEI solutions was measured with pH indicator paper.

19.1.3 PEG-NHS/PEG-AM/Chitosan Hydrogels

The following example is directed to PEG-MA/PEG-NHS/Chitosan hydrogels. Chitosan can be added to the PEG-AM/PEG-NHS hydrogels for impartation of a positive charge to the hydrogel, for the purpose of sequestration of the hydrogel to the skin.

PEG-NHS/Chitosan gel formation was investigated to see if chitosan could replace PEG-AM. Chitosan Batch #FP-211-03 was purchased from NovaMatrix, Because Chitosan is not soluble at pH 7 in phosphate buffer, Chitosan solution in water at pH 5-6 has been used. The addition of Chitosan water solutions at concentrations 0.25% and 0.65% to the solid PEG-NETS failed to produce gels. The mixture of PEG-NETS with Chitosan remained in a liquid form after 20 hours from the start of the reaction. This experiment demonstrated that chitosan could not replace PEG-AM.

The next experiment was to test if chitosan could be added to PEG-AM. Therefore, a three component system was developed, a chitosan solution was added to PEG-NHS and PEG-AM.

Two methods of introducing chitosan into PEG-AM/PEG-NHS hydrogels were tested. In Method 1, a 2.5% w/w chitosan aqueous solution was mixed with 5% w/w PEG-AM in 0.1M phosphate buffer at pH 7. This solution was added to solid PEG-NETS. In Method 2, a 2.5% w/w chitosan aqueous solution was added to solid PEG-NETS and dissolved. 5% w/w PEG-AM in 0.1M Phosphate buffer at pH 7 was added to this solution. Chitosan solutions at 0.22-0.27% and 0.57-0.64% were obtained using these methods (Table 38). The experimental conditions, final reagent concentrations, and gel times for PEG-NHS/PEG-AM/chitosan hydrogels are shown in Table 38.

In both methods, partial precipitation of chitosan was observed, but gels became transparent as the reaction proceeded. This indicated that chitosan was incorporated into the hydrogel matrix as the reaction proceeded. The gel times of the three-component system PEG-NHS/PEG-AM/chitosan hydrogel were compared with a control—the two component PEG-NHS/PEG-AM hydrogel system. As outlined in Table 38, at chitosan concentrations of 0.22-0.27%, the gel times were either longer (first method of chitosan introduction) or close to the gel time of the controls (second method of chitosan introduction). For chitosan at concentrations of 0.57-0.64%, gel times were longer than for controls independently of the way chitosan was introduced into the gel. Thus, incorporation of chitosan into PEG-AM/PEG-NHS HYDROGELS slows down the reaction significantly at higher concentrations.

TABLE 38

Gel times of PEG-NHS/PEG-AM/Chitosan Hydrogels (0.1M Phosphate buffer, pH 7.0)

| Experiment | Method* | PEG-NHS conc., % | PEG-AM conc., % | Chitosan conc., % | Gel time |
|---|---|---|---|---|---|
| 08-13 Mix12 | 1 | 4.6 | 4.6 | 0.22 | 13' 44" |
| 08-17 Mix8 | 1 | 4.4 | 4.5 | 0.27 | 12' 19" |
| 08-17 Mix4 | 2 | 5.0 | 4.6 | 0.22 | 9' 24" |
| 08-17 Mix7 | 2 | 4.5 | 4.5 | 0.27 | 7' 5" |
| 08-17 Mix10 | control | 4.6 | 4.5 | 0.00 | 8' 24" |
| 08-17 Mix5 | control | 5.0 | 4.5 | 0.00 | 8' 03" |
| 08-18-mix4 | 1 | 3.9 | 4.0 | 0.64 | 21' 09" |
| 08-18-mix5 | 2 | 4.1 | 4.1 | 0.57 | 21' 30" |
| 08-I8-mix6 | control | 4.1 | 4.0 | 0.00 | 13' 11" |

The PEG-NHS/PEG-AM/Chitosan hydrogel has disadvantages compared with the PEG-NHS/PEG-AM hydrogel and PEG-NHS/PEI hydrogel. At a pH ~7, Chitosan precipitates and cannot be covalently bonded to the gel matrix.

(1) Determination of Equilibrium Swelling

Equilibrium swelling measures the crosslink density of a covalently cross-linked hydrogel. A highly cross-linked hydrogel swells less, due to its high mesh density. Hydrogels that have high equilibrium swelling can also delaminate from the tissue surface. Thus, low equilibrium swelling is desired to prevent delamination from the tissue surface.

Factors that affect equilibrium swelling include concentration of the PEGs and the number of reactive groups per molecule. Thus, a 4-armed PEG-AM reacting with a 4-armed PEG-NHS would have a lower equilibrium swelling than a 2-armed PEG-AM/PEG-NHS hydrogel due to lower crosslink density.

In this experiment, the solid PEG-NETS was mixed with solutions of PEG-AM. The mixed solutions were withdrawn by a 1.0 mL disposable syringe (Henke Sass Wolf GmbH) and gels were formed inside the syringes. This method allowed formation of hydrogel molds with a fixed geometry. The syringes were cut into small cylindrical pieces. The gel plugs were 5-6 mm in length and 5 mm in diameter. The gel plugs were weighed and placed into Falcon tubes filled with 10 mL of 1×PBS at pH 7.4. The Falcon tubes were placed into a 37° C. water bath for 24 hours. After 24 hours, the gel plugs were removed from the Falcon tubes and excess PBS was wiped off. The gel plugs were weighed after swelling. The percent swell was calculated by dividing the change in weight by the original weight, and expressing the result as a percentage:

Percentage Swell=((Weight after swelling−Weight before swelling)/Weight before swelling)×100

As outlined in Table 39, as a general rule, the swelling of PEG-AM/PEG-NHS hydrogels increased with increasing concentration of each PEG component, due to the high binding of polyethylene glycol polymers with water.

a. PEG-NHS/PEG-AM Hydrogels: PEG-AM at 2.5% (25 mg/ml), 5.0% (50 mg/ml) and 7.5% (75.0 mg/ml) in 0.1M Phosphate buffer at pH 7.5 was added to solid PEG-NHS to obtain equal final concentrations of both reagents 2.5%, 5% and 7.5%.

b. PEG-NHS/PEI Hydrogels: PEI at concentration 0.125%, 0.25% and 0.5% in 0.1M Phosphate buffer at pH 7.0 was added to solid PEG-NETS to obtain 5% concentration.

c. PEG-NHS/PEG-AM/Chitosan Hydrogels: Aqueous chitosan solution at concentration 2.5% was added to solid PEG-NHS. PEG-AM in 0.1M Phosphate at pH 7 was added to this solution.

d. Gel plugs were fabricated to test equilibrium swelling at room temperature.

TABLE 39

Preparation of Hydrogels for Equilibrium Swelling

PEG-NHS/PEG-AM

| Experiment | PEG-NHS mg | PEG-AM µl | PEG-NHS Conc., % | PEG-AM Conc., % |
|---|---|---|---|---|
| 08-25-mix1 | 13.2 | 528 | 2.500 | 2.5 |
| 08-25-mix2 | 25.2 | 510 | 5.000 | 5.00 |
| 08-25-mix3 | 38.2 | 509 | 7.505 | 7.5 |

PEG-NHS/PEI

| Experiment | PEG-NHS Mg | PEI µl | PEG-NHS Conc., % | PEI Conc., % |
|---|---|---|---|---|
| 08-25-mix4 | 25.3 | 500 | 5.060 | 0.125 |
| 08-25-mix5 | 24.4 | 500 | 5.000 | 0.25 |
| 08-25-mix6 | 25.1 | 500 | 5.000 | 0.5 |

PEG-NHS/PEG-AM/Chitosan

| Experiment | PEG-NHS Mg | PEG-AM µl | Chitosan µl | PEG-NHS Conc., % | PEG-AM Conc., % | Chitosan Conc., % |
|---|---|---|---|---|---|---|
| 08-25-mix7 | 26.4 | 500 | 50 | 4.5 | 4.5 | 0.23 |

Figure 27:
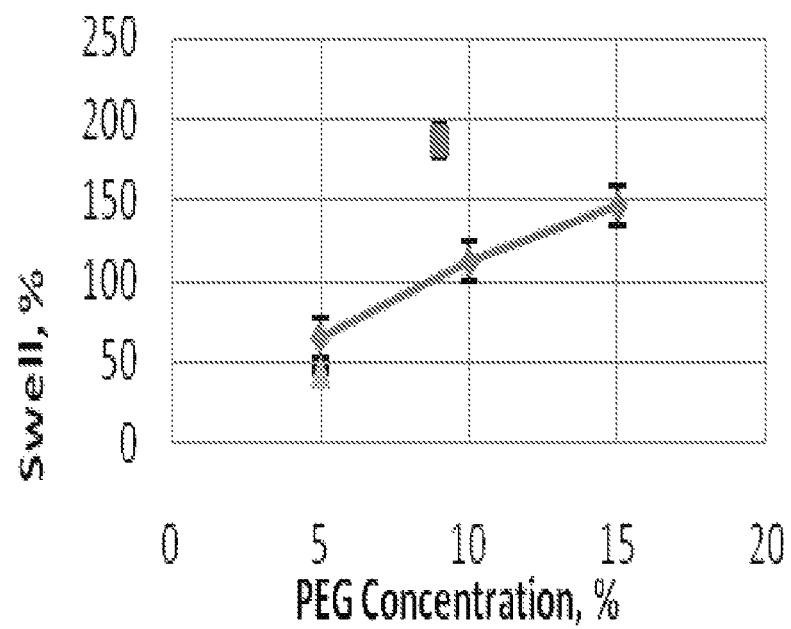
FIG. 27 is a graph depicting the degree of swelling (y-axis) as a function of PEG concentration (x-axis) for PEG-NHS/PEG-Amine hydrogels (diamonds), PEG-NHS/PEG-Amine/Chitosan hydrogels (squares), and PEG-NHS/PEI hydrogels (triangles).
Figure 28:
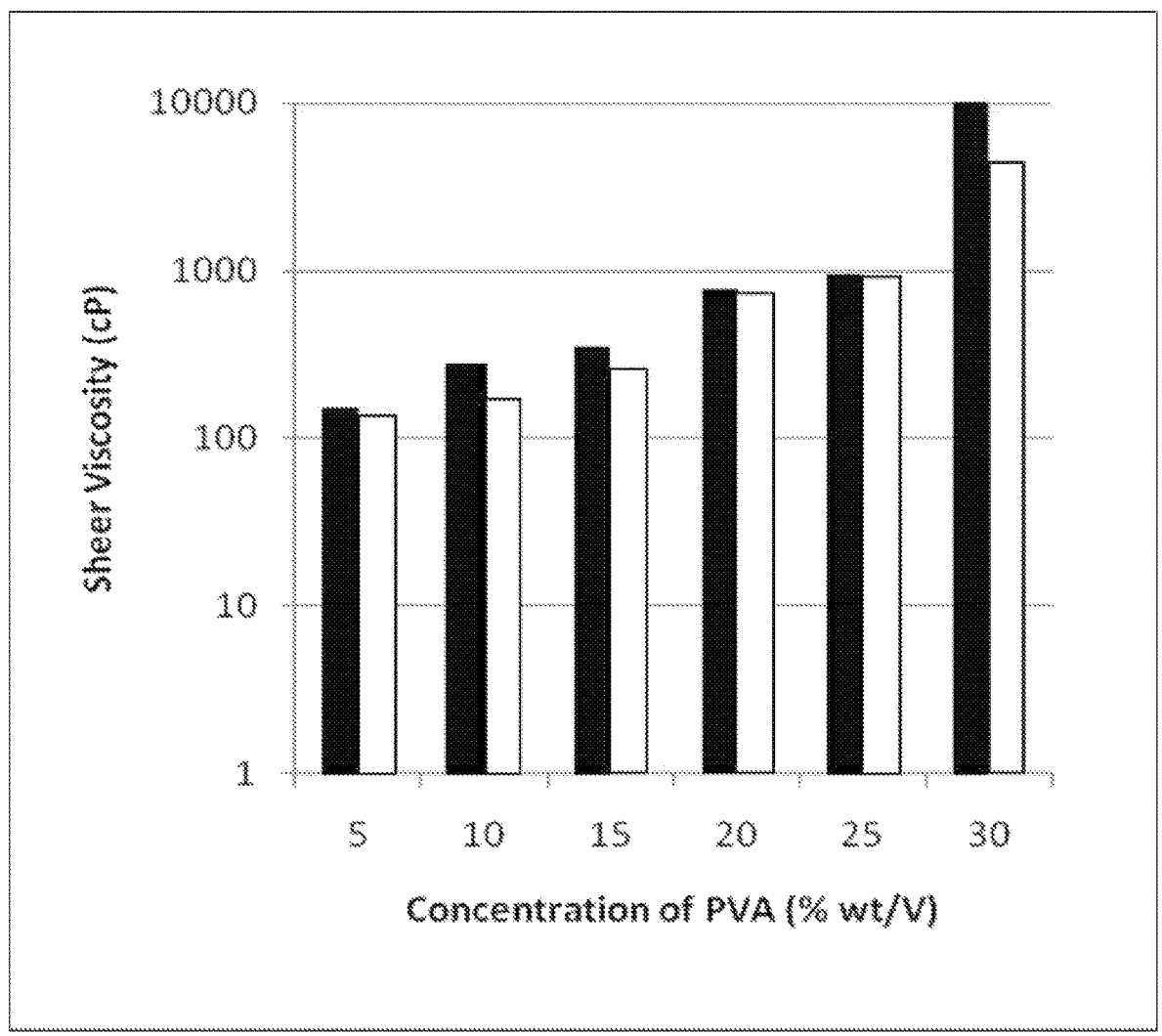
FIG. 28 is a graph depicting the viscosity of PVA solutions as a function of temperature and PVA concentration. The left-hand bar for each concentration (x-axis) represents the sheer viscosity (cP) at 25° C. and the right-hand bar for each concentration (x-axis) represents the sheer viscosity (cP) at 30° C.

The results of equilibrium swelling for PEG-NHS/PEG-AM hydrogels, PEG-NHS/PEI hydrogels, and PEG-NHS/PEG-AM/Chitosan hydrogels are shown in Table 40 and FIG. 27. The degree of swelling increased for PEG-NHS/PEG-AM hydrogels from 65.3% to 146.9% with the increasing of total PEG concentration from 5% to 15% (Table 40, FIG. 27). The degree of swelling is a function of cross-linking density, with higher degrees corresponding to a higher density. In this case, the effect of higher PEG concentration overwhelms the increase of cross-linking density. This is due to the high affinity of polyethylene glycol for water.

For PEG-NHS/PEI hydrogels, increase in PEI concentration did not change the degree of swelling and was close to the degree of cross-linking of PEG-NHS/PEG-AM hydrogels, indicating similar cross-linking density in both hydrogels (FIG. 27). In contrast, the degree of swelling was significantly higher for PEG-NHS/PEG-AM/Chitosan hydrogels (187%) when compared to PEG-NHS/PEG-AM hydrogels (112%) at 10% PEG concentrations. This is an indication of lower cross-linking density for the PEG-NHS/PEG-AM/chitosan hydrogels, due to the interference of chitosan in the reaction between PEG-NHS and PEG-AM.

TABLE 40

Swelling Properties of Hydrogels.

PEG-NHS/PEG-AM

| Experiment | PEG-NHS Conc., % | PEG-AM Conc., % | PEG, total Conc., % | Weight b.s.* mg | Weight a.s.* mg | Swell % |
|---|---|---|---|---|---|---|
| 08-25-mix1a | 2.5 | 2.5 | 5.0 | 86.4 | 142 | 64.4 |
| 08-25 -mix1b | 2.5 | 2.5 | 5.0 | 87.9 | 148 | 68.4 |
| 08-25 -mix1c | 2.5 | 2.5 | 5.0 | 78.5 | 128 | 63.1 |
| 08-25-mix2a | 5.0 | 5.0 | 10.0 | 99 | 202.1 | 104.1 |
| 08-25 -mix2b | 5.0 | 5.0 | 10.0 | 93.7 | 192.7 | 105.7 |
| 08-25 -mix2c | 5.0 | 5.0 | 10.0 | 91.8 | 208.6 | 127.2 |
| 08-25-mix3a | 7.5 | 7.5 | 15.0 | 102.9 | 259.6 | 152.3 |
| 08-25 -mix3b | 7.5 | 7.5 | 15.0 | 104.1 | 258.9 | 148.7 |
| 08-25 -mix3c | 7.5 | 7.5 | 15.0 | 102.3 | 245.1 | 139.6 |

TABLE 40-continued

Swelling Properties of Hydrogels.

PEG-NHS/PEI

| | PEG-NHS Conc., % | PEI Conc., % | PEG, total Conc., % | Weight b.s. mg | Weight a.s. mg | Swell % |
|---|---|---|---|---|---|---|
| 08-25-mix4a | 5.0 | 0.125 | 5.0 | n.d. | n.d. | n.d. |
| 08-25-mix4b | 5.0 | 0.125 | 5.0 | 97.5 | 134 | 37.4 |
| 08-25-mix4c | 5.0 | 0.125 | 5.0 | 93.9 | 128 | 36.3 |
| 08-25-mix5a | 5.0 | 0.250 | 5.0 | 91 | 95.5 | 4.9 |
| 08-25-mix5b | 5.0 | 0.250 | 5.0 | 90.7 | 97.8 | 7.8 |
| 08-25-mix5c | 5.0 | 0.250 | 5.0 | 102.8 | 109.7 | 6.7 |
| 08-25-mix6a | 5.0 | 0.500 | 5.0 | 99.2 | 142.1 | 43.2 |
| 08-25-mix6b | 5.0 | 0.500 | 5.0 | 79.5 | 115.5 | 45.3 |
| 08-25-mix6c | 5.0 | 0.500 | 5.0 | n.d | n.d | n.d |

PEG-NHS/PEG-AM/Chitosan

| | PEG-NHS Conc., % | PEG-AM Conc., % | Chitosan Conc., % | PEG, total Conc., % | Weight b.s. mg | Weight a.s. mg | Swell % |
|---|---|---|---|---|---|---|---|
| 08-25-mix7a | 4.5 | 4.5 | 0.23 | 9 | 101.1 | 280.8 | 177.7 |
| 08-25-mix7b | 4.5 | 4.5 | 0.23 | 9 | 98.4 | 279.9 | 184.5 |
| 08-25-mix7c | 4.5 | 4.5 | 0.23 | 9 | 100.9 | 301.6 | 198.9 |

*Weight b.s.—weight of gel plugs before swelling; Weight a.s.—weight of gel plugs after swelling

19.2 Hydrogel Testing on Skin

PEG-NHS/PEG-AM Hydrogel: 5% w/w PEG-AM in 0.1M Phosphate buffer at pH 7.5 was added to solid PEG-NETS (Table 41). The mixture was applied to intact skin. The liquid formed a sticky solution that coalesced within few minutes into a thin film that adhered well to skin. The film remained attached to the skin for few hours.

PEG-NHS/PEI Hydrogel: 0.5% PEI in 0.1M Phosphate buffer at pH 7.0 was added to solid PEG-NETS. The liquid formed a sticky solution that coalesced within few minutes into a thin, skin-adherent film. The hydrogel was applied to intact skin, and remained attached to the skin for few hours. The PEG-NHS/PEI hydrogel transformed to a thin film faster and seemed to be attached more tightly to the skin than PEG-NHS/PEG-AM hydrogel.

PEG-NHS/PEG-AM/Chitosan Hydrogel: Aqueous chitosan solution (2.5% w/w) was added to solid PEG-NETS. PEG-AM (in 0.1M Phosphate at pH 7) was added to this solution. The hydrogel was applied to intact skin. The gel did not adhere well to the skin.

TABLE 41

Preparation of Hydrogels for Testing on Skin

PEG-NHS/PEG-AM

| Experiment | PEG-NHS mg | PEG-AM µl | PEG-NHS Conc., % | PEG-AM Conc., % |
|---|---|---|---|---|
| 08-27-mix1 | 25.9 | 500 | 5.0 | 5.0 |

PEG-NHS/PEI

| Experiment | PEG-NHS mg | PEI µl | PEG-NHS Conc., % | PEI Conc., % |
|---|---|---|---|---|
| 08-27-mix4 | 25.7 | 500 | 5.0 | 0.5 |

PEG-NHS/PEG-AM/Chitosan

| Experiment | PEG-NHS mg | PEG-AM µl | Chitosan µl | PEG-NHS Conc., % | PEG-AM Conc., % | Chitosan Conc., % |
|---|---|---|---|---|---|---|
| 08-27-mix3 | 24.0 | 500 | 49.6 | 4.4 | 4.5 | 0.23 |

20. EXAMPLE: SOLID-LIQUID IN-SITU CROSS-LINKING SPRAY ON A BIODEGRADABLE SCAFFOLD THAT RELEASES DRUG

Described above is a formulation for sustained release of drug from PLG microspheres sequestered to the dermis via an in-situ cross-linking, biodegradable hydrogel. Because the drug delivery system may be applied to a dynamic wound healing environment, drug uptake into the dermis may become limited as the skin heals and slowly re-establishes its barrier function. Thus, sustained transport of drug into the dermis may diminish as a thick, fibrous scab is formed on the wound. Accordingly, drug will be released from the microspheres sequestered in the hydrogel, but transport of the drug through the scab will likely be limited.

When the problem is transport of drug through a scab, a solution can be to incorporate the delivery system into the scab. Once the delivery system is incorporated into the scab, the release of drug will be from the scab into the healing dermis. Thus, the scab becomes part of the delivery system.

In the present example, a drug-containing thin, gauze-like, pliable biodegradable scaffold is placed on the fresh wound. The material properties of the scaffold can be adjusted such that the gauze is able to absorb the blood and other exudates from the wound. Thus, the biodegradable scaffold will have a high content of void space in order to absorb blood, fibrin, and fibrinogen. This incorporation of the scaffold into the fibrin clot during its formation, results in its incorporation into the fibrous network, also called a scab, after it solidifies. After placement of the drug-containing biodegradable scaffold into the wound, an in-situ cross-linking hydrogel will be applied on top to cover the entire site as a wound dressing.

In the previous example, the drug is contained within PLG microspheres co-lyophilized with Polymer 1 (PEG-NETS) in chamber 1 of the sprayer. In the present example, the sprayer contains only the in-situ cross-linking polymer components. The drug is incorporated in the biodegradable scaffold.

This concept is advantageous and important implications for wound healing. The scaffold allows close contact of the drug system with the wound, and in some embodiments, the drug system comprises agents with antimicrobial properties. Close contact with the wound may prevent infections in the wound, thus aiding in effective wound healing. The fibrin-incorporated drug delivery system is an excellent "scaffold" for cells to attach to.

20.1 Description

In this example, (a) a two-chamber sprayer that contains a liquid in one chamber and a lyophilized solid in the other and (b) a biodegradable pre-fabricated scaffold that contains the drug is used.

The biodegradable scaffold is in the form a pliable, gauze-like material that is a blend of PLG polymers. Other polymers may be added to the main component (PLG) to impart characteristics such as biodegradability, pliability, etc. Drug will be incorporated in the biodegradable scaffold.

The biodegradable scaffold will have an "open-cell" structure that allows cells to (a) attach themselves, (b) differentiate, and (c) proliferate. The scaffold may have other components such as RGD peptides, etc. incorporated in order to promote cell attachment. The scaffold will have bioadhesive attributes to keep it "in place."

20.2 Method of Use

After placement of the scaffold on the fresh wound, the blood oozing from the site is allowed to be soaked into the gauze. The sprayer is then engaged to mix the two components contained in chamber 1 and chamber 2.

The lyophilized solid component contained in chamber 1 is comprised of a polymer macromonomer (Polymer 1) (a polymer that can further cross-link with another component). The component in the other chamber (chamber 2) contains another polymer macromonomer (Polymer 2) that is capable of reacting with the lyophilized polymer (Polymer 1). Polymer 2 is dissolved in a phosphate buffer of pH 6-8. Polymer 2 does not contain hydrolytically labile linkages and is therefore, stable in water. Thus, Polymer 2 can be stored in the reconstitution buffer. Accordingly, the solution containing Polymer 2 reconstitutes the lyophilized Polymer 1 when the polymers are mixed together in the sprayer. The mixed solution is then rapidly sprayed onto the wound site. Upon spraying, the solution cross-links, thereby forming a hydrogel.

In this example, the scaffold in the drug delivery carrier and the hydrogel is the wound dressing.

20.3 the Example

The objective of this experiment is to develop prototypes of biodegradable scaffold patches that could be placed on wounded tissue to deliver a drug to the wound. The "scaffold" is a three-dimensional structure that can provide a high surface area for cell attachment. Varying the polymer composition of the scaffold matrix can modulate drug release rates from 3 days to 14 days.

Drug is dissolved in water at a concentration of 50 mg/mL. Poly(lactide-co-glycolide) (PLG), MW 12000 g/mole, poly(lactic acid) (PLA), MW 30,000 g/mole and blends thereof, were used to prepare fibrous scaffolds. The blends of polymers were 100/0 PLA/PLG, 50/50 PLA/PLG, 25/75 PLA/PLG and 0/100 PLA/PLG, respectively. PLA and PLG were purchased from Purac, Inc.

A cotton candy machine (Gold Medal Floss, Cat #3024) was set at a setting of 3 (there are five settings in total, ranging from temperatures of 40° C. to 200° C. One gram of a blend of 100/0 PLA and 1 ml of drug-containing solution is fed into the hopper, which resulted in fine fibers collecting (much like a spider web) in the collection chamber. The fibers with the incorporated drug are collected and pressed into patches of 1 g each using a low pressure Carver press. The patches are then punched out into 1-inch by 1-inch squares. A similar procedure is followed for the other blends of 50/50 PLA/PLG, 25/75 PLA/PLG and 0/100 PLA/PLG.

Scanning electron micrographs (SEM) are taken of the patches. By SEM, the mesh size, or open-cell size is estimated to be approximately 100-200 microns. Estimated thickness of the fabricated patches can range from 500-1000 microns. The patches are placed into mesh buckets in dissolution baths containing phosphate buffered saline at 37° C. and a pH of 7.4, to simulate physiological conditions. Aliquots of the dissolution media can be retrieved at pre-determined time-points and analyzed for drug content by, e.g., flame-emission atomic adsorption spectroscopy (AA).

20.4 Results

Solutions of drug are prepared in distilled water at a concentration of 50 mg/ml. Poly(lactide-co-glycolide)

(PLG), MW 12000 g/mole, poly(lactic acid) (PLA), MW 30,000 g/mole and blends thereof, are used to prepare fibrous scaffolds. The blends of polymers are 100/0 PLA/PLG, 50/50 PLA/PLG, 25/75 PLA/PLG and 0/100 PLA/PLG, respectively. PLA and PLG were purchased from Purac, Inc.

A cotton candy machine (Gold Medal Floss, Cat #3024) is set at a setting at 3 (there are five settings in total, ranging from temperatures of 40° C. to 200° C.).

1 g of a blend of 100/0 PLA and 1 ml of drug solution is fed into the hopper, which results in fine fibers collecting (much like spider web) in the collection chamber. The fibers with incorporated drug are collected and pressed into patches of 1 g each, a low pressure Carver press. The patches are then punched out into 1 square inch squares.

A similar procedure is followed for the other blends of 50/50 PLA/PLG, 25/75 PLA/PLG and 0/100 PLA/PLG.

Scanning electron micrographs (SEM) can be used to determine the texture of the patches. The following attributes are also tested:

Visual and Flexural Modulus. The pressed fiber patches are tested for flexural strength by a simple flex method of bending the patch between the thumb and the index finger. Brittleness of the patches can be reduced by incorporating some plasticizing polymers such as PEGs, or silicones, to impart some flexibility to the patches.

Release Rates. The release of drug could be modulated by varying the ratio of PLA to PLG. As a rule of thumb, the higher crystallinity of the poly(lactide) (PLA) slows down the release of drug from the matrix. The amorphous nature of poly (lactide-co-glycolide) (PLG) result in higher release rates of drug. The approach of blending various ratios of PLA: PLG can be utilized effectively to modulate the release rate of drug from the matrix.

Biodegradability. The biodegradability of the patches can be tested in vitro, by incubation of pre-weighed patches in phosphate buffer saline, pH 7.4 at 37° C. Over time, the patches are removed from the bath and dried in a vacuum oven maintained at 30° C. The weight of the patches at T=0 and t=t provides biodegradation profile. Since the polymers degrade by hydrolysis and not by enzymolysis, the degradation buffer would not contain enzymes.

Bioadhesion. The bioadhesiveness of the drug-loaded patches can be assessed by placing the patch of wet tissue, inverting the tissue and measuring the rate at which the patch detaches from the tissue.

Cell Adhesion. The propensity of the drug-loaded patches to adhere to cells is measured by in-vitro culture of COS cells or keratinocytes in the presence of the scaffolds.

21. EXAMPLE: SIMULTANEOUS ADMINISTRATION OF TWO OR MORE DRUGS VIA A TWO CHAMBER LIQUID-LIQUID SPRAYER

Occasionally, multiple drugs need to be administered simultaneously. For a dermal application, application of one drug followed by the other is possible, but has practical issues such as accidentally rubbing off the first drug during administration of the second. If these drugs can be co-formulated, then a single application of a combined formulation offers ease of use and administration. An example of this could be a dermal cream with two co-formulated drugs. However, many drugs cannot be formulated together, either due to differences in solubility properties of one drug relative to another or physical/chemical incompatibilities arising from being co-formulated. For example, an excipient that stabilizes or solubilizes one of the drugs may initiate precipitation for the other. Ionic binding of drugs to each other can create additional issues such as unpredictable bioavailability, absorption and clearance. Thus, what is needed is a pharmaceutically compliant way of co-administering two drugs at the target site, without co-formulation. A precise volume of delivery and the ability to cover a large site in a homogenous fashion would be additionally desired attributes.

A drug delivery device that co-administers two separate formulations can be used to address the above-described problems associated with administering multiple drugs simultaneously. One example of a drug delivery system that can administer multiple drugs simultaneously is a co-ointment tube, through which both the formulations are extruded together. Another example of a drug delivery system that can administer multiple drugs simultaneously is a dual chamber delivery spray device that contains a formulated drug in each chamber and co-sprays the drug formulations in a precise volume. Alternatively, the spray device can be engaged for spraying each drug separately, if required. For example, an alcoholic solution (±drug) may be used to first "prepare" the wound by thorough cleansing, followed by spraying of a drug formulation. The spraying mechanism may be at high energy or low energy, depending upon the application. In another application, both chambers could contain the same drug, but in different forms and formulated differently to achieve different release profiles. For example, chamber 1 could contain one drug or form thereof suspended in a FDA-approved liquid excipient. Chamber 2 could contain dissolved drug in another form (e.g., for sustained release), or another drug, in an aqueous sprayable gel. Co-spraying both provides instantly-bioavailable, drug and a sustained form of drug or a second drug made available as it dissolves.

A drug sprayer that can apply drug combinations has large implications in the treatment of dermatological conditions and can be used to (a) deliver a precise combination of the drug combination and (2) provide uniform coverage over large areas. Additionally, for treatment of wounds, wound cleansing can be combined with administration of a drug-containing gel to the target site.

The solutions that are contained in chamber 1 and chamber 2 sprayer (a) must be sprayable, (b) must not "run-off" the skin, and (c) must form a uniform coating on skin. The first two are dependent on the modulation of viscosity and the last is dependent upon the surface wettability of the formulation. In terms of a formulation being fluid enough to spray, but viscous enough to "stay on the skin", one of the formulations has the added requirement of adding viscosity to the spray. This can be accomplished by using thermo-reversible polymers that have the property of being a liquid while cold, but "gels" when the solution reaches skin temperatures. One such polymer is of the PEO-PPO-PEO (polyethylene oxide-co-polypropylene oxide-co-polyethylene oxide) structure. At low temperatures (0-15° C.), both the PPO and the PEO are fully dissolved and the polymer exists in a random-coil conformation. At higher temperatures (T>15° C.), the PPO segments begin to collapse, while the PEO segments are still soluble. The polymer begins to undergo a state of "critical gelation," brought on by higher temperatures. Physically, the polymer solution attains a higher viscosity like a gel. This allows the drug-containing polymer solution to be sprayed while still attaining a homogeneous gel coating on the skin. In Example Sections 28 and 29 the in-situ cross-linking reaction was covalent in nature and triggered by a change in pH. In this concept, the in-situ gelation is non-covalent in nature and in triggered by change in pH. The "gelation" phenomenon is physical cross-linking, caused by a collapse of polymer segments, creating a solution of higher viscosity. A physical cross-link is not covalent or permanent in nature but accomplishes the task of minimizing or preventing "run-off."

Another way to develop a sprayable formulation that does not "run off" the skin after administration is to accomplish the gelation in-situ while spraying. This can be achieved by lecithin/polyethylene glycol/water solutions which gel instantly when mixed. The drug can be dissolved in a polyethylene glycol/water solution and included in the first chamber. Lecithin included in the second chamber and co-sprayed with the contents of the first chamber, will result in a "gel" on the skin.

Provided below are some examples of the two-chamber liquid-liquid drug delivery system.

21.1 Delivery of Drug PEO-PPO-PEO Formulations from a Two Chamber Liquid-Liquid Spray Delivery System This experiment is directed to delivering one drug in two forms (e.g., ionized and micronized) or two drugs for a sustained period of time from an in-situ gelling system, triggered by change in temperature. The block copolymer was 12,600 daltons in molecular weight, with each polymer segment approximately 4000 daltons. Benzyl alcohol was used as a preservative. Allantoin and sodium alginate was used as wound healing aids A solution (solution 1) is prepared that contains drug dissolved in a solution that contains 1% benzyl alcohol, 3% allantoin, 20% F127 and 3% sodium alginate and water (Q.S). Another solution (solution 2) is prepared that contains micronized drug dispersed in a solution that contains 78% propylene glycol, 1% tween 20 and 10% polyethylene glycol 400. Solution 1 can be contained in chamber 1 of the liquid-liquid sprayer and solution 2 can be contained in chamber 2. The viscosity of each solution is measured using a Brookefield Viscometer at 4° C., 25° C. and 32° C. (skin temperature). Gel times are measured by mixing 1:1, 1:2 and 1:3 ratios of each solution. The gelling concept is tested on skin to estimate if the gelled formulation stayed on the surface.

Solution 2 contains excipients that are water-soluble. The excipients are all soluble in water because the ingredients in solution 2 would need to be miscible with all ingredients in solution 1. Propylene glycol and polyethylene glycol are included as surface wetting agents. The viscosity of solution 1 should not vary with temperature, whereas the viscosity of solution 2 can vary significantly with temperature. Optimally, mixing of a 1:1 ratio of solution 1 and solution 2, results in a solution with little "run off." The thinner the film on the skin, the lower the "run-off" Optimally, mixing of a 1:2 and 1:3 ratio of solution 1 and 2 results in a solution with no "run off" All three mixes are gels. An in-vitro release experiment of the 1:3 ratio gel optimally demonstrates some sustained release of ionized drug.

21.2 Determination of the Viscosity that can be Sprayed from a Sprayer

This experiment was to generate a series of polyvinyl alcohol solutions formulated in distilled water and measure the viscosities of these solutions, with the purpose of ascertaining whether these solutions could be effectively sprayed from a spraying apparatus.

Materials

Polyvinyl Alcohol (PVA); 5, 10, 15, 20, 25, 30% solutions—Lot #D14T017, Alfa Aesar
Distilled Water
Brookfield Rheometer, DV III

Methods a. Six solutions of PVA were prepared by weighing out the appropriate amounts of PVA solid and dissolving it into distilled water.

b. To measure viscosity, a Brookfield DV-III Ultra programmable rheometer was utilized, and the temperature was regulated by a Neslab RTE-111 water bath. When the temperature was stable at 25° C., mineral oil calibration standards at 9.5, 98, 4800, and 12500 cP were used to calibrate the instrument.

c. The solutions were then applied and the RPM adjusted until the viscosity reading remained stable over several RPM values. The procedure was then repeated at 30° C.

Data

Table 42 summarizes the range of viscosities obtained by the PVA solutions, with the lowest viscosity at ~150 cP (5% w/v PVA) and the highest viscosity at 9900 cP (30% w/v PVA), measured at 25° C. All solutions had flow characteristics.

TABLE 42

Viscosity as a function of concentration in % w/v

| Concentration (% wt/V) | Viscosity (25 deg. C.) | Viscosity (30 deg. C.) | Flow Properties | TESTED WITH SPRAYER |
|---|---|---|---|---|
| 5 | 154 | 135 | Yes, flows quickly, watery | Can be sprayed |
| 10 | 265 | 164 | Yes, flows quickly, watery | Can be sprayed |
| 15 | 357 | 258 | Yes, moderately fast, like olive oil | difficult |
| 20 | 773 | 730 | Yes, flows slowly, like syrup | no |
| 25 | 952 | 920 | Yes, flows very slowly, like molasses | no |
| 30 | 9900 | 4500 | Yes, but flows extremely slowly | no |

Consistent with the properties of Newtonian fluids, PVA lessens in viscosity as temperature increases, as shown in FIG. 28. Table 42 includes the actual viscosity values obtained and the flow properties were recorded qualitatively by observing the flow of solution down their vials.

The purpose of this experiment was to ascertain the viscosity of PVA, which will be used to determine the limits of a spraying apparatus designed to expel a liquid formulation that will eventually solidify into a gel on the target surface. The usage of PVA as a test mechanism will determine how viscous the formulation can be without jamming or damaging the sprayer. The two temperatures chosen were 25° C. and 30° C. because the temperature of the apparatus will be approximately room temperature, while the temperature of the body is at 32° C. The results of PVA are consistent with the known properties of Newtonian fluids, as the viscosity decreases as the temperature increases. Therefore, a PVA solution expelled from a sprayer would be less viscous if applied to the surface of the body. As outlined in Table 42, (a) solutions having a concentration of 5% and 10% could be sprayed easily, (b) the solution having a concentration of 15% was difficult to spray, and (c) solutions with concentrations greater than 15% (~337 cP-9900 cP) could not be sprayed.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the illustrative embodiments and/or appended claims.

What is claimed is:

1. A method of treating a human subject suffering from baldness, wherein the method comprises:
   a) integumental perturbation of an area of the bald scalp of the human subject, wherein the integumental perturbation is performed using microneedles; and
   b) administering a hair growth promoting agent;
   wherein the integumental perturbation is to a skin depth of about 500 to 1000 μm.

2. The method of claim 1, wherein the hair growth promoting agent is selected from the group consisting of: a potassium channel opener, an ATP-sensitive potassium channel (KATP opener), minoxidil, diazoxide, phenytoin, a 5α-reductase inhibitor, finasteride, dutasteride, turosteride, bexlosteride, izonsteride, epristeride, epigallocatechin, MK-386, azelaic acid, FCE 28260, SKF 105,111, ketoconazole, fluconazole, spironolactone, flutamide, 17-alpha-hydroxyprogesterone, 11-alpha-hydroxyprogesterone, RU58841, fluridil, QLT-7704, an antiandrogen oligonucleotide, a prostaglandin F2α analogs, prostaglandin analogs, a prostaglandin, bimatoprost, latanoprost, travoprost, tafluprost, unoprostone, dinoprost, AS604872, BOL303259X, PF3187207, carboprost, kopexil, $CaCl_2$, botilinum toxin A, adenosine, DoxoRx, docetaxel, FK506, GP11046, GP11511, LGD 1331, ICX-TRC, MTS-01, NEOSH101, HYG-102440, HYG-410, HYG-420, HYG-430, HYG-440, CB-03-01, RK-023, abatacept, MorrF, ASC-J9, NP-619, AS101, Metron-F-1, PSK 3841, bexrotene, MedinGel, THG11331, PF-277343, PF-3004459, efalizumab, caffeine, coffee, a herb, triamcinolone acetonide, a topical irritant or sensitizer, clomipramine, unsaturated fatty acids, a fatty acid derivative, a thickener, a hair loss concealer, niacin, nicotinate esters and salts, methionine, an androgen receptor inhibitor, a copper peptide, a compound with superoxide dismutation activity, an agent that increases nitric oxide production, a compound that mobilizes bone marrow-derived stem cells, a compound that regulates the differentiation of stem cells into gender-specific specialized human hair follicles, cyoctol, topical progesterone, topical estrogen, cyproterone acetate, combination 5α-reductase inhibitors, oral contraceptive pills, an antiestrogen, an estrogen, or estrogen-like drug, an anti-oxidant, inhibitors of reactive oxygen species (ROS) generation, an agent that induces an immune response or causes inflammation, and an antiapoptotic compound.

3. The method of claim 1, wherein, at 3 months after the integumental perturbation, the area of the scalp of the subject has at least 5%, 10%, 15%, 20%, 25%, 30%, 35%, 40%, 45%, 50%, 55%, 60%, 65%, 70%, 75%, 80%, 85%, 90%, 95%, or at least 100% more vellus hair compared to immediately before the integumental perturbation.

4. The method of claim 1 further comprising: applying a wound healing dressing.

5. The method of claim 4, wherein the wound healing dressing is non-occlusive.

6. The method of claim 5, wherein the wound healing dressing is a cream, gel, lotion, emulsion, suspension, oil, non-aqueous solution, aqueous solution, or drop.

7. The method of claim 4, wherein the wound healing dressing is applied for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days after the integumental perturbation.

8. The method of claim 1, wherein the hair growth promoting agent is administered topically.

9. The method of claim 1, wherein the hair growth promoting agent is administered once reepithelization is completed, or 1, 2, 3, 4, 5, 6, 7, 8, 9, 10, 11, 12, 13, 14, 15, or 16 weeks after integumental perturbation.

10. The method of claim 1, wherein the hair growth promoting agent is administered before and after integumental perturbation.

11. The method of claim 1, wherein the hair growth promoting agent is administered for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 weeks.

12. The method of claim 1, wherein the subject has androgenetic alopecia (AGA), scarring alopecia, male pattern baldness, female pattern baldness, discoid lupus erythematosis, or lichen planopilaris.

13. A method of treating a human subject suffering from baldness, wherein the method comprises:
   i) integumental perturbation of an area of the bald scalp of the human subject, wherein the integumental perturbation is performed by dermabrasion, wherein the dermabrasion is performed with a dermabrader having a dermabrasion hand piece with dermabrasion tip comprising:
      a housing having a first opening substantially aligned with a longitudinal axis of the housing and a second opening disposed at an angle to the longitudinal axis;
      transmission unit disposed in the housing, the transmission unit comprising:
         a first set of gears;
         a second set of gears; and
         a linkage assembly disposed between the first set of gears and the second set of gears; and
      an abrasive disk; and
      wherein the transmission unit converts a rotational motion of the dermabrasion hand piece to a reciprocating motion causing the abrasive disk to reciprocate, and
      wherein the abrasive disk is disposed at an angle with the longitudinal axis of the housing; and
   ii) administering a hair growth promoting agent;
   wherein the integumental perturbation is to a skin depth of about 500 to 1000 μm.

14. The method of claim 2, wherein:
   i) the herb is saw palmetto, glycine soja, Panax ginseng, Castanea Sativa, Amica Montana, or Hedera Helix Geranium Maculatum;
   ii) the topical irritant is anthralin;

iii) the topical sensitizer is squaric acid dibutyl ester (SADBE) or di phenyl cyclopropenone (DPCP);
iv) the unsaturated fatty acid is gamma linolenic acid;
v) the thickener is carbomer, glycol distearate, or cetearyl alcohol;
vi) the agent that increases nitric oxide production is arginine, citrulline, nitroglycerin, amyl nitrite, or sildenafil;
vii) the compound that mobilizes bone marrow-derived stem cells is a growth factor, G-CSF, and/or a chemical agent;
viii) the compound that regulates the differentiation of stem cells into gender-specific specialized human hair follicles is finasteride, fluconazole, spironolactone, flutamide, diazoxide, 11-alpha-hydroxyprogesterone, ketoconazole, RU 5 8 841, dutasteride, fluridil, or QL T-7704, an antiandrogen oligonucleotide, cyoctol, topical progesterone, topical estrogen, cyproterone acetate, ru58841, combination 5α-reductase inhibitors, or an oral contraceptive pill;
ix) the anti-oxidant is glutathione, ascorbic acid, tocopherol, uric acid, or polyphenol antioxidants;
x) the inhibitor of ROS generation is a superoxide dismutase inhibitor, a stimulator or ROS breakdown, an mTOR inhibitor, or a sirtuin or activator thereof; or
xi) the agent that induces an immune response or causes inflammation is a tetanus toxoid, a topical non-specific irritant, or a sensitizer.

15. The method of claim 14, wherein:
i) the chemical agent is plerixafor;
ii) the stimulator of ROS breakdown is selenium;
iii) the mTOR inhibitor is rapamycin;
iv) the sirtuin or activator thereof is resveratrol, or another SIRT1, SIRT3 activator, or a nicotinamide inhibitor;
v) the topical non-specific irritant is anthralin; or
vi) the topical sensitizer is squaric acid dibutyl ester (SADBE) or diphenyl cyclopropenone (DPCP).

16. The method of claim 1, wherein the hair growth promoting agent is administered following the new appearance of vellus hair on the area of the bald scalp that has been subjected to integumental perturbation.

17. The method of claim 1, wherein the microneedles are in a microneedle array.

18. The method of claim 1, wherein the method promotes vellus hair growth in the human subject suffering from baldness.

19. The method of claim 13, wherein the method promotes vellus hair growth in the human subject.

* * * * *